US011767332B2

(12) United States Patent
Kruse et al.

(10) Patent No.: US 11,767,332 B2
(45) Date of Patent: Sep. 26, 2023

(54) GLUCOSE-SENSITIVE ALBUMIN-BINDING DERIVATIVES

(71) Applicant: Novo Nordisk A/S, Bagsvaerd (DK)

(72) Inventors: Thomas Kruse, Herlev (DK); Mikael Kofod-Hansen, Broenshoej (DK); Martin Werner Borchsenius Muenzel, Broenshoej (DK); Henning Thoegersen, Farum (DK); Per Sauerberg, Farum (DK); Jakob Ewald Rasmussen, Koebenhavn (DK); Carsten Behrens, Koebenhavn (DK); Thomas Hoeg-Jensen, Broenshoej (DK); Vojtech Balsanek, Prague (CZ); Zuzana Drobnakova, Prague (CZ); Ladislav Droz, Prague (CZ); Miroslav Havranek, Strancice-Praha (CZ); Vladislav Kotek, Prague (CZ); Milan Stengl, Klatovy (CZ); Ivan Snajdr, Prague (CZ); Hana Drusanova, Kromeriz (CZ)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/500,242

(22) Filed: Oct. 13, 2021

(65) Prior Publication Data

US 2022/0081451 A1 Mar. 17, 2022

Related U.S. Application Data

(63) Continuation of application No. 16/759,378, filed as application No. PCT/EP2018/080650 on Nov. 8, 2018, now Pat. No. 11,186,595.

(30) Foreign Application Priority Data

Nov. 9, 2017 (EP) .................................... 17200734
Jun. 18, 2018 (EP) .................................... 18178294

(51) Int. Cl.
*C07F 5/02* (2006.01)
*A61K 47/54* (2017.01)

(52) U.S. Cl.
CPC .............. *C07F 5/025* (2013.01); *A61K 47/54* (2017.08)

(58) Field of Classification Search
CPC ...................................................... C07F 5/025
See application file for complete search history.

(56) References Cited

U.S. PATENT DOCUMENTS

| | | | |
|---|---|---|---|
| 7,316,999 B2 | 1/2008 | Hoeg-Jensen et al. | |
| 7,317,000 B2 | 1/2008 | Hoeg-Jensen et al. | |
| 11,186,595 B2 * | 11/2021 | Kruse | G01N 33/542 |
| 2014/0005398 A1 | 1/2014 | Li et al. | |
| 2015/0320837 A1 | 11/2015 | Anderson et al. | |
| 2018/0057559 A1 | 3/2018 | Weiss | |
| 2018/0299462 A1 | 10/2018 | Wu et al. | |
| 2019/0247468 A1 | 8/2019 | Mahdavi | |

FOREIGN PATENT DOCUMENTS

| | | | |
|---|---|---|---|
| DE | 102008052314 | A1 | 4/2010 |
| EP | 0424168 | A1 | 4/1991 |
| JP | 2003535106 | A | 11/2003 |
| JP | 2005-526009 | A | 9/2005 |
| WO | 0192334 | | 12/2001 |
| WO | 03/048195 | | 6/2003 |
| WO | 2003/105860 | A1 | 12/2003 |
| WO | 2009/112583 | A2 | 9/2009 |
| WO | 2011/000823 | A1 | 1/2011 |
| WO | 2014093696 | | 6/2014 |
| WO | 2015106292 | A1 | 7/2015 |
| WO | 2019092125 | A1 | 5/2019 |
| WO | 2019204206 | A1 | 10/2019 |

OTHER PUBLICATIONS

C.M. Donmoyer et al., "Fructose augments infection-impaired net hepatic glucose uptake during TPN administration," Am. J. Physiol. Endocrinol. Metab. 2001, vol. 280, pp. E703-E711.
H.C. Chou et al., "Glucose-responsive insulin activity by covalent modification with aliphatic phenylboronic acid conjugates," Proc. Nat. Acad. Sci., 2015, vol. 112, No. 8, pp. 2401-2406.
Hansen et al., "Arylboronic Acids: A Diabetic Eye on Glucose Sensing," Sensors Actuators B, 2012, vol. 161, pp. 45-79.
Hansen et al., "Ortho-substituted aryl monoboronic acids have improved selectivity for D-glucose relative to D-fructose and L-lactate," Tetrahedron, 2011, vol. 67, No. 6, pp. 1334-1340.
M.L. Goodwin et al., "Blood lactate measurements and analysis during exercise: a guide for clinicians," J Diabetes Sci Technol, 2007, vol. 1, No. 4, pp. 558-569.
SB van Witteloostuijn et al., "Half-Life Extension of Biopharmaceuticals using Chemical Methods: Alternatives to PEGylation," Chem Med Chem, 2016, vol. 11, pp. 2474-2495.
T. Arai et al., "A Comparison of the Plasma Fructose Concentrations in Dogs and Cats and Changes in the Fructose Concentrations in Dogs Following Intravenous Administration of Fructose," Vet. Res. Commun., 1999, vol. 23, No. 4, pp. 203-209.
Tan et al., "Glucose and pH-Responsive Nanogated Ensemble Based on Polymeric Network Capped Mesoporous Silica," XP002779955, retrieved from STN Database accession No. 2015:373548 on Apr. 10, 2018.

(Continued)

*Primary Examiner* — Golam M Shameem

(74) *Attorney, Agent, or Firm* — Jianjie Hu

(57) ABSTRACT

This invention relates to glucose-sensitive albumin-binding diboron conjugates. More particularly the invention provides novel diboron compounds, and in particular diboronate or diboroxole compounds, useful as intermediate compounds for the synthesis of diboron conjugates.

3 Claims, 6 Drawing Sheets

(56) References Cited

OTHER PUBLICATIONS

Tan et al., "Glucose and pH-Responsive Nanogated Ensemble Based on Polymeric Network Capped Mesoporous Silica," ACS Applied Materials & Interfaces, 2015, vol. 7, No. 11, pp. 6310-6316.

Thomas Hoeg-Jensen, "Preparation and Screening of Diboronate Arrays for Identification of Carbohydrate Binders," QSAR & Combinatorial Science, 2004, vol. 23, No. 5, pp. 344-351.

Brownlee et al.,"A glucose-controlled insulin-delivery system: semisynthetic insulin bound to lectin", Science, Dec. 1979, vol. 206, No. 4423, pp. 1190-1191.

Chou, Danny Hung-Chieh, et al., "Glucose-responsive insulin activity by covalent modification with aliphatic phenylboronic acid conjugates." Proceedings of the National Academy of Sciences, Feb. 2015, vol. 112, No. 8, pp. 2401-2406.

Hansen et al.,"Arylboronic acids: A diabetic eye on glucose sensing." Sensors and Actuators B: Chemical, Sep. 2012, vol. 161, No. 1, pp. 45-79.

Hoeg-Jensen et al., "Insulins with built-in glucose sensors for glucose responsive insulin release." Journal of peptide science: an official publication of the European Peptide Society, Aug. 2005, vol. 11, No. 6, pp. 339-346.

Kowalczyk, Wioleta, et al. "The binding of boronated peptides to low affinity mammalian saccharides." Peptide Science, May 2018, vol. 110, No. 3, p. 1-12e23101.

Takei et al., Sugar-Responsive Layer-by-Layer Film Composed of Phenylboronic Acid-Appended Insulin and Poly(vinyl alcohol), Chemical and Pharmaceutical Bulletin, Jan. 2018, vol. 66, No. 4, p. 368-374.

Wu et al.,"Responsive Materials for Self-Regulated Insulin Delivery." Macromolecular bioscience, Jul. 2013, vol. 13, No. 11, pp. 1464-1477.

Zaykov et al., "Pursuit of a perfect insultin", Nature Reviews Drug Discovery, Jun. 2016, vol. 15, No. 6, pp. 125-439.

* cited by examiner $^{19}$F-NMR, Compound of Example 26

GLUCOSE-SENSITIVE ALBUMIN-BINDING DERIVATIVES

CROSS-REFERENCE TO RELATED APPLICATIONS

This application is a continuation of U.S. patent application Ser. No. 16/759,378, filed Apr. 27, 2020, which is a 35 U.S.C. § 371 National Stage application of International Application PCT/EP2018/080650 (WO 2019/092125), filed Nov. 8, 2018, which claims priority to European Patent Applications 17200734.6, filed Nov. 9, 2017 and 18178294.7, filed Jun. 18, 2018; the contents of which are incorporated herein by reference.

TECHNICAL FIELD

This invention relates to glucose-sensitive albumin-binding diboron conjugates. More particularly the invention provides novel diboron compounds, and in particular diboronate or diboroxole compounds, useful as intermediate compounds for the synthesis of diboron conjugates.

BACKGROUND ART

Boronic acids are known for their capability to bind glucose and other carbohydrates and polyols via the formation of boronate esters. This glucose binding is covalent, but the binding equilibrium is fast and reversible, so the binding appears as a complex formation, with displacement constants (Kd) in the millimolar range.

Simple boronic acids have pKa values around 9, but since it is the boronate form that binds glucose the strongest (see FIG. 2), tuning of boronic acid pKa-values using electron-withdrawing groups can provide stronger glucose affinity at physiological pH 7.5. Notably, monoboronates bind glucose with Kd values in the range 10-50 millimolar, which does not match well with the physiological range for glucose fluctuations (usually 1-30 mM in diabetes patients).

Stronger glucose affinity can be secured by using diboronic acids, as extensively researched in pursuit of optical glucose sensors. However, diboronates for use as optical glucose sensors are typically coloured and fluorescent (Hansen, Hoeg-Jensen et al, Sensors and Actuators B 161 (2012) 45), and such properties are not always desirable for other applications, and in particular for therapeutic use.

Diboronate selectivity for glucose over other polyols is a desirable property for in vivo use of the compounds. The bulk of diboronate literature focus on selectivity towards glucose over fructose, but millimolar blood concentrations of fructose never happen, not even after a fructose-rich meal. Blood lactate concentrations, on the other hand, are in the low millimolar values at rest, but can increase to 10-20 mM during extreme exercise. Diboron compounds with selectivity for glucose over lactate therefore are advantageous for therapeutic use (Hansen, Hoeg-Jensen et al, Tetrahedron 67 (2011) 1334).

The diboronic acids identified for developing optical glucose sensors typically lack a conjugation handle, and therefore are not particularly well suited for attachment to protein and peptide-based drugs.

A number of protein and peptide-based drugs, and in particular insulin, GLP-1, and amylin, are used in treatment of diabetes. However, such therapeutics have roughly the same bioactivity at low and as well as high glucose blood values, and the use of such drugs can lead to very low blood glucose values, with a concomitant risk of hypoglycemia, which is a life-threatening condition.

SUMMARY OF THE INVENTION

While blood glucose lowering drugs are successfully used for the treatment of diabetes, such drugs are also capable of lowering blood glucose levels even in situations where the patients do not want glucose levels to change. This may in particular be the case when blood glucose is below the normal fasting value of approx. 5 mM glucose. Therefore it would be advantageous to equip diabetes-related peptide and protein drugs with a glucose-regulated bioactivity, e.g. a weaker glucose-lowering activity of insulin at low blood glucose values.

According to the present invention certain diboronates and diboroxoles are provided, which diboron compounds bind glucose with Kd values in the low millimolar range (of approx. 0.2-5 mM), and which compounds have good selectivity for glucose over lactate. Moreover, the diboron compounds of the invention contain a conjugation handle, e.g. a carboxy group, so they may be conjugated to diabetes-related protein and peptide-based drugs, e.g. via attachment to a (native or substituted/introduced) lysine residue or an N-terminal of the protein or peptide.

Moreover, the diboron compounds of the invention are capable of binding to human serum albumin (HSA), thus possessing a dual action, as this binding also is glucose-sensitive (the HSA-bound fraction of the diboron peptide is inactive due to blocking of the receptor binding sites on the peptide). Albumin binding can in general prolong the in vivo half-life of peptides and protein-based drugs. The prolonged effect is achieved as the albumin bound fraction is protected from enzymatic degradation and kidney elimination, and only the free fraction is biological active, thus preventing receptor mediated clearance of the albumin bound fraction.

HSA-binding of fatty acid-conjugated protein and peptide-based drugs is an established method for making the peptide/proteins long-acting in vivo. However, the fact that the diboron-conjugated peptides and proteins of the invention, comprising no fatty acids, are capable of binding to HSA, and that the binding is sensitive to glucose, has never been reported.

Therefore, in its first aspect, the invention provides novel diboron compounds represented by the general Formula I, as described herein.

In other aspects the invention provides novel diboron compounds of Formula Ia, and more particular of Formulas Ia, Ib, Ic, Id, Ie, If, Ig, Ih, and Ii as described herein.

In further aspects the invention relates to the use of the diboron compounds as intermediates in the manufacture of diboron conjugates of the invention.

In yet another aspect, the invention provides novel diboron conjugates represented by the general Formula I', as described herein.

Other objects of the invention will be apparent to the person skilled in the art from the following detailed description and examples.

BRIEF DESCRIPTION OF THE DRAWINGS

The present invention is further illustrated by reference to the accompanying drawing, in which.

DETAILED DISCLOSURE OF THE INVENTION

The Diboron Conjugates of the Invention

Figure 1:
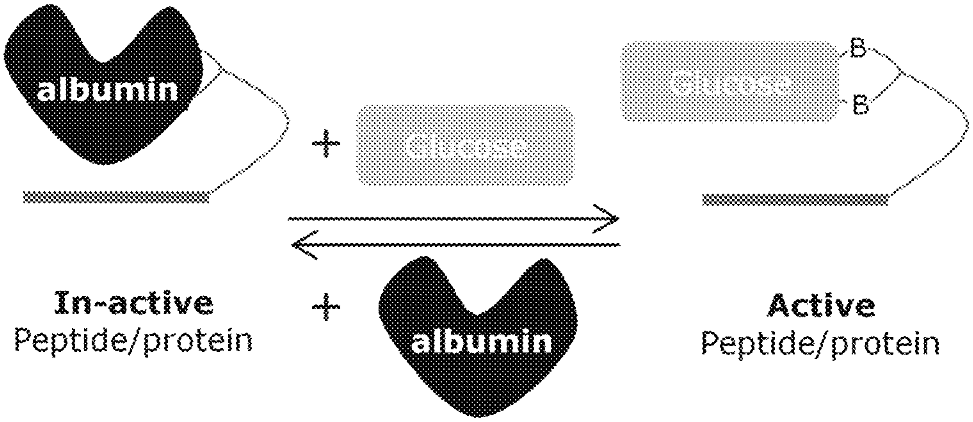
FIG. 1 shows an illustration of glucose-sensitive albumin binding.
Figure 2:
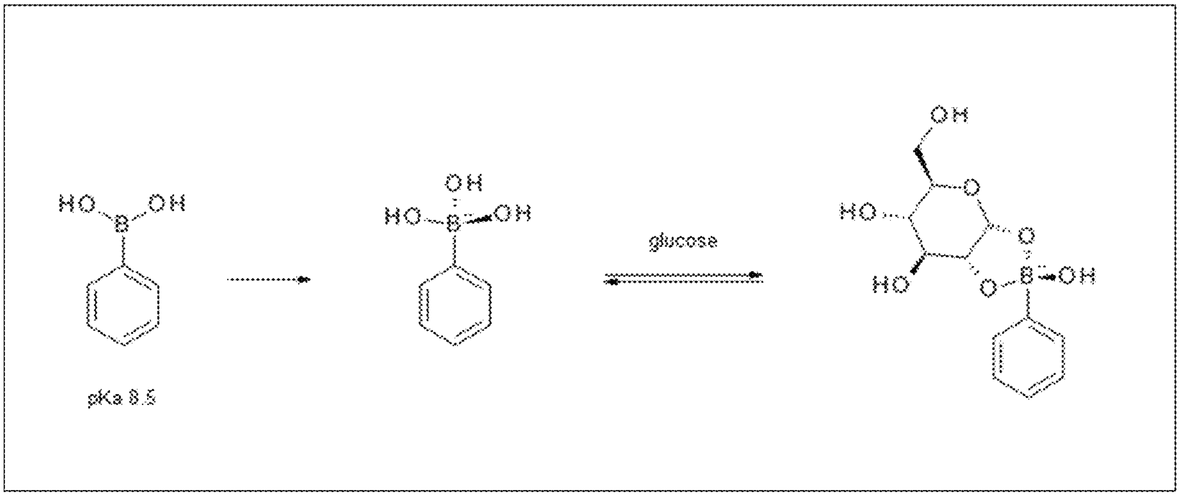
FIG. 2 shows how glucose is binding boronate, illustrated for the pyranose form.

In one aspect the invention provides diboron conjugates represented by the general Formula I'

$R^{1'}$—X'—$R^{2'}$ in which Formula I',

X' represents a linker of Formula Ia':

(Formula Ia')

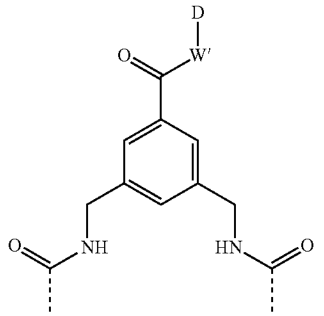

wherein

---- represents a covalent bond towards $R^{1'}$ or $R^{2'}$;

D represents a drug substance; and

W' represents a covalent bond, or a linker selected from the group consisting of $—NHCH_2(C{=}O)—$, $—NHCH_2CH_2(C{=}O)—$, $—NHCH_2CH_2CH_2(C{=}O)—$, and $—NHCH(COOH)CH_2CH_2(C{=}O)—$ (the latter representing an L-gamma-Glu or a D-gamma-Glu residue); or X' represents a linker of Formula Ib':

(Formula Ib')

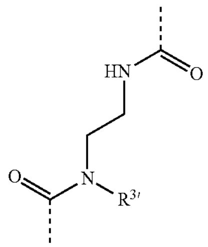

wherein,

---- represents a covalent bond towards $R^{1'}$ or $R^{2'}$; and $R^{3'}$ represent $—(CH_2)_{m'}(C{=}O)—W'\text{-}D$, wherein m' represents an integer in the range of 1 to 4;

W' represents a covalent bond or a linker selected from the group consisting of $—NHCH_2(C{=}O)—$, $—NHCH_2CH_2(C{=}O)—$, $—NHCH_2CH_2CH_2(C{=}O)—$, and $—NHCH(COOH)CH_2CH_2(C{=}O)—$ (the latter representing an L-gamma-Glu or a D-gamma-Glu residue); and D represents a drug substance; or X' represents a linker of Formula Ic':

(Formula Ic')

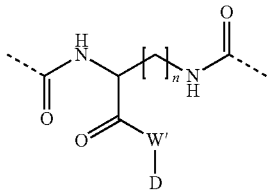

which represents a D- or an L-amino acid form; and wherein,

---- represents a covalent bond towards $R^{1'}$ or $R^{2'}$;

n' represents an integer in the range of 1 to 4;

W' represents a covalent bond or a linker selected from the group consisting of $—NHCH_2(C{=}O)—$, $—NHCH_2CH_2(C{=}O)—$, $—NHCH_2CH_2CH_2(C{=}O)—$, and $—NHCH(COOH)CH_2CH_2(C{=}O)—$ (the latter representing an L-gamma-Glu or a D-gamma-Glu residue); and D represents a drug substance; or X' represents a linker of Formula Id':

(Formula Id')

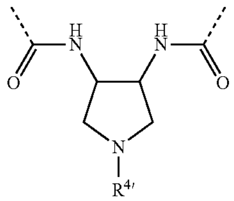

which represents a R,R or S,S, or R,S or R,S stereoisomer of the 3,4-diaminopyrrolidine;

wherein,

---- represents a covalent bond towards $R^{1'}$ or $R^{2'}$;

$R^{4'}$ represents $—(C{=}O)(CH_2)_{p'}(C{=}O)—W'\text{-}D$; where

W' represents a covalent bond or a linker selected from the group consisting of $—NHCH_2(C{=}O)—$, $—NHCH_2CH_2(C{=}O)—$, $—NHCH_2CH_2CH_2(C{=}O)—$, and $—NHCH(COOH)CH_2CH_2(C{=}O)—$ (the latter representing an L-gamma-Glu or a D-gamma-Glu residue);

wherein p' represents an integer in the range of 1 to 4; and

D represents a drug substance; or

X' represents a linker of Formula Ie':

(Formula Ie')

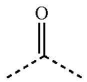

wherein,

---- represents a covalent bond towards $R^{1'}$ or $R^{2'}$; or

X' represents a linker of Formula If':

(Formula If')

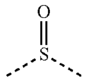

wherein,

---- represents a covalent bond towards $R^{1'}$ or $R^{2'}$; or

X' represents a linker of Formula Ig':

(Formula Ig')

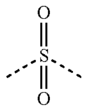

wherein,

---- represents a covalent bond towards $R^{1'}$ or $R^{2'}$; or

X' represents a linker of Formula Ih':

(Formula Ih')

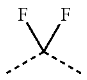

wherein,

---- represents a covalent bond towards $R^{1'}$ or $R^{2'}$; or

X' represents a linker of Formula Ii':

(Formula Ii')

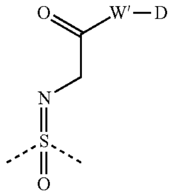

wherein,

---- represents a covalent bond towards $R^{1'}$ or $R^{2'}$; and

W' represents a covalent bond, or a linker selected from the group consisting of —$NHCH_2(C{=}O)$—, —$NHCH_2CH_2(C{=}O)$—, —$NHCH_2CH_2CH_2(C{=}O)$—, or —$NHCH(COOH)CH_2CH_2(C{=}O)$— (the latter representing an L-gamma-Glu or a D-gamma-Glu residue); and D represents a drug substance; and $R^{1'}$ and $R^{2'}$, which may be identical or different, each represents a group of Formula IIa' or Formula IIb':

(Formula IIa')

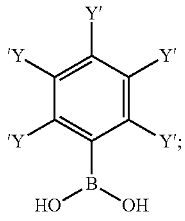

or

-continued (Formula IIb')

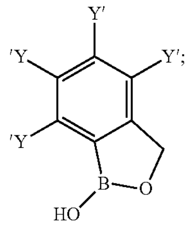

wherein, one to four Y' represents H; and none, one or two Y' represents F, Cl, $CF_2$, $CF_3$, $SF_5$, $OCF_3$, $SO_2CH_3$ and/or $SO_2CF_3$; and one Y' represents (a covalent bond representing) the attachment point to X' of Formula I'; and when X' is Formula Ie', If', Ig' or Ih', one Y' in either $R^{1'}$ or $R^{2'}$ represents —(C═O)—W'-D, where W' represents a covalent bond, or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing an L-gamma-Glu or a D-gamma-Glu residue); and wherein D represents a drug substance.

The drug substance D to be conjugated according to the invention may be selected from a number of protein and peptide-based drugs, and in particular insulin, GLP-1, and amylin, which are used in treatment of diabetes.

In one embodiment the diboron conjugate of the invention may in particular be a compound according to the general Formula I', wherein D represents insulin or an insulin analogue.

In another embodiment the diboron compound of the invention is a compound according to the general Formula I', wherein D represents GLP-1 or a GLP-1 analogue.

In a third embodiment the diboron compound of the invention is a compound according to the general Formula I', wherein D represents amylin or an amylin analogue.

The diboron compound of the invention may in particular be a compound according to the general Formula I', wherein the diboron compound represented by the general Formula I' is conjugated to the drug substance D via a lysine (K) residue, which may be a native or an introduced lysine residue, or to an N-terminal of the drug substance.

In another embodiment, the diboron compound of the invention may in particular be a compound according to the general Formula I', wherein the diboron compound is conjugated to the drug substance D via a native lysine (K) residue, or to an N-terminal of the drug substance.

In a third embodiment, the diboron compound of the invention may in particular be a compound according to the general Formula I', wherein the diboron compound is conjugated to the drug substance D via two or more (native and/or introduced) lysine residues, and/or one or two N-terminals of the drug substance.

The Diboron Compounds of the Invention

In another aspect the invention provides diboron compounds, and in particular a diboronate or a diboroxole derivative, represented by Formula I:

$$R^1—X'—R^2$$

in which Formula I,

X represents a linker of Formula Ia:

(Formula Ia)

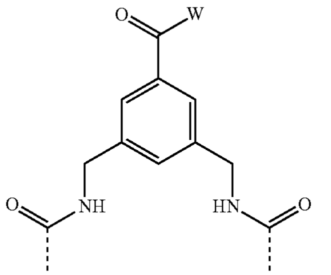

wherein

---- represents a covalent bond towards $R^1$ or $R^2$;

W represents OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); or X represents a linker of Formula Ib:

(Formula Ib)

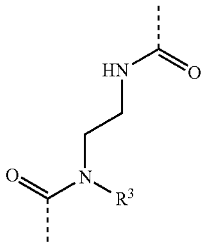

wherein,

---- represents a covalent bond towards $R^1$ or $R^2$; and $R^3$ represent —$(CH_2)_m(C{=}O)$—W;

wherein m represents an integer in the range of 1 to 4; and

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); or X represents a linker of Formula Ic:

(Formula Ic)

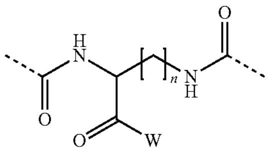

which represents a D- or an L-amino acid form; and wherein,

---- represents a covalent bond towards $R^1$ or $R^2$;

n represents an integer in the range of 1 to 4;

W represents OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); or wherein X represents a linker of Formula Id:

(Formula Id)

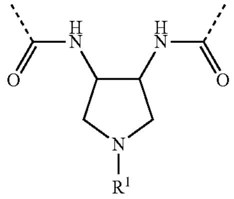

which represents a R,R or S,S, or R,S or R,S stereoisomer of the 3,4-diaminopyrrolidine;

wherein,

---- represents a covalent bond towards $R^1$ or $R^2$;

$R^4$ represents —$(C{=}O)(CH_2)_m(C{=}O)$—W;

wherein m represents an integer in the range of 1 to 4;

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); or X represents a linker of Formula Ie:

(Formula Ie)

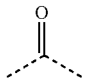

wherein,

---- represents a covalent bond towards $R^1$ or $R^2$; or

X represents a linker of Formula If:

(Formula If)

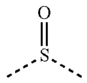

wherein,

---- represents a covalent bond towards $R^1$ or $R^2$; or

X represents a linker of Formula Ig:

(Formula Ig)

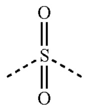

wherein,

---- represents a covalent bond towards $R^1$ or $R^2$; or

X represents a linker of Formula Ih:

(Formula Ih)

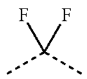

wherein,

---- represents a covalent bond towards $R^1$ or $R^2$; or

X represents a linker of Formula Ii:

(Formula Ii)

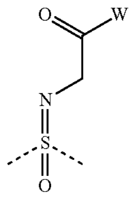

wherein,

---- represents a covalent bond towards $R^1$ or $R^2$; and

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); and $R^1$ and $R^2$, which may be identical or different, each represents a group of Formula IIa or IIb:

(Formula IIa)

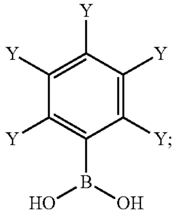

or (Formula IIb)

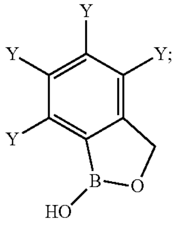

wherein, one to four Y represents H; and none, one or two Y represents F, Cl, $CF_2$, $CF_3$, $SF_5$, $OCF_3$, $SO_2CH_3$ and/or $SO_2CF_3$; and one Y represents (a covalent bond representing) the attachment point to X of Formula I; and when X is Formula Ie, If, Ig or Ih, one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue).

In one embodiment, the diboron compound of the invention is represented by Formula I, wherein X represents a linker of Formula Ia:

(Formula Ia)

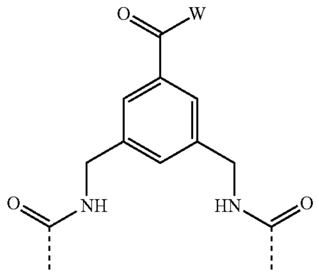

wherein

---- represents a covalent bond towards $R^1$ or $R^2$;

W represents OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); and $R^1$ and $R^2$, which may be identical or different, each represents a group of Formula IIa or IIb:

(Formula IIa)

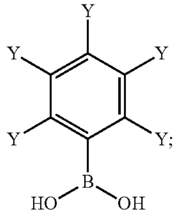

or (Formula IIb)

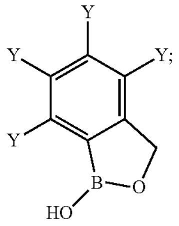

wherein, one Y represents (a covalent bond representing) the attachment point to the linker X of Formula Ia;

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Ia as defined above, wherein W represents —OH.

In a further embodiment, the diboron compound of the invention is represented by Formula I, wherein X represents a linker of Formula Ia as defined above, wherein W represents —OH;

one of Y represents F or $CF_3$; and the remaining Y represents H.

In a further embodiment, the diboron compound of the invention is represented by Formula I, wherein X represents a linker of Formula Ia as defined above, wherein W represents —OH;

one of Y represents F; and the remaining Y represents H.

In a further embodiment, the diboron compound of the invention is represented by Formula I, wherein X represents a linker of Formula Ia as defined above, wherein W represents —OH;

$R^1$ and $R^2$ are identical and represent a group of Formula IIa;

one of Y represents F; and the remaining Y represents H.

In a further embodiment, the diboron compound of the invention is represented by Formula I, wherein X represents a linker of Formula Ia as defined above, wherein W represents —OH;

$R^1$ and $R^2$ are identical and represent a group of Formula IIb;

one of Y represents F; and the remaining Y represents H.

In another embodiment, the diboron compound of the invention is represented by Formula I, wherein X represents a linker of Formula Ib:

(Formula Ib)

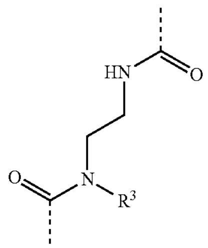

wherein,

---- represents a covalent bond towards $R^1$ or $R^2$; and $R^3$ represent $—(CH_2)_m(C{=}O)—W$;

wherein m represents an integer in the range of 1 to 4; and

W represents —OH, $—NHCH_2COOH$, $—NHCH_2CH_2COOH$, $—NHCH_2CH_2CH_2COOH$, or $—NHCH(COOH)CH_2CH_2COOH$ (the latter representing an L-gamma-Glu or a D-gamma-Glu residue);

$R^1$ and $R^2$, which may be identical or different, each represents a group of Formula IIa or IIb:

(Formula IIa)

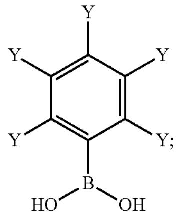

or (Formula IIb)

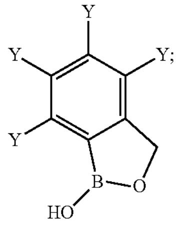

wherein, one Y represents (a covalent bond representing) the attachment point to the linker X of Formula Ib;

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Ib as defined above, wherein m is 1 and W is —OH.

In a third embodiment, the diboron compound of the invention is represented by Formula I, wherein X represents a linker of Formula Ic:

(Formula Ic)

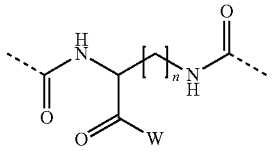

which represents a D- or an L-amino acid form; and wherein,

---- represents a covalent bond towards $R^1$ or $R^2$;

n represents an integer in the range of 1 to 4;

W represents OH, $—NHCH_2COOH$, $—NHCH_2CH_2COOH$, $—NHCH_2CH_2CH_2COOH$, or $—NHCH(COOH)CH_2CH_2COOH$ (the latter representing an L-gamma-Glu or a D-gamma-Glu residue); and $R^1$ and $R^2$, which may be identical or different, each represents a group of Formula IIa or IIb:

(Formula IIa)

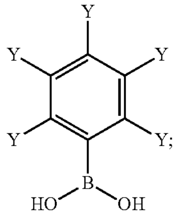

or (Formula IIb)

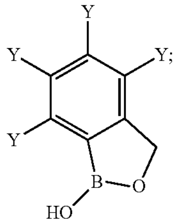

wherein, one Y represents (a covalent bond representing) the attachment point to the linker X of Formula Ic;

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Ic as defined above, wherein n is an integer in the range of 1 to 3 and W is —OH.

In a further embodiment, the diboron compound of the invention is represented by Formula I, wherein X represents a linker of Formula Ic as defined above, wherein n is 1, 2 or 3;

W represents —OH;

$R^1$ and $R^2$ are identical and represent a group of Formula IIa or IIb;

one of Y represents F or $CF_3$; and the remaining Y represents H.

In a further embodiment, the diboron compound of the invention is represented by Formula I, wherein X represents a linker of Formula Ic as defined above, wherein n is 1, 2 or 3;

W represents —OH;

$R^1$ and $R^2$ are identical and represent a group of Formula IIa;

one of Y represents F; and the remaining Y represents H.

In a further embodiment, the diboron compound of the invention is represented by Formula I, wherein X represents a linker of Formula Ic as defined above, wherein n is 1 or 2;

W represents —OH;

$R^1$ and $R^2$ are identical and represent a group of Formula IIb;

one of Y represents F or $CF_3$; and the remaining Y represents H.

In a fourth embodiment, the diboron compound of the invention is represented by Formula I, wherein X represents a linker of Formula Id:

(Formula Id)

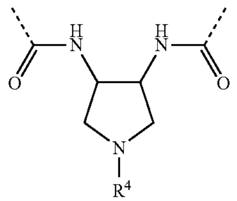

which represents a R,R or S,S, or R,S or R,S stereoisomer of the 3,4-diaminopyrrolidine;

wherein,

---- represents a covalent bond towards $R^1$ or $R^2$;

$R^4$ represents $—(C{=}O)(CH_2)_p(C{=}O)—W$;

wherein p represents an integer in the range of 1 to 4;

W represents —OH, $—NHCH_2COOH$, $—NHCH_2CH_2COOH$, $—NHCH_2CH_2CH_2COOH$, or $—NHCH(COOH)CH_2CH_2COOH$ (the latter representing an L-gamma-Glu or a D-gamma-Glu residue); and $R^1$ and $R^2$, which may be identical or different, each represents a group of Formula IIa or IIb:

(Formula IIa)

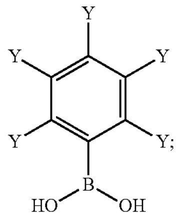

or

-continued (Formula IIb)

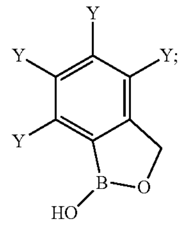

wherein, one Y represents (a covalent bond representing) the attachment point to the linker X of Formula Id;

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Id as defined above, wherein p is 2 and W is —OH.

In a further embodiment, the diboron compound of the invention is represented by Formula I, wherein X represents a linker of Formula Id as defined above, wherein p represents 2;

W represents —OH;

$R^1$ and $R^2$ are identical and represent a group of Formula IIb;

one of Y represents F or $CF_3$; and the remaining Y represents H.

In a fifth embodiment, the diboron compound of the invention is represented by Formula I, wherein X represents a linker of Formula Ie:

(Formula Ie)

wherein,

---- represents a covalent bond towards $R^1$ or $R^2$; and $R^1$ and $R^2$, which may be identical or different, each represents a group of Formula IIa or IIb:

(Formula IIa)

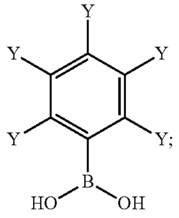

or (Formula IIb)

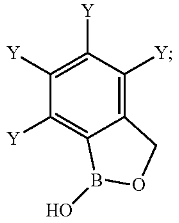

wherein, one Y represents (a covalent bond representing) the attachment point to the linker —CO— of Formula Ie;

one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue);

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Id as defined above, wherein W is —OH.

In a further embodiment, the diboron compound of the invention is represented by Formula I, wherein X represents a linker of Formula Ie as defined above, wherein $R^1$ and $R^2$ are identical and represent a group of Formula IIa;

W represents —OH;

one Y represents —COOH or —$CONHCH_2COOH$;

one Y represents F or $CF_3$; and the remaining of Y represents H.

In a sixth embodiment, the diboron compound of the invention is represented by Formula I, wherein X represents a linker of Formula If:

(Formula If)

wherein,

---- represents a covalent bond towards $R^1$ or $R^2$; and $R^1$ and $R^2$, which may be identical or different, each represents a group of Formula IIa or IIb:

(Formula IIa)

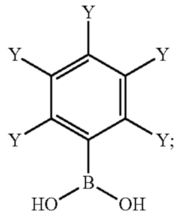

or (Formula IIb)

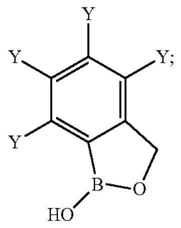

wherein, one Y represents (a covalent bond representing) the attachment point to the linker —SO— of Formula If;

one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue);

none, one or two of Y represent F, Cl, $CF_2$, $CF_3$, $SF_5$, $OCF_3$, $SO_2CH_3$ and/or $SO_2CF_3$; and the remaining Y represents H.

In a seventh embodiment, the diboron compound of the invention is represented by Formula I, wherein X represents a linker of Formula Ig:

(Formula Ig)

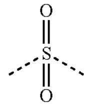

wherein,

---- represents a covalent bond towards $R^1$ or $R^2$; and $R^1$ and $R^2$, which may be identical or different, each represents a group of Formula IIa or IIb:

(Formula IIa)

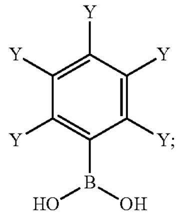

or (Formula IIb)

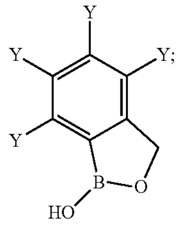

wherein, one Y represents (a covalent bond representing) the attachment point to the linker —($SO_2$)— of Formula Ig;

one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue);

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Ig as defined above, wherein $R^1$ and $R^2$ are identical and represent a group of Formula IIa;

one Y in either $R^1$ or $R^2$ represents —(C═O)—W, where W represents —OH or —$NHCH_2COOH$;

one Y represents F, $CF_3$ or $SF_5$; and the remaining of Y represents H.

In an eighth embodiment, the diboron compound of the invention is represented by Formula I, wherein X represents a linker of Formula Ih:

(Formula Ih)

wherein,

---- represents a covalent bond towards $R^1$ or $R^2$; and $R^1$ and $R^2$, which may be identical or different, each represents a group of Formula IIa or IIb:

(Formula IIa)

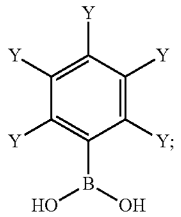

or (Formula IIb)

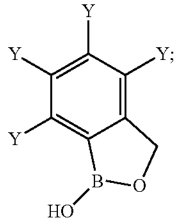

wherein, one Y represents (a covalent bond representing) the attachment point to the linker —($CF_2$)— of Formula Ih;

one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue);

none, one or two of Y represent F, Cl, $CF_2$, $CF_3$, $SF_5$, $OCF_3$, $SO_2CH_3$ and/or $SO_2CF_3$; and the remaining Y represents H.

In an further embodiment, the diboron compound of the invention is represented by Formula I, wherein X represents a linker of Formula Ih as defined above, wherein $R^1$ and $R^2$ are identical and represent a group of Formula IIa;

one Y in either $R^1$ or $R^2$ represents —(C═O)—W, where W represents —OH or —$NHCH_2COOH$;

one Y represents $CF_3$; and the remaining of Y represents H.

In a ninth embodiment, the diboron compound of the invention is represented by Formula I, wherein X represents a linker of Formula Ii:

(Formula Ii)

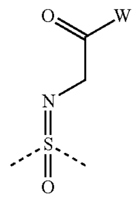

wherein,

---- represents a covalent bond towards $R^1$ or $R^2$;

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue); and $R^1$ and $R^2$, which may be identical or different, each represents a group of Formula IIa or IIb:

(Formula IIa)

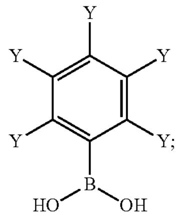

or (Formula IIb)

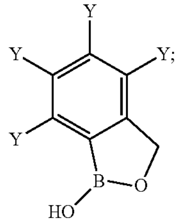

wherein, one Y represents (a covalent bond representing) the attachment point to the linker X of Formula Ii;

none, one or two of Y represent F, Cl, $CF_2$, $CF_3$, $SF_5$, $OCF_3$, $SO_2CH_3$ and/or $SO_2CF_3$; and the remaining Y represents H.

In a further embodiment, the diboron compound of the invention is represented by Formula I, wherein X represents a linker of Formula Ii as defined above, wherein W is —OH.

In a further embodiment, the diboron compound of the invention is represented by Formula I, wherein X is represented by Formula Ia, Ib, Ic, Id, Ie, If, Ig, Ih, or Ii as defined above, and wherein $R^1$ and $R^2$, which may be identical or different, each represents a group of Formula IIa:

(Formula IIa)

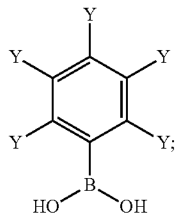

wherein, one to four Y represents H; and none, one or two of Y represents F, Cl, $CF_2$, $CF_3$, $SF_5$, $OCF_3$, $SO_2CH_3$ and/or $SO_2CF_3$; and one Y represents (a covalent bond representing) the attachment point to X of Formula I; and when X is Formula Ie, If, Ig or Ih, one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing an L-gamma-Glu or a D-gamma-Glu residue).

In a further embodiment, the diboron compound of the invention is represented by Formula I, wherein X is represented by Formula Ia, Ib, Ic, Id, Ie, If, Ig, Ih, or Ii as defined above, and wherein $R^1$ and $R^2$, which may be identical or different, each represents a group of Formula IIb:

(Formula IIb)

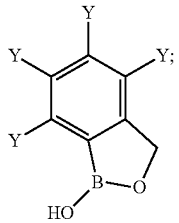

wherein, one to four Y represents H; and none, one or two of Y represents F, Cl, $CF_2$, $CF_3$, $SF_5$, $OCF_3$, $SO_2CH_3$ and/or $SO_2CF_3$; and one Y represents (a covalent bond representing) the attachment point to X of Formula I; and when X is Formula Ie, If, Ig or Ih, one Y in either $R^1$ or $R^2$ represents —(C═O)—W, where W represents —OH, $—NHCH_2COOH$, $—NHCH_2CH_2COOH$, $—NHCH_2CH_2CH_2COOH$, or —NHCH(COOH) $CH_2CH_2COOH$ (the latter representing an L-gamma-Glu or a D-gamma-Glu residue).

In a further embodiment, the diboron compound of the invention is selected from the group consisting of 3,5-Bis((4-borono-2-fluorobenzamido)methyl)benzoic acid;
3,5-Bis((4-borono-3-fluorobenzamido)methyl)benzoic acid;
N,N'-bis(4-borono-3-fluorobenzamido)-N-ethyl-glycine amide;
(S)-2,4-bis(4-borono-3-fluorobenzamido)butanoic acid;
N-(7-Fluoro-1-hydroxy-1,3-dihydrobenzo[c][1,2]oxaborole-6-carbonyl)-N-(2-(7-fluoro-1-hydroxy-1,3-dihydrobenzo[c][1,2]oxaborole-6-carboxamido)ethyl)glycine;
3,5-Bis((7-fluoro-1-hydroxy-1,3-dihydrobenzo[c][1,2]oxaborole-6-carboxamido) methyl) benzoic acid;
N-(5-Fluoro-1-hydroxy-1,3-dihydrobenzo[c][1,2]oxaborole-6-carbonyl)-N-(2-(5-fluoro-1-hydroxy-1,3-dihydrobenzo[c][1,2]oxaborole-6-carboxamido)ethyl)glycine;
N-(4-Fluoro-1-hydroxy-1,3-dihydrobenzo[c][1,2]oxaborole-6-carbonyl)-N-(2-(4-fluoro-1-hydroxy-1,3-dihydrobenzo[c][1,2]oxaborole-6-carboxamido)ethyl)glycine;
N-(6-Fluoro-1-hydroxy-1,3-dihydrobenzo[c][1,2]oxaborole-5-carbonyl)-N-(2-(6-fluoro-1-hydroxy-1,3-dihydrobenzo[c][1,2]oxaborole-5-carboxamido)ethyl)glycine;
$N^2$,$N^6$-Bis(6-fluoro-1-hydroxy-1,3-dihydrobenzo[c][1,2]oxaborole-5-carbonyl)-L-lysine;
3-Borono-5-((3-borono-4-fluorophenyl)sulfonyl)-4-fluorobenzoic acid;
3-Borono-5-(3-borono-5-fluorobenzoyl)benzoic acid;
3-Borono-5-(5-borono-2,4-difluorobenzoyl)benzoic acid;
$N^6$-(4-Borono-2-fluorobenzoyl)-$N^2$-(6-fluoro-1-hydroxy-1,3-dihydrobenzo[c][1,2]-oxaborole-5-carbonyl)-L-lysine;
(S)-2,3-Bis(7-fluoro-1-hydroxy-1,3-dihydrobenzo[c][1,2]oxaborole-6-carboxamido)propanoic acid;
(S)-2,3-Bis(5-fluoro-1-hydroxy-1,3-dihydrobenzo[c][1,2]oxaborole-6-carboxamido)propanoic acid;
(S)-2,3-Bis(4-fluoro-1-hydroxy-1,3-dihydrobenzo[c][1,2]oxaborole-6-carboxamido)propanoic acid;
(3-Borono-5-((3-borono-5-(trifluoromethyl)phenyl)difluoromethyl)benzoyl) glycine;
(3-Borono-5-(3-borono-5-(trifluoromethyl)benzoyl)benzoyl)glycine;
(3-Borono-5-((3-borono-5-(trifluoromethyl)phenyl)sulfonyl)glycine;
4-((3S,4S)-3,4-Bis(7-fluoro-1-hydroxy-1,3-dihydrobenzo[c][1,2]oxaborole-6-carboxamido)pyrrolidin-1-yl)-4-oxobutanoic acid;
(3-Borono-5-(3-borono-5-fluorobenzoyl)benzoyl)glycine;
(3-(6-Borono-2-(ethoxycarbonyl)-8-fluoro-1,1-dioxido-4H-benzo[b][1,4]thiazin-4-yl)-5-fluorophenyl)boronic acid;
(3-Borono-5-((3-borono-5-fluorophenyl)sulfonyl)benzoyl)glycine;
N-(1-Hydroxy-4-(trifluoromethyl)-1,3-dihydrobenzo[c][1,2]oxaborole-6-carbonyl)-N-(2-(1-hydroxy-4-(trifluoromethyl)-1,3-dihydrobenzo[c][1,2]oxaborole-6-carboxamido)ethyl)glycine;
(S)-2,3-Bis(1-hydroxy-4-(trifluoromethyl)-1,3-dihydrobenzo[c][1,2]oxaborole-6-carboxamido)propanoic acid;
4-((3S,4S)-3,4-Bis(1-hydroxy-4-(trifluoromethyl)-1,3-dihydrobenzo[c][1,2]oxaborole-6-carboxamido)pyrrolidin-1-yl)-4-oxobutanoic acid;
(3-Borono-5-((3-borono-5-(pentafluoro-$\lambda^6$-sulfanyl)phenyl)sulfonyl)benzoyl) glycine;
4-[(3R,4R)-3,4-bis[[1-hydroxy-4-(trifluoromethyl)-3H-2,1-benzoxaborole-6-carbonyl]-amino]pyrrolidin-1-yl]-4-oxobutanoic acid;
2-((Bis(3-borono-5-(trifluoromethyl)phenyl)(oxo)-λ6-sulfanylidene)amino)acetic acid;
N-(4-(Difluoromethyl)-1-hydroxy-1,3-dihydrobenzo[c][1,2]oxaborole-6-carbonyl)-N-(2-(4-(difluoromethyl)-1-hydroxy-1,3-dihydrobenzo[c][1,2]oxaborole-6-carboxamido)ethyl)glycine;
N-(4-Chloro-1-hydroxy-1,3-dihydrobenzo[c][1,2]oxaborole-6-carbonyl)-N-(2-(4-chloro-1-hydroxy-1,3-dihydrobenzo[c][1,2]oxaborole-6-carboxamido)ethyl)glycine;
3-(2,3-Bis(4-chloro-1-hydroxy-1,3-dihydrobenzo[c][1,2]oxaborole-6-carboxamido)propanamido)propanoic acid;
2-((Bis(3-borono-5-(difluoromethyl)phenyl)(oxo)-λ6-sulfanylidene)amino)acetic acid;
2-((Bis(3-borono-5-chlorophenyl)(oxo)-λ6-sulfanylidene)amino)acetic acid; and
2-((Bis(3-boronophenyl)(oxo)-λ6-sulfanylidene)amino)acetic acid.

Medical Use

Viewed from another aspect the invention provides novel diboron conjugates for use as medicaments, and in particular for use as medicaments for the treatment of metabolic disorders or conditions.

It is found that the binding constant of the diboron compounds of the invention toward glucose is in the low millimolar range (with a Kd in the range of 0.2-5 mM), thus matching the physiological range of glucose fluctuations (1-30 mM), in particular the glucose range where protection against low blood sugar is desired (1-5 mM).

While the diboroxole compounds are found to provide the best selectivity for glucose vs lactate (see Table 1), the diboronate compounds also hold potential, as blood lactate values do not fluctuate as much, or go as high as glucose values.

Pharmaceutical Compositions

Viewed from another aspect the invention provides novel pharmaceutical compositions comprising a therapeutically effective amount of a diboron conjugate of the invention. In one embodiment, the invention provides a pharmaceutical composition comprising a diboron conjugate of the invention and one or more excipients.

Intermediate Compounds

Viewed from another aspect the invention provides novel diboron compounds for use as an intermediate compound in the manufacture of the novel diboron conjugates of the invention.

Therefore, in one embodiment, the invention relates to the use of a diboron compound, and in particular a diboronate or a diboroxole compound represented by Formula I, as a starting material for the manufacture of the diboron conjugate of the invention.

Methods of Preparation

The diboron compounds of the invention may be prepared by conventional methods for chemical synthesis, e.g. those described in the working examples.

The diboron compounds of the invention may subsequently be use as a starting material for the preparation of the diboron conjugates of the invention.

Methods of Therapy

Viewed from another aspect the invention provides methods of treatment, prevention or alleviation of a metabolic disease or a disorder or a condition of a living animal body, which method comprises the step of administering to such a living animal body in need thereof, a therapeutically effective amount of the diboron conjugate of the invention.

Particular Embodiments

The invention is further described by the following non-limiting embodiments:

1. A diboron conjugate represented by the general Formula I'

$R^1—X—R^2$ in which Formula I', X, $R^1$ and $R^2$, are as defined herein.

2. A diboron compound represented by Formula I $R^1—X—R^2$ in which Formula I,

X represents a linker of Formula Ia:

(Formula Ia)

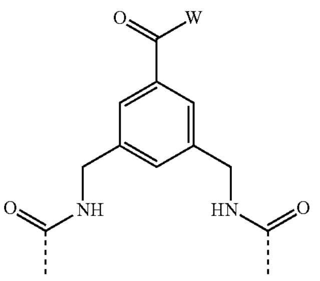

wherein

---- represents a covalent bond towards $R^1$ or $R^2$;

W represents —OH or —$NHCH_2COOH$; or

X represents a linker of Formula Ib:

(Formula Ib)

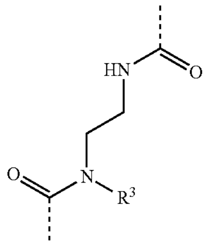

wherein,

---- represents a covalent bond towards $R^1$ or $R^2$; and $R^3$ represent —$(CH_2)_m$COOH;

wherein m represents an integer in the range 1-4; or

X represents a linker of Formula Ic:

(Formula Ic)

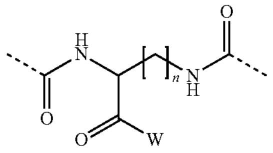

which represents a D- or an L-amino acid form; and wherein,

---- represents a covalent bond towards $R^1$ or $R^2$;

n represents an integer in the range 1-4;

W represents —OH or —$NHCH_2COOH$; or wherein X represents a linker of Formula Id:

(Formula Id)

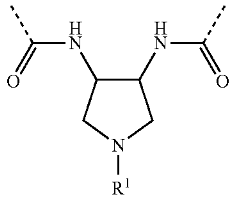

which represents a R,R or S,S, or R,S or R,S stereoisomer of the 3,4-diaminopyrrolidine;

wherein,

---- represents a covalent bond towards $R^1$ or $R^2$;

$R^4$ represents —(C═O)$(CH_2)_m$(COOH);

wherein m represents an integer in the range 1-4; or

X represents a linker of Formula Ie:

(Formula Ie)

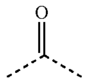

wherein,

---- represents a covalent bond towards $R^1$ or $R^2$; or

X represents a linker of Formula If:

(Formula If)

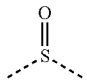

wherein,

---- represents a covalent bond towards $R^1$ or $R^2$; or

X represents a linker of Formula Ig:

(Formula Ig)

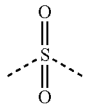

wherein,

---- represents a covalent bond towards $R^1$ or $R^2$; or

X represents a linker of Formula Ih:

(Formula Ih)

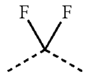

wherein,

---- represents a covalent bond towards $R^1$ or $R^2$; and in which Formulas Ia, Ib, Ic, Id, Ie, If, Ig and Ih, $R^1$ and $R^2$, which may be identical or different, each represents a group of Formula IIa or IIb:

(Formula IIa)

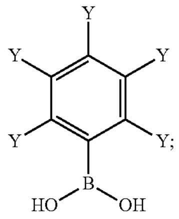

or (Formula IIb)

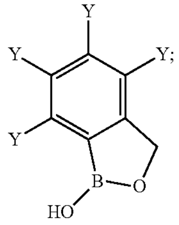

wherein, one to four Y represents H; and none, one or two of Y represents F, $CF_3$, and/or $SF_5$; and one Y represents (a covalent bond representing) the attachment point to X of Formula I; and in Formulas Ie, If, Ig and Ih, Y represents —COOH or $CONHCH_2COOH$.

3. The diboron compound of embodiment 2, represented by Formula I, wherein represents a linker of Formula Ia:

(Formula Ia)

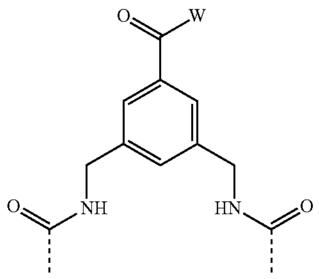

wherein

---- represents a covalent bond towards $R^1$ or $R^2$;

W represents —OH or —$NHCH_2COOH$; and $R^1$ and $R^2$, which may be identical or different, each represents a group of Formula IIa or IIb:

(Formula IIa)

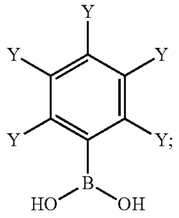

or (Formula IIb)

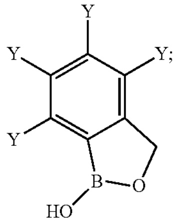

wherein, one Y represents (a covalent bond representing) the attachment point to the linker X of Formula Ia;

none, one or two of Y represent F, $CF_3$, and/or $SF_5$; and the remaining Y represents H.

4. The diboron compound of embodiment 2, represented by Formula I, wherein X represents a linker of Formula Ib:

(Formula Ib)

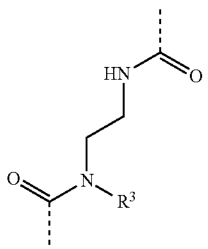

wherein,

---- represents a covalent bond towards $R^1$ or $R^2$; and $R^3$ represent —$(CH_2)_mCOOH$;

wherein m represents an integer in the range 1-4; and $R^1$ and $R^2$, which may be identical or different, each represents a group of Formula IIa or IIb:

(Formula IIa)

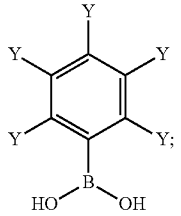

or (Formula IIb)

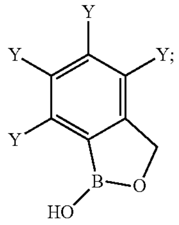

wherein, one Y represents (a covalent bond representing) the attachment point to the linker X of Formula Ib;

none, one or two of Y represent F, $CF_3$, and/or $SF_5$; and the remaining Y represents H.

5. The diboron compound of embodiment 2, represented by Formula I, wherein X represents a linker of Formula Ic:

(Formula Ic)

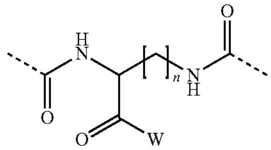

which represents a D- or an L-amino acid form; and wherein,

---- represents a covalent bond towards $R^1$ or $R^2$;

n represents an integer in the range 1-4;

W represents —OH or —$NHCH_2COOH$; and $R^1$ and $R^2$, which may be identical or different, each represents a group of Formula IIa or IIb:

(Formula IIa)

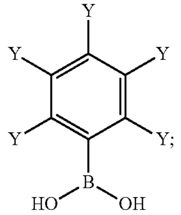

or (Formula IIb)

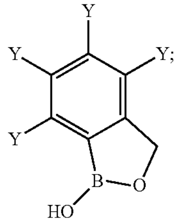

wherein, one Y represents (a covalent bond representing) the attachment point to the linker X of Formula Ic;

none, one or two of Y represent F, $CF_3$, and/or $SF_5$; and the remaining Y represents H.

6. The diboron compound of embodiment 2, represented by Formula I, wherein X represents a linker of Formula Id:

(Formula Id)

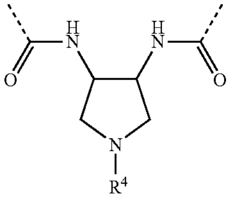

which represents a R,R or S,S, or R,S or R,S stereoisomer of the 3,4-diaminopyrrolidine;

wherein,

---- represents a covalent bond towards $R^1$ or $R^2$;

$R^4$ represents —$(C{=}O)(CH_2)_m(COOH)$;

wherein m represents an integer in the range 1-4; and $R^1$ and $R^2$, which may be identical or different, each represents a group of Formula IIa or IIb:

(Formula IIa)

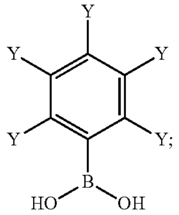

or (Formula IIb)

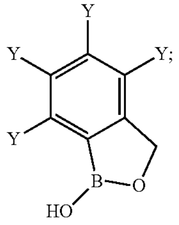

wherein, one Y represents (a covalent bond representing) the attachment point to the linker X of Formula Id;

none, one or two of Y represent F, $CF_3$, and/or $SF_5$; and the remaining Y represents H.

7. The diboron compound of embodiment 2, represented by Formula I, wherein X represents a linker of Formula Ie:

(Formula Ie)

wherein,

---- represents a covalent bond towards $R^1$ or $R^2$; and $R^1$ and $R^2$, which may be identical or different, each represents a group of Formula IIa or IIb:

(Formula IIa)

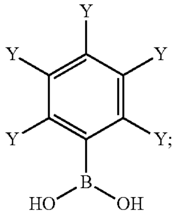

or (Formula IIb)

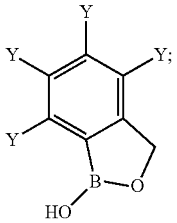

wherein, one Y represents (a covalent bond representing) the attachment point to the linker —CO— of Formula Ie;

one Y represents —COOH or —$CONHCH_2COOH$;

none, one or two of Y represent F, $CF_3$, and/or $SF_5$; and the remaining of Y represents H.

8. The diboron compound of embodiment 2, represented by Formula I, wherein X represents a linker of Formula If:

(Formula If)

wherein,

---- represents a covalent bond towards $R^1$ or $R^2$; and $R^1$ and $R^2$, which may be identical or different, each represents a group of Formula IIa or IIb:

(Formula IIa)

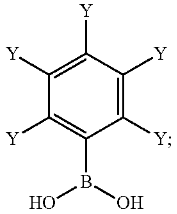

or (Formula IIb)

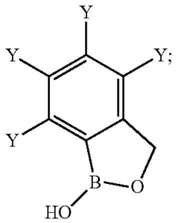

wherein, one Y represents (a covalent bond representing) the attachment point to the linker —SO— of Formula If;

one Y represents —COOH or —$CONHCH_2COOH$;

none, one or two of Y represent F, $CF_3$, and/or $SF_5$; and the remaining Y represents H.

9. The diboron compound of embodiment 2, represented by Formula I, wherein X represents a linker of Formula Ig:

(Formula Ig)

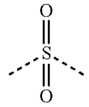

wherein,

---- represents a covalent bond towards $R^1$ or $R^2$; and $R^1$ and $R^2$, which may be identical or different, each represents a group of Formula IIa or IIb:

(Formula IIa)

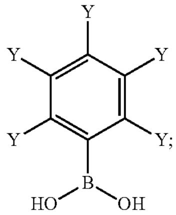

or (Formula IIb)

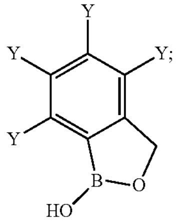

wherein, one Y represents (a covalent bond representing) the attachment point to the linker —($SO_2$)— of Formula Ig;

one Y represents —COOH or —$CONHCH_2COOH$;

none, one or two of Y represent F, $CF_3$, and/or $SF_5$; and the remaining Y represents H.

10. The diboron compound of embodiment 2, represented by Formula I, wherein X represents a linker of Formula Ih:

(Formula Ih)

wherein,

---- represents a covalent bond towards $R^1$ or $R^2$; and $R^1$ and $R^2$, which may be identical or different, each represents a group of Formula IIa or IIb:

(Formula IIa)

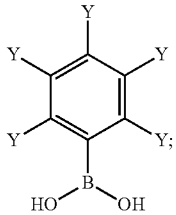

or

-continued (Formula IIb)

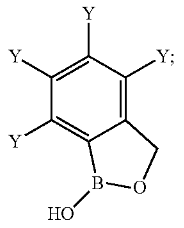

wherein, one Y represents (a covalent bond representing) the attachment point to the linker —$(CF_2)$— X of Formula Ih;

one Y represents —COOH or —$CONHCH_2COOH$;

none, one or two of Y represent F, $CF_3$, and/or $SF_5$; and the remaining Y represents H.

11. A diboron compound selected from the group consisting of 3,5-Bis((4-borono-2-fluorobenzamido)methyl)benzoic acid; 3,5-Bis((4-borono-3-fluorobenzamido)methyl) benzoic acid; N,N'-bis(4-borono-3-fluorobenzamido)-N-ethyl-glycine amide; (S)-2,4-bis(4-borono-3-fluorobenzamido)butanoic acid; N-(7-Fluoro-1-hydroxy-1,3-dihydrobenzo[c][1,2]oxaborole-6-carbonyl)-N-(2-(7-fluoro-1-hydroxy-1,3-dihydrobenzo[c][1,2]oxaborole-6-carboxamido)ethyl)glycine; 3,5-Bis((7-fluoro-1-hydroxy-1,3-dihydrobenzo[c][1,2]oxaborole-6-carboxamido) methyl) benzoic acid; N-(5-Fluoro-1-hydroxy-1,3-dihydrobenzo[c][1,2]oxaborole-6-carbonyl)-N-(2-(5-fluoro-1-hydroxy-1,3-dihydrobenzo[c][1,2]oxaborole-6-carboxamido)ethyl)glycine; N-(4-Fluoro-1-hydroxy-1,3-dihydrobenzo[c][1,2] oxaborole-6-carbonyl)-N-(2-(4-fluoro-1-hydroxy-1,3-dihydrobenzo[c][1,2]oxaborole-6-carboxamido)ethyl) glycine; N-(6-Fluoro-1-hydroxy-1,3-dihydrobenzo[c][1,2] oxaborole-5-carbonyl)-N-(2-(6-fluoro-1-hydroxy-1,3-dihydrobenzo[c][1,2]oxaborole-5-carboxamido)ethyl) glycine; $N^2$,$N^6$-Bis(6-fluoro-1-hydroxy-1,3-dihydrobenzo [c][1,2]oxaborole-5-carbonyl)-L-lysine; 3-Borono-5-((3-borono-4-fluorophenyl)sulfonyl)-4-fluorobenzoic acid]; 3-Borono-5-(3-borono-5-fluorobenzoyl)benzoic acid; 3-Borono-5-(5-borono-2,4-difluorobenzoyl)benzoic acid; $N^6$-(4-Borono-2-fluorobenzoyl)-$N^2$-(6-fluoro-1-hydroxy-1,3-dihydrobenzo[c][1,2] oxaborole-5-carbonyl)-L-lysine; (S)-2,3-Bis(7-fluoro-1-hydroxy-1,3-dihydrobenzo-[c][1,2] oxaborole-6-carboxamido)-propanoic acid; (S)-2,3-Bis(5-fluoro-1-hydroxy-1,3-dihydrobenzo[c][1,2]oxaborole-6-carboxamido)-propanoic acid; (S)-2,3-Bis(4-fluoro-1-hydroxy-1,3-dihydrobenzo[c][1,2]oxaborole-6-carboxamido)-propanoic acid; (3-Borono-5-((3-borono-5-(trifluoromethyl)phenyl)difluoromethyl)benzoyl) glycine; (3-Borono-5-(3-borono-5-(trifluoromethyl)benzoyl)benzoyl)glycine; (3-Borono-5-((3-borono-5-(trifluoromethyl) phenyl)sulfonyl)glycine; 4-((3S,4S)-3,4-Bis(7-fluoro-1-hydroxy-1,3-dihydrobenzo[c][1,2]oxaborole-6-carboxamido) pyrrolidin-1-yl)-4-oxobutanoic acid; (3-Borono-5-(3-borono-5-fluorobenzoyl)benzoyl)glycine; (3-(6-Borono-2-(ethoxycarbonyl)-8-fluoro-1,1-dioxido-4H-benzo[b][1,4] thiazin-4-yl)-5-fluorophenyl)boronic acid; (3-Borono-5-((3-borono-5-fluorophenyl)sulfonyl)benzoyl)glycine; N-(1-Hydroxy-4-(trifluoromethyl)-1,3-dihydrobenzo[c][1,2] oxaborole-6-carbonyl)-N-(2-(1-hydroxy-4-(trifluoromethyl)-1,3-dihydrobenzo[c][1,2]oxaborole-6-carboxamido)-ethyl)glycine; (S)-2,3-Bis(1-hydroxy-4-(trifluoromethyl)-1,3-dihydrobenzo[c][1,2]oxaborole-6-carboxamido)propanoic acid; 4-((3S,4S)-3,4-Bis(1-hydroxy-4-(trifluoromethyl)-1,3-dihydrobenzo[c][1,2] oxaborole-6-carboxamido)pyrrolidin-1-yl)-4-oxobutanoic acid; (3-Borono-5-((3-borono-5-(pentafluoro-λ$^6$-sulfanyl) phenyl)sulfonyl)benzoyl) glycine; and 4-[(3R,4R)-3,4-bis [[1-hydroxy-4-(trifluoromethyl)-3H-2,1-benzoxaborole-6-carbonyl]-amino]pyrrolidin-1-yl]-4-oxobutanoic acid.

12. The diboron conjugate of embodiment 1 for use as a medicament.

13. The diboron compound of any one of embodiments 2-11 for use as an intermediate compounds for the manufacture of the diboron conjugate according to embodiment 1.

14. A method of treatment, prevention or alleviation of a metabolic disease or a disorder or a condition of a living animal body, which method comprises the step of administering to such a living animal body in need thereof, a therapeutically effective amount of the diboron conjugate of embodiment 1.

The invention is even further described by the following non-limiting embodiments:

15. A diboron conjugate represented by the general Formula I'

$$R^{1'}—X'—R^{2'}$$

in which Formula I',

X' represents a linker of Formula Ia':

(Formula Ia')

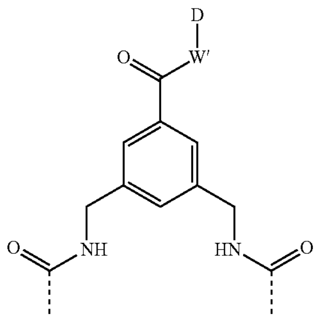

wherein

---- represents a covalent bond towards $R^{1'}$ or $R^{2'}$;

D represents a drug substance; and

W' represents a covalent bond, or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing a L-gamma-Glu or D-gamma-Glu residue); or X' represents a linker of Formula Ib':

(Formula Ib')

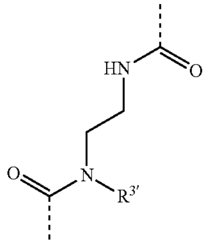

wherein,

---- represents a covalent bond towards $R^{1'}$ or $R^{2'}$; and $R^{3'}$ represent —$(CH_2)_{m'}(C{=}O)$—W'-D, wherein m' represents an integer in the range of 1 to 4;

W' represents a covalent bond or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing a L-gamma-Glu or D-gamma-Glu residue); and D represents a drug substance; or X' represents a linker of Formula Ic':

(Formula Ic')

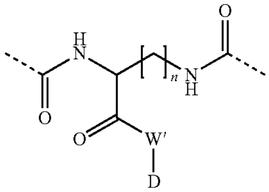

which represents a D- or an L-amino acid form; and wherein,

---- represents a covalent bond towards $R^{1\prime}$ or $R^{2\prime}$;

n' represents an integer in the range of 1 to 4;

W' represents a covalent bond or a linker selected from the group consisting of

—$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing a L-gamma-Glu or D-gamma-Glu residue); and D represents a drug substance; or X' represents a linker of Formula Id':

(Formula Id')

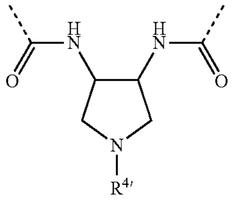

which represents a R,R or S,S, or R,S or R,S stereoisomer of the 3,4-diaminopyrrolidine;

wherein,

---- represents a covalent bond towards $R^{1\prime}$ or $R^{2\prime}$;

$R^{4\prime}$ represents —$(C{=}O)(CH_2)_{p'}(C{=}O)$—W'-D; where

W' represents a covalent bond or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$—

(the latter representing a L-gamma-Glu or D-gamma-Glu residue);

wherein p' represents an integer in the range of 1 to 4; and

D represents a drug substance; or

X' represents a linker of Formula Ie':

(Formula Ie')

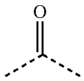

wherein,

---- represents a covalent bond towards $R^{1\prime}$ or $R^{2\prime}$; or

X' represents a linker of Formula If':

(Formula If')

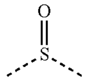

wherein,

---- represents a covalent bond towards $R^{1\prime}$ or $R^{2\prime}$; or

X' represents a linker of Formula Ig':

(Formula Ig')

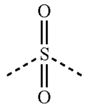

wherein,

---- represents a covalent bond towards $R^{1\prime}$ or $R^{2\prime}$; or

X' represents a linker of Formula Ih':

(Formula Ih')

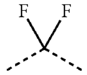

wherein,

---- represents a covalent bond towards $R^{1\prime}$ or $R^{2\prime}$; or

X' represents a linker of Formula Ii':

(Formula Ii')

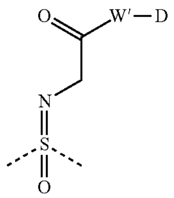

wherein,

---- represents a covalent bond towards $R^{1\prime}$ or $R^{2\prime}$; and

W' represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue); and $R^{1\prime}$ and $R^{2\prime}$, which may be identical or different, each represents a group of Formula IIa' or Formula IIb':

(Formula IIa')

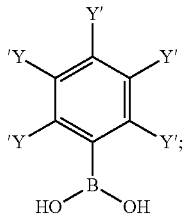

or

-continued (Formula IIb')

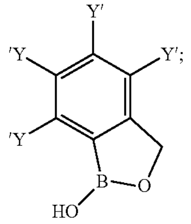

wherein, one to four Y' represents H; and none, one or two Y' represents F, Cl, $CF_2$, $CF_3$, and/or $SF_5$; and one Y' represents (a covalent bond representing) the attachment point to X' of Formula I'; and when X' is Formula Ie', If', Ig' or Ih', one Y in either $R^{1'}$ or $R^{2'}$ represents —(C═O)—W'-D, where W' represents a covalent bond, or a linker selected from the group consisting of —$NHCH_2$(C═O)—, —$NHCH_2CH_2$(C═O)—, —$NHCH_2CH_2CH_2$(C═O)—, and —NHCH(COOH)$CH_2CH_2$(C═O)— (the latter representing a L-gamma-Glu or D-gamma-Glu residue); and wherein D represents a drug substance.

16. A diboron compound represented by Formula I $R^1$—X—$R^2$ in which Formula I, X represents a linker of Formula Ia:

(Formula Ia)

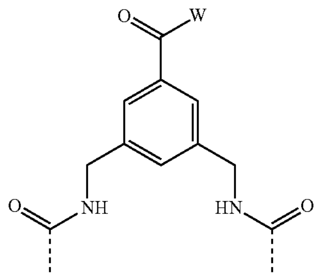

wherein

---- represents a covalent bond towards $R^1$ or $R^2$;

W represents —OH, —$NHCH_2COOH$, —$NHCH_2CH_2COOH$, —$NHCH_2CH_2CH_2COOH$, or —NHCH(COOH)$CH_2CH_2COOH$ (the latter representing a L-gamma-Glu or D-gamma-Glu residue); or X represents a linker of Formula Ib:

(Formula Ib)

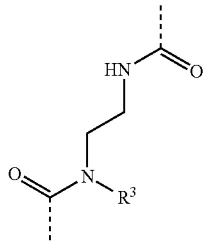

wherein,

---- represents a covalent bond towards $R^1$ or $R^2$; and $R^3$ represent —$(CH_2)_m$(C═O)—W;

wherein m represents an integer in the range of 1 to 4; and

W represents OH, $NHCH_2COOH$; $NHCH_2CH_2COOH$; $NHCH_2CH_2CH_2COOH$; or NHCH(COOH)$CH_2CH_2COOH$ (the latter representing a L-gamma-Glu or D-gamma-Glu residue); or X represents a linker of Formula Ic:

(Formula Ic)

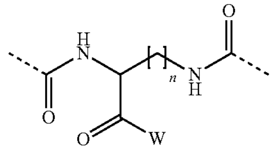

which represents a D- or an L-amino acid form; and wherein,

---- represents a covalent bond towards $R^1$ or $R^2$;

n represents an integer in the range of 1 to 4;

W represents —OH, —$NHCH_2COOH$, —$NHCH_2CH_2COOH$, —$NHCH_2CH_2CH_2COOH$, or —NHCH(COOH)$CH_2CH_2COOH$ (the latter representing a L-gamma-Glu or D-gamma-Glu residue); or wherein X represents a linker of Formula Id:

(Formula Id)

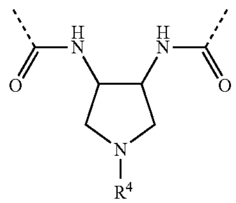

which represents a R,R or S,S, or R,S or R,S stereoisomer of the 3,4-diaminopyrrolidine;

wherein,

---- represents a covalent bond towards $R^1$ or $R^2$;

$R^4$ represents —(C═O)$(CH_2)_p$(C═O)—W;

wherein p represents an integer in the range of 1 to 4;

W represents —OH, —$NHCH_2COOH$, —$NHCH_2CH_2COOH$, —$NHCH_2CH_2CH_2COOH$, or —NHCH(COOH)$CH_2CH_2COOH$ (the latter representing a L-gamma-Glu or D-gamma-Glu residue); or X represents a linker of Formula Ie:

(Formula Ie)

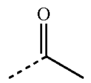

wherein,

---- represents a covalent bond towards $R^1$ or $R^2$; or

X represents a linker of Formula If:

(Formula If)

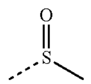

wherein,

---- represents a covalent bond towards $R^1$ or $R^2$; or

X represents a linker of Formula Ig:

(Formula Ig)

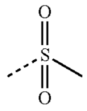

wherein,

---- represents a covalent bond towards $R^1$ or $R^2$; or

X represents a linker of Formula Ih:

(Formula Ih)

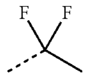

wherein,

---- represents a covalent bond towards $R^1$ or $R^2$; or

X represents a linker of Formula Ii:

(Formula Ii)

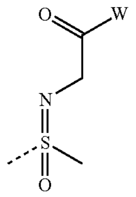

wherein,

---- represents a covalent bond towards $R^1$ or $R^2$; and

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue); and $R^1$ and $R^2$, which may be identical or different, each represents a group of Formula IIa or IIb:

(Formula IIa)

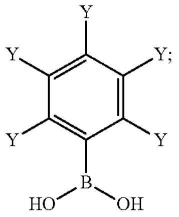

(Formula IIb)

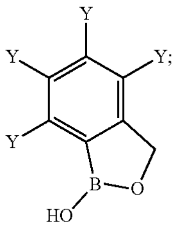

wherein, one to four Y represents H; and none, one or two of Y represents F, Cl, $CF_2$, $CF_3$, and/or $SF_5$; and one Y represents (a covalent bond representing) the attachment point to X of Formula I; and when X is Formula Ie, If, Ig or Ih, one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue).

17. The diboron compound of embodiment 16, represented by Formula I, wherein X represents a linker of Formula Ia:

(Formula Ia)

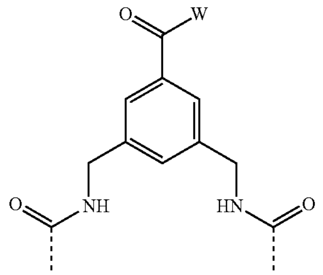

wherein

---- represents a covalent bond towards $R^1$ or $R^2$;

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue); and $R^1$ and $R^2$, which may be identical or different, each represents a group of Formula IIa or IIb:

(Formula IIa)

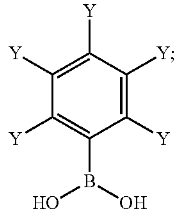

(Formula IIb)

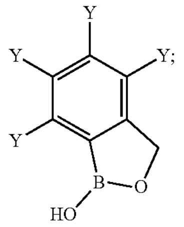

wherein, one Y represents (a covalent bond representing) the attachment point to the linker X of Formula Ia;

none, one or two of Y represent F, Cl, $CF_2$, $CF_3$, and/or $SF_5$; and the remaining Y represents H.

18. The diboron compound of embodiment 16, represented by Formula I, wherein X represents a linker of Formula Ib:

(Formula Ib)

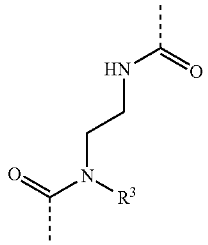

wherein,

---- represents a covalent bond towards $R^1$ or $R^2$; and $R^3$ represent —$(CH_2)_m$(C═O)—W;

wherein m represents an integer in the range of 1 to 4;

W represents OH, $NHCH_2COOH$; $NHCH_2CH_2COOH$; $NHCH_2CH_2CH_2COOH$; or $NHCH(COOH)CH_2CH_2COOH$ (the latter representing a L-gamma-Glu or D-gamma-Glu residue); and $R^1$ and $R^2$, which may be identical or different, each represents a group of Formula IIa or IIb:

(Formula IIa)

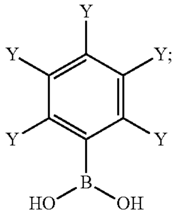

(Formula IIb)

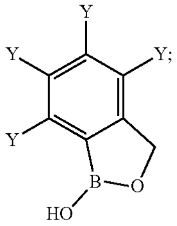

wherein, one Y represents (a covalent bond representing) the attachment point to the linker X of Formula Ib;

none, one or two of Y represent F, Cl, $CF_2$, $CF_3$, and/or $SF_5$; and the remaining Y represents H.

19. The diboron compound of embodiment 16, represented by Formula I, wherein X represents a linker of Formula Ic:

(Formula Ic)

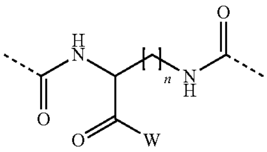

which represents a D- or an L-amino acid form; and wherein,

---- represents a covalent bond towards $R^1$ or $R^2$;

n represents an integer in the range of 1 to 4;

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue); and $R^1$ and $R^2$, which may be identical or different, each represents a group of Formula IIa or IIb:

(Formula IIa)

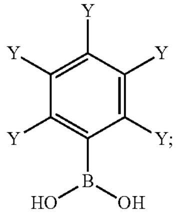

or (Formula IIb)

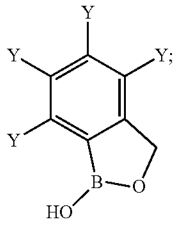

wherein, one Y represents (a covalent bond representing) the attachment point to the linker X of Formula Ic;

none, one or two of Y represent F, Cl, $CF_2$, $CF_3$, and/or $SF_5$; and the remaining Y represents H.

20. The diboron compound of embodiment 16, represented by Formula I, wherein X represents a linker of Formula Id:

(Formula Id)

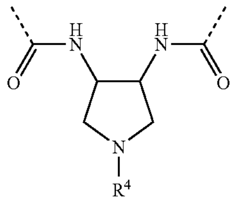

which represents a R,R or S,S, or R,S or R,S stereoisomer of the 3,4-diaminopyrrolidine;

wherein,

---- represents a covalent bond towards $R^1$ or $R^2$;

$R^4$ represents —(C═O)$(CH_2)_p$(C═O)—W;

wherein p represents an integer in the range of 1 to 4;

W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue); and $R^1$ and $R^2$, which may be identical or different, each represents a group of Formula IIa or IIb:

(Formula IIa)

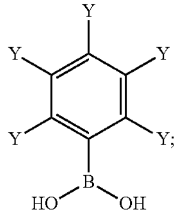

or (Formula IIb)

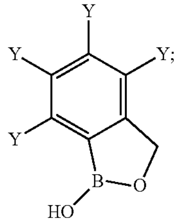

wherein, one Y represents (a covalent bond representing) the attachment point to the linker X of Formula Id;

none, one or two of Y represent F, Cl, $CF_2$, $CF_3$, and/or $SF_5$; and the remaining Y represents H.

21. The diboron compound of embodiment 16, represented by Formula I, wherein X represents a linker of Formula Ie:

(Formula Ie)

wherein,

---- represents a covalent bond towards $R^1$ or $R^2$; and $R^1$ and $R^2$, which may be identical or different, each represents a group of Formula IIa or IIb:

(Formula IIa)

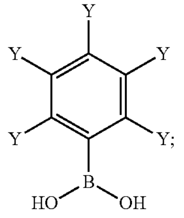

or (Formula IIb)

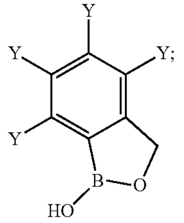

wherein, one Y represents (a covalent bond representing) the attachment point to the linker —CO— of Formula Ie;

one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue);

none, one or two of Y represent F, Cl, $CF_2$, $CF_3$, and/or $SF_5$; and the remaining of Y represents H.

22. The diboron compound of embodiment 16, represented by Formula I, wherein X represents a linker of Formula If:

(Formula If)

wherein,

---- represents a covalent bond towards $R^1$ or $R^2$; and $R^1$ and $R^2$, which may be identical or different, each represents a group of Formula IIa or IIb:

(Formula IIa)

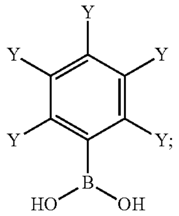

or (Formula IIb)

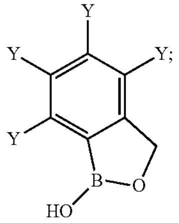

wherein, one Y represents (a covalent bond representing) the attachment point to the linker —SO— of Formula If;

one Y in either $R^1$ or $R^2$ represents —(C═O)—W, where W represents —OH, —$NHCH_2COOH$, —$NHCH_2CH_2COOH$, —$NHCH_2CH_2CH_2COOH$, or —$NHCH(COOH)CH_2CH_2COOH$ (the latter representing a L-gamma-Glu or D-gamma-Glu residue);

none, one or two of Y represent F, Cl, $CF_2$, $CF_3$, and/or $SF_5$; and the remaining Y represents H.

23. The diboron compound of embodiment 16, represented by Formula I, wherein X represents a linker of Formula Ig:

(Formula Ig)

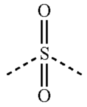

wherein,

---- represents a covalent bond towards $R^1$ or $R^2$; and $R^1$ and $R^2$, which may be identical or different, each represents a group of Formula IIa or IIb:

(Formula IIa)

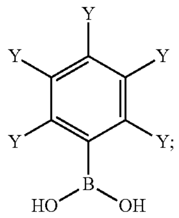

or (Formula IIb)

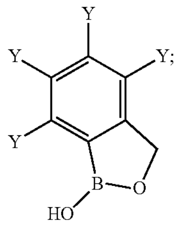

wherein, one Y represents (a covalent bond representing) the attachment point to the linker $-(SO_2)-$ of Formula Ig;

one Y in either $R^1$ or $R^2$ represents $-(C{=}O)-W$, where W represents $-OH$, $-NHCH_2COOH$, $-NHCH_2CH_2COOH$, $-NHCH_2CH_2CH_2COOH$, or $-NHCH(COOH)CH_2CH_2COOH$ (the latter representing a L-gamma-Glu or D-gamma-Glu residue);

none, one or two of Y represent F, Cl, $CF_2$, $CF_3$, and/or $SF_5$; and the remaining Y represents H.

24. The diboron compound of embodiment 16, represented by Formula I, wherein X represents a linker of Formula Ih:

(Formula Ih)

wherein,

---- represents a covalent bond towards $R^1$ or $R^2$; and $R^1$ and $R^2$, which may be identical or different, each represents a group of Formula IIa or IIb:

(Formula IIa)

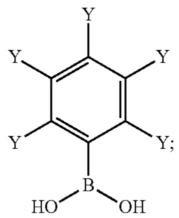

or

-continued (Formula IIb)

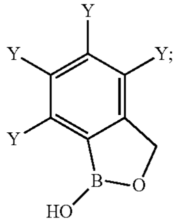

wherein, one Y represents (a covalent bond representing) the attachment point to the linker $-(CF_2)-$ of Formula Ih;

one Y in either $R^1$ or $R^2$ represents $-(C{=}O)-W$, where W represents $-OH$, $-NHCH_2COOH$, $-NHCH_2CH_2COOH$, $-NHCH_2CH_2CH_2COOH$, or $-NHCH(COOH)CH_2CH_2COOH$ (the latter representing a L-gamma-Glu or D-gamma-Glu residue);

none, one or two of Y represent F, Cl, $CF_2$, $CF_3$, and/or $SF_5$; and the remaining Y represents H.

25. The diboron compound of embodiment 16, represented by Formula I, wherein X represents a linker of Formula Ii:

(Formula Ii)

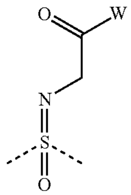

wherein

---- represents a covalent bond towards $R^1$ or $R^2$;

W represents $-OH$, $-NHCH_2COOH$, $-NHCH_2CH_2COOH$, $-NHCH_2CH_2CH_2COOH$, or $-NHCH(COOH)CH_2CH_2COOH$ (the latter representing a L-gamma-Glu or D-gamma-Glu residue); and $R^1$ and $R^2$, which may be identical or different, each represents a group of Formula IIa or IIb:

(Formula IIa)

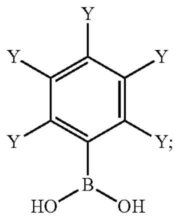

or (Formula IIb)

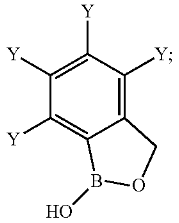

wherein, one Y represents (a covalent bond representing) the attachment point to the linker X of Formula Ii;

none, one or two of Y represent F, Cl, $CF_2$, $CF_3$, and/or $SF_5$; and the remaining Y represents H.

26. A diboron compound selected from the group consisting of 3,5-Bis((4-borono-2-fluorobenzamido)methyl) benzoic acid; 3,5-Bis((4-borono-3-fluorobenzamido) methyl)benzoic acid; N,N'-bis(4-borono-3-fluorobenzamido)-N-ethyl-glycine amide; (S)-2,4-bis(4-borono-3-fluorobenzamido)butanoic acid; N-(7-Fluoro-1-hydroxy-1,3-dihydrobenzo[c][1,2]oxaborole-6-carbonyl)-N-(2-(7-fluoro-1-hydroxy-1,3-dihydrobenzo[c][1,2] oxaborole-6-carboxamido)ethyl)glycine; 3,5-Bis((7-fluoro-1-hydroxy-1,3-dihydrobenzo[c][1,2]oxaborole-6-carboxamido)methyl) benzoic acid; N-(5-Fluoro-1-hydroxy-1,3-dihydrobenzo[c][1,2]oxaborole-6-carbonyl)-N-(2-(5-fluoro-1-hydroxy-1,3-dihydrobenzo[c][1,2] oxaborole-6-carboxamido)ethyl)glycine; N-(4-Fluoro-1-hydroxy-1,3-dihydrobenzo[c][1,2]oxaborole-6-carbonyl)-N-(2-(4-fluoro-1-hydroxy-1,3-dihydrobenzo[c][1,2] oxaborole-6-carboxamido)ethyl)glycine; N-(6-Fluoro-1-hydroxy-1,3-dihydrobenzo[c][1,2]oxaborole-5-carbonyl)-N-(2-(6-fluoro-1-hydroxy-1,3-dihydrobenzo[c][1,2] oxaborole-5-carboxamido)ethyl)glycine; $N^2$,$N^6$-Bis(6-fluoro-1-hydroxy-1,3-dihydrobenzo[c][1,2]oxaborole-5-carbonyl)-L-lysine; 3-Borono-5-((3-borono-4-fluorophenyl) sulfonyl)-4-fluorobenzoic acid; 3-Borono-5-(3-borono-5-fluorobenzoyl)benzoic acid; 3-Borono-5-(5-borono-2,4-difluorobenzoyl)benzoic acid; $N^6$-(4-Borono-2-fluorobenzoyl)-$N^2$-(6-fluoro-1-hydroxy-1,3-dihydrobenzo [c][1,2]-oxaborole-5-carbonyl)-L-lysine; (S)-2,3-Bis(7-fluoro-1-hydroxy-1,3-dihydrobenzo-[c][1,2]oxaborole-6-carboxamido)propanoic acid; (S)-2,3-Bis(5-fluoro-1-hydroxy-1,3-dihydrobenzo[c][1,2]oxaborole-6-carboxamido)propanoic acid; (S)-2,3-Bis(4-fluoro-1-hydroxy-1,3-dihydrobenzo[c][1,2]oxaborole-6-carboxamido) propanoic acid; (3-Borono-5-((3-borono-5-(trifluoromethyl)phenyl)difluoromethyl)benzoyl)-glycine; (3-Borono-5-(3-borono-5-(trifluoromethyl)benzoyl)benzoyl)glycine; (3-Borono-5-((3-borono-5-(trifluoromethyl) phenyl)sulfonyl)glycine; 4-((3S,4S)-3,4-Bis(7-fluoro-1-hydroxy-1,3-dihydrobenzo[c][1,2]oxaborole-6-carboxamido) pyrrolidin-1-yl)-4-oxobutanoic acid; (3-Borono-5-(3-borono-5-fluorobenzoyl)benzoyl)glycine; (3-(6-Borono-2-(ethoxycarbonyl)-8-fluoro-1,1-dioxido-4H-benzo[b][1,4] thiazin-4-yl)-5-fluorophenyl)boronic acid; (3-Borono-5-((3-borono-5-fluorophenyl)sulfonyl)benzoyl)glycine; N-(1-Hydroxy-4-(trifluoromethyl)-1,3-dihydrobenzo[c][1,2] oxaborole-6-carbonyl)-N-(2-(1-hydroxy-4-(trifluoromethyl)-1,3-dihydrobenzo[c][1,2]oxaborole-6-carboxamido)ethyl)glycine; (S)-2,3-Bis(1-hydroxy-4-(trifluoromethyl)-1,3-dihydrobenzo[c][1,2]oxaborole-6-carboxamido)propanoic acid; 4-((3S,4S)-3,4-Bis(1-hydroxy-4-(trifluoromethyl)-1,3-dihydrobenzo[c][1,2] oxaborole-6-carboxamido)pyrrolidin-1-yl)-4-oxobutanoic acid; (3-Borono-5-((3-borono-5-(pentafluoro-$\lambda^6$-sulfanyl) phenyl)sulfonyl)benzoyl) glycine; 2-((Bis(3-borono-5-(trifluoromethyl)phenyl)(oxo)-λ6-sulfanylidene)amino)acetic acid; N-(4-(Difluoromethyl)-1-hydroxy-1,3-dihydrobenzo [c][1,2]oxaborole-6-carbonyl)-N-(2-(4-(difluoromethyl)-1-hydroxy-1,3-dihydrobenzo[c][1,2]oxaborole-6-carboxamido)ethyl)glycine; N-(4-Chloro-1-hydroxy-1,3-dihydrobenzo[c][1,2]oxaborole-6-carbonyl)-N-(2-(4-chloro-1-hydroxy-1,3-dihydrobenzo[c][1,2]oxaborole-6-carboxamido)ethyl)glycine; 3-(2,3-Bis(4-chloro-1-hydroxy-1,3-dihydrobenzo[c][1,2]oxaborole-6-carboxamido) propanamido)propanoic acid; 2-((Bis(3-borono-5-(difluoromethyl)phenyl)(oxo)-λ6-sulfanylidene)amino) acetic acid; 2-((Bis(3-borono-5-chlorophenyl)(oxo)-λ6-sulfanylidene)amino)acetic acid; and 2-((Bis(3-boronophenyl)(oxo)-λ6-sulfanylidene)amino)acetic acid.

27. The diboron conjugate of anyone of embodiments 15-26 for use as a medicament.

28. The diboron compound of any one of embodiments 15-26 for use as an intermediate compounds for the manufacture of the diboron conjugate according to embodiment 15.

29. A method of treatment, prevention or alleviation of a metabolic disease or a disorder or a condition of a living animal body, which method comprises the step of administering to such a living animal body in need thereof, a therapeutically effective amount of the diboron conjugate of anyone of embodiments 15-26.

EXAMPLES

The invention is further illustrated with reference to the following examples, which are not intended to be in any way limiting to the scope of the invention as claimed.

Abbreviations Used Herein

AA acetic acid

AIBN 2,2'-azobis(2-methylpropionitrile)

ARS Alizarin Red Sodium

DAST (diethylamino)sulfur trifluoride

DCC N,N'-dicyclohexylcarbodiimide

DMSO dimethylsulfoxide

EDC N-(3-dimethylaminopropyl)-N'-ethylcarbodiimide

ELSD electrospray detection

F-NMR fluorine-19 nuclear magnetic resonance spectroscopy

FA formic acid

HATU 1-((dimethylamino)(dimethyliminio)methyl)-1H-[1,2,3]triazolo[4,5-b]pyridine 3-oxide hexafluorophosphate HSA human serum albumin LCMS liquid chromatography mass spectrometry NBS N-bromosuccinimide (1-bromopyrrolidine-2,5-dione)

NIS N-iodosuccinimide (1-iodobromopyrrolidine-2,5-dione)

NMR nuclear magnetic resonance spectroscopy

HOSu, NOHSu N-hydroxysuccinimide

PCC pyridinium chlorochromate

XPhos 2-dicyclohexylphosphino-2',4',6'-triisopropylbiphenyl

Preparation of Diboron Compounds of the Invention

Example 1

3,5-Bis((4-borono-2-fluorobenzamido)methyl)benzoic acid

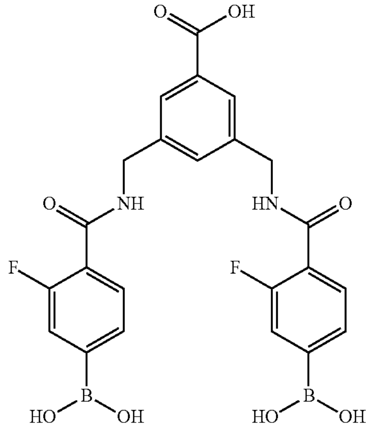 [SMILES: O=C(O)c1cc(CNC(=O)c2ccc(B(O)O)cc2F)cc(CNC(=O)c2ccc(B(O)O)cc2F)c1]

3,5-Bis((4-borono-2-fluorobenzamido)methyl)benzoic acid was synthesized according to the reaction schemes shown in Chem. 1 and Chem. 2 and following the procedure described below.

Chem. 1

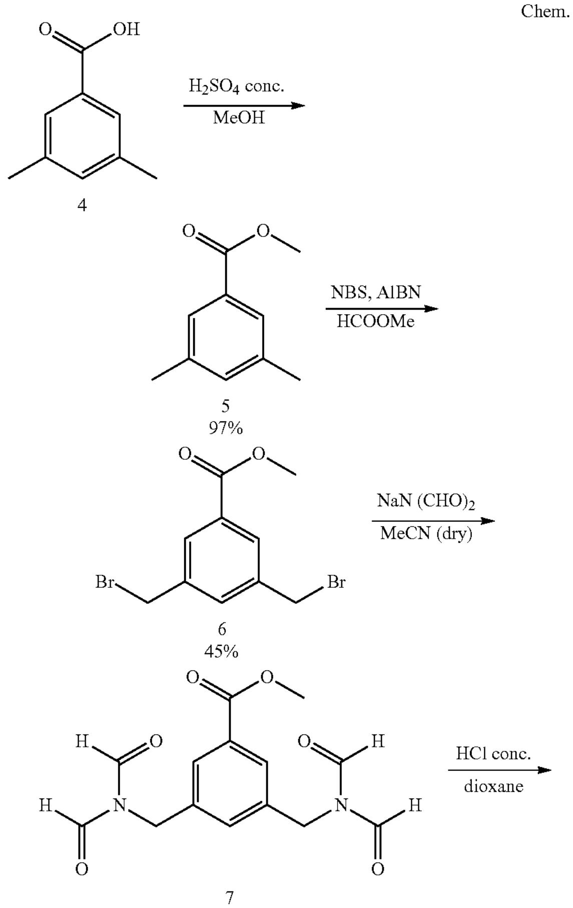

4

5
97%

6
45%

7
88%

-continued

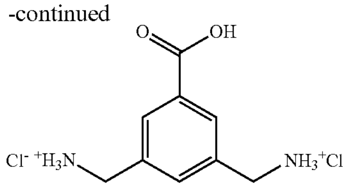

8
98%

3,5-Dimethylbenzoic acid (4, 27.6 g, 18.4 mmol) was suspended in methanol (80 mL) and treated with concentrated sulfuric acid (8 mL). The mixture was refluxed for 2 days. After neutralization with sodium carbonate (50 g), the mixture was dissolved in water (250 mL) and extracted with diethyl ether (2×300 mL). The organic phases were dried over anhydrous sodium sulfate, filtered and evaporated to dryness affording methyl 3,5-dimethylbenzoate 5 as pale yellow oil.

Yield: 29.3 g (97%).

$^1$H NMR spectrum (300 MHz, $CDCl_3$, $\delta_H$): 7.67 (s, 2H); 7.19 (s, 1H); 3.91 (s, 3H); 2.37 (s, 6H).

A mixture of the above methyl 3,5-dimethylbenzoate (5, 29.3 g, 178 mmol), N-bromosuccinimide (NBS, 111 g, 623 mmol) and a spatula of azobisisobutyronitrile in methyl formate (450 mL) was irradiated with visible light while heating to reflux for 20 hours. The solvent was evaporated and the residue was dissolved in dichloromethane (200 mL). The precipitated succinimide was filtered off and the filtrate was washed with saturated aqueous solution of sodium sulfite (2×150 mL). The organic layer was dried over anhydrous sodium sulfate, filtered and evaporated. The residue was purified by flash column chromatography (Silicagel 60, 0.040-0.063 mm; eluent: hexane/ethyl acetate 15:1). The product was crystallized from ethyl acetate/cyclohexane mixture giving methyl 3,5-bis(bromomethyl)benzoate 6 as white solid.

Yield: 25.6 g (45%).

$R_F$ ($SiO_2$, hexanes/ethyl acetate 9:1): 0.50.

$^1$H NMR spectrum (300 MHz, $CDCl_3$, $\delta_H$): 8.02-7.95 (m, 2H); 7.62 (s, 1H); 4.51 (s, 4H); 3.94 (s, 3H).

A suspension of the above bromide 6 (25.3 g, 78.6 mmol) and sodium diformylamide (20.9 g, 220 mmol) in dry acetonitrile (350 mL) was refluxed for 4 hours. After removal of a white solid by filtration, the solvent was evaporated. Recrystallization from ethyl acetate/cyclohexane mixture afforded methyl 3,5-bis((N-formylformamido)methyl)benzoate 7 as white powder.

Yield: 21.0 g (88%).

$^1$H NMR spectrum (300 MHz, DMSO-$d_6$, $\delta_H$): 9.08 (s, 4H); 7.72 (s, 2H); 7.44 (s, 1H); 4.70 (s, 4H); 3.84 (s, 3H).

Benzoate (7, 20.9 g, 68.5 mmol) was dissolved in a mixture of 1,4-dioxane (220 mL) and concentrated hydrochloric acid (280 mL) and heated for 2 hours to reflux. After cooling down to room temperature, a flow of air was passed through the solution. Product began to precipitate. After 1 hour, the solvent was evaporated and product was recrystallized from methanol/diethyl ether mixture affording 3,5-bis(aminomethyl) benzoic acid dihydrochloride 8 as white powder.

Yield: 17.1 g (98%).

$^1$H NMR spectrum (300 MHz, DMSO-$d_6$, $\delta_H$): 13.26 (bs, 1H); 8.65 (bs, 6H); 8.10 (s, 2H); 7.88 (s, 1H); 4.08 (s, 4H).

Chem. 2

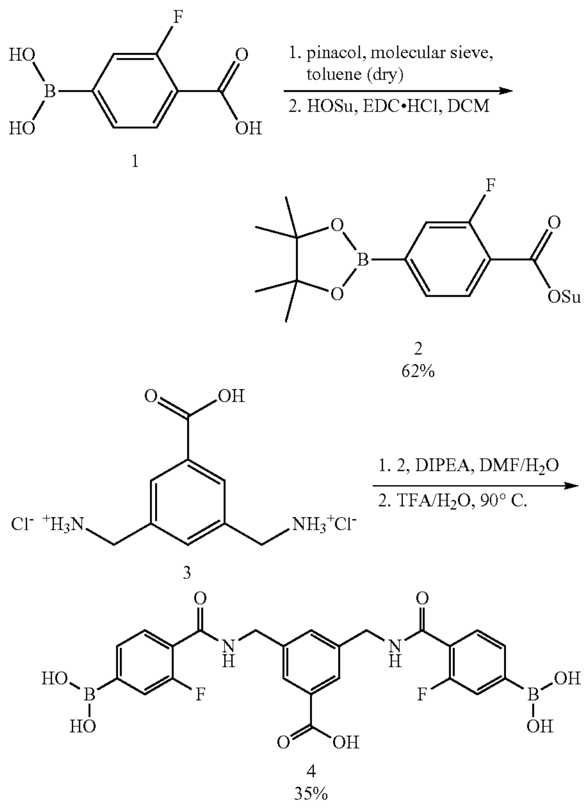

Mixture of 4-borono-2-fluorobenzoic acid (1, 1.14 g, 6.20 mmol), pinacol (0.74 g, 6.20 mmol) and molecular sieves (2.60 g) in dry toluene (40 mL) was stirred overnight at room temperature. The suspension was filtered; solid residue was suspended in dichloromethane (50 mL). Subsequently hydroxysuccinimide (HOSu, 1.43 g, 12.4 mmol) and N-(3-dimethylaminopropyl)-N'-ethylcarbodiimide hydrochloride (EDC.HCl, 2.38 g, 12.4 mmol) were added. Resulting mixture was stirred overnight at room temperature. The suspension was filtered and the filtrate was partitioned between ethyl acetate (80 mL) and 0.1 M aqueous solution of hydrochloric acid (50 mL). Organic layer was washed with 0.1 M aqueous solution of hydrochloric acid (2×75 mL) and brine (1×75 mL), dried over anhydrous sodium sulfate, filtered and evaporated to yield 2,5-dioxopyrrolidin-1-yl 2-fluoro-4-(4,4,5,5-tetramethyl-1,3,2-dioxaborolan-2-yl) benzoate (2) as white powder.

Yield: 1.36 g (62%).

$^1$H NMR spectrum (400 MHz, $CDCl_3$, $\delta_H$): 8.07-8.03 (m, 1H); 7.69-7.65 (m, 1H); 7.65-7.60 (m, 1H); 2.92 (bs, 4H); 1.37 (s, 12H).

3,5-Bis(aminomethyl)benzoic acid dihydrochloride (3, 152 mg, 0.60 mmol) was dissolved in water (2 mL). Subsequently N,N-diisopropylethylamine (0.04 mL, 0.24 mmol), N,N-dimethylformamide (4 mL) and 2,5-dioxopyrrolidin-1-yl 2-fluoro-4-(4,4,5,5-tetramethyl-1,3,2-dioxaborolan-2-yl)benzoate (2, 0.44 g, 1.20 mmol) were added. The mixture was stirred overnight at room temperature; then solvent was evaporated. The liquid residue was dissolved in aqueous trifluoroacetic acid (50%, 10 mL) and stirred overnight at 90° C. Precipitate was collected by filtration and washed with acetonitrile to yield the title compound (4) as white powder.

Yield: 105 mg (35%).

$^1$H NMR spectrum (400 MHz, DMSO-$d_6$, $\delta_H$): 12.94 (bs, 1H); 9.03-8.88 (m, 2H); 8.36 (s, 4H); 7.83 (s, 2H); 7.67-7.53 (m, 7H); 4.51 (d, J=5.9 Hz, 4H).

LC-MS purity: 99% (ELSD).

LC-MS Rt (Kinetex C18, 4.6 mm×50 mm, acetonitrile/water 20:80 to 100:0+0.1% FA): 2.21 min.

LC-MS m/z: 513.4 $(M+H)^+$.

Example 2

3,5-Bis((4-borono-3-fluorobenzamido)methyl)benzoic acid

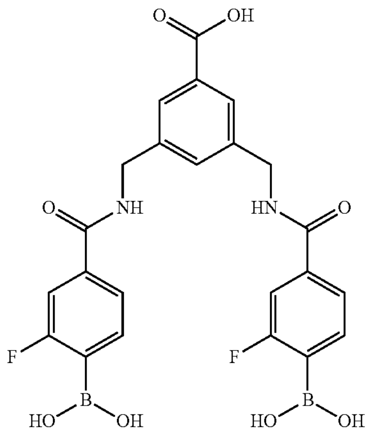 [SMILES: O=C(O)c1cc(CNC(=O)c2ccc(B(O)O)c(F)c2)cc(CNC(=O)c2ccc(B(O)O)c(F)c2)c1]

3,5-Bis((4-borono-3-fluorobenzamido)methyl)benzoic acid was prepared similarly to the compound of Example 1 from 4-borono-3-fluorobenzoic acid.

Example 3

N,N'-bis(4-borono-3-fluorobenzamido)-N-ethyl-glycine amide

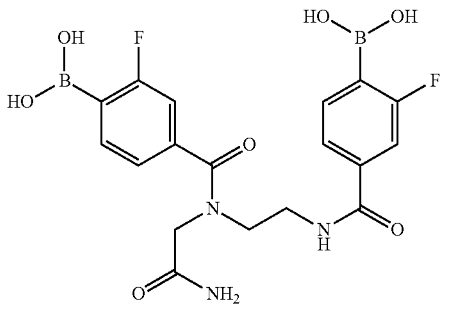 [SMILES: NC(=O)CN(CCNC(=O)c1ccc(B(O)O)c(F)c1)C(=O)c1ccc(B(O)O)c(F)c1]

N,N'-bis(4-borono-3-fluorobenzamido)-N-ethyl-glycine amide was prepared similar to the compound of Example 5 from 4-borono-3-fluorobenzoic acid.

Example 4

(S)-2,4-bis(4-borono-3-fluorobenzamido)butanoic acid

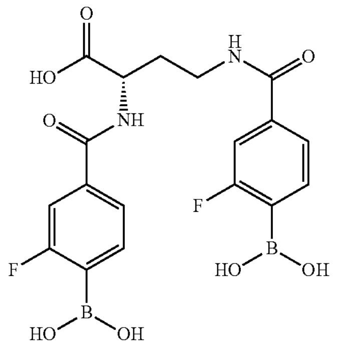 [SMILES: O=C(NCC[C@H](NC(=O)c1ccc(B(O)O)c(F)c1)C(=O)O)c1ccc(B(O)O)c(F)c1]

(S)-2,4-bis(4-borono-3-fluorobenzamido)butanoic acid was synthesized according to the reaction scheme shown in Chem. 3 and following the procedure described below.

Chem. 3

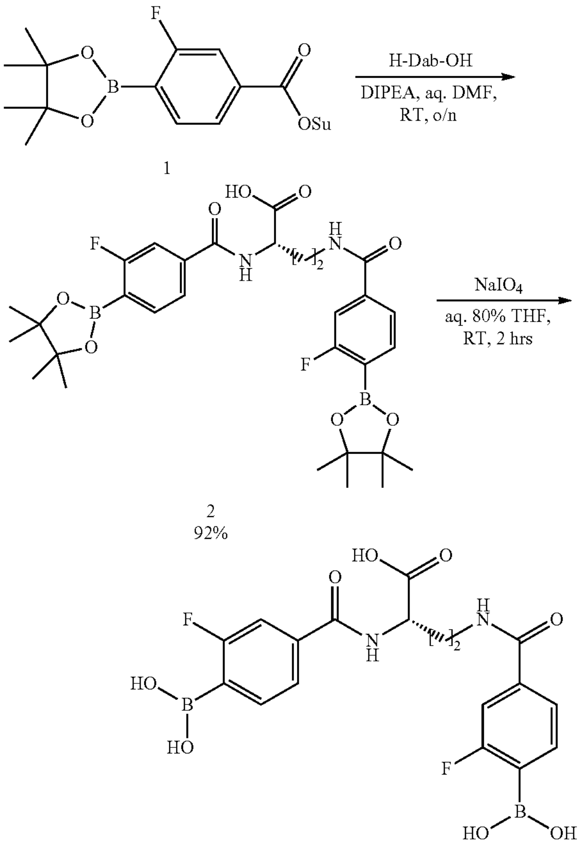

1

2
92%

3
26%

L-2,4-Diaminobutyric acid dihydrochloride (0.20 g, 1.69 mmol) was dissolved in water (3.6 mL). Subsequently N,N-diisopropylethylamine (1.18 mL, 6.76 mmol), N,N-dimethylformamide (7.2 mL) and 2,5-dioxopyrrolidin-1-yl 3-fluoro-4-(4,4,5,5-tetramethyl-1,3,2-dioxaborolan-2-yl) benzoate (1, 1.23 g, 3.38 mmol) were added. The mixture was stirred overnight at room temperature; then it was acidified by 1 M aqueous solution of hydrochloric acid. The solvent was co-evaporated with toluene three times. The residue was dissolved in dichloromethane/toluene mixture (1:1, 100 mL). The residue was dissolved in ethyl acetate (60 mL) and washed with water (3×40 mL). Organic layer was dried over anhydrous sodium sulfate, filtered and evaporated. The residue was dissolved in dichloromethane (3 mL) and product started to precipitate. Cyclohexane was added (35 mL). The precipitate was collected by filtration, washed with cyclohexane and dried in vacuo to yield 2,4-bis(4-(1,3,2-dioxaborolan-2-yl)-3-fluorobenzamido)butanoic acid (2) as transparent oil.

Yield: 960 mg (92%).

$^1$H NMR spectrum (300 MHz, $CDCl_3$, $\delta_H$): 7.90-7.75 (m, 2H); 7.65-7.40 (m, 5H); 7.11-7.02 (m, 1H); 4.91-4.79 (m, 1H); 3.58-3.50 (s, 2H); 2.10-1.70 (m, 4H); 1.36 (s, 24H).

LC-MS purity: 100% (ELSD).

LC-MS Rt (Kinetex C18, 4.6 mm×50 mm, acetonitrile/water 05:95 to 100:0+0.1% FA): 2.82 min, 3.56 min, 4.53 min.

LC-MS m/z: 615.6 $(M+H)^+$, 533.5 $(M+H\text{-pinacol})^+$, 451.4 $(M+H\text{-}2\times\text{pinacol})^+$.

The above acid (2, 200 mg, 0.32 mmol) was dissolved in tetrahydrofuran (3 mL) and water (0.75 mL). Sodium metaperiodate (0.35 g, 1.63 mmol) was added and the resulting mixture was vigorously stirred at ambient temperature (24° C.) for 2 hours and the resulting suspension was evaporated in vacuo. The residue was purified by preparative LC/MS (SunFire Prep C18, 5 μm, 19×100 mm, acetonitrile/water 5:95 to 100:0+0.1% FA) to give the title compound (3) as white solid.

Yield: 50.0 mg (26%).

$^1$H NMR spectrum (300 MHz, DMSO-$d_6$, $\delta_H$): 8.73 (d, J=7.5 Hz, 1H); 8.58 (t, J=5.5 Hz, 1H); 8.35 (d, J=7.9 Hz, 4H); 7.70-7.50 (m, 6H); 4.49-4.42 (m, 1H); 3.54-3.43 (m, 2H); 2.19-1.95 (m, 2H).

LC-MS purity: 100% (ELSD).

LC-MS Rt (Kinetex C18, 4.6 mm×50 mm, acetonitrile/water 5:95 to 100:0+0.1% FA): 2.80 min.

LC-MS m/z: 450.4 $(M+H)^+$.

Example 5

N-(7-Fluoro-1-hydroxy-1,3-dihydrobenzo[c][1,2]oxaborole-6-carbonyl)-N-(2-(7-fluoro-1-hydroxy-1,3-dihydrobenzo[c][1,2]oxaborole-6-carboxamido)ethyl)glycine

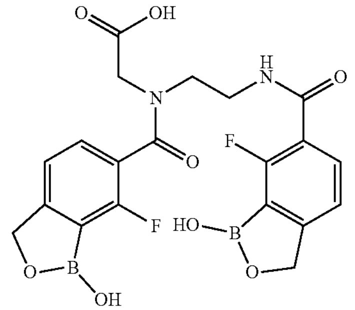 [SMILES: O=C(O)CN(CCNC(=O)c1ccc2c(c1F)B(O)OC2)C(=O)c1ccc2c(c1F)B(O)OC2]

N-(7-Fluoro-1-hydroxy-1,3-dihydrobenzo[c][1,2]oxaborole-6-carbonyl)-N-(2-(7-fluoro-1-hydroxy-1,3-dihydrobenzo[c][1,2]oxaborole-6-carboxamido)ethyl)glycine was synthesized according to the reaction schemes shown in Chem. 4 and Chem. 5 and following the procedure described below.

Chem. 4

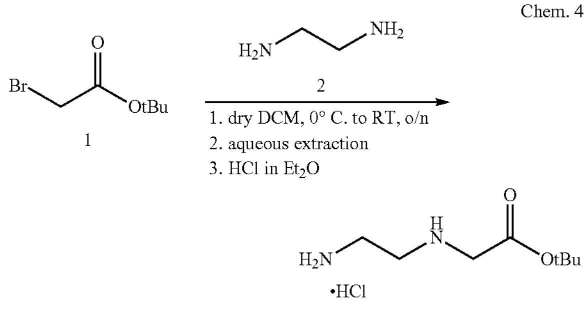

1

2

3

63%

Ethane-1,2-diamine (2, 44.0 mL, 659 mmol) was dissolved in anhydrous dichloromethane (300 mL) and tert-butyl 2-bromoacetate (1, 11.0 mL, 81.7 mmol) in anhydrous dichloromethane (20 mL) was added using syringe pump (3 mL/hour) at 0° C. under argon atmosphere. The reaction mixture was stirred for 10 hours at room temperature. Resulting mixture was extracted with water (200 mL), organic phase was dried with anhydrous sodium sulfate and concentrated under reduced pressure. Residue was dissolved in cold diethyl ether (150 mL) and precipitated with 3 M solution of hydrogen chloride in diethyl ether to give tert-butyl (2-aminoethyl)glycinate hydrochloride (3) as white solid.

Yield: 10.8 g (63%).

$^1$H NMR spectrum (300 MHz, $CDCl_3$, $\delta_H$): 3.31 (s, 2H); 2.83-2.75 (m, 2H); 2.73-2.64 (m, 2H); 1.47 (s, 9H).

Chem. 5

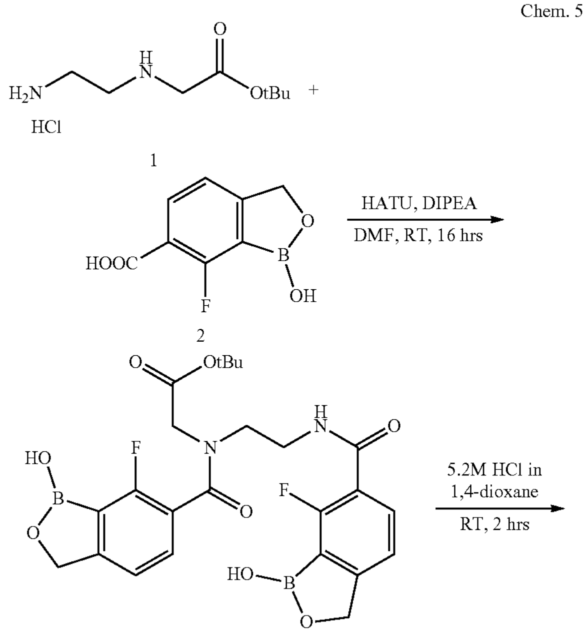

1

2

3

-continued

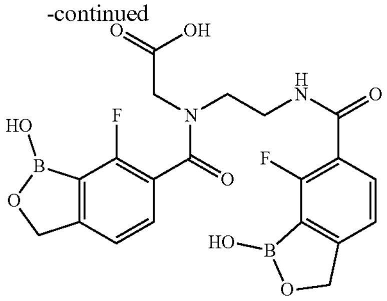

4

22%

7-Fluoro-1-hydroxy-1,3-dihydrobenzo[c][1,2]oxaborole-6-carboxylic acid (2, 0.30 g, 1.53 mmol) was dissolved in N,N-dimethylformamide (15 mL) and 1-((dimethylamino)(dimethyliminio)methyl)-1H-[1,2,3]triazolo[4,5-b]pyridine 3-oxide hexafluorophosphate(V) (HATU, 0.58 g, 1.53 mmol) and N,N-diisopropylethylamine (1.06 mL, 6.12 mmol) were added. After 5 minutes, tert-butyl (2-aminoethyl)glycinate hydrochloride (1, 0.16 g, 0.77 mmol) was added to the reaction mixture at room temperature and the reaction was stirred for 16 hours. Volatiles were then evaporated under reduced pressure and the ester 3 was used for the next step without further purification.

LC-MS purity: 40% (ELSD).

LC-MS Rt (Kinetex C18, 4.6 mm×50 mm, acetonitrile/water 5:95 to 100:0+0.1% FA): 3.48 min.

LC-MS m/z: 531.7 $(M+H)^+$.

tert-Butyl N-(7-fluoro-1-hydroxy-1,3-dihydrobenzo[c][1,2]oxaborole-6-carbonyl)-N-(2-(7-fluoro-1-hydroxy-1,3-dihydrobenzo[c][1,2]oxaborole-6-carboxamido) ethyl)glycinate (3, <0.77 mmol) was dissolved in 5.2 M solution of hydrogen chloride in 1,4-dioxane (10 mL) and the mixture was stirred for 2 hours at room temperature. Volatiles were then evaporated under reduced pressure and the residue was purified by preparative HPLC (Column X-Bridge, C18, 15 μm; 50×250 mm; acetonitrile/water 3:97 to 30:70+0.05% AA) and freeze-dried to afford N-(7-fluoro-1-hydroxy-1,3-dihydrobenzo[c][1,2]oxaborole-6-carbonyl)-N-(2-(7-fluoro-1-hydroxy-1,3-dihydrobenzo[c][1,2]oxaborole-6-carboxamido)ethyl)glycine 4 as white solid.

Yield: 81 mg (22%).

$^1$H NMR spectrum (300 MHz, DMSO-$d_6$, $\delta_H$): 9.41-9.33 (m, 2H); 8.42-8.18 (m, 1H); 7.81-7.64 (m, 1H); 7.43-7.11 (m, 3H); 5.07-4.97 (m, 4H); 4.22 (s, 1H); 3.98 (s, 1H); 3.68 (t, J=6.5 Hz, 1H); 3.60-3.40 (m, 3H).

LC-MS purity: 96% (ELSD).

LC-MS Rt (Kinetex C18, 4.6 mm×50 mm, acetonitrile/water 5:95 to 100:0+0.1% FA): 2.98 min.

LC-MS m/z: 475.5 $(M+H)^+$.

Example 6

3,5-Bis((7-fluoro-1-hydroxy-1,3-dihydrobenzo[c][1,2]oxaborole-6-carboxamido)methyl) benzoic acid

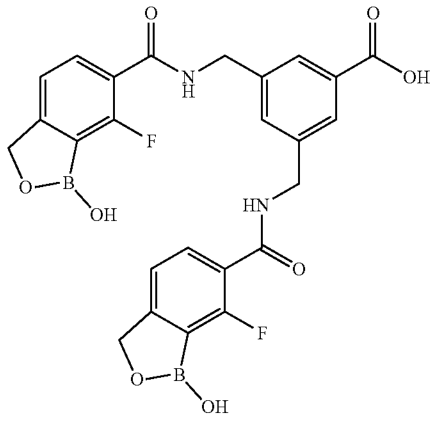 [SMILES: O=C(O)c1cc(CNC(=O)c2ccc3c(c2F)B(O)OC3)cc(CNC(=O)c2ccc3c(c2F)B(O)OC3)c1]

3,5-Bis((7-fluoro-1-hydroxy-1,3-dihydrobenzo[c][1,2]oxaborole-6-carboxamido)methyl) benzoic acid was synthesized according to the reaction scheme shown in Chem. 6 and following the procedure described below.

Chem. 6

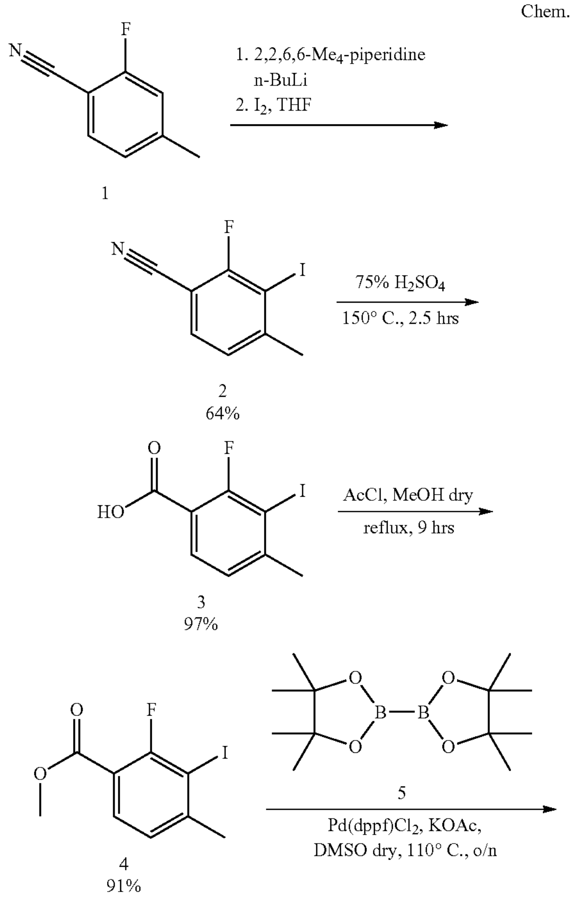

-continued

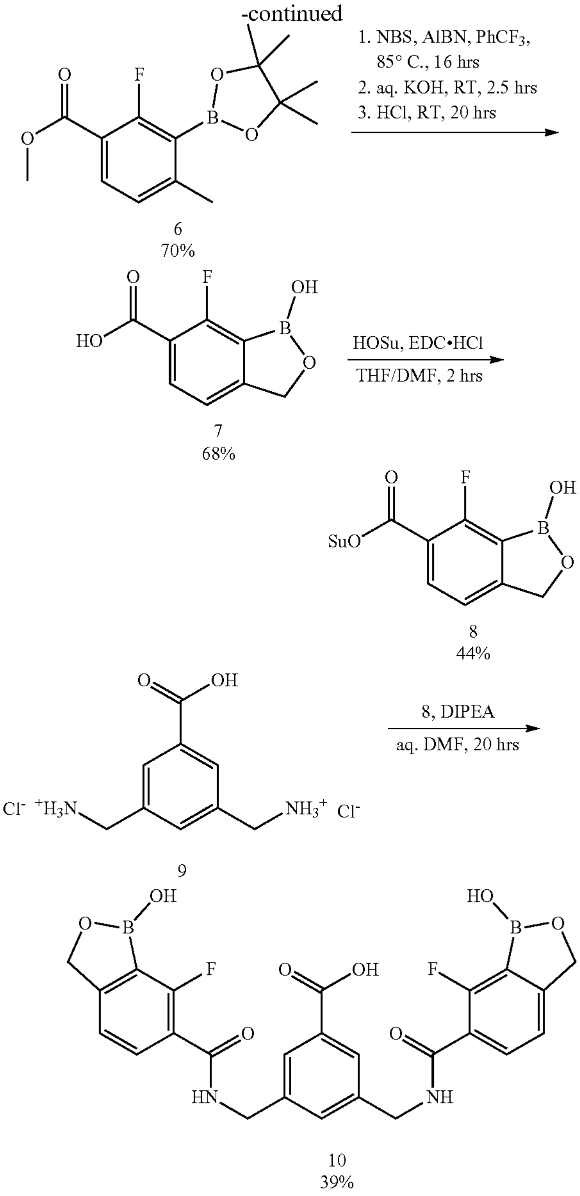

Butyllithium (2.35 M in hexane, 53.0 ml, 125 mmol) was drop-wise added to an nitrogen purged solution of 2,2,6,6-tetramethylpiperidine (17.7 g, 125 mmol) in anhydrous tetrahydrofuran (100 mL) over 20 minutes maintaining internal temperature below −35° C. A solution of 2-fluoro-4-methylbenzonitrile (1, 15.0 g, 111 mmol) in dry tetrahydrofuran (50 mL) was drop-wise added to the above mixture at a rate keeping internal temperature below −70° C. Then the mixture was warmed up to −50° C. for 45 minutes. A solution of iodine (31.0 g, 122 mmol) in tetrahydrofuran (50 mL) was drop-wise added to the reaction mixture keeping internal temperature below −60° C. The mixture was stirred for 12 hours at ambient temperature, then it was quenched by pouring to a stirred solution of sodium thiosulfate (10 g) in water (500 mL). The mixture was stirred for 1 hour. The mixture was treated with ethyl acetate (300 mL), aqueous phase was separated and re-extracted (100 mL). Combined organics were dried over anhydrous sodium sulfate and evaporated. The residue was loaded on silica by co-evaporation and column chromatography (Silicagel 60, 0.063-

0.200 mm; eluent: cyclohexane/diethyl ether 10:1) afforded crude product, which was crystallized from methanol to give 2-fluoro-3-iodo-4-methylbenzonitrile (2) as a white crystalline solid.

Yield: 18.49 g (64%).

$R_F$ ($SiO_2$, cyclohexane/diethyl ether 9:1): 0.35

$^1$H NMR spectrum (300 MHz, $CDCl_3$, $\delta_H$): 7.48 (dd, J=7.9 and 6.5 Hz, 1H); 7.17-7.12 (m, 1H), 2.56 (s, 3H).

A slurry of 2-fluoro-3-iodo-4-methylbenzonitrile (2, 18.5 g, 70.7 mmol) in 75% sulfuric acid (29 mL) was stirred at 150° C. for 2 hours. After cooling, the mixture was poured over ice/water (275 g), the precipitated solid was filtered off, washed with water and dried to yield 2-fluoro-3-iodo-4-methylbenzoic acid (3) as a creamy solid.

Yield: 19.18 g (97%).

$^1$H NMR spectrum (300 MHz, DMSO-$d_6$, $\delta_H$): 13.30 (s, 1H); 7.75 (t, J=7.8 Hz, 1H); 7.27 (d, J=8.0 Hz, 1H); 2.47 (s, 3H).

Acetyl chloride (4.90 mL, 68.7 mmol) was drop-wise added to a stirred suspension of 2-fluoro-3-iodo-4-methylbenzoic acid (3, 19.1 g, 68.3 mmol) in dry methanol (75 mL) at 0° C. The mixture was refluxed for 9 hours. The volatiles were removed by evaporation under reduced pressure and the residue was treated with ethyl acetate (100 mL) and saturated aqueous solution of sodium bicarbonate (100 mL). The mixture was filtered through a cotton plug (200 ml ethyl acetate washing). Phases were separated and the organic phase was dried over anhydrous magnesium sulfate and evaporated. The residue was crystallized from isopropanol/water (1:1, 30 mL) to furnish methyl 2-fluoro-3-iodo-4-methylbenzoate (4) as an off-white needles.

Yield: 18.36 g (91%).

$R_F$ ($SiO_2$, cyclohexane/diethyl ether 9:1): 0.50

$^1$H NMR spectrum (300 MHz, $CDCl_3$, $\delta_H$): 7.80 (t, J=7.7 Hz, 1H); 7.10 (d, J=8.0 Hz, 1H); 3.93 (s, 3H); 2.52 (s, 3H).

Solution of 2-fluoro-3-iodo-4-methylbenzoate (4, 18.5 g, 62.9 mmol), bis(pinacolato)diboron (5, 24.0 g, 94.4 mmol), anhydrous potassium acetate (18.5 g, 189 mmol) and [1,1'-bis(diphenylphosphino)ferrocene]dichloropalladium(II) complex with dichloromethane (1.02 g, 1.25 mmol) in anhydrous dimethylsulfoxide (250 mL) was stirred at 110° C. under argon atmosphere for 20 hours. Then the reaction mixture was cooled to ambient temperature, diluted with water (2000 mL) and extracted with ethyl acetate (4×500 mL). Organic layer was separated, dried over anhydrous sodium sulfate, filtered and concentrated under reduced pressure. Crude product was purified by flash chromatography (Silicagel 60, 0.063-0.200 mm; eluent: cyclohexane/dichloromethane 9:1) to provide methyl 2-fluoro-4-methyl-3-(4,4,5,5-tetramethyl-1,3,2-dioxaborolan-2-yl)benzoate (6).

Yield: 13.0 g (70%).

$R_F$ ($SiO_2$, cyclohexane/dichloromethane 9:1): 0.30

$^1$H NMR spectrum (300 MHz, $CDCl_3$, $\delta_H$): 7.84 (t, J=8.0 Hz, 1H); 7.00 (d, J=8.1 Hz, 1H); 3.90 (s, 3H); 2.47 (s, 3H); 1.39 (s, 12H).

Solution of methyl 2-fluoro-4-methyl-3-(4,4,5,5-tetramethyl-1,3,2-dioxaborolan-2-yl)benzoate (6, 11.7 g, 39.8 mmol), 1-bromopyrrolidine-2,5-dione (NBS, 9.20 g, 51.7 mmol) and 2,2'-azobis(2-methylpropionitrile) (AIBN, 0.33 g, 1.99 mmol) in benzotrifluoride (170 mL) was stirred at 85° C. for 16 hours. The reaction mixture was cooled to ambient temperature and 12% aqueous solution of potassium hydroxide (80 mL) was added and the reaction mixture was stirred for 2 hours at room temperature. Aqueous layer was separated and another portion of 12% aqueous solution of potassium hydroxide (50 mL) was added to the organic layer and the reaction mixture was stirred for another 30 minutes at room temperature. Combined aqueous layers were then acidified with 1 M aqueous solution of hydrochloric acid to pH<1 and allowed to stir at ambient temperature for 20 hours. Precipitate was filtered to provide 7-fluoro-1-hydroxy-1,3-dihydrobenzo[c][1,2]oxaborole-6-carboxylic acid (7) as beige solid.

Yield: 5.34 g (68%).

$^1$H NMR spectrum (300 MHz, DMSO-$d_6$, $\delta_H$): 9.39 (s, 1H); 7.97 (t, J=7.3 Hz, 1H); 7.32 (d, J=7.9 Hz, 1H); 5.04 (s, 2H).

LC-MS purity: 100% (ELSD).

LC-MS Rt (Kinetex C18, 4.6 mm×50 mm, acetonitrile/water 35:65 to 100:0+0.1% FA): 3.95 min.

LC-MS m/z: 373.4 $(M+H)^+$.

1-Hydroxy-2,5-pyrrolidinedione (HOSu, 1.17 g, 10.2 mmol) and 3-(ethyliminomethyleneamino)-N,N-dimethyl-propan-1-amine hydrochloride (EDC.HCl, 1.95 g, 10.2 mmol) were added to a solution of 7-fluoro-1-hydroxy-1,3-dihydrobenzo[c][1,2]oxaborole-6-carboxylic acid (7, 2.00 g, 10.2 mmol) in mixture of tetrahydrofuran/N,N-dimethylformamide (5:1, 50 mL) at room temperature. Reaction mixture was allowed to stir at ambient temperature for 2 hours. Volatiles were then evaporated, the residue was dissolved in ethyl acetate (200 mL) and extracted with 1 M aqueous solution of hydrochloric acid (2×80 mL) and brine (1×50 mL). Organic layer was separated, dried over anhydrous sodium sulfate, filtered and concentrated under reduced pressure. Crude product was recrystallized from hot 2-propanol (50 mL) to provide 2,5-dioxopyrrolidin-1-yl 7-fluoro-1-hydroxy-1,3-dihydrobenzo[c][1,2]oxaborole-6-carboxylate (8) as pale yellow solid.

Yield: 1.30 mg (44%).

$^1$H NMR spectrum (300 MHz, DMSO-$d_6$, $\delta_H$): 9.56 (s, 1H); 8.15 (dd, J=7.9 and 6.6 Hz, 1H); 7.50 (d, J=8.1 Hz, 1H); 5.12 (s, 2H); 2.84 (s, 4H).

LC-MS purity: 100% (ELSD).

LC-MS Rt (Kinetex C18, 4.6 mm×50 mm, acetonitrile/water 5:95 to 100:0+0.1% FA): 3.20 min.

LC-MS m/z: 294.4 $(M+H)^+$.

Solution of 2,5-dioxopyrrolidin-1-yl 7-fluoro-1-hydroxy-1,3-dihydrobenzo [c][1,2]oxaborole-6-carboxylate (8, 200 mg, 0.68 mmol), 3,5-bis(aminomethyl)benzoic acid dihydrochloride (9, 86.0 mg, 0.34 mmol) and N,N-diisopropylethylamine (0.36 mL) in mixture of N,N-dimethylformamide/water (4:1, 10 mL) was allowed to stir at ambient temperature for 20 hours. Reaction mixture was then evaporated and the rest was precipitated with 20% aqueous acetonitrile (15 mL). Resulting suspension was diluted with additional portion of water (20 mL) and centrifuged. Solids were then collected and purified by preparative LC/MS (SunFire Prep C18, 5 μm, 19×100 mm, acetonitrile/water 5:95 to 100:0+0.1% FA) and freeze-dried to afford 3,5-bis((7-fluoro-1-hydroxy-1,3-dihydrobenzo[c][1,2]oxaborole-6-carboxamido)methyl)benzoic acid (10) as white solid.

Yield: 71.0 mg (39%).

$^1$H NMR spectrum (300 MHz, DMSO-$d_6$, $\delta_H$): 9.38 (s, 2H); 8.99-8.87 (m, 2H); 7.83 (s, 2H); 7.76 (t, J=7.3 Hz, 2H); 7.55 (s, 1H); 7.30 (d, J=7.9 Hz, 2H); 5.03 (s, 4H); 4.52 (d, J=5.7 Hz, 4H).

LC-MS purity: 100% (ELSD).

LC-MS Rt (Kinetex C18, 4.6 mm×50 mm, acetonitrile/water 5:95 to 100:0+0.1% FA): 3.16 min.

LC-MS m/z: 537.7 $(M+H)^+$.

Example 7

N-(5-Fluoro-1-hydroxy-1,3-dihydrobenzo[c][1,2]oxaborole-6-carbonyl)-N-(2-(5-fluoro-1-hydroxy-1,3-dihydrobenzo[c][1,2]oxaborole-6-carboxamido)ethyl)glycine

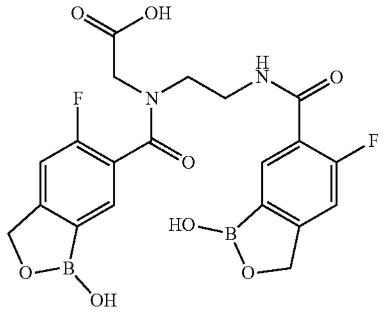 [SMILES: O=C(O)CN(CCNC(=O)c1cc2c(cc1F)COB2O)C(=O)c1cc2c(cc1F)COB2O]

N-(5-Fluoro-1-hydroxy-1,3-dihydrobenzo[c][1,2]oxaborole-6-carbonyl)-N-(2-(5-fluoro-1-hydroxy-1,3-dihydrobenzo[c][1,2]oxaborole-6-carboxamido)ethyl)glycine was synthesized according to the reaction scheme shown in Chem. 7 and following the procedure described below.

Chem. 7

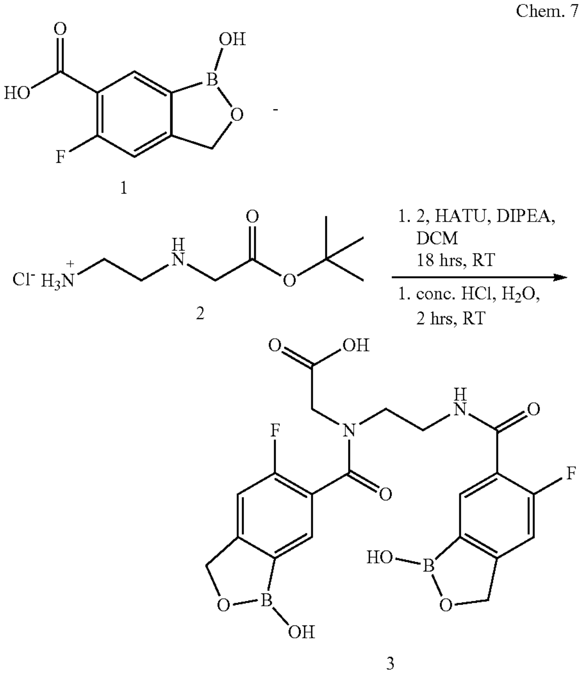

1

2

3
6%

Solution of 5-fluoro-1-hydroxy-1,3-dihydrobenzo[c][1,2]oxaborole-6-carboxylic acid (1, 140 mg, 0.71 mmol), 1-((dimethylamino)(dimethyliminio)methyl)-1H-[1,2,3]triazolo[4,5-b]pyridine 3-oxide hexafluorophosphate(V) (HATU, 265 mg, 0.70 mmol) and N,N-diisopropylethylamine (0.31 mL, 1.79 mmol) in dichloromethane (5 mL) was allowed to stir at ambient temperature. After 5 minutes, tert-butyl (2-aminoethyl)glycinate hydrochloride (2, 0.09 g, 0.36 mmol) was added to the reaction mixture at room temperature and the reaction was stirred for 18 hours. Volatiles were then evaporated under reduced pressure and concentrated hydrochloric acid (2 mL) was added. Reaction mixture was allowed to stir at room temperature for 2 hours. Then saturated aqueous solution of sodium bicarbonate was added to adjust neutral pH. Aqueous layer was extracted with acetonitrile (3×10 mL) and ethyl acetate (2×10 mL). Organic solutions were then evaporated under reduced pressure. The crude product 3 was purified by preparative LC/MS (SunFire Prep C18, 5 μm, 19×100 mm, acetonitrile/water 5:95 to 100:0+0.1% FA) with no success. Isolated compound 3 was then purified by preparative HPLC (Column X-Select, C18, 15 μm; 30×150 mm; acetonitrile/water 3:97 to 30:70+0.05% AA) and freeze-dried to afford N-(5-fluoro-1-hydroxy-1,3-dihydrobenzo[c][1,2]oxaborole-6-carbonyl)-N-(2-(5-fluoro-1-hydroxy-1,3-dihydrobenzo[c][1,2]oxaborole-6-carboxamido)ethyl)glycine (3) as white solid.

Yield: 10 mg (6%).

$^1$H NMR spectrum (300 MHz, DMSO-$d_6$, $\delta_H$): 9.39-9.23 (m, 2H); 8.55-8.22 (m, 1H); 8.05-7.93 (m, 1H); 7.67-7.63 (m, 1H); 7.36-7.21 (m, 2H); 5.00-4.97 (m, 4H); 4.20 (s, 1H); 3.88 (s, 1H); 3.70-3.65 (m, 2H); 3.57-3.53 (m, 2H).

LC-MS purity: 100% (ELSD).

LC-MS Rt (Kinetex C18, 4.6 mm×50 mm, acetonitrile/water 5:95 to 100:0+0.1% FA): 2.98 min.

LC-MS m/z: 475.5 $(M+H)^+$.

Example 8

N-(4-Fluoro-1-hydroxy-1,3-dihydrobenzo[c][1,2]oxaborole-6-carbonyl)-N-(2-(4-fluoro-1-hydroxy-1,3-dihydrobenzo[c][1,2]oxaborole-6-carboxamido)ethyl)glycine

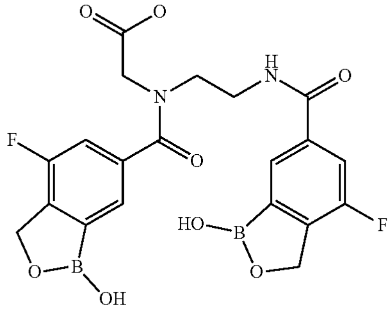

N-(4-Fluoro-1-hydroxy-1,3-dihydrobenzo[c][1,2]oxaborole-6-carbonyl)-N-(2-(4-fluoro-1-hydroxy-1,3-dihydrobenzo[c][1,2]oxaborole-6-carboxamido)ethyl)glycine was synthesized according to the reaction schemes shown in Chem. 8 and Chem. 9 and following the procedure described below.

Chem. 8

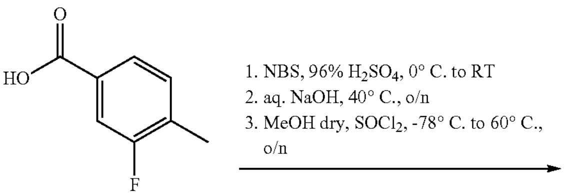

1

-continued

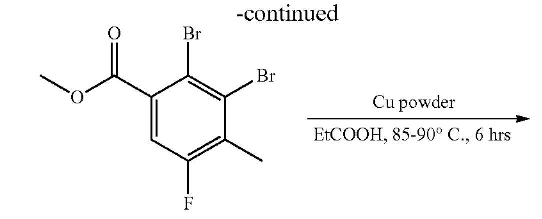

2
60%

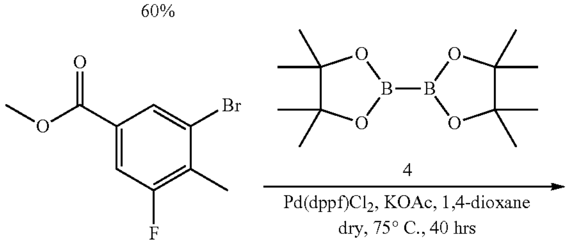

3
92%

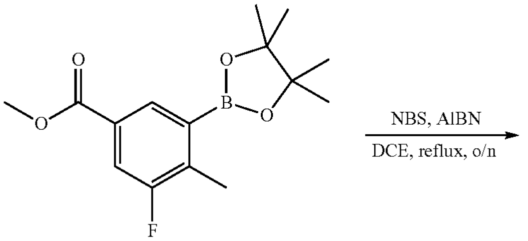

5
81%

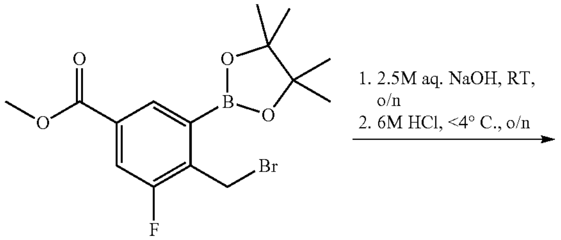

6
70%

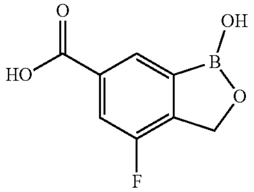

7
96%

Intensively stirred solution of 3-fluoro-4-methylbenzoic acid (1, 61.7 g, 400 mmol) in sulfuric acid (96%, 400 mL) was cooled by external ice water bath and N-bromosuccinimide (72.0 g, 405 mmol) was added in three portions during 20 minutes. The mixture was stirred at room temperature for 4 hours then another portion of N-bromosuccinimide (72.0 g, 405 mmol) was added at once and the whole mixture was stirred at room temperature overnight. Resulting suspension was diluted with ice water (3.00 L) and stirred for 10 minutes. The solid was filtered off, washed with water (200 mL), triturated with water (3×600 mL) and sucked off as much as possible. Wet solid was suspended in water (400 mL), stirred at room temperature and solution of sodium hydroxide (50.0 g, 1.25 mol in 200 mL water) was added.

Resulting solution was heated to 40° C. overnight. Filtration of slightly cloudy solution afforded clear yellowish filtrate to which solution of potassium bisulfate (180 g, 1.32 mol in 400 mL water) was added. White precipitate was extracted with a mixture of dichloromethane/tetrahydrofuran 4:1 (2×500 mL). Organic extracts were dried over anhydrous sodium sulfate and evaporated to dryness to give white solid residue. Thionyl chloride (30.0 mL, 413 mmol) was added to stirred cooled (−78° C.) suspension of this residue in anhydrous methanol (500 mL). Reaction mixture was allowed to warm to room temperature and then heated to 60° C. overnight. The solution was cooled to room temperature and kept 4° C. overnight. Crystalline material was filtered off washed by methanol (2×50 mL), tert-butyl methyl ether (2×50 mL) and dried in vacuo to afford methyl 2,3-dibromo-5-fluoro-4-methylbenzoate (2) as colorless crystals.

Yield: 78.2 g (60%).

$^1$H NMR spectrum (300 MHz, $CDCl_3$, $\delta_H$): 7.37 (d, J=9.0 Hz, 1H); 3.94 (s, 3H); 2.46 (d, J=2.3 Hz, 3H).

LC-MS purity: 98% (UV).

LC-MS Rt (Kinetex C18, 4.6 mm×50 mm, acetonitrile/water 40:60 to 100:0+0.1% FA): 4.55 min.

LC-MS m/z: 327.2 $(M+H)^+$.

A suspension of fine powdered copper (44.0 g, 692 mmol) and methyl 2,3-dibromo-5-fluoro-4-methylbenzoate (2, 75.2 g, 231 mmol) in propionic acid (100 mL) was stirred and heated at 85-90° C. for 6 hours, cooled to room temperature and diluted with mixture of cyclohexane/toluene (3:1, 800 mL). Reaction mixture was washed with water (3×200 mL), 10% aqueous solution of potassium bisulfate (2×200 mL) and brine (2×300 mL). Organic solution was dried over anhydrous sodium sulfate and evaporated to dryness to give yellowish oil which was purified by flash column chromatography (Silicagel 60, 0.040-0.060 mm; eluent: cyclohexane/toluene 3:1) to afford methyl 3-bromo-5-fluoro-4-methylbenzoate (3) as colorless crystals.

Yield: 52.5 g (92%).

$^1$H NMR spectrum (300 MHz, $CDCl_3$, $\delta_H$): 7.51 (s, 1H); 7.37 (d, J=9.0 Hz, 1H); 3.86 (s, 3H); 2.37 (d, J=2.4 Hz, 3H).

LC-MS purity: 99% (UV).

LC-MS Rt (Kinetex C18, 4.6 mm×50 mm, acetonitrile/water 40:60 to 100:0+0.1% FA): 3.72 min.

LC-MS m/z: 347.3 $(M+H)^+$.

Methyl 3-bromo-5-fluoro-4-methylbenzoate (3, 51.9 g, 210 mmol) was dissolved in anhydrous 1,4-dioxane (400 mL), anhydrous potassium acetate (65.3 g, 666 mmol) and bis(pinacolato)diboron (4, 75.1 g, 296 mmol) was added at room temperature and this mixture was degassed. 1,1'-Bis(diphenylphosphino)ferrocene] dichloropalladium(II) (1.88 g, 2.57 mmol) was added and the mixture was heated to 75° C. in an argon atmosphere for 40 hours. The mixture was concentrated under reduced pressure and dissolved in toluene (1.1 L) and extracted with water (2×200 mL). Organic solution was dried using anhydrous sodium sulfate, evaporated under reduced pressure and then purified by flash column chromatography (Silicagel 60, 0.040-0.063 mm; eluent: toluene/ethyl acetate 9:1) to afford methyl 3-fluoro-4-methyl-5-(4,4,5,5-tetramethyl-1,3,2-dioxaborolan-2-yl) benzoate (5) as white solid.

Yield: 50.0 g (81%).

$^1$H NMR spectrum (300 MHz, $CDCl_3$, $\delta_H$): 8.20 (s, 1H); 7.70 (d, J=10.0 Hz, 1H); 3.85 (s, 3H); 2.50 (s, 3H); 1.36 (s, 12H).

LC-MS purity: 100% (ELSD).

LC-MS Rt (Kinetex C18, 4.6 mm×50 mm, acetonitrile/water 40:60 to 100:0+0.1% FA): 6.12 min.

LC-MS m/z: 295.4 $(M+H)^+$.

Azobisisobutyronitrile (AIBN, 0.86 g, 5.20 mmol) and N-bromosuccinimide (NBS, 25.4 g, 143 mmol) were added to a solution of methyl 3-fluoro-4-methyl-5-(4,4,5,5-tetramethyl-1,3,2-dioxaborolan-2-yl)benzoate (5, 40.0 g, 136 mmol) in 1,2-dichloroethane (200 mL). The mixture was refluxed overnight. Reaction mixture was cooled to room temperature, diluted with dichloromethane (500 mL) and extracted with water (2×500 mL). Organic solution was dried over anhydrous magnesium sulfate and evaporated to dryness to give methyl 4-(bromomethyl)-3-fluoro-5-(4,4,5,5-tetramethyl-1,3,2-dioxaborolan-2-yl)benzoate (6) as yellowish crystals. The product was used in the next step without further purification.

Yield: 35.5 g (70%).

LC-MS purity: 96% (ELSD).

LC-MS Rt (Kinetex C18, 4.6 mm×50 mm, acetonitrile/water 40:60 to 100:0+0.1% FA): 6.53 min.

LC-MS m/z: 373.4 $(M+H)^+$.

Methyl 4-(bromomethyl)-3-fluoro-5-(4,4,5,5-tetramethyl-1,3,2-dioxaborolan-2-yl)benzoate (6, 7.46 g, 20.0 mmol) stirred with 2.5 M aqueous solution of sodium hydroxide (40.0 mL, 100 mmol) at room temperature overnight. 6 M aqueous solution of hydrochloric acid (20.0 mL, 120 mmol) was added and the mixture was stirred for 30 minutes and kept 4° C. overnight. White precipitate was collected by filtration and washed with water (2×100 mL) and air dried to afford 4-fluoro-1-hydroxy-1,3-dihydrobenzo[c][1,2]oxaborole-6-carboxylic acid (7) as a white solid which was used in the next step without further purification.

Yield: 3.76 g (96%).

$^1H$ NMR spectrum (300 MHz, DMSO-$d_6$, $\delta_H$): 12.8 (s, 1H); 9.57 (s, 1H); 8.20 (s, 1H); 7.72 (d, J=7.1 Hz, 1H); 5.14 (s, 2H).

LC-MS purity: 95% (ELSD).

LC-MS Rt (Kinetex C18, 4.6 mm×50 mm, acetonitrile/water 5:95 to 100:0+0.1% FA): 3.22 min.

LC-MS m/z: 197.4 $(M+H)^+$.

Chem. 9

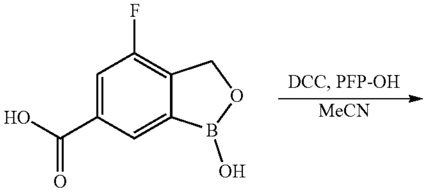

1

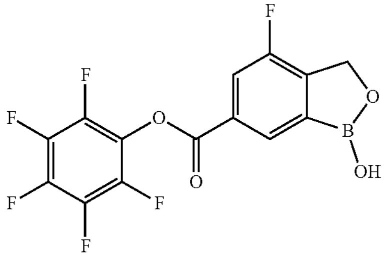

2
74%

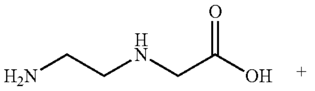

3

-continued

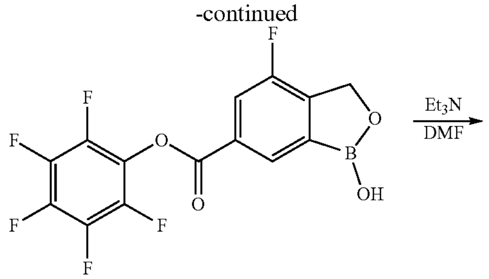

2

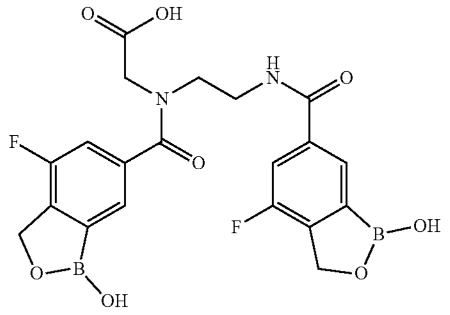

4
20%

4-Fluoro-1-hydroxy-1,3-dihydrobenzo[c][1,2]oxaborole-6-carboxylic acid (1, 0.30 g, 1.53 mmol) was dissolved in acetonitrile (5 mL). 2,3,4,5,6-Pentafluorophenol (0.28 g, 1.53 mmol) and N,N-dicyclohexylcarbodiimide (0.32 g, 1.53 mmol) were added at room temperature. After stirring for 16 hours, precipitate was filtered off and filtrate was evaporated under reduced pressure to give perfluorophenyl 4-fluoro-1-hydroxy-1,3-dihydrobenzo[c][1,2]oxaborole-6-carboxylate (2) as a white solid.

Yield: 0.41 g (74%).

$^1H$ NMR spectrum (300 MHz, DMSO-$d_6$, $\delta_H$): 9.72 (s, 1H); 8.46 (s, 1H); 8.05 (d, J=8.1 Hz, 1H); 5.23 (s, 2H).

(2-Aminoethyl)glycine (3, 0.06 g, 0.50 mmol) was dissolved in N,N-dimethylformamide (3 mL), triethylamine (0.42 mL, 3.00 mmol) and perfluorophenyl 4-fluoro-1-hydroxy-1,3-dihydrobenzo[c][1,2]oxaborole-6-carboxylate (2, 0.40 g, 1.00 mmol) were added at room temperature. After stirring for 16 hours at room temperature, all volatiles were then evaporated under reduced pressure and the residue was precipitated from ethyl acetate (40 mL) and purified by preparative HPLC (SunFire Prep C18, 5 μm, 19×100 mm, acetonitrile/water 5:95 to 100:0+0.1% FA) and freeze-dried to afford N-(4-fluoro-1-hydroxy-1,3-dihydrobenzo[c][1,2]oxaborole-6-carbonyl)-N-(2-(4-fluoro-1-hydroxy-1,3-dihydrobenzo[c][1,2]oxaborole-6-carboxamido)ethyl)glycine (4) as white solid.

Yield: 47.0 mg (20%).

$^1H$ NMR spectrum (300 MHz, DMSO-$d_6$, $\delta_H$): 12.83 (bs, 1H); 9.63-9.41 (m, 2H); 8.78-8.52 (m, 1H); 8.13-7.92 (m, 1H); 7.79-7.45 (m, 2H); 7.22-6.99 (m, 1H); 5.19-5.01 (m, 4H); 4.20 (s, 1H); 4.00 (s, 1H); 3.71-3.36 (m, 4H).

LC-MS purity: 100% (ELSD).

LC-MS Rt (Kinetex C18, 4.6 mm×50 mm, acetonitrile/water 5:95 to 100:0+0.1% FA): 3.19 min.

LC-MS m/z: 475.3 $(M+H)^+$.

Example 9

N-(6-Fluoro-1-hydroxy-1,3-dihydrobenzo[c][1,2]oxaborole-5-carbonyl)-N-(2-(6-fluoro-1-hydroxy-1,3-dihydrobenzo[c][1,2]oxaborole-5-carboxamido)ethyl)glycine

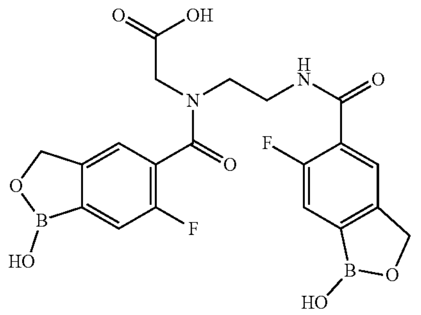 [SMILES: O=C(O)CN(CCNC(=O)c1cc2c(cc1F)B(O)OC2)C(=O)c1cc2c(cc1F)B(O)OC2]

N-(6-Fluoro-1-hydroxy-1,3-dihydrobenzo[c][1,2]oxaborole-5-carbonyl)-N-(2-(6-fluoro-1-hydroxy-1,3-dihydrobenzo[c][1,2]oxaborole-5-carboxamido)ethyl)glycine was synthesized according to the reaction scheme shown in Chem. 10 and following the procedure described below.

Chem. 10

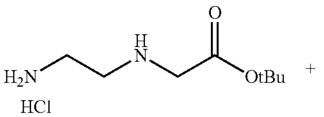

1

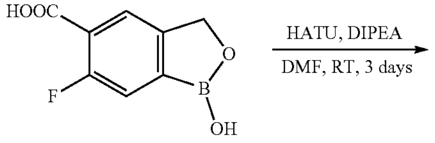

2

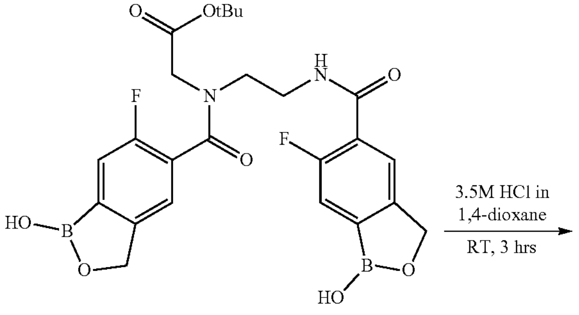

3

-continued

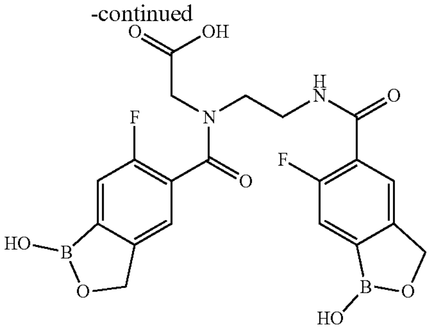

4

14%

6-Fluoro-1-hydroxy-1,3-dihydrobenzo[c][1,2]oxaborole-5-carboxylic acid (2, 0.25 g, 1.27 mmol) was dissolved in N,N-dimethylformamide (15 mL) and 1-((dimethylamino)(dimethyliminio)methyl)-1H-[1,2,3]triazolo[4,5-b]pyridine 3-oxide hexafluorophosphate (HATU, 0.49 g, 1.27 mmol) and N,N-diisopropylethylamine (0.89 mL, 5.10 mmol) were added. After 5 minutes, tert-butyl (2-aminoethyl)glycinate hydrochloride (1, 0.13 g, 0.64 mmol) was added to the reaction mixture at room temperature and the reaction was stirred for 3 days. Volatiles were then evaporated under reduced pressure and the ester 3 was used for the next step without further purification.

LC-MS purity: 66% (ELSD).

LC-MS Rt (Kinetex C18, 4.6 mm×50 mm, acetonitrile/water 5:95 to 100:0+0.1% FA): 3.55 min.

LC-MS m/z: 531.5 $(M+H)^+$.

tert-Butyl N-(6-fluoro-1-hydroxy-1,3-dihydrobenzo[c][1,2]oxaborole-5-carbonyl)-N-(2-(6-fluoro-1-hydroxy-1,3-dihydrobenzo[c][1,2]oxaborole-5-carboxamido)ethyl)glycinate (3, <0.64 mmol) was dissolved in 3.5 M solution of hydrogen chloride in 1,4-dioxane (20 mL) and the mixture was stirred for 3 hours at room temperature. Volatiles were then evaporated under reduced pressure and the residue was purified by preparative HPLC (Column X-Select, C18, 15 μm; 30×150 mm; acetonitrile/water 3:97 to 30:70+0.05% AA) and freeze-dried to afford N-(6-fluoro-1-hydroxy-1,3-dihydrobenzo[c][1,2]oxaborole-5-carbonyl)-N-(2-(6-fluoro-1-hydroxy-1,3-dihydrobenzo[c][1,2]oxaborole-5-carboxamido)ethyl)glycine 4 as white solid.

Yield: 0.04 g (14%).

$^1$H NMR spectrum (300 MHz, DMSO-$d_6$, $\delta_H$): 9.53-9.40 (m, 2H); 8.55-8.23 (m, 1H); 7.67-7.40 (m, 3H); 7.36-7.22 (m, 1H); 5.04-4.94 (m, 3H); 4.76 (bs, 1H); 4.22 (s, 1H); 3.97 (s, 1H); 3.73-3.64 (m, 2H); 3.58-3.52 (m, 2H).

LC-MS purity: 100% (ELSD).

LC-MS Rt (Kinetex C18, 4.6 mm×50 mm, acetonitrile/water 5:95 to 100:0+0.1% FA): 2.97 min.

LC-MS m/z: 475.4 $(M+H)^+$.

Example 10

N[2],N[6]-Bis(6-fluoro-1-hydroxy-1,3-dihydrobenzo[c][1,2]oxaborole-5-carbonyl)-L-lysine

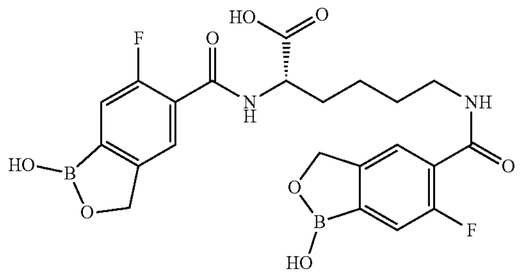 [SMILES: O=C(NCCCC[C@H](NC(=O)c1cc2c(cc1F)B(O)OC2)C(=O)O)c1cc2c(cc1F)B(O)OC2]

N[2],N[6]-Bis(6-fluoro-1-hydroxy-1,3-dihydrobenzo[c][1,2]oxaborole-5-carbonyl)-L-lysine was synthesized according to the reaction scheme shown in Chem. 11 and following the procedure described below.

Chem. 11

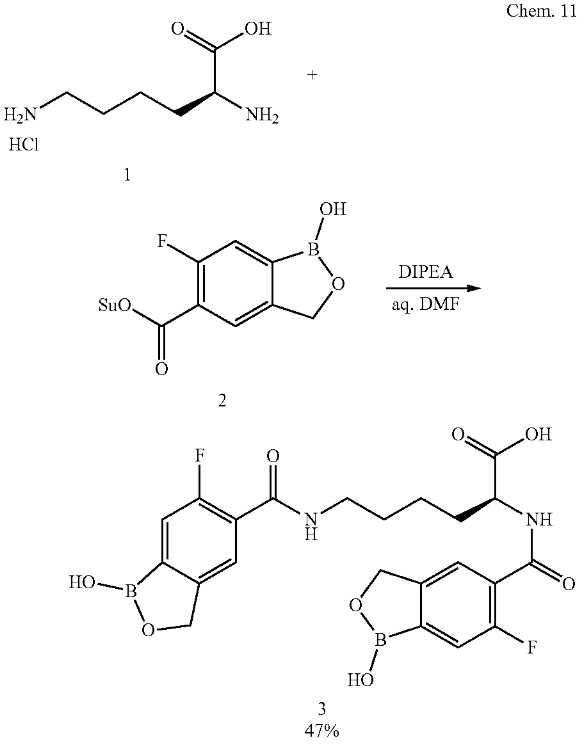

L-Lysine hydrochloride (1, 68.0 mg, 0.38 mmol) was dissolved in N,N-dimethylformamide (6 mL) and water (3 mL). N,N-Diisopropylethylamine (0.39 mL, 2.25 mmol) and 2,5-dioxopyrrolidin-1-yl 6-fluoro-1-hydroxy-1,3-dihydrobenzo[c][1,2] oxaborole-5-carboxylate (2, 0.22 g, 0.75 mmol) were added at room temperature. After stirring for 3 hours, volatiles were evaporated under reduced pressure and the residue was purified by preparative HPLC (Column X-Bridge, C18, 15 μm; 30×150 mm, acetonitrile/water 3:97 to 30:70+0.05% AA) and freeze-dried to afford N[2],N[6]-bis (6-fluoro-1-hydroxy-1,3-dihydrobenzo[c][1,2]oxaborole-5-carbonyl)-L-lysine (3) as a white solid.

Yield: 89.0 mg (47%).

$^1$H NMR spectrum (300 MHz, DMSO-$d_6$, $\delta_H$): 12.65 (bs, 1H); 9.41 (d, J=5.9 Hz, 2H); 8.60 (d, J=1.5 Hz, 1H); 8.39 (t, J=5.3 Hz, 1H); 7.62-7.53 (m, 2H); 7.53-7.43 (m, 2H); 4.97 (d, J=5.5 Hz, 4H); 4.41-4.29 (m, 1H); 3.30-3.20 (m, 2H); 1.88-1.68 (m, 2H); 1.60-1.37 (m, 4H).

LC-MS purity: 97% (ELSD).

LC-MS Rt (Kinetex C18, 4.6 mm×50 mm, acetonitrile/water 5:95 to 100:0+0.1% FA): 3.08 min.

LC-MS m/z: 503.5 $(M+H)^+$.

Example 11

3-Borono-5-((3-borono-4-fluorophenyl)sulfonyl)-4-fluorobenzoic acid

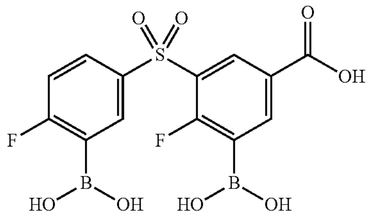 [SMILES: O=C(O)c1cc(B(O)O)c(F)c(S(=O)(=O)c2ccc(F)c(B(O)O)c2)c1]

3-Borono-5-((3-borono-4-fluorophenyl)sulfonyl)-4-fluorobenzoic acid was synthesized according to the reaction scheme shown in Chem. 12 and following the procedure described below.

Chem. 12

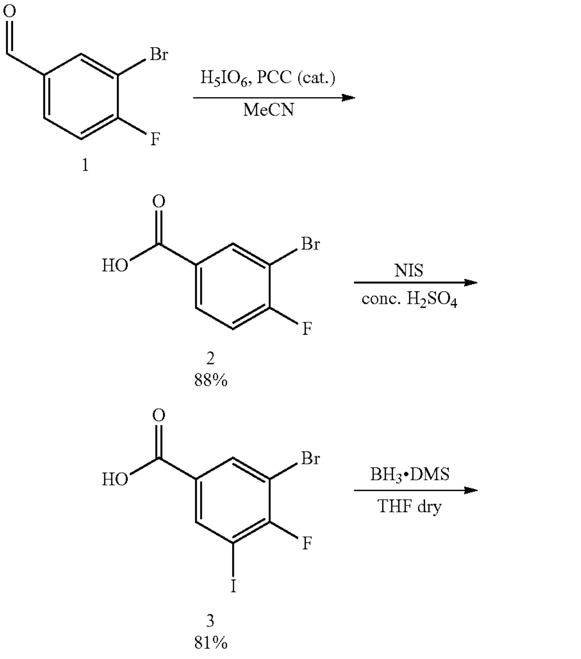

-continued

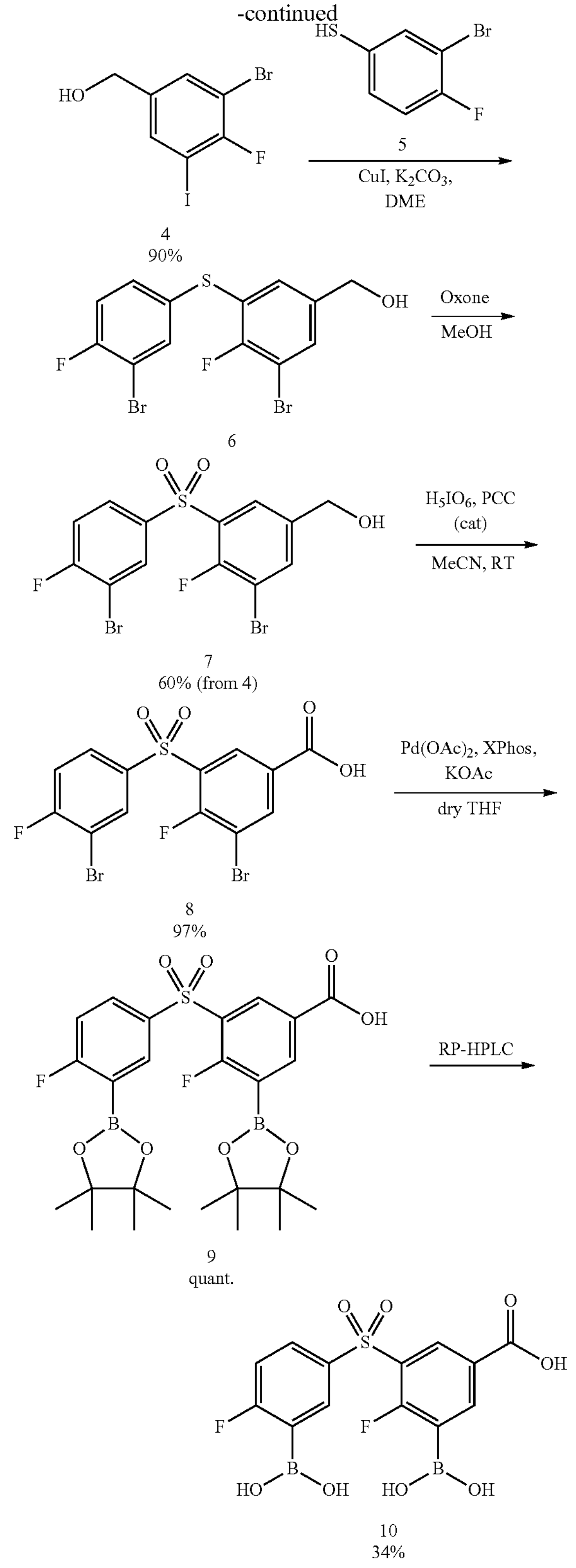

3-Bromo-4-fluorobenzaldehyde (1, 4.06 g, 20.0 mmol) and periodic acid (5.02 g, 22.0 mmol) were suspended in acetonitrile (100 mL) and pyridinium chlorochromate (PCC, 86.0 mg, 0.40 mmol) was added with stirring. The resulting viscous suspension was stirred for two hours and then concentrated to half its volume. Water (300 mL) was added with stirring, resulting in the precipitation of a white solid, which was collected by filtration, washed with water (2×50 mL) and air dried to give 3-bromo-4-fluorobenzoic acid (2).

Yield: 3.85 g (88%).

3-Bromo-4-fluorobenzoic acid (2, 2.19 g, 10.0 mmol) was dissolved in sulfuric acid (25 mL) and N-iodosuccinimide (NIS, 2.47 g, 3.00 mmol) was added in portions with stirring. The reaction mixture was then stirred for an hour and then it was poured into ice-cold water (150 mL) to precipitate the product, which was washed with water (2×20 mL) and air dried. The crude acid was recrystallized from toluene to give the title compound 3-bromo-4-fluoro-5-iodobenzoic acid (3) as off-white solid.

Yield: 2.46 g (81%).

$^1H$ NMR spectrum (300 MHz, $CDCl_3$, $\delta_H$): 9.60 (bs, 1H); 8.30 (s, 1H); 8.13 (s, 1H).

3-Bromo-4-fluoro-5-iodobenzoic acid (3, 1.72 g, 5.00 mmol) was dissolved in dry tetrahydrofuran (15 mL) and cooled to 0° C. in an ice-bath. Neat borane-dimethyl sulfide (1.00 ml, 10.0 mmol) was added (gas evolution) and the resulting mixture was stirred for 16 hours (overnight). The reaction mixture was carefully quenched with methanol (2 mL), evaporated to dryness and the residue was co-distilled with methanol (2×10 mL). The resulting solid was triturated with n-hexane and filtered to give the (3-bromo-4-fluoro-5-iodophenyl)methanol (4) as white solid.

Yield: 1.48 g (90%).

$^1H$ NMR spectrum (300 MHz, $CDCl_3$, $\delta_H$): 7.74-7.66 (m, 1H); 7.58-7.50 (m, 1H); 4.64 (s, 2H); 1.87 (bs, 1H).

(3-Bromo-4-fluoro-5-iodophenyl)methanol (4, 825 mg, 2.50 mmol), anhydrous potassium carbonate (690 mg, 5.00 mmol), copper iodide (95.0 mg, 0.50 mmol) and 3-bromo-4-fluorobenzenethiol (5, 776 mg, 3.75 mmol) were suspended in dry 1,2-dimethoxyethane (10 mL) and the resulting suspension was stirred for 48 hours at 80° C. After cooling to ambient temperature, the reaction mixture was diluted with ethyl acetate (20 mL), filtered through Celite (washed with ethyl acetate) and evaporated. The residue was purified by flash chromatography (Silicagel 60, 0.063-0.200 mm; eluent: cyclohexane/ethyl acetate 3:1) to give 6 as colorless oil. It was dissolved in methanol (10 mL) and water (5 mL) and potassium peroxymonosulfate (2.30 g, 3.75 mmol) was added in portions. After stirring for 16 hours, the reaction mixture was taken up in ethyl acetate (50 mL) and washed with water (30 mL) and brine (30 mL). After drying the organic layer with anhydrous sodium sulfate, filtration and evaporation. The crude product was purified by flash chromatography (Silicagel 60, 0.063-0.200 mm; eluent: cyclohexane/ethyl acetate 3:1 to 1:1) to give (3-bromo-5-((3-bromo-4-fluorophenyl)sulfonyl)-4-fluorophenyl) methanol (7) as colorless solid.

Yield: 663 mg (60%).

$^1H$ NMR spectrum (300 MHz, $CDCl_3$, $\delta_H$): 8.26-8.19 (m, 1H); 8.05-7.97 (m, 2H); 7.89-7.83 (m, 1H); 7.36-7.26 (m, 1H, overlapping with $CHCl_3$); 4.79 (s, 2H); 2.18 (bs, 1H).

LC-MS purity: 100% (ELSD).

LC-MS Rt (Kinetex C18, 4.6 mm×50 mm, acetonitrile/water 50:50 to 100:0+0.1% FA): 2.14 min.

LC-MS m/z: 443.2 $(M+H)^+$.

(3-bromo-5-((3-bromo-4-fluorophenyl)sulfonyl)-4-fluorophenyl)methanol (7, 621 mg, 1.405 mmol) and periodic acid (707 mg, 3.1 mmol) were suspended in acetonitrile (10 mL) and pyridinium chlorochromate (PCC, 15 mg, 0.07 mmol) was added with stirring. The resulting viscous suspension was stirred for 16 hours and then mixture was taken up in ethyl acetate (30 mL) and washed with water (30 mL)

and brine (30 mL). The organic layer dried with anhydrous sodium sulfate, filtered and evaporated to give pure 3-bromo-5-((3-bromo-4-fluorophenyl)sulfonyl)-4-fluorobenzoic acid (8) as colorless solid.

Yield: 620 mg (97%).

$^1$H NMR spectrum (300 MHz, $CDCl_3$, $\delta_H$): 8.52-8.46 (m, 1H); 8.33-8.26 (m, 1H); 8.07-8.00 (m, 1H), 7.86-7.79 (m, 1H), 7.22-7.13 (s, 1H); 4.24 (bs, 1H).

LC-MS purity: 100% (ELSD).

LC-MS Rt (Kinetex C18, 4.6 mm×50 mm, acetonitrile/water 50:50 to 100:0+0.1% FA): 2.66 min.

LC-MS m/z: 457.8 $(M+H)^+$.

A 25 mL reaction vessel was charged with potassium acetate (392 mg, 4.00 mmol) and the salt was dried for 1 hour at 110° C. in vacuo. After cooling to room temperature, the reaction vessel was backfilled with nitrogen and charged 3-bromo-5-((3-bromo-4-fluorophenyl)sulfonyl)-4-fluorobenzoic acid (8, 364 mg, 0.80 mmol), palladium acetate (9.0 mg, 0.04 mmol), 2-dicyclohexylphosphino-2',4',6'-triisopropylbiphenyl (XPhos, 38.0 mg, 0.08 mmol) and bis(pinacolato)diboron (447 mg, 1.76 mmol). The reaction vessel was then evacuated and backfilled with nitrogen (this procedure was repeated twice), anhydrous tetrahydrofuran (4 mL) was added with syringe, the vessel was sealed with rubber septum and submerged in the heating bath preheated to 60° C. After stirring at 400 rpm for 20 hours (overnight) the reaction mixture was diluted with dichloromethane (15 mL) and quickly filtered through a short plug of Celite (3.00 g) with the aid of more dichloromethane (3×5 mL). The filtrate was concentrated under reduced pressure to afford the crude 4-fluoro-3-((4-fluoro-3-(4,4,5,5-tetramethyl-1,3,2-dioxaborolan-2-yl)phenyl)sulfonyl)-5-(4,4,5,5-tetramethyl-1,3,2-dioxaborolan-2-yl)benzoic acid (9) a beige foam. A part of this material was purified (pinacol ester hydrolysis occurred spontaneously) by preparative LC-MS (SunFire Prep C18, 5 μm, 19×100 mm, acetonitrile/water 5:95 to 100:0+0.1% FA). The fractions were pooled and freeze-dried to give 3-borono-5-((3-borono-4-fluorophenyl)sulfonyl)-4-fluorobenzoic acid (10) as white solid.

Yield: 34 mg (11%).

$^1$H NMR spectrum (300 MHz, Acetone-$d_6$/$D_2O$, 10:1, $\delta_H$): 8.70-8.64 (m, 1H); 8.59-8.53 (m, 1H); 8.35-8.28 (m, 1H), 8.14-8.05 (m, 1H), 7.38-7.28 (s, 1H).

LC-MS purity: 100% (ELSD).

LC-MS Rt (Kinetex C18, 4.6 mm×50 mm, acetonitrile/water 20:80 to 100:0+0.1% FA): 3.28 min.

LC-MS m/z: 387.4 $(M+H)^+$.

Example 12

3-Borono-5-(3-borono-5-fluorobenzoyl)benzoic acid

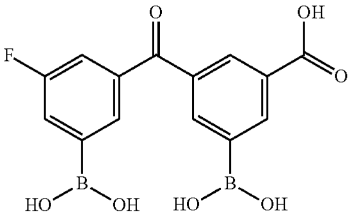 [SMILES: O=C(O)c1cc(B(O)O)cc(C(=O)c2cc(F)cc(B(O)O)c2)c1]

3-Borono-5-(3-borono-5-fluorobenzoyl)benzoic acid was synthesized according to the reaction scheme shown in Chem. 13 and following the procedure described below.

Chem. 13

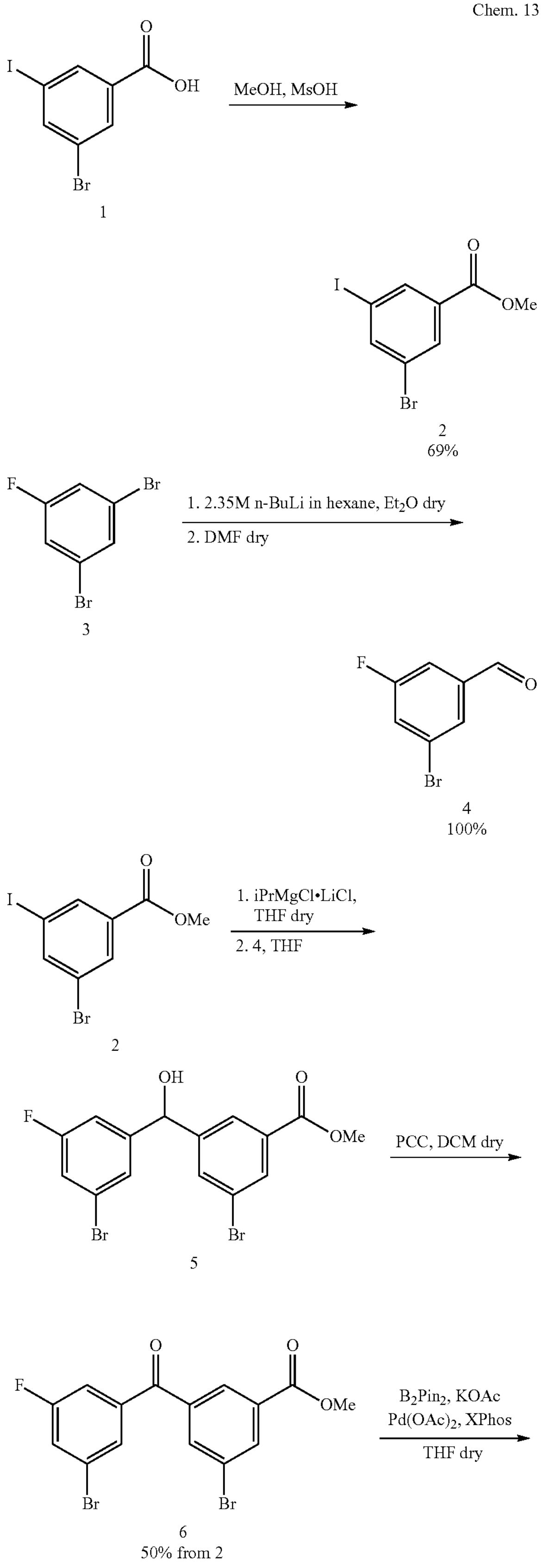

-continued

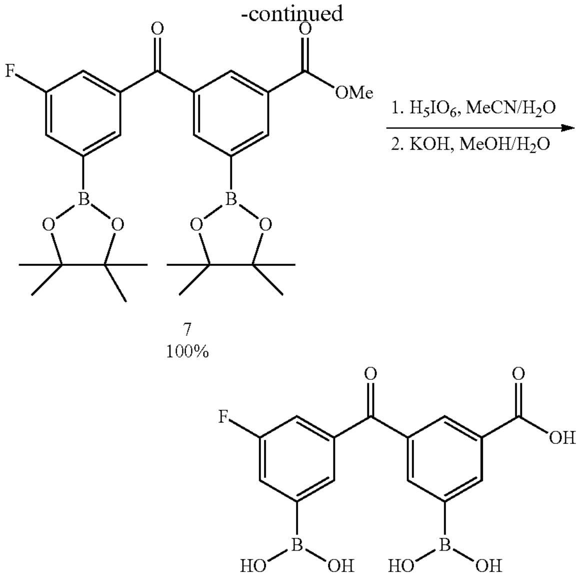

7
100%

8
83% from 6

3-Bromo-5-iodobenzoic acid (1, 6.52 g, 20.0 mmol) was suspended in methanol (40 mL) and methanesulfonic acid (0.4 mL) was added. The resulting mixture was stirred for 16 hours at 60° C. (oil bath). The resulting clear solution was cooled to −20° C. in the freezer for 16 hours and the resulting solid was collected by filtration, washed with chilled (−20° C.) methanol and dried in vacuo to give methyl 3-bromo-5-iodobenzoate (2) as an off-white solid.

Yield: 4.70 g (69%).

$^1$H NMR spectrum (300 MHz, $CDCl_3$, $\delta_H$): 8.30 (s, 1H); 8.14 (s, 1H); 8.04 (s, 1H); 3.93 (s, 1H).

1,3-Dibromo-5-fluorobenzene (3, 0.63 mL, 5.00 mmol) was dissolved in dry diethyl ether (15 mL) and cooled down to −78° C. 2.35 M n-Butyllithium in hexane (2.20 mL, 2.35 M in hexane, 5.25 mmol) was added drop-wise with stirring. After 15 minutes, dry N,N-dimethylformamide (0.77 mL, 10.0 mmol) was added and the resulting mixture was stirred at for 15 minutes and then allowed to warm to ambient temperature. After one hour, the reaction mixture was quenched with 1 M aqueous solution of hydrochloric acid (15 mL). Layers were separated and the organic layer was washed with brine (15 mL), dried over anhydrous magnesium sulfate and evaporated to give 3-bromo-5-fluorobenzaldehyde (4) as yellowish oil which solidified on storage in freezer.

Yield: 1.02 g (100%).

$^1$H NMR spectrum (300 MHz, $CDCl_3$, $\delta_H$): 9.92 (s, 1H); 7.80 (bs, 1H); 7.50 (bs, 2H).

Methyl 3-bromo-5-iodobenzoate (2, 341 mg, 1.00 mmol) was dissolved in dry tetrahydrofuran (4 mL) under nitrogen atmosphere and cooled down to −40° C. 1.3 M Isopropylmagnesium chloride-lithium chloride complex in tetrahydrofuran (0.80 mL, 1.05 mmol) was added slowly dropwise. After 30 minutes 3-bromo-5-fluorobenzaldehyde (4, 243 mg, 1.20 mmol) was added with the aid of dry tetrahydrofuran (0.5 mL). The resulting mixture was allowed to warm to room temperature overnight (16 hours). The reaction was quenched by addition of 0.5 M aqueous solution of hydrochloric acid (5 mL) and extracted with ethyl acetate (1×20 mL). Organic layer was washed with brine (15 mL) and dried over anhydrous sodium sulfate, filtered and evaporated. The residue was purified by flash column chromatography (Silicagel 60, 0.063-0.200 mm; eluent: cyclohexane/ethyl acetate 10:1 to 6:1) to give methyl 3-bromo-5-((3-bromo-5-fluorophenyl)(hydroxy)methyl)benzoate (5) as a colorless oil. It was dissolved in dry dichloromethane (5 mL) and pyridinium chlorochromate (PCC, 200 mg, 0.93 mmol) was added. The reaction mixture was then stirred overnight (16 hours) before it was quenched with 2-propanol (0.3 mL). After stirring for one hour at room temperature, the reaction mixture was filtered through a silica gel plug (5 g) topped with Celite S and washed with dichloromethane (2×10 mL). The solvent was removed in vacuo and the residue was purified by flash column chromatography (Silicagel 60, 0.063-0.200 mm; eluent: cyclohexane/dichloromethane 6:1 to 2:1) to give methyl 3-bromo-5-(3-bromo-5-fluorobenzoyl)benzoate (6) as colorless solid.

Yield: 208 mg (50%).

$^1$H NMR spectrum (300 MHz, $CDCl_3$, $\delta_H$): 8.43 (s, 1H); 8.30 (s, 1H); 8.11 (s, 1H); 7.71 (s, 1H); 7.53 (d, J=7.6 Hz, 1H); 7.41 (d, J=8.3 Hz, 1H); 3.97 (s, 3H).

LC-MS purity: 100% (ELSD).

LC-MS Rt (Kinetex C18, 4.6 mm×50 mm, acetonitrile/water 70:30 to 100:0+0.1% FA): 2.84 min.

LC-MS m/z: neither molecular oil nor fragments could be detected.

A 25 mL reaction vessel was charged with potassium acetate (188 mg, 1.92 mmol) and the salt was dried for 1 hour at 110° C. in vacuo. After cooling to room temperature, the reaction vessel was backfilled with nitrogen and charged with methyl 3-bromo-5-(3-bromo-5-fluorobenzoyl)benzoate (6, 200 mg, 0.48 mmol), palladium acetate (5.40 mg, 0.24 mmol), 2-dicyclohexylphosphino-2',4',6'-triisopropylbiphenyl (XPhos, 23.0 mg, 0.48 mmol) and bis(pinacolato)diboron (270 mg, 1.06 mmol). The reaction vessel was then evacuated and backfilled with nitrogen (this procedure was repeated twice), anhydrous tetrahydrofuran (3 mL) was added with syringe, the vessel was sealed with rubber septum and submerged in the heating bath preheated to 60° C. After stirring at 400 rpm for 16 hours (overnight) the reaction mixture was cooled to ambient temperature, diluted with cyclohexane (24 mL) and filtered through a short plug of silica (5 g) topped with Celite S with the aid of dichloromethane (3×10 mL). The filtrate was concentrated under reduced pressure to afford the methyl 3-(3-fluoro-5-(4,4,5,5-tetramethyl-1,3,2-dioxaborolan-2-yl)benzoyl)-5-(4,4,5,5-tetramethyl-1,3,2-dioxaborolan-2-yl)benzoate (7) as yellowish waxy solid.

Yield: 245 mg (100%).

$^1$H NMR spectrum (300 MHz, $CDCl_3$, $\delta_H$): 8.69 (s, 1H); 8.48 (s, 1H); 8.38 (s, 1H); 7.97 (s, 1H); 7.72 (d, J=8.5 Hz, 1H); 7.54 (d, J=9.0 Hz, 1H); 3.95 (s, 3H); 1.36 (s, 12H); 1.35 (s, 12H).

LC-MS purity: 100% (ELSD).

LC-MS Rt (Kinetex C18, 4.6 mm×50 mm, acetonitrile/water 70:30 to 100:0+0.1% FA): 3.79 min.

LC-MS m/z: 511.6 $(M+H)^+$.

Methyl 3-(3-fluoro-5-(4,4,5,5-tetramethyl-1,3,2-dioxaborolan-2-yl)benzoyl)-5-(4,4,5,5-tetramethyl-1,3,2-dioxaborolan-2-yl)benzoate (7, 245 mg, 0.48 mmol) was dissolved in acetonitrile (3 mL) and water (0.6 mL). Periodic acid (438 mg, 1.92 mmol) was added and the resulting mixture was vigorously stirred at ambient temperature for an hour. The reaction mixture was taken up in ethyl acetate (20 mL) and washed with water (20 mL) and brine (20 mL), dried over anhydrous sodium sulfate, filtered and evaporated. The residue was dissolved in methanol (3 mL) and water (0.3 mL) and potassium hydroxide (270 mg, 4.80 mmol) was added in one portion. The reaction mixture was stirred for 48 hours, diluted with 1 M aqueous solution of potassium hydroxide (5 mL) and water (10 mL) and washed with dichloromethane (2×7 mL).The aqueous phase was acidified by the addition of concentrated hydrochloric acid (3 mL) and extracted with ethyl acetate (15 mL). The organic layer was washed with brine (15 mL), dried over anhydrous sodium sulfate, filtered and evaporated. The crude product was dissolved in a minimum amount of wet (shaken thoroughly with water) 2-methyltetrahydrofuran and the solution added drop-wise to an ice-cold n-hexane (5 mL) with stirring, resulting in the precipitation of a product. The solid was collected by filtration and washed with cyclohexane (2×5 mL) to give the title 3-borono-5-(3-borono-5-fluorobenzoyl)benzoic acid (8) as off-white solid.

Yield: 133.0 mg (83%).

$^1H$ NMR spectrum (300 MHz, Acetone-$d_6$/$D_2O$; 10:1, $\delta_H$): 8.75 (s, 1H); 8.47-8.40 (m, 2H); 8.05 (s, 1H); 7.85-7.78 (m, 1H); 7.60-7.53 (m, 1H).

LC-MS purity: 100% (ELSD).

LC-MS Rt (Kinetex C18, 4.6 mm×50 mm, acetonitrile/water 20:80 to 100:0+0.1% FA): 2.52 min.

LC-MS m/z: 333.4 $(M+H)^+$.

Example 13

3-Borono-5-(5-borono-2,4-difluorobenzoyl)benzoic acid

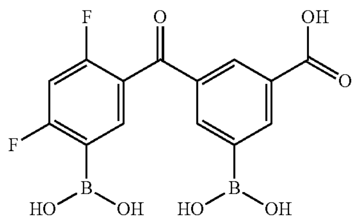 [SMILES: O=C(O)c1cc(B(O)O)cc(C(=O)c2cc(B(O)O)c(F)cc2F)c1]

3-Borono-5-(5-borono-2,4-difluorobenzoyl)benzoic acid was synthesized according to the reaction schemes shown in Chem. 14 and Chem. 15 and following the procedure described below.

Chem. 14

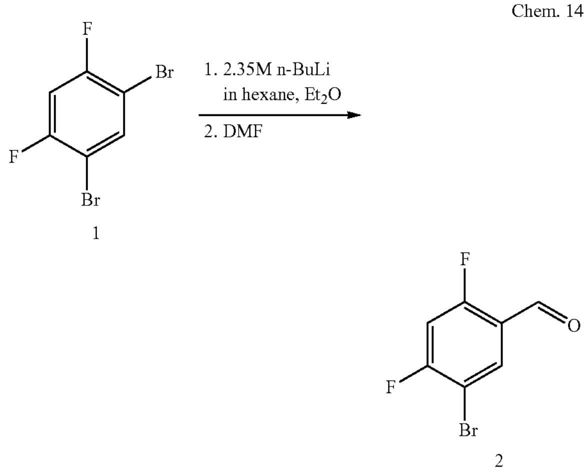

1

2
70%

-continued

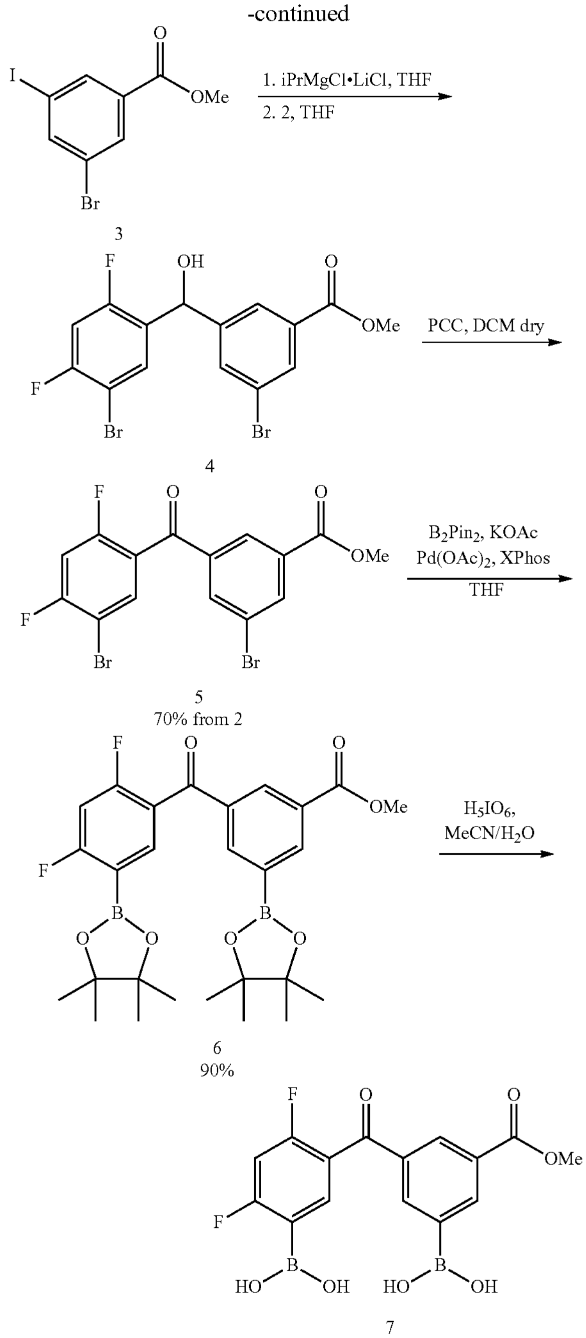

3

4

5
70% from 2

6
90%

7
90% from 5

1,5-Dibromo-2,4-difluorobenzene (1, 1.36 g, 5.00 mmol) was dissolved in dry diethyl ether (15 mL) and cooled down to −78° C. 2.35 M n-Butyllithium in hexane (2.20 mL, 5.25 mmol) was added drop-wise with stirring. After 15 minutes, dry N,N-dimethylformamide (0.77 mL, 10.0 mmol) was added and the resulting mixture was stirred at for 15 minutes and then allowed to warm to ambient temperature. After one hour, the reaction mixture was quenched with 1.0 M aqueous solution of hydrochloric acid (15 mL). Layers were separated and the organic layer was washed with brine (15 mL), dried over anhydrous magnesium sulfate and evaporated. The residue was purified by flash column chromatography (Silicagel 60, 0.063-0.200 mm; eluent: cyclohexane/ethyl acetate 20:1) 5-bromo-2,4-difluorobenzaldehyde (2) as colorless oil which solidified on storage in freezer.

Yield: 780 mg (70%).

$^1$H NMR spectrum (300 MHz, $CDCl_3$, $\delta_H$): 10.26 (s, 1H); 8.14 (dd, J=9.6 and 8.0 Hz, 1H); 7.05 (d, J=8.0 Hz, 1H).

Methyl 3-bromo-5-iodobenzoate (3, 681 mg, 2.00 mmol) was dissolved in dry tetrahydrofuran (4 mL) under nitrogen atmosphere and cooled down to −40° C. 1.3 M Isopropylmagnesium chloride-lithium chloride complex in tetrahydrofuran (1.7 mL, 2.20 mmol) was added slowly drop-wise. After 30 minutes 5-bromo-2,4-difluorobenzaldehyde (2, 530 mg, 2.40 mmol) was added with the aid of dry tetrahydrofuran (0.5 mL). The resulting mixture was allowed to warm to room temperature overnight (16 hours). The reaction was quenched by addition of 0.5 M aqueous solution of hydrochloric acid (15 mL) and extracted with ethyl acetate (1×30 mL). Organic layer was washed with brine (20 mL) and dried over anhydrous sodium sulfate, filtered and evaporated. The residue was purified by flash column chromatography (Silicagel 60, 0.063-0.200 mm; eluent: cyclohexane/ethyl acetate 8:1) to give methyl 3-bromo-5-((5-bromo-2,4-difluorophenyl) (hydroxy)methyl)benzoate (4) as a colorless oil. It was dissolved in dry dichloromethane (7 mL) and pyridinium chlorochromate (PCC, 491 mg, 2.28 mmol) was added. The reaction mixture was then stirred overnight (16 hours) before it was quenched with 2-propanol (0.6 mL). After stirring for one hour at room temperature, the reaction mixture was filtered through a silica gel plug (10 g) topped with Celite S and washed with dichloromethane (2×20 mL). The solvent was removed in vacuo and the residue was purified by flash column chromatography (Silicagel 60, 0.063-0.200 mm; eluent: cyclohexane/dichloromethane 6:1 to 2:1) to give methyl 3-bromo-5-(5-bromo-2,4-difluorobenzoyl)benzoate (5) as colorless solid.

Yield: 606 mg (70%).

$^1$H NMR spectrum (300 MHz, $CDCl_3$, $\delta_H$): 8.41 (s, 1H); 8.29 (d, J=1.6 Hz, 1H); 8.12 (d, J=1.2 Hz, 1H); 7.87 (t, J=7.3 Hz, 1H); 7.04 (dd, J=9.3 and 8.1 Hz, 1H); 3.96 (s, 3H).

LC-MS purity: 100% (ELSD).

LC-MS Rt (Kinetex C18, 4.6 mm×50 mm, acetonitrile/water 70:30 to 100:0+0.1% FA): 2.76 min.

LC-MS m/z: 435.3 $(M+H)^+$

A 25 mL reaction vessel was charged with potassium acetate (524 mg, 5.35 mmol) and the salt was dried for 1 hour at 110° C. in vacuo. After cooling to room temperature, the reaction vessel was backfilled with nitrogen and charged with methyl methyl 3-bromo-5-(5-bromo-2,4-difluorobenzoyl)benzoate (5, 581 mg, 1.34 mmol), palladium acetate (9.00 mg, 0.04 mmol), 2-dicyclohexylphosphino-2',4',6'-triisopropylbiphenyl (XPhos, 38.0 mg, 0.08 mmol) and bis(pinacolato)diboron (748 mg, 2.94 mmol). The reaction vessel was then evacuated and backfilled with nitrogen (this procedure was repeated twice), anhydrous tetrahydrofuran (6 mL) was added with syringe, the vessel was sealed with rubber septum and submerged in the heating bath preheated to 60° C. After stirring at 400 rpm for 16 hours (overnight) the reaction mixture was cooled to ambient temperature, diluted with cyclohexane (18 mL) and filtered through a short plug of silica (5.0 g) topped with Celite S with the aid of dichloromethane (3×10 mL). The filtrate was concentrated under reduced pressure to afford the methyl 3-(2,4-difluoro-5-(4,4,5,5-tetramethyl-1,3,2-dioxaborolan-2-yl) benzoyl)-5-(4,4,5,5-tetramethyl-1,3,2-dioxaborolan-2-yl) benzoate (6) as yellowish waxy solid. It was dissolved in acetonitrile (8 mL) and water (2 mL). Periodic acid (1.22 g, 5.35 mmol) was added and the resulting mixture was vigorously stirred at ambient temperature for two hours. The reaction mixture was taken up in ethyl acetate (30 mL) and washed with water (20 mL) and brine (20 mL), dried over anhydrous sodium sulfate, filtered and evaporated. The crude product was dissolved in the minimum amount of wet ethyl acetate (shaken thoroughly with water) and the solution added drop-wise to an ice-cold n-hexane (5 mL) with stirring, resulting in the precipitation of a product. The solid was collected by filtration and washed with cold n-hexane (2×5 mL) to give the title (5-(3-borono-5-(methoxycarbonyl)benzoyl)-2,4-difluorophenyl)boronic acid (7) as off-white solid.

Yield: 443.0 mg (90%).

$^1$H NMR spectrum (300 MHz, Acetone-$d_6$/$D_2O$ 10:1, $\delta_H$): 8.82-8.68 (m, 1H); 8.46 (dd, J=16.8 and 1.4 Hz, 2H); 8.01 (dd, J=8.7 and 7.0 Hz, 1H); 7.12 (dd, J=10.4 and 9.5 Hz, 1H); 3.91 (s, 3H).

LC-MS purity: 100% (ELSD).

LC-MS Rt (Kinetex C18, 4.6 mm×50 mm, acetonitrile/water 20:80 to 100:0+0.1% FA): 3.99 min.

LC-MS m/z: 365.3 $(M+H)^+$.

Chem. 15

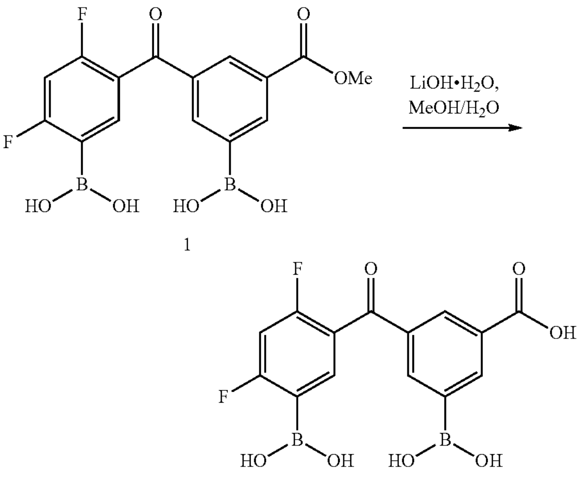

1

2
73%

(5-(3-Borono-5-(methoxycarbonyl)benzoyl)-2,4-difluorophenyl)boronic acid (1, 200 mg, 548 μmol) was dissolved in methanol (2 mL) and water (0.7 mL). Lithium hydroxide monohydrate (116 mg, 2.76 mmol) was added and the resulting mixture was vigorously stirred at ambient temperature for six hours. The reaction mixture was taken up in ethyl acetate (15 mL) and washed with 1 M aqueous solution of hydrochloric acid (15 mL) and brine (15 mL), dried over anhydrous sodium sulfate, filtered and evaporated. The crude product was dissolved in the minimum amount of wet ethyl acetate (shaken thoroughly with water) and the solution added drop-wise to an ice-cold n-hexane (5 mL) with stirring, resulting in the precipitation of a product. The solid was collected by filtration and washed with cold n-hexane (2×5 mL) to give the title 3-borono-5-(5-borono-2,4-difluorobenzoyl)benzoic acid (2) as colorless solid.

Yield: 140 mg (73%).

$^1$H NMR spectrum (300 MHz, Acetone-$d_6$/$D_2O$ 10:1, $\delta_H$): 8.77 (s, 1H); 8.46 (dd, J=10.7 and 1.1 Hz, 2H); 8.00 (dd, J=8.7 and 7.0 Hz, 1H); 7.11 (dd, J=10.4 and 9.5 Hz, 1H).

LC-MS purity: 100% (ELSD).

LC-MS Rt (Kinetex C18, 4.6 mm×50 mm, acetonitrile/water 5:95 to 100:0+0.1% FA): 3.13 min.

LC-MS m/z: 351.3 $(M+H)^+$.

Example 14

N$^6$-(4-Borono-2-fluorobenzoyl)-N$^2$-(6-fluoro-1-hydroxy-1,3-dihydrobenzo[c][1,2] oxaborole-5-carbonyl)-L-lysine

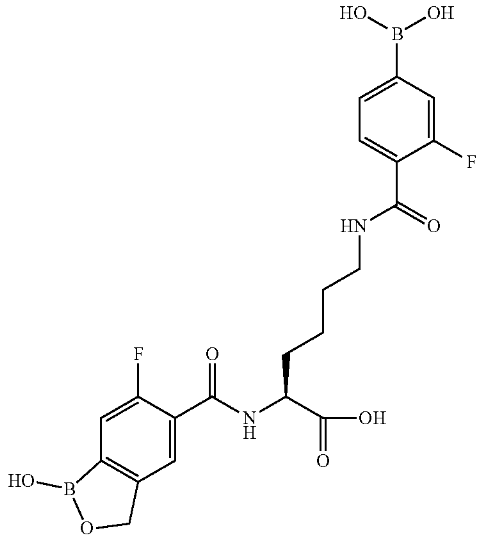 [SMILES: O=C(NCCCC[C@H](NC(=O)c1cc2c(cc1F)B(O)OC2)C(=O)O)c1ccc(B(O)O)cc1F]

N$^6$-(4-Borono-2-fluorobenzoyl)-N$^2$-(6-fluoro-1-hydroxy-1,3-dihydrobenzo[c][1,2] oxaborole-5-carbonyl)-L-lysine was synthesized according to the reaction scheme shown in Chem. 16 and following the procedure described below.

Chem. 16

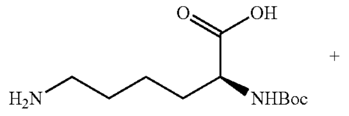

1

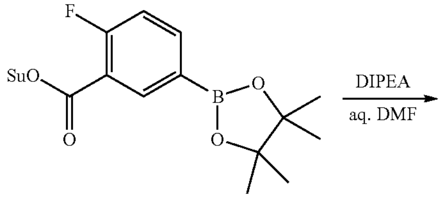

2

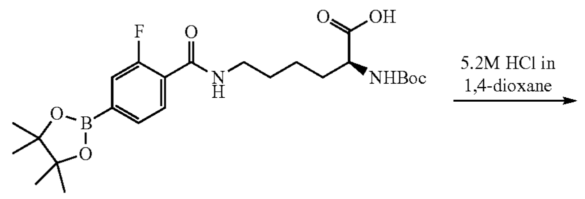

3 quant.

-continued

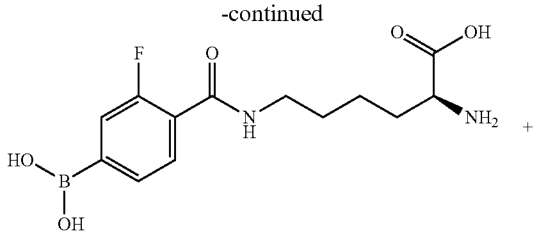

4 quant.

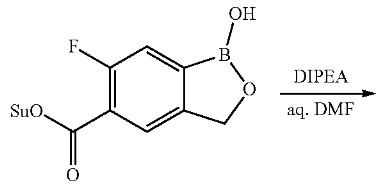

5

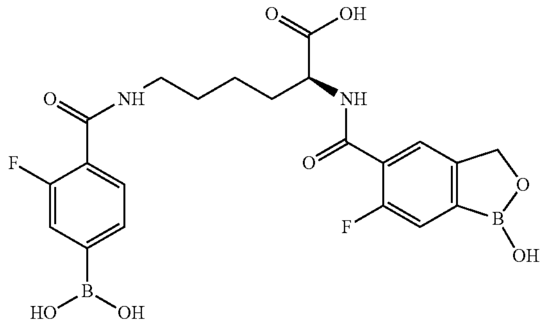

6 62%

N$_\alpha$-(tert-Butoxycarbonyl)-L-lysine (1, 75.0 mg, 0.31 mmol) was dissolved in N,N-dimethylformamide (3 mL) and water (1 mL). N,N-Diisopropylethylamine (0.27 mL, 1.53 mmol) and 2,5-dioxopyrrolidin-1-yl 2-fluoro-4-(4,4,5,5-tetramethyl-1,3,2-dioxaborolan-2-yl)benzoate (2, 0.20 g, 0.71 mmol) were added at room temperature. After stirring for 3 hours, volatiles were evaporated under reduced pressure. The compound 3 was dissolved in anhydrous 1,4-dioxane (2 mL) and 5.2 M solution of hydrogen chloride in 1,4-dioxane was added (5 mL), then the reaction mixture was stirred at room temperature. After stirring for 1 hour, volatiles were evaporated under reduced pressure to give compound 4, which was re-dissolved in N,N-dimethyl formamide (3 mL) and water (1 mL). N,N-Diisopropylethylamine (0.32 mL, 1.80 mmol) and 2,5-dioxopyrrolidin-1-yl 6-fluoro-1-hydroxy-1,3-dihydrobenzo[c][1,2]oxaborole-5-carboxylate (5, 89.0 mg, 0.31 mmol) were added at room temperature. After stirring for 2 hours, volatiles were evaporated under reduced pressure and the residue was purified by preparative HPLC (SunFire Prep C18, 5 μm, 19×100 mm, acetonitrile/water 5:95 to 100:0+0.1% FA) and freeze-dried to afford N$^6$-(4-borono-2-fluorobenzoyl)-N$^2$-(6-fluoro-1-hydroxy-1,3-dihydrobenzo[c][1,2]oxaborole-5-carbonyl)-L-lysine (6) as a white solid.

Yield: 88.0 mg (62%).

$^1$H NMR spectrum (300 MHz, DMSO-d$_6$, $\delta_H$): 9.43 (bs, 1H); 8.70 (bs, 1H); 8.47 (d, J=6.4 Hz, 1H); 8.35-8.21 (m, 1H); 7.68-7.42 (m, 5H); 4.99 (s, 2H); 4.39-4.24 (m, 1H); 3.28-3.18 (m, 2H); 1.93-1.66 (m, 2H); 1.62-1.33 (m, 4H).

LC-MS purity: 100% (ELSD).

LC-MS Rt (Kinetex C18, 4.6 mm×50 mm, acetonitrile/water 5:95 to 100:0+0.1% FA): 3.48 min.

LC-MS m/z: 491.5 (M+H)$^+$.

Example 15

(S)-2,3-Bis(7-fluoro-1-hydroxy-1,3-dihydrobenzo[c][1,2]oxaborole-6-carboxamido)propanoic acid

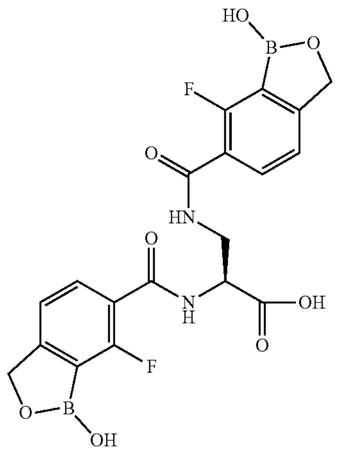 [SMILES: O=C(NC[C@H](NC(=O)c1ccc2c(c1F)B(O)OC2)C(=O)O)c1ccc2c(c1F)B(O)OC2]

(S)-2,3-Bis(7-fluoro-1-hydroxy-1,3-dihydrobenzo[c][1,2]oxaborole-6-carboxamido)propanoic acid was synthesized according to the reaction scheme shown in Chem. 17 and following the procedure described below.

Chem. 17

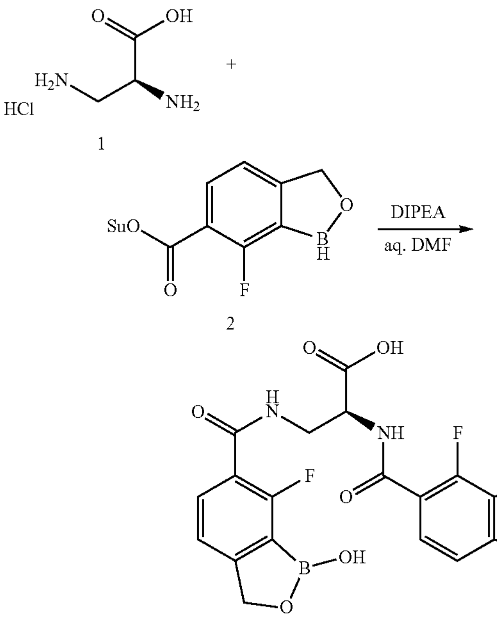

1
2
3 34%

(S)-2,3-Diaminopropanoic acid hydrochloride (1, 50.0 mg, 0.36 mmol) was dissolved in N,N-dimethylformamide (2 mL) and water (1 mL). N,N-Diisopropylethylamine (0.37 mL, 2.13 mmol) and 2,5-dioxopyrrolidin-1-yl 7-fluoro-1-hydroxy-1,3-dihydrobenzo[c][1,2]oxaborole-6-carboxylate (2, 0.20 g, 0.71 mmol) were added at room temperature. After stirring for 2 hours, volatiles were evaporated under reduced pressure and the residue was washed with 1 M aqueous hydrochloric acid (3 mL). Precipitate was collected and purified by preparative HPLC (SunFire Prep C18, 5 μm, 19×100 mm, acetonitrile/water 5:95 to 100:0+0.1% FA) and freeze-dried to afford (S)-2,3-bis(7-fluoro-1-hydroxy-1,3-dihydrobenzo[c][1,2]oxaborole-6-carboxamido)propanoic acid (3) as a white solid.

Yield: 55.0 mg (34%).

$^1$H NMR spectrum (300 MHz, DMSO-$d_6$, $\delta_H$): 12.90 (bs, 1H); 9.38 (d, J=8.8 Hz, 2H); 8.57-8.38 (m, 2H); 7.88-7.69 (m, 2H); 7.31 (t, J=7.4 Hz, 2H); 5.03 (d, J=4.2 Hz, 4H); 4.72-4.59 (m, 1H); 3.82-3.65 (m, 2H).

LC-MS purity: 100% (ELSD).

LC-MS Rt (Kinetex C18, 4.6 mm×50 mm, acetonitrile/water 5:95 to 100:0+0.1% FA): 4.22 min.

LC-MS m/z: 461.5 $(M+H)^+$.

Example 16

(S)-2,3-Bis(5-fluoro-1-hydroxy-1,3-dihydrobenzo[c][1,2]oxaborole-6-carboxamido)propanoic acid

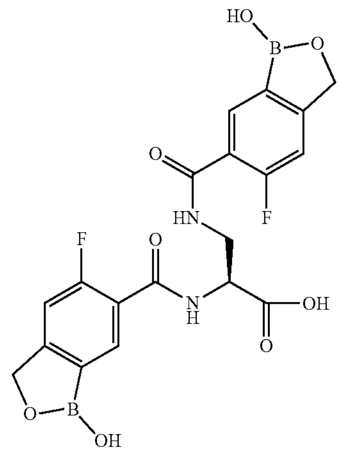 [SMILES: O=C(NC[C@H](NC(=O)c1cc2c(cc1F)COB2O)C(=O)O)c1cc2c(cc1F)COB2O]

(S)-2,3-Bis(5-fluoro-1-hydroxy-1,3-dihydrobenzo[c][1,2]oxaborole-6-carboxamido)propanoic acid was synthesized according to the reaction schemes shown in Chem. 18 and Chem. 19 and following the procedure described below.

Chem. 18

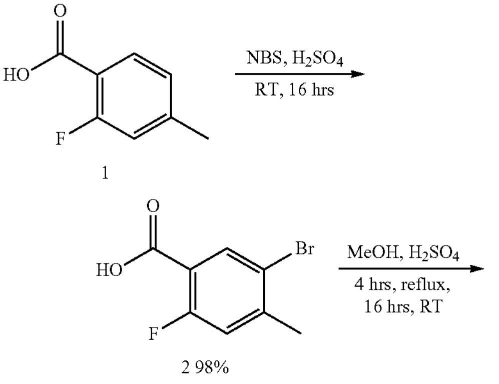

1
2 98%

-continued

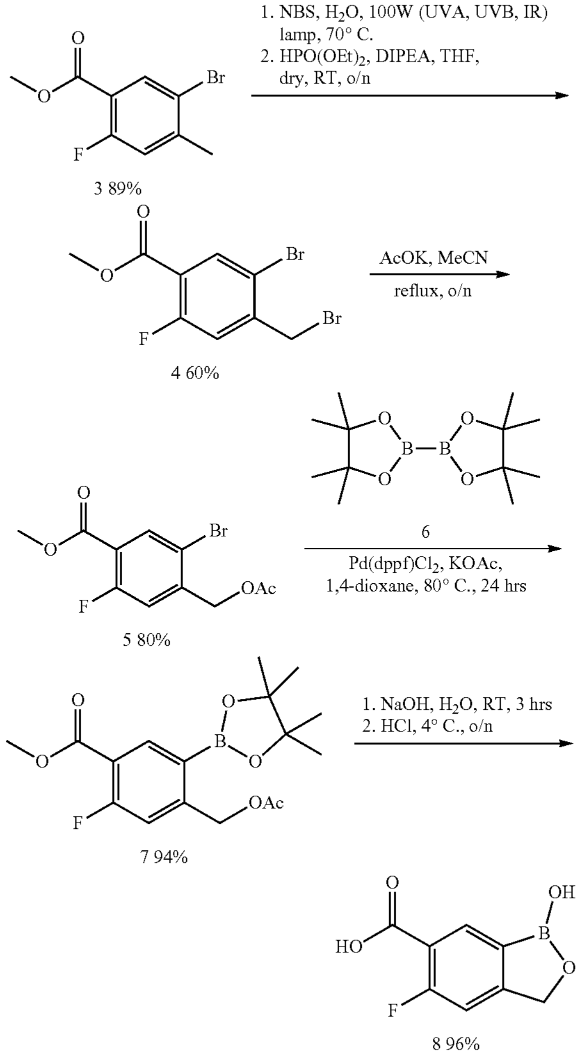

1-Bromopyrrolidine-2,5-dione (NBS, 105 g, 584 mmol) was added to a solution of 2-fluoro-4-methylbenzoic acid (1, 90.0 g, 584 mol) in concentrated sulfuric acid (1.1 L) and the reaction mixture was allowed to stir at ambient temperature for 16 hours. The reaction mixture was then poured into ice-water (5 L). Resulting precipitate was filtered off, washed with water (1.5 L) and dissolved in ethyl acetate (1.2 L); dried over anhydrous sodium sulfate, filtered and evaporated to provide 5-bromo-2-fluoro-4-methylbenzoic acid (2) as white solid.

Yield: 133.5 g (98%).

$^1H$ NMR spectrum (300 MHz, $CDCl_3$, $\delta_H$): 8.20 (d, J=6.9 Hz, 1H); 7.11 (d, J=11.4 Hz, 1H); 2.47 (s, 3H).

Concentrated sulfuric acid (10 mL) was added to a solution of 5-bromo-2-fluoro-4-methylbenzoic acid (2, 133 g, 570 mmol) in methanol (1 L) and the reaction mixture was allowed to stir under reflux for 4 hours and at ambient temperature for 16 hours. The reaction mixture was then evaporated under reduced pressure, dissolved in diethyl ether (800 mL), extracted with water (2×600 mL) and mixture of saturated solution of potassium carbonate (300 mL) and brine (300 mL). Organic layer was separated, dried over anhydrous sodium sulfate, filtered and evaporated to provide methyl 5-bromo-2-fluoro-4-methylbenzoate (3) as white solid.

Yield: 125 g (89%).

$^1H$ NMR spectrum (300 MHz, $CDCl_3$, $\delta_H$): 8.10 (d, J=6.6 Hz, 1H); 7.06 (d, J=11.1 Hz, 1H); 3.92 (s, 3H); 2.43 (s, 3H).

The suspension of 1-bromopyrrolidine-2,5-dione (NBS, 131 g, 735 mmol) and 5-bromo-2-fluoro-4-methylbenzoate (3, 120 g, 490 mmol) in water (1 L) was stirred for two days under 100 W light bulb at 70° C. If the reaction rate is slow, an extra 0.5 equivalent of NBS is added. The solution at 70° C. should stay clear to prevent the absorption of the radiation. Reaction mixture was extracted with diethyl ether (2×1 L). Organic layers were washed with brine (1 L). To reduce bromine sodium metabisulfite pentahydrate was added to separatory funnel until the solution discoloured. Organic layer was separated, dried over anhydrous sodium sulfate, filtered and evaporated. The crude product was purified by flash chromatography (Silicagel, 0.063-0.200 mm; eluent: cyclohexane/ethyl acetate 15:1 to 9:1) to provide a mixture of methyl 5-bromo-2-fluoro-4-(bromomethyl)benzoate (4) and a product of radical dibromination. The mixture was diluted in dry tetrahydrofuran (600 mL), N,N-diisopropylethylamine (26.0 ml, 200 mmol) and diethylphosphite (35.0 mL, 200 mmol) were added to the solution at 0° C. The reaction mixture was then allowed to stir at ambient temperature for 18 hours. The solvent was evaporated and the crude product was dissolved in ethyl acetate and washed with water (1 L) and 1 M hydrochloric acid (300 mL), brine (500 mL), 1 M aqueous solution of potassium hydrogen carbonate (500 mL). Organic layer was separated, dried over anhydrous sodium sulfate, filtered and evaporated. The crude product was purified by column chromatography (Silicagel, 0.063-0.200 mm; eluent: cyclohexane/ethyl acetate 9:1) to give methyl 5-bromo-2-fluoro-4-(bromomethyl) benzoate (4).

Yield: 96 g (60%).

$R_F$ ($SiO_2$, cyclohexane/ethyl acetate 9:1): 0.50.

$^1H$ NMR spectrum (300 MHz, $CDCl_3$, $\delta_H$): 8.16 (d, J=6.6 Hz, 1H); 7.31 (d, J=10.2 Hz, 1H); 4.54 (s, 2H); 3.95 (s, 3H).

Solution of methyl 5-bromo-2-fluoro-4-(bromomethyl) benzoate (4, 96.0 g, 290 mmol) and potassium acetate (59.0 g, 601 mmol) in acetonitrile (1 L) was stirred at 75° C. overnight. The suspension was filtered through cotton-wool and evaporated. The crude product was dissolved in dichloromethane and filtered again. Purification by column chromatography (Silicagel, 0.063-0.200 mm; eluent: cyclohexane/ethyl acetate 9:1 to 1:1) provided methyl 5-bromo-2-fluoro-4-(acetylmethyl)benzoate (5).

Yield: 70 g (80%).

$R_F$ ($SiO_2$, cyclohexane/ethyl acetate 9:1): 0.30.

$^1H$ NMR spectrum (300 MHz, $CDCl_3$, $\delta_H$): 8.15 (d, J=6.3 Hz, 1H); 7.24 (d, J=11.1 Hz, 1H); 5.18 (s, 2H); 3.95 (s, 3H); 2.21 (s, 3H).

Solution of methyl 5-bromo-2-fluoro-4-(acetylmethyl) benzoate (5, 70.0 g, 230 mmol), bis(pinacolato)diboron (6, 64.3 g, 253 mmol), potassium acetate (67.6 g, 690 mmol) and [1,1'-bis(diphenylphosphino)ferrocene]dichloropalladium(II) (3.00 g, 4.00 mmol) in dry 1,4-dioxane (600 mL) was allowed to stir at 80° C. under argon atmosphere for 24 hours. Then the reaction mixture was cooled to ambient temperature, filtered and evaporated. The crude product was filtered through silica gel (Silicagel, 0.063-0.200 mm; eluent: cyclohexane/ethyl acetate 9:1 to 4:1) to provide methyl 2-fluoro-4-(acetylmethyl)-5-(4,4,5,5-tetramethyl-1,3,2-dioxaborolan-2-yl)benzoate (7).

Yield: 76.2 g (94%).

$R_F$ ($SiO_2$, cyclohexane/ethyl acetate 9:1): 0.30.

$^1H$ NMR spectrum (300 MHz, $CDCl_3$, $\delta_H$): 8.42 (d, J=8.4 Hz, 1H); 7.19 (d, J=12 Hz, 1H); 5.42 (s, 2H); 3.94 (s, 3H); 2.16 (s, 3H); 1.35 (s, 12H).

Solution of methyl 2-fluoro-4-(acetylmethyl)-5-(4,4,5,5-tetramethyl-1,3,2-dioxaborolan-2-yl)benzoate (7, 76.2 g, 216 mmol) and sodium hydroxide (43.0 g, 1.08 mol) in water (700 mL) was stirred at ambient temperature for 3 hours. Then solution of hydrochloric acid (35%, 120 mL) in water (200 mL) was added to lower the pH to 1. The reaction mixture was put into the fridge for 16 hours. Precipitate was filtered and freeze dried to provide 5-fluoro-1-hydroxy-1,3-dihydrobenzo[c][1,2]oxaborole-6-carboxylic acid (8) as white solid.

Yield: 40.7 g (96%).

$^1$H NMR spectrum (300 MHz, DMSO-$d_6$, $\delta_H$): 13.17 (bs, 1H); 9.38 (bs, 1H); 8.29 (d, J=7.7 Hz, 1H); 7.36 (d, J=11.2 Hz, 1H); 5.02 (s, 2H).

LC-MS purity: 98% (ELSD).

LC-MS Rt (Kinetex C18, 4.6 mm×50 mm, acetonitrile/water 5:95 to 100:0+0.1% FA): 4.18 min.

LC-MS m/z: 197.3 (M+H)$^+$.

Chem. 19

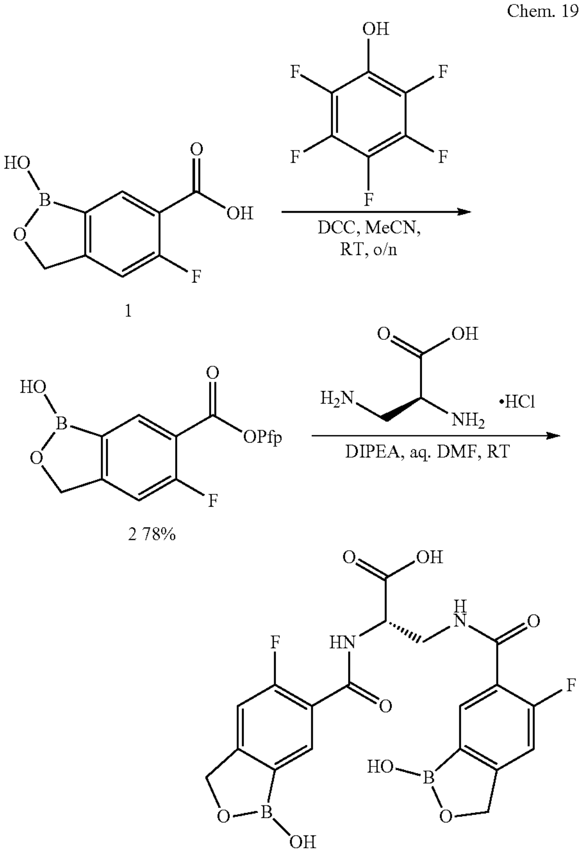

1
2 78%
3 14%

Solution of 2,3,4,5,6-pentafluorophenol (939 mg, 5.10 mmol), 5-fluoro-1-hydroxy-1,3-dihydrobenzo[c][1,2]oxaborole-6-carboxylic acid (1, 1.00 g, 5.10 mmol) and N,N'-dicyclohexylcarbodiimide (DCC, 1.05 g, 5.10 mmol) in acetonitrile (30 mL) was stirred at ambient temperature overnight. The reaction mixture was filtered, washed with acetonitrile and evaporated. Crude product 2 (618 mg, 1.71 mmol) reacted with 2,3-diaminopropionic acid hydrochloride (120 mg, 854 μmol) in N,N-dimethylformamide (12 mL) and water (6 mL) at ambient temperature overnight. Crude product 3 was purified by preparative HPLC (SunFire Prep C18, 5 μm, 19×100 mm, acetonitrile/water 20:80 to 100:0+0.1% FA) and freeze-dried to afford (S)-2,3-bis(5-fluoro-1-hydroxy-1,3-dihydrobenzo[c][1,2]oxaborole-6-carboxamido)propanoic acid (3) as a white solid.

Yield: 54.0 mg (14%).

$^1$H NMR spectrum (300 MHz, DMSO-$d_6$, $\delta_H$): 12.88 (bs, 1H); 9.37 (d, J=5.9 Hz, 2H); 8.55 (dd, J=7.3 and 3.4 Hz, 1H); 8.50-8.38 (m, 1H); 8.09 (d, J=7.5 Hz, 1H); 8.02 (d, J=7.5 Hz, 1H); 7.36 (dd, J=10.8 Hz and 8.3 Hz, 2H); 5.01 (d, J=4.2 Hz, 4H); 4.70-4.59 (m, 1H); 3.84-3.65 (m, 2H).

LC-MS purity: 100% (ELSD).

LC-MS Rt (Kinetex C18, 4.6 mm×50 mm, acetonitrile/water 20:80 to 100:0+0.1% FA): 4.43 min.

LC-MS m/z: 461.4 (M+H)$^+$.

Example 17

(S)-2,3-Bis(4-fluoro-1-hydroxy-1,3-dihydrobenzo[c][1,2]oxaborole-6-carboxamido) propanoic acid

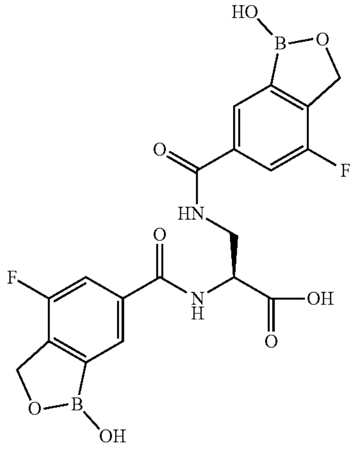 [SMILES: O=C(NC[C@H](NC(=O)c1cc(F)c2c(c1)B(O)OC2)C(=O)O)c1cc(F)c2c(c1)B(O)OC2]

(S)-2,3-Bis(4-fluoro-1-hydroxy-1,3-dihydrobenzo[c][1,2]oxaborole-6-carboxamido) propanoic acid was synthesized according to the reaction scheme shown in Chem. 20 and following the procedure described below.

Chem. 20

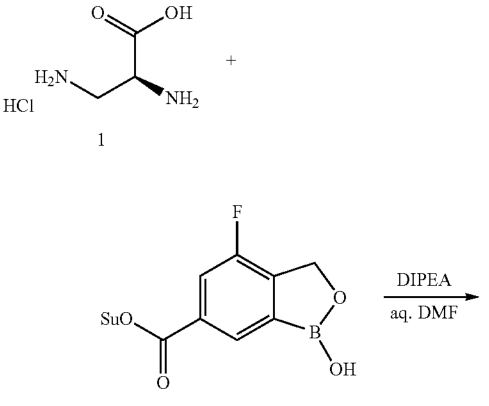

1
2

-continued

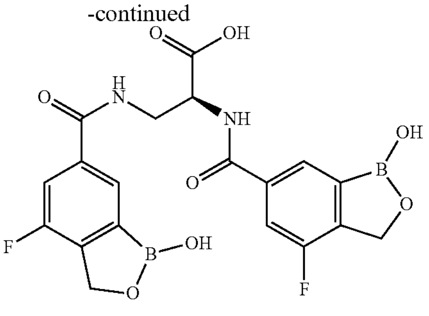

3 40%

(S)-2,3-Diaminopropanoic acid hydrochloride (1, 72.0 mg, 0.36 mmol) was dissolved in N,N-dimethylformamide (6 mL) and water (2 mL). N,N-Diisopropylethylamine (0.54 mL, 3.07 mmol) and 2,5-dioxopyrrolidin-1-yl 4-fluoro-1-hydroxy-1,3-dihydrobenzo[c][1,2]oxaborole-6-carboxylate (2, 0.30 g, 1.02 mmol) were added at room temperature. After stirring for 2 hours, volatiles were evaporated under reduced pressure and the residue was purified by preparative HPLC (SunFire Prep C18, 5 μm, 19×100 mm, acetonitrile/water 5:95 to 100:0+0.1% FA) and freeze-dried to afford (S)-2,3-bis(4-fluoro-1-hydroxy-1,3-dihydrobenzo[c][1,2]oxaborole-6-carboxamido)propanoic acid (3) as a white solid.

Yield: 95.0 mg (40%).

$^1$H NMR spectrum (300 MHz, DMSO-$d_6$, $\delta_H$): 9.55 (d, J=6.2 Hz, 2H); 8.85 (d, J=7.5 Hz, 1H); 8.78 (t, J=5.5 Hz, 1H); 8.07 (d, J=16.7 Hz, 2H); 7.79-7.62 (m, 2H); 5.13 (d, J=6.1 Hz, 4H); 4.75-4.60 (m, 1H); 3.90-3.64 (m, 2H).

LC-MS purity: 97% (ELSD).

LC-MS Rt (Kinetex C18, 4.6 mm×50 mm, acetonitrile/water 5:95 to 100:0+0.1% FA): 3.30 min.

LC-MS m/z: 461.4 $(M+H)^+$.

Example 18

(3-Borono-5-((3-borono-5-(trifluoromethyl)phenyl)difluoromethyl)benzoyl)glycine

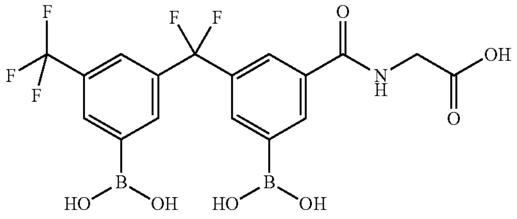 [SMILES: O=C(O)CNC(=O)c1cc(B(O)O)cc(C(F)(F)c2cc(B(O)O)cc(C(F)(F)F)c2)c1]

(3-Borono-5-((3-borono-5-(trifluoromethyl)phenyl)difluoromethyl)benzoyl)glycine was synthesized according to the reaction schemes shown in Chem. 21 and Chem. 22 and following the procedure described below.

Chem. 21

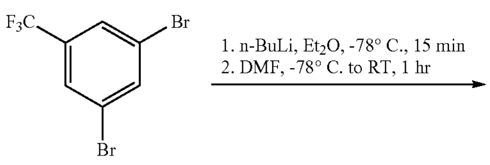

1

-continued

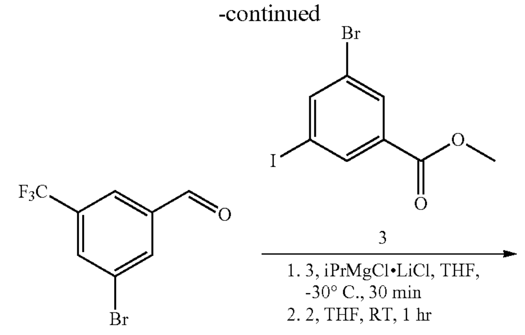

2 54%

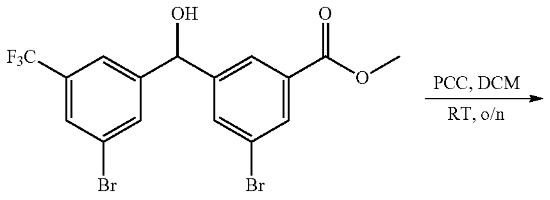

4

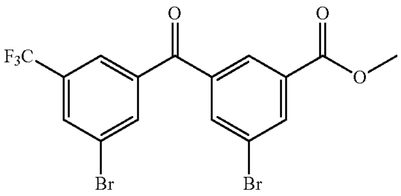

5 87% (from 3)

1,3-dibromo-5-(trifluoromethyl)benzene (1, 3.03 g, 10.00 mmol) was dissolved in dry diethyl ether (25 mL) and cooled to −78° C. n-Butyllithium (4.24 mL, 2.35 M in hexanes, 10.0 mmol) was added drop-wise with stirring. After 15 minutes, dry N,N-dimethylformamide (1.44 mL, 20.0 mmol) was added in one portion and the resulting mixture was allowed to warm to ambient temperature over an hour. 1 M aqueous solution of hydrochloric acid (30 mL) was then added to quench the reaction and the reaction mixture was taken up in diethyl ether (30 mL) and washed with water (20 mL) and brine (20 mL), dried over anhydrous sodium sulfate, filtered and evaporated. The crude product was purified by flash column chromatography (Silicagel 60, 0.040-0.063 mm; eluent: cyclohexane/ethyl acetate 20:1) to give 3-bromo-5-(trifluoromethyl) benzaldehyde (2) as colorless oil.

Yield: 1366 mg (54%).

$^1$H NMR spectrum (300 MHz, $CDCl_3$, $\delta_H$): 10.02 (s, 1H); 8.20 (bs, 1H); 8.07 (bs, 1H); 8.02 (bs, 1H).

Methyl 3-bromo-5-iodobenzoate (3, 1.36 g, 4.00 mmol) was dissolved in dry tetrahydrofuran (12 mL) and cooled to −30° C. Isopropylmagnesium chloride-lithium chloride complex (3.11 mL, 1.3 M solution in tetrahydrofuran, 4.20 mmol) was added drop-wise with stirring. After 30 minutes, 3-bromo-5-(trifluoromethyl)benzaldehyde (2, 1.21 g, 4.80 mmol) was added with aid of 3 mL of tetrahydrofuran. The resulting mixture was allowed to warm to ambient temperature and quenched after one hour by the addition of 1 M aqueous solution of hydrochloric acid (15 mL). The reaction mixture was taken up in diethyl ether (50 mL), washed with water (30 mL) and brine (30 mL), dried over anhydrous sodium sulfate, filtered and evaporated. The crude product (4) was dissolved in dry dichloromethane (20 mL) and pyridinium chlorochromate (1.29 g, 6.00 mmol) was added with stirring. After stirring for 17 hours, the reaction mixture was filtered through a plug of silica (15 g) topped with Celite and the bed was washed with dichloromethane (3×20 mL). The yellowish solution was concentrated in vacuo and the residue was purified by flash column chromatography (Silicagel 60, 0.040-0.063 mm; eluent: cyclohexane/dichloromethane 6:1 to 1:1) to give methyl 3-bromo-5-(3-bromo-5-(trifluoromethyl)benzoyl)benzoate (5) as colorless solid.

Yield: 1620 mg (87%).

$^1$H NMR spectrum (300 MHz, $CDCl_3$, $\delta_H$): 8.45 (t, J=1.4 Hz, 1H); 8.29 (m, 1H); 8.12 (t, J=1.6 Hz, 1H); 8.08 (bs, 1H); 8.04 (bs, 1H); 7.95 (bs, 1H); 3.97 (s, 3H).

Chem. 22

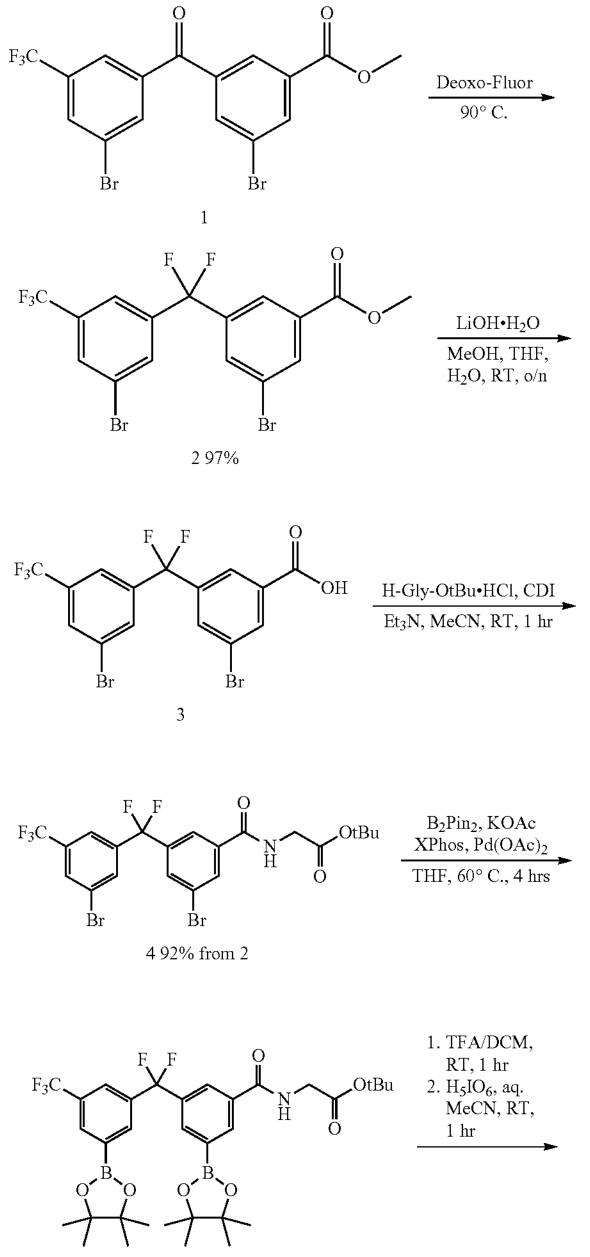

-continued

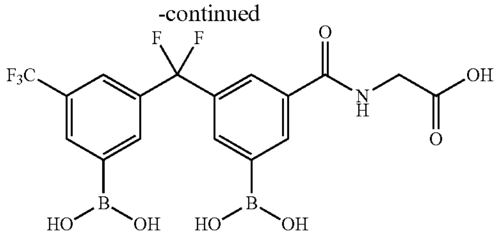

6 81% (from 5)

Methyl 3-bromo-5-(3-bromo-5-(trifluoromethyl)benzoyl) benzoate (1, 1071 mg, 2.30 mmol) and Deoxo-Fluor (3.00 mL) were charged to a 25 mL reaction vessel. The vessel was sealed, purged with nitrogen and heated to 90° C. (oil bath) for 16 hours. The reaction mixture was cooled to ambient temperature and diluted with dichloromethane (50 mL). The resulting solution was added slowly to a saturated aqueous potassium hydrogencarbonate solution (100 mL) and the biphasic mixture was stirred for an hour to decompose the excess of fluorinating reagent. The layers were separated and the organic layer was dried over anhydrous sodium sulfate, filtered and evaporated. The crude product was purified by flash column chromatography (Silicagel 60, 0.040-0.063 mm; eluent: cyclohexane/ethyl acetate 30:1 to 15:1) to give methyl 3-bromo-5-((3-bromo5-(trifluoromethyl)phenyl)difluoromethyl) benzoate (2) as yellowish oil.

Yield: 1096 mg (97%)

$^1$H NMR spectrum (300 MHz, $CDCl_3$, $\delta_H$): 8.30 (s, 1H); 8.08 (s, 1H); 7.88 (s, 1H); 7.83 (s, 1H); 7.81 (s, 1H); 7.71 (s, 1H); 3.96 (s, 3H).

$^{19}$F NMR spectrum (282 MHz, $CDCl_3$, $\delta_F$): −62.87 (s, 3H); −90.00 (s, 2H).

3-Bromo-5-((3-bromo-5-(trifluoromethyl)phenyl)difluoromethyl) benzoate (2, 1096 mg, 2.25 mmol) dissolved in tetrahydrofuran (8 mL), methanol (4 mL) and water (2 mL). Lithium hydroxide monohydrate (377 mg, 9.00 mmol) was added and the resulting mixture was stirred for 16 hours; and then it was taken up in ethyl acetate (40 mL) and washed with 1 M aqueous solution of hydrochloric acid (30 mL) and brine (30 mL); dried over anhydrous sodium sulfate; filtered and evaporated to give the crude 3-bromo-5-((3-bromo-5-(trifluoromethyl)phenyl)difluoromethyl)benzoic acid (3) as a white solid. It was dissolved in anhydrous acetonitrile (10 mL) and carbonyldiimidazole (CDI, 437 mg, 2.69 mmol) was added. After 30 minutes, glycine tert-butyl ester hydrochloride (564 mg, 3.37 mmol) was added and the resulting mixture was stirred for an hour at ambient temperature. The reaction mixture was evaporated in vacuo and the residue was taken up in ethyl acetate (40 mL) and the organic layer was washed 1 M aqueous solution of hydrochloric acid (30 mL) and brine (30 mL), dried over anhydrous sodium sulfate and evaporated. The resulting gum was triturated with n-hexane (12 mL) to induce crystallization and the resulting solid was collected by filtration, washed with n-hexane (2×6 mL) and dried in vacuo to give tert-butyl (3-bromo-5-((3-bromo-5-(trifluoromethyl)phenyl)difluoromethyl)benzoyl) glycinate (4) as colorless solid.

Yield: 1220 mg (92%).

$^1$H NMR spectrum (300 MHz, $CDCl_3$, $\delta_H$): 8.03 (s, 1H); 7.88 (s, 1H); 7.86 (s, 1H); 7.79 (s, 1H); 7.75 (s, 1H); 6.86 (m, 1H); 6.86 (s, 1H); 4.12 (d, J=4.9 Hz, 2H); 1.50 (s, 9H).

$^{19}F$ NMR spectrum (282 MHz, $CDCl_3$, $\delta_F$): −62.85 (s, 3H); −89.85 (s, 2H).

LC-MS purity: 100% (ELSD).

LC-MS Rt (Kinetex C18, 4.6 mm×50 mm, acetonitrile/water 70:30 to 100:0+0.1% FA): 2.70 min.

LC-MS m/z: 532.2 $(M+H)^+$

A 100 mL reaction vessel was charged with potassium acetate (735 mg, 7.50 mmol) and the salt was dried for 1 hour at 110° C. in vacuo. After cooling to room temperature, the reaction vessel was backfilled with nitrogen and charged with tert-butyl (3-bromo-5-((3-bromo-5-(trifluoromethyl)phenyl)difluoromethyl)benzoyl)glycinate (4, 880 mg, 1.50 mmol), palladium acetate (4.6 mg, 60.0 μmol), 2-dicyclohexylphosphino-2',4',6'-triisopropylbiphenyl (XPhos, 57 mg, 120 μmol) and bis(pinacolato)diboron (838 mg, 3.30 mmol). The reaction vessel was then evacuated and backfilled with nitrogen (this procedure was repeated twice). Anhydrous tetrahydrofuran (8.0 mL) was added with syringe, the vessel was sealed with a plastic stopper and submerged in the heating bath preheated to 60° C. After stirring at 400 rpm for 4 hours the reaction mixture was cooled to ambient temperature, diluted with dichloromethane (15 mL) and filtered through a short plug of silica (10 g) topped with Celite S with the aid of dichloromethane (3×20 mL). The filtrate was concentrated under reduced pressure to afford tert-butyl (3-(difluoro(3-(4,4,5,5-tetramethyl-1,3,2-dioxaborolan-2-yl)-5-(trifluoromethyl)phenyl) methyl)-5-(4,4,5,5-tetramethyl-1,3,2-dioxaborolan-2-yl)benzoyl) glycinate (5) as orange foam.

It was dissolved in dry dichloromethane (4.0 mL) and trifluoroacetic acid (4.0 mL) was added and the resulting mixture was stirred for 1 hour at room temperature. Volatiles were evaporated under reduced pressure and the residue was co-distilled with toluene (3×10 mL). The residue was dissolved in acetonitrile (9.0 mL) and water (3.0 mL), periodic acid (1368 mg, 6.00 mmol) was added and reaction mixture was stirred for 2 hours. The mixture was diluted with ethyl acetate (40 mL) and washed with water (2×30 mL) and brine (30 mL). Organic phase was dried over anhydrous sodium sulphate, filtered and concentrated under reduced pressure to give a yellowish foam. The foam was dissolved in wet ethyl acetate (5 mL) and n-hexane (15 mL) was added. The mixture was left to stir overnight and the precipitated product was collected by filtration, washed with n-hexane (2×6 mL) and dissolved in acetonitrile (15 mL). The solution was freeze-dried to afford the title (3-borono-5-((3-borono-5-(trifluoromethyl)phenyl) difluoromethyl)benzoyl)glycine (6) as colorless solid.

Yield: 558 mg (81%).

$^1H$ NMR spectrum (300 MHz, Acetone-$d_6$/$D_2O$ 10:1, $\delta_H$): 8.48 (s, 1H); 8.38 (m, 1H, exchanges with $D_2O$); 8.29 (s, 1H); 8.25 (s, 1H); 8.20 (app. s, 2H); 7.94 (s, 1H); 4.16-4.09 (m, 2H).

$^{19}F$ NMR spectrum (282 MHz, Acetone-$d_6$/$D_2O$ 10:1, $\delta_F$): −63.07 (s, 3H); −89.89 (s, 2H).

LC-MS purity: 100% (ELSD).

LC-MS Rt (Kinetex C18, 4.6 mm×50 mm, acetonitrile/water 5:95 to 100:0+0.1% FA): 2.92 min.

LC-MS m/z: 462.4 $(M+H)^+$.

Example 19

(3-Borono-5-(3-borono-5-(trifluoromethyl)benzoyl)benzoyl)glycine

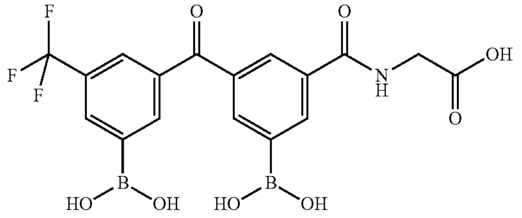 [SMILES: O=C(O)CNC(=O)c1cc(B(O)O)cc(C(=O)c2cc(B(O)O)cc(C(F)(F)F)c2)c1]

(3-Borono-5-(3-borono-5-(trifluoromethyl)benzoyl)benzoyl)glycine was synthesized according to the reaction scheme shown in Chem. 23 and following the procedure described below.

Chem. 23

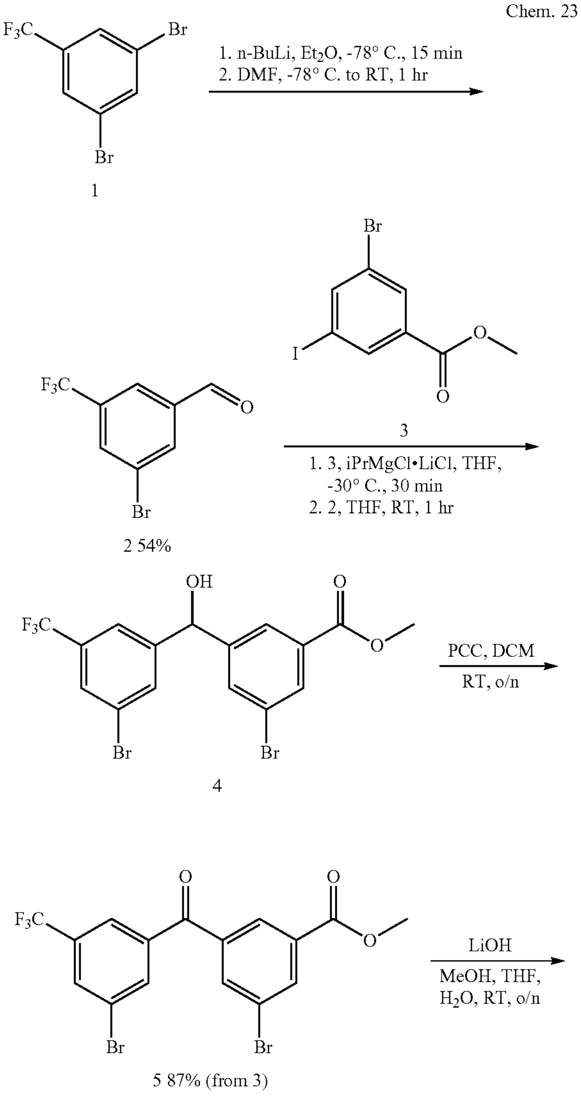

-continued

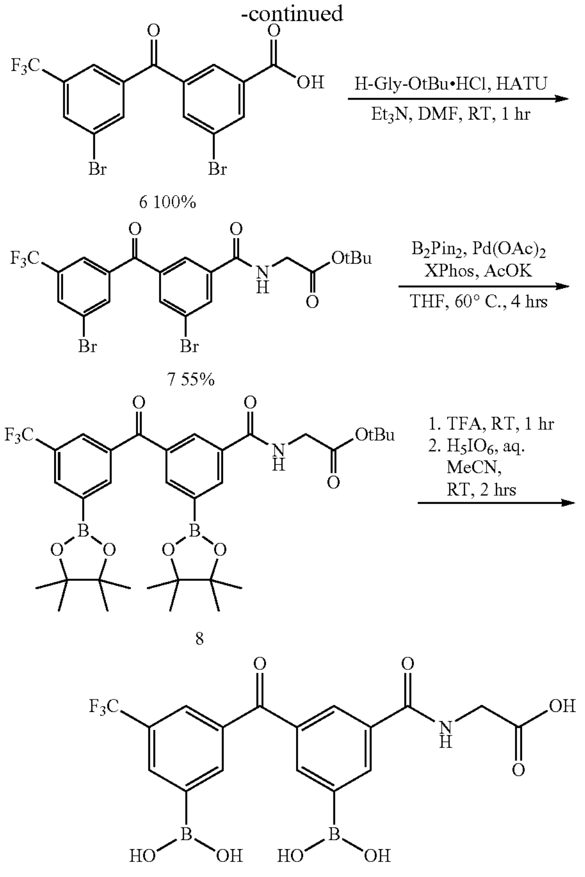

6 100%

7 55%

8

9 49% (from 7)

1,3-dibromo-5-(trifluoromethyl)benzene (1, 3.03 g, 10.00 mmol) was dissolved in dry diethyl ether (25 mL) and cooled to −78° C. n-Butyllithium (4.24 mL, 2.35 M in hexanes, 10.0 mmol) was added drop-wise with stirring. After 15 minutes, dry N,N-dimethylformamide (1.44 mL, 20.0 mmol) was added in one portion and the resulting mixture was allowed to warm to ambient temperature over an hour. 1 M aqueous solution of hydrochloric acid (30 mL) was then added to quench the reaction and the reaction mixture was taken up in diethyl ether (30 mL) and washed with water (20 mL) and brine (20 mL), dried over anhydrous sodium sulfate, filtered and evaporated. The crude product was purified by flash column chromatography (Silicagel 60, 0.040-0.063 mm; eluent: cyclohexane/ethyl acetate 20:1) to give 3-bromo-5-(trifluoromethyl) benzaldehyde (2) as colorless oil.

Yield: 1366 mg (54%).

$^1$H NMR spectrum (300 MHz, $CDCl_3$, $\delta_H$): 10.02 (s, 1H); 8.20 (bs, 1H); 8.07 (bs, 1H); 8.02 (bs, 1H).

Methyl 3-bromo-5-iodobenzoate (3, 1.36 g, 4.00 mmol) was dissolved in dry tetrahydrofuran (12 mL) and cooled to −30° C. Isopropylmagnesium chloride-lithium chloride complex (3.11 mL, 1.3 M solution in tetrahydrofuran, 4.20 mmol) was added drop-wise with stirring. After 30 minutes, 3-bromo-5-(trifluoromethyl)benzaldehyde (2, 1.21 g, 4.80 mmol) was added with aid of 3 mL of tetrahydrofuran. The resulting mixture was allowed to warm to ambient temperature and quenched after one hour by the addition of 1 M aqueous solution of hydrochloric acid (15 mL). The reaction mixture was taken up in diethyl ether (50 mL), washed with water (30 mL) and brine (30 mL), dried over anhydrous sodium sulfate, filtered and evaporated. The crude product (4) was dissolved in dry dichloromethane (20 mL) and pyridinium chlorochromate (1.29 g, 6.00 mmol) was added with stirring. After stirring for 17 hours, the reaction mixture was filtered through a plug of silica (15 g) topped with Celite and the bed was washed with dichloromethane (3×20 mL). The yellowish solution was concentrated in vacuo and the residue was purified by flash column chromatography (Silicagel 60, 0.040-0.063 mm; eluent: cyclohexane/dichloromethane 6:1 to 1:1) to give methyl 3-bromo-5-(3-bromo-5-(trifluoromethyl)benzoyl)benzoate (5) as colorless solid.

Yield: 1620 mg (87%).

$^1$H NMR spectrum (300 MHz, $CDCl_3$, $\delta_H$): 8.45 (t, J=1.4 Hz, 1H); 8.29 (m, 1H); 8.12 (t, J=1.6 Hz, 1H); 8.08 (bs, 1H); 8.04 (bs, 1H); 7.95 (bs, 1H); 3.97 (s, 3H).

Methyl 3-bromo-5-(3-bromo-5-(trifluoromethyl)benzoyl) benzoate (5, 466 mg, 1.00 mmol) was dissolved in tetrahydrofuran (3 mL), methanol (2 mL) and water (1 mL). Lithium hydroxide monohydrate (210 mg, 5.00 mmol) was added and the resulting mixture was stirred for 16 hours; and then it was taken up in ethyl acetate (30 mL) and washed with 1 M aqueous solution of hydrochloric acid (15 mL) and brine (15 mL); dried over anhydrous sodium sulfate; filtered and evaporated. The resulting solid (6) was added to a solution of 1-[bis(dimethylamino)methylene]-1H-1,2,3-triazolo[4,5-b]pyridinium 3-oxide hexafluorophosphate (HATU, 399 mg, 1.05 mmol) in dry N,N-dimethylformamide (5 mL), followed by addition of triethylamine (0.70 mL, 5.00 mmol). After ten minutes, glycine tert-butyl ester hydrochloride (250 mg, 1.50 mmol) was added and the resulting mixture was stirred for one hour at ambient temperature. The reaction mixture was diluted 1 M aqueous solution of hydrochloric acid (15 mL) and the precipitated gummy solid was collected by filtration and dried in air. The resulting solid was triturated with n-hexane (5 mL), collected by filtration and dried in vacuo to give tert-butyl 2-(3-bromo-5-(3-bromo-5-(trifluoromethyl)benzoyl)benzamido)acetate (7) as colorless solid.

Yield: 311 mg (55%).

$^1$H NMR spectrum (300 MHz, $CDCl_3$, $\delta_H$): 8.23 (t, J=1.7 Hz, 1H); 8.09 (t, J=1.5 Hz, 1H); 8.07 (bs, 1H); 8.06-8.01 (m, 2H); 7.96 (bs, 1H); 6.67 (t, J=3.8 Hz, 1H); 4.15 (d, J=4.8 Hz, 2H); 1.52 (s, 9H).

LC-MS purity: 100% (ELSD).

LC-MS Rt (Kinetex C18, 4.6 mm×50 mm, acetonitrile/water 70:30 to 100:0+0.1% FA): 2.18 min.

LC-MS m/z: 566.3 (M+H)+

A 20 mL reaction vessel was charged with potassium acetate (202 mg, 2.06 mmol) and the salt was dried for 1 hour at 110° C. in vacuo. After cooling to room temperature, the reaction vessel was backfilled with nitrogen and charged with tert-butyl 2-(3-bromo-5-(3-bromo-5-(trifluoromethyl) benzoyl)benzamido)acetate (7, 290 mg, 513 μmol), palladium acetate (4.6 mg, 10 μmol), 2-dicyclohexylphosphino-2',4',6'-triisopropylbiphenyl (XPhos, 19.5 mg, 51 μmol) and bis(pinacolato)diboron (287 mg, 1.13 mmol). The reaction vessel was then evacuated and backfilled with nitrogen (this procedure was repeated twice). Anhydrous tetrahydrofuran (4 mL) was added with syringe, the vessel was sealed with a plastic stopper and submerged in the heating bath preheated to 60° C. After stirring at 400 rpm for 4 hours the reaction mixture was cooled to ambient temperature, diluted with dichloromethane (15 mL) and filtered through a short plug of silica (15 g) topped with Celite S with the aid of dichloromethane (3×10 mL). The filtrate was concentrated under reduced pressure to afford tert-butyl (3-(4,4,5,5-tetramethyl-1,3,2-dioxaborolan-2-yl)-5-(3-(4,4,5,5-tetramethyl-1,3,2-dioxaborolan-2-yl)-5-(trifluoromethyl)benzoyl)benzoyl)glycinate (8) as yellow waxy foam.

Yield: 340 mg (quantitative).

LC-MS purity: 100% (ELSD).

LC-MS Rt (Kinetex C18, 4.6 mm×50 mm, acetonitrile/water 35:65 to 100:0+0.1% FA): 5.57 min, 3.97 min LC-MS m/z: 604.5 $(M+H-tBu)^+$, 522.5 $(M\text{-pinacol-tBu}+H)^+$ tert-Butyl (3-(4,4,5,5-tetramethyl-1,3,2-dioxaborolan-2-yl)-5-(3-(4,4,5,5-tetramethyl-1,3,2-dioxaborolan-2-yl)-5-(trifluoromethyl)benzoyl)benzoyl)glycinate (8, 340 mg, 513 μmol) was mixed with trifluoroacetic acid (2 mL) and stirred for 1 hour at room temperature. Volatiles were evaporated under reduced pressure. The residue and periodic acid (600 mg, 2.63 mmol) were dissolved in acetonitrile/water mixture (4:1, 2.5 mL), and reaction mixture was stirred for 2 hours. The mixture was diluted with ethyl acetate (5 mL) and washed with water (5 mL) and brine (5 mL). Organic phase was concentrated under reduced pressure to give yellow solid, which was purified by preparative LC/MS (SunFire Prep C18, 5 μm, 19×100 mm, acetonitrile/water 5:95 to 100:0+0.1% FA). Pure fractions were collected and freeze-dried to afford the title product (9) as white solid.

Yield: 101 mg (49%).

$^1$H NMR spectrum (300 MHz, Acetone-$d_6$/$D_2O$ 10:1, $\delta_H$): 8.66 (s, 1H); 8.48 (s, 1H); 8.40 (m, 3H); 8.15 (s, 1H); 4.16 (m, 2H).

$^{19}$F NMR spectrum (282 MHz, Acetone-$d_6$/$D_2O$ 10:1, $\delta_F$): 63.13 (s).

LC-MS purity: 100% (ELSD).

LC-MS Rt (Kinetex C18, 4.6 mm×50 mm, acetonitrile/water 5:95 to 100:0+0.1% FA): 3.34 min.

LC-MS m/z: 440.3 $(M+H)^+$.

Example 20

(3-Borono-5-((3-borono-5-(trifluoromethyl)phenyl)sulfonyl)glycine

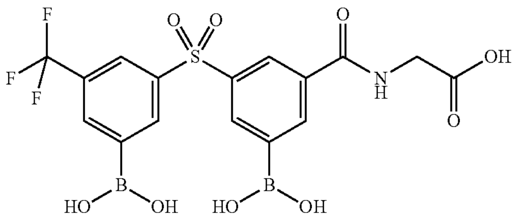 [SMILES: O=C(O)CNC(=O)c1cc(B(O)O)cc(S(=O)(=O)c2cc(B(O)O)cc(C(F)(F)F)c2)c1]

(3-Borono-5-((3-borono-5-(trifluoromethyl)phenyl)sulfonyl)glycine was synthesized according to the reaction scheme shown in Chem. 24 and following the procedure described below.

Chem. 24

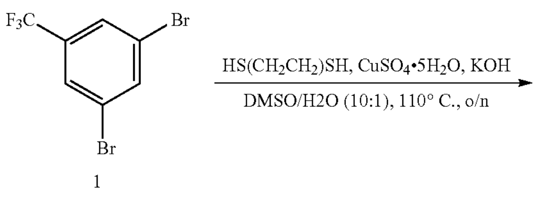

-continued

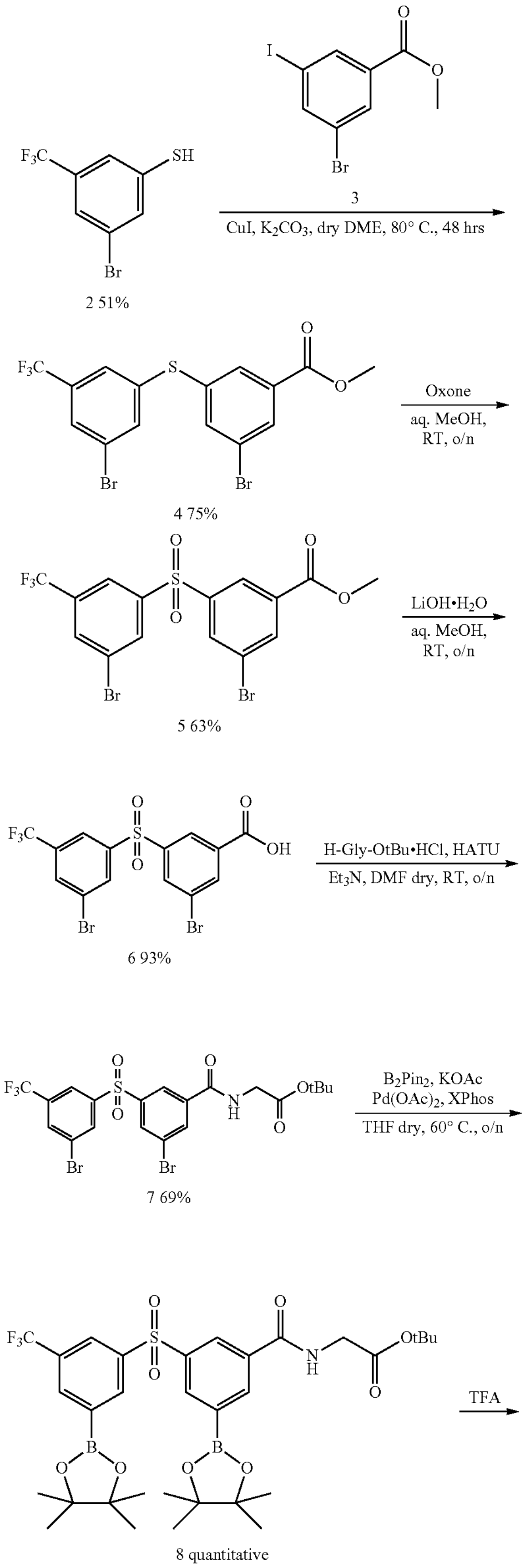

-continued

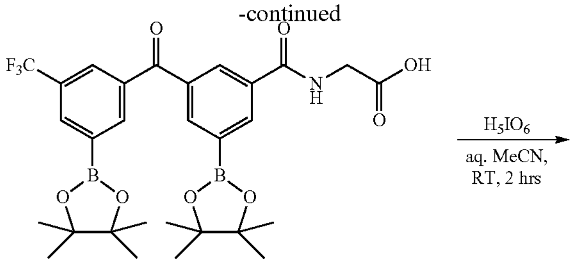

9 quantitative

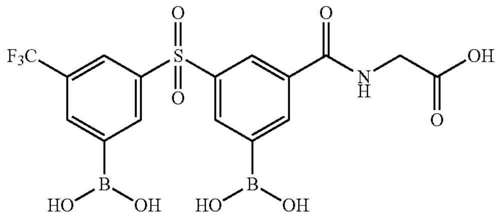

10 14%

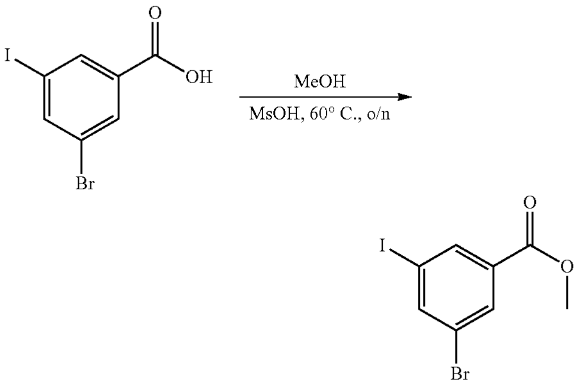

3 83%

1,3-Dibromo-5-(trifluoromethyl)benzene (1, 5.74 g, 18.0 mmol) was added to a mixture of copper(II) sulfate pentahydrate (225 mg, 1.80 mmol) and potassium hydroxide (5.03 g, 180 mmol) in mixture dimethyl sulfoxide/water (10:1, 38 mL), reaction flask was filled with nitrogen and at the end was added 1,2-ethanedithiol (2.68 mL, 60.0 mmol) through the septum. Reaction mixture was heated to 110° C. overnight. Then was mixture acidified to pH=2 with 1 M aqueous solution of hydrochloric acid and extracted with ethyl acetate. After drying over anhydrous sodium sulfate and filtration solvent was evaporated under reduced pressure. Residue was purified by column chromatography (Silicagel 60, 0.063-0.200 mm; eluent: cyclohexane) to give 3-bromo-5-(trifluoromethyl)benzenethiol (2) as yellow oil.

Yield: 2.27 g (51%).

$^1$H NMR spectrum (300 MHz, $CDCl_3$, $\delta_H$): 7.61 (s, 1H); 7.56 (s, 1H); 7.46 (s, 1H); 3.66 (s, 1H).

3-Bromo-5-iodobenzoic acid (40.0 g, 122 mmol) was dissolved in methanol, methanesulfonic acid (3 mL) was added and reaction mixture was heated to 60° C. overnight, then was reaction cooled to 0° C. with stirring and then was kept in freezer overnight. Methyl 3-bromo-5-iodobenzoate (3) was obtained by filtration as white solid.

Yield: 34.5 g (83%).

$^1$H NMR spectrum (300 MHz, $CDCl_3$, $\delta_H$): 8.31 (t, J=1.34 Hz, 1H); 8.15 (t, J=1.50 Hz, 1H); 8.05 (t, J=1.59 Hz, 1H); 3.95 (s, 3H).

3-Bromo-5-(trifluoromethyl)benzenethiol (2, 2.27 g, 8.80 mmol), methyl 3-bromo-5-iodobenzoate (3, 1.85 g, 5.50 mmol), potassium carbonate (1.51 g, 10.9 mmol) and copper (I) iodide (207 mg, 1.09 mmol) were dissolved in dry dimethoxyethane (22 mL). Reaction flask was heated to 80° C. for 48 hours. After this time was mixture diluted with ethyl acetate and filtrated through the Celite S, solvent was then evaporated under reduced pressure. Residue was purified by column chromatography (Silicagel 60, 0.063-0.200 mm; eluent: cyclohexane/ethyl acetate 1:0 to 20:1) to give methyl 3-bromo-5-((3-bromo-5-(trifluoromethyl)phenyl)thio)benzoate (4) as yellow oil.

Yield: 1.93 g (75%).

$^1$H NMR spectrum (300 MHz, $CDCl_3$, $\delta_H$): 7.82 (m, 1H); 7.68 (m, 3H); 7.52 (m, 1H); 2.54 (s, 3H).

Methyl 3-bromo-5-((3-bromo-5-(trifluoromethyl)phenyl)thio)benzoate (4, 1.93 g, 4.10 mmol) and potassium peroxymonosulfate (3.80 g, 6.30 mmol) were suspended in methanol (22 mL) and water (11 mL) was added. The reaction was stirred overnight at room temperature. Then was mixture diluted with ethyl acetate (20 mL), washed with water (30 mL) and then with brine (30 mL). Organic phase was evaporated under reduced pressure, residue was chromatographed by column chromatography (Silicagel 60, 0.063-0.200 mm; eluent: cyclohexane/ethyl acetate 9:1 to 3:1) to give methyl 3-bromo-5-((3-bromo-5-(trifluoromethyl)phenyl)sunfonyl)benzoate (5) as white solid.

Yield: 1.30 g (63%).

$^1$H NMR spectrum (300 MHz, $CDCl_3$, $\delta_H$): 8.53 (m, 1H); 8.43 (m, 1H); 8.27 (m, 2H); 8.16 (m, 1H); 8.01 (m, 1H); 4.00 (s, 3H).

Methyl 3-bromo-5-((3-bromo-5-(trifluoromethyl)phenyl)sunfonyl)benzoate (5, 1.30 g 2.60 mmol) and lithium hydroxide monohydrate (330 mg, 7.80 mmol) were dissolved in mixture of methanol/water/tetrahydrofurane (4:2:5, 23 mL), reaction mixture was stirred overnight at room temperature. After this time was mixture acidified to pH=2 with 1 M aqueous solution of hydrochloric acid and extracted with ethyl acetate. After evaporation of all volatiles was obtained 3-bromo-5-((3-bromo-5-(trifluoromethyl)phenyl)sulfonyl)benzoic acid (6) as white solid.

Yield: 1.18 g (93%).

$^1$H NMR spectrum (300 MHz, DMSO-$d_6$, $\delta_H$): 13.91 (bs, 1H); 8.68 (s, 2H); 8.50 (s, 1H); 8.45 (s, 1H); 8.41 (s, 1H); 8.32 (s, 1H).

3-Bromo-5-((3-bromo-5-(trifluoromethyl)phenyl)sunfonyl)benzoic acid (6, 1.18 g, 2.40 mmol) mixed with 1-((dimethylamino)(dimethyliminio)methyl)-1H-[1,2,3]triazolo[4,5-b]pyridine 3-oxide hexafluorophosphate(V) (HATU, 1.01 g, 2.64 mmol) in dry N,N'-dimethylformamide (30 mL) for 30 minutes, then triethylamine (1.22 g, 12.0 mmol) was added and glycine tert-butyl ester hydrochloride (810 mg, 4.80 mmol), after end of reaction was added water and reaction mixture was extracted with ethyl acetate (25 mL), after evaporation of all volatiles under reduced pressure was residue purified by column chromatography (Silicagel 60, 0.063-0.200 mm; eluent: cyclohexane/ethyl acetate 3:1) to give tert-butyl (3-bromo-5-((3-bromo-5-(trifluoromethyl)phenyl)sulfonyl)benzoyl)glycinate (7) as white solid.

Yield: 1.00 g (69%).

LC-MS purity: 100% (ELSD).

LC-MS Rt (Kinetex C18, 4.6 mm×50 mm, acetonitrile/water 35:65 to 100:0+0.1% FA): 4.30 min.

LC-MS m/z: 602.3 $(M+H)^+$.

A 50 mL reaction flask was charged with potassium acetate (815 mg, 8.30 mmol) and the salt was dried for 1 hour at 110° C. in vacuo. After cooling to room temperature, the reaction flask was backfilled with nitrogen and charged with tert-butyl (3-bromo-5-((3-bromo-5-(trifluoromethyl)

phenyl)sulfonyl)benzoyl)glycinate (7, 1.00 g, 1.66 mmol), palladium acetate (19.0 mg, 82.0 μmol), 2-dicyclohexylphosphino-2',4',6'-triisopropylbiphenyl (XPhos, 79 mg, 165 μmol) and bis(pinacolato)diboron (930 mg, 3.60 mmol). The reaction flask was then evacuated and backfilled with nitrogen (this procedure was repeated twice), anhydrous tetrahydrofuran (8 mL) was added with syringe, the flask was sealed with a plastic stopper and heated to 60° C. Reaction mixture was stirred overnight and then was cooled to ambient temperature, diluted with dichloromethane (30 mL) and filtered through a short plug of silicagel topped with Celite S and washed with dichloromethane (3×10 mL). The filtrate was concentrated under reduced pressure to afford the tert-butyl (3-(4,4,5,5-tetramethyl-1,3,2-dioxaboroloan-2-yl)-5-((3-(4,4,5,5-tetramethyl-1,3,2-dioxaborolan-2-yl)-5-(trifluoromethyl)phenyl) sulfonyl)benzoyl)glycinate (8) as brown waxy foam.

Yield: 1.16 g (quantitative).

LC-MS purity: 100% (ELSD).

LC-MS Rt (Kinetex C18, 4.6 mm×50 mm, acetonitrile/water 35:65 to 100:0+0.1% FA): 5.40 min, 3.97 min, 2.62 min LC-MS m/z: 640.5 $(M+H-tBu)^+$, 558.4 $(M-pinacol-tBu+H)^+$, 476.3 $(M-2pinacol-tBu+H)^+$.

tert-Butyl (3-(4,4,5,5-tetramethyl-1,3,2-dioxaboroloan-2-yl)-5-((3-(4,4,5,5-tetramethyl-1,3,2-dioxaborolan-2-yl)-5-(trifluoromethyl)phenyl)sulfonyl)benzoyl) glycinate (8, 1.16 g, 1.66 mmol) was mixed with trifluoroacetic acid (5 mL) and stirred 1 hour at room temperature, after this time all volatiles was evaporated under reduced pressure. (3-(4,4,5,5-Tetramethyl-1,3,2-dioxaboroloan-2-yl)-5-((3-(4,4,5,5-tetramethyl-1,3,2-dioxaborolan-2-yl)-5-(trifluoromethyl)phenyl)sulfonyl)benzoyl)glycine (9) was obtained as brown waxy foam.

Yield: 1.06 g (quantitative).

LC-MS purity: 100% (ELSD).

LC-MS Rt (Kinetex C18, 4.6 mm×50 mm, acetonitrile/water 35:65 to 100:0+0.1% FA): 4.31 min, 2.89 min, 1.12

LC-MS m/z: 640.5 $(M+H)^+$, 558.4 $(M-pinacol+H)^+$, 476.3 $(M-2pinacol+H)^+$.

(3-(4,4,5,5-Tetramethyl-1,3,2-dioxaboroloan-2-yl)-5-((3-(4,4,5,5-tetramethyl-1,3,2-dioxaborolan-2-yl)-5-(trifluoromethyl)phenyl)sulfonyl)benzoyl)glycine (9, 1.16 g, 1.16 mmol) and periodic acid (430 mg, 4.64 mmol) were dissolved in acetonitrile/water (mixture 4:1, 5 mL), reaction mixture was stirred 2 hours. Then was mixture diluted with ethyl acetate (10 mL) and washed with water (10 mL) and brine (10 mL). Organic phase was concentrated under reduced pressure, as residue was obtained yellow solid, from which was removed part, which was purified by preparative LC/MS (SunFire Prep C18, 5 μm, 19×100 mm, acetonitrile/water 5:95 to 100:0+0.1% FA). All solvents were freeze-dried and (3-borono-5-((3-borono-5-(trifluoromethyl)phenyl)sulfonyl)benzoyl)glycine (10) was obtained as white solid.

Yield: 110 mg (14%).

$^1H$ NMR spectrum (300 MHz, Acetone-$d_6$/$D_2O$ 10:1, $\delta_H$): 8.69 (s, 1H); 8.59 (m, 3H); 8.36 (s, 1H); 8.33 (s, 1H); 4.13 (m, 2H).

$^{19}F$ NMR spectrum (282 MHz, Acetone-$d_6$/$D_2O$ 10:1, $\delta_F$): 63.16 (s).

LC-MS purity: 100% (ELSD).

LC-MS Rt (Kinetex C18, 4.6 mm×50 mm, acetonitrile/water 5:95 to 100:0+0.1% FA): 3.34 min.

LC-MS m/z: 476.3 $(M+H)^+$.

Example 21

4-((3S,4S)-3,4-Bis(7-fluoro-1-hydroxy-1,3-dihydrobenzo[c][1,2]oxaborole-6-carboxamido)pyrrolidin-1-yl)-4-oxobutanoic acid

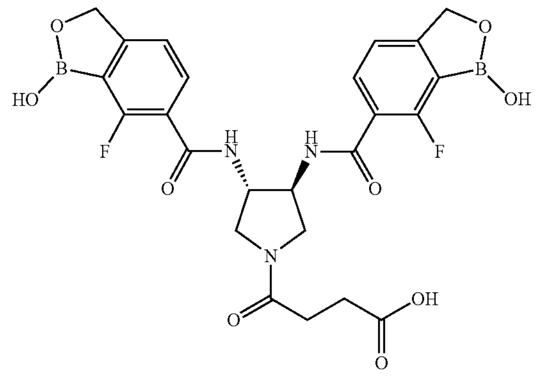 [SMILES: O=C(O)CCC(=O)N1C[C@H](NC(=O)c2ccc3c(c2F)B(O)OC3)[C@@H](NC(=O)c2ccc3c(c2F)B(O)OC3)C1]

4-((3S,4S)-3,4-Bis(7-fluoro-1-hydroxy-1,3-dihydrobenzo[c][1,2]oxaborole-6-carboxamido)pyrrolidin-1-yl)-4-oxobutanoic acid was synthesized according to the reaction schemes shown in Chem. 25 and Chem. 26 and following the procedure described below.

Chem. 25

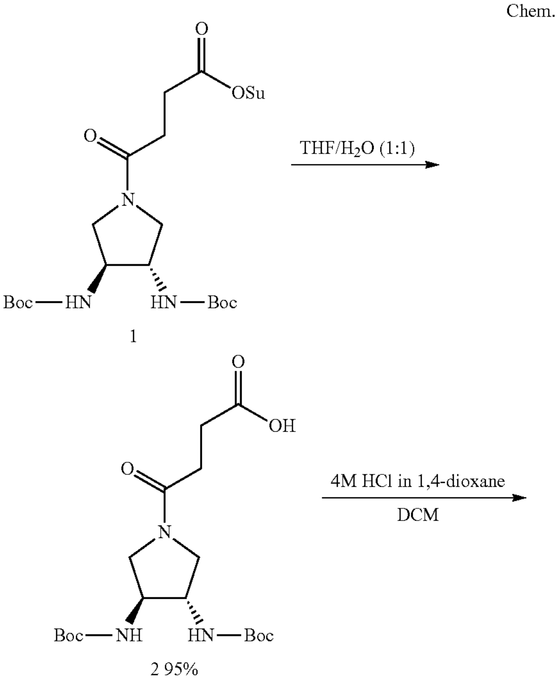

-continued

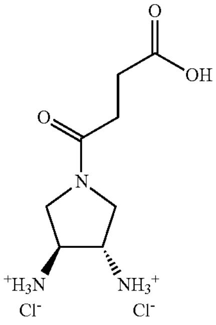

3 quant.

2,5-Dioxopyrrolidin-1-yl 4-((3S,4S)-3,4-bis((tert-butoxycarbonyl)amino) pyrrolidin-1-yl)-4-oxobutanoate (1, 1.50 g, 3.01 mmol) was dissolved in tetrahydrofuran/water mixture (1:1, 10 mL) and left to stay for 7 days. The mixture was diluted with ethyl acetate (50 mL) and washed with water (2×50 mL) and brine (1×50 mL). Organic layer was dried over anhydrous sodium sulfate, filtered and evaporated to dryness affording 4-((3S,4S)-3,4-bis((tert-butoxycarbonyl) amino) pyrrolidin-1-yl)-4-oxobutanoic acid (2) as white solid.

Yield: 1.15 g (95%).

$^1$H NMR spectrum (300 MHz, $CDCl_3$, $\delta_H$): 5.58-5.45 (m, 1H); 5.41-5.30 (m, 1H); 4.12-3.80 (m, 4H); 3.35-3.17 (m, 2H); 2.76-2.39 (m, 4H); 1.45 (s, 18H).

LC-MS purity: 100% (ELSD).

LC-MS Rt (Kinetex C18, 4.6 mm×50 mm, acetonitrile/water 20:80 to 100:0+0.1% FA): 2.97 min.

LC-MS m/z: 401.4 $(M+H)^+$.

The acid (2, 1.14 g, 2.83 mmol) was dissolved in dichloromethane (5 mL) and 4 M solution of hydrogen chloride in 1,4-dioxane (20 mL) was added. After 30 minutes the solvent was evaporated. The residue was suspended in diethyl ether (10 mL), decanted and dried in vacuo to yield 4-((3S,4S)-3,4-diaminopyrrolidin-1-yl)-4-oxobutanoic acid dihydrochloride (3) as pale brown powder.

Yield: 0.78 g (100%).

$^1$H NMR spectrum (300 MHz, $D_2O$, $\delta_H$): 4.33-4.17 (m, 3H); 4.10-3.99 (m, 1H); 3.92-3.83 (m, 1H); 3.78-3.68 (m, 1H); 2.67 (s, 4H).

Chem. 26

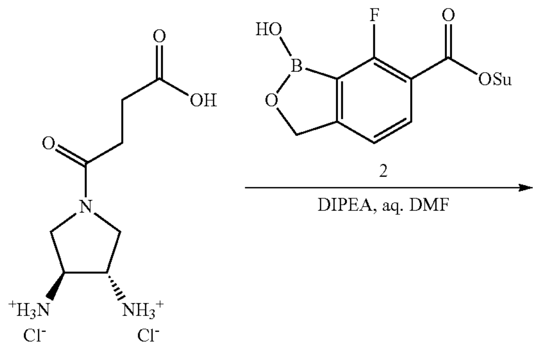

1

-continued

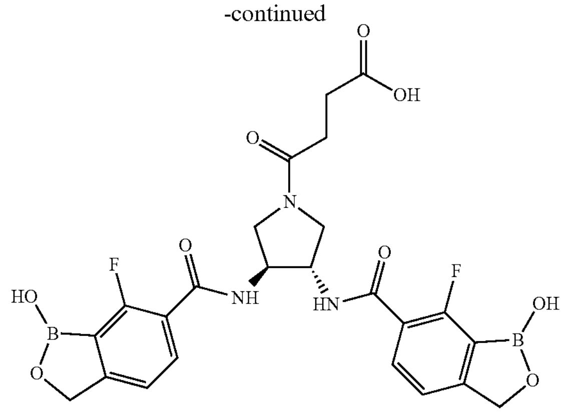

3 5%

4-((3S,4S)-3,4-Diaminopyrrolidin-1-yl)-4-oxobutanoic acid dihydrochloride (1, 0.16 g, 0.59 mmol) was dissolved in water (3 mL). Then N,N-dimethylformamide (3 mL), N,N-diisopropylethylamine (0.51 mL, 2.95 mmol) and 2,5-dioxopyrrolidin-1-yl 7-fluoro-1-hydroxy-1,3-dihydrobenzo [c][1,2]oxaborole-6-carboxylate (2, 0.34 g, 1.17 mmol) were added. Resulting mixture was stirred overnight at room temperature. The mixture was acidified with 1 M aqueous solution of hydrochloric acid and solvents were evaporated. The residue was dissolved in ethyl acetate (40 mL) and washed with water (2×20 mL). Organic layer was dried over anhydrous sodium sulfate, filtered and evaporated. The residue was purified by preparative LC/MS (SunFire Prep C18, 5 μm, 19×100 mm, acetonitrile/water 5:95 to 100:0+0.1% FA) to give the title compound (3) as white solid.

Yield: 16.0 mg (5%).

Total yield: 16.0 mg (5%).

$^1$H NMR spectrum (300 MHz, DMSO-$d_6$, $\delta_H$): 9.39 (s, 2H); 8.73-8.63 (m, 2H); 7.75-7.65 (m, 2H); 7.34-7.27 (m, 2H); 5.03 (s, 4H); 4.63-4.48 (m, 2H); 3.99-3.88 (m, 1H); 3.82-3.72 (m, 1H); 3.47-3.22 (m, 2H); 2.47-2.39 (m, 4H).

LC-MS purity: 100% (ELSD).

LC-MS Rt (Kinetex C18, 4.6 mm×50 mm, acetonitrile/water 5:95 to 100:0+0.1% FA): 3.05 min.

LC-MS m/z: 557.0 $(M+H)^+$.

Example 22

(3-Borono-5-(3-borono-5-fluorobenzoyl)benzoyl)glycine

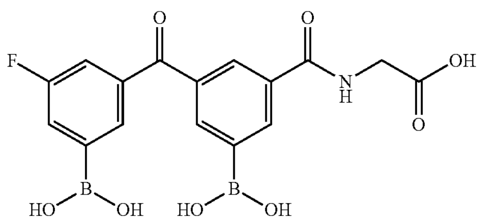 [SMILES: O=C(O)CNC(=O)c1cc(B(O)O)cc(C(=O)c2cc(F)cc(B(O)O)c2)c1]

(3-Borono-5-(3-borono-5-fluorobenzoyl)benzoyl)glycine was synthesized according to the reaction scheme shown in Chem. 27 and following the procedure described below.

Chem. 27

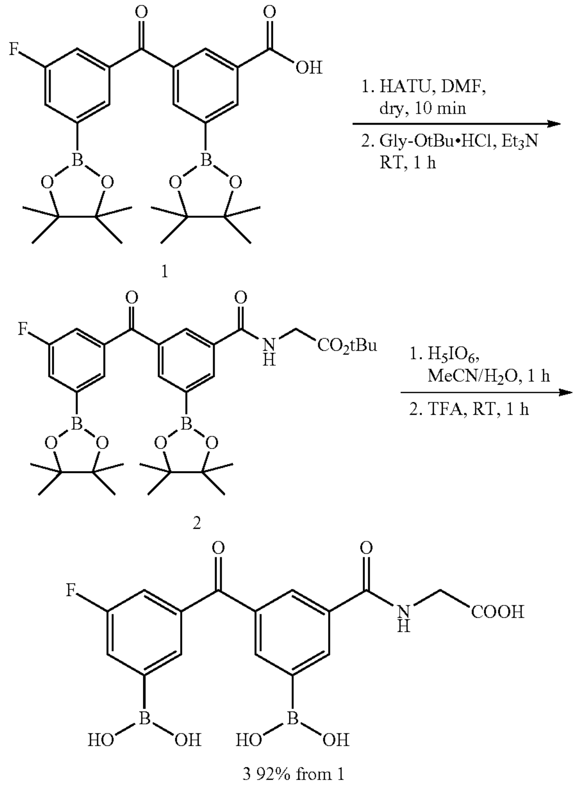

3-(3-Fluoro-5-(4,4,5,5-tetramethyl-1,3,2-dioxaborolan-2-yl)benzoyl)-5-(4,4,5,5-tetramethyl-1,3,2-dioxaborolan-2-yl) benzoic acid (1, 546 mg, 1.10 mmol) and 1-[bis(dimethyl-amino)methylene]-1H-1,2,3-triazolo[4,5-b]pyridinium 3-oxide hexafluorophosphate (HATU, 439 mg, 1.16 mmol) were dissolved in dry DMF (5 mL) and triethylamine (0.76 mL, 5.50 mmol) was added. After ten minutes, glycine tert-butyl ester hydrochloride (277 mg, 1.65 mmol) was added and the resulting mixture was stirred for an hour at ambient temperature. The reaction mixture was taken up in ethyl acetate (25 mL) and washed with 0.5 M aqueous solution of hydrochloric acid (2×15 mL), 5% aqueous solution of lithium chloride (2×15 mL), 5% aqueous solution of potassium hydrogencarbonate (1×15 mL) and brine (15 mL), dried over anhydrous sodium sulfate and evaporated to give a compound 2 as yellowish powder. Solid was dissolved in acetonitrile (6 mL) and water (1.5 mL) and periodic acid (912 mg, 4.00 mmol) was added. After one hour, the reaction mixture was taken up in ethyl acetate (25 mL) and washed with water (2×15 mL) and brine (15 mL), dried over anhydrous sodium sulfate and evaporated to give a yellowish foam, which was dissolved in trifluoroacetic acid (5 mL) and stirred for one hour. Volatiles were removed in vacuo and the residue co-evaporated with ethyl acetate (3×15 mL) to give a beige solid, which was triturated with diethyl ether (5 mL) and cyclohexane (5 mL). The resulting solid was collected by filtration, washed with cyclohexane (2×5 mL) and dried in vacuo to give the title 3-borono-5-(3-borono-5-fluorobenzoyl)benzoyl)glycine (3) as colorless solid.

Yield: 394 mg (92%).

$^1$H NMR spectrum (300 MHz, Acetone-$d_6$/$D_2O$, $\delta_H$): 8.60 (d, J=0.6 Hz, 1H); 8.35 (dd, J=8.2, 1.5 Hz, 2H); 8.04 (s, 1H); 7.80 (ddd, J=9.2, 2.7, 0.8 Hz, 1H); 7.62-7.49 (m, 1H); 4.12 (s, 2H).

LC-MS purity: 100% (ELSD).

LC-MS Rt (Kinetex C18, 4.6 mm×50 mm, acetonitrile/water 05:95 to 100:0+0.1% FA): 3.11 min.

LC-MS m/z: 390.4 (M+H)$^+$

Example 24

(3-Borono-5-((3-borono-5-fluorophenyl)sulfonyl) benzoyl)glycine

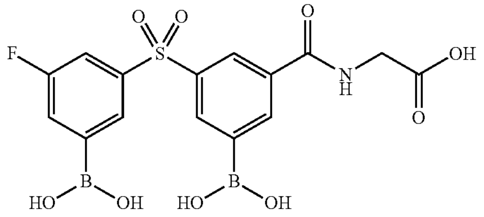 [SMILES: O=C(O)CNC(=O)c1cc(B(O)O)cc(S(=O)(=O)c2cc(F)cc(B(O)O)c2)c1]

(3-Borono-5-((3-borono-5-fluorophenyl)sulfonyl)benzoyl)glycine was synthesized according to the reaction scheme shown in Chem. 29 and following the procedure described below.

Chem. 29

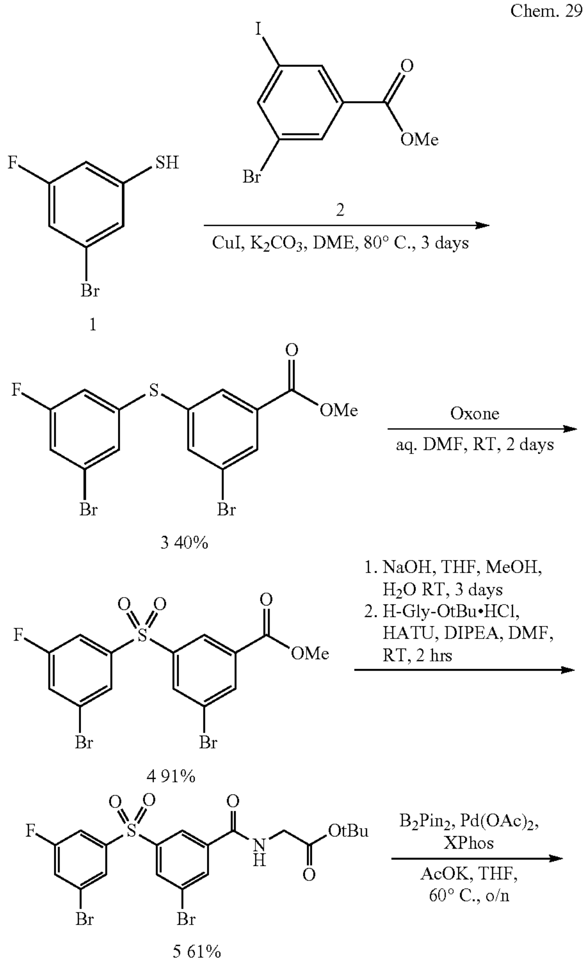

-continued

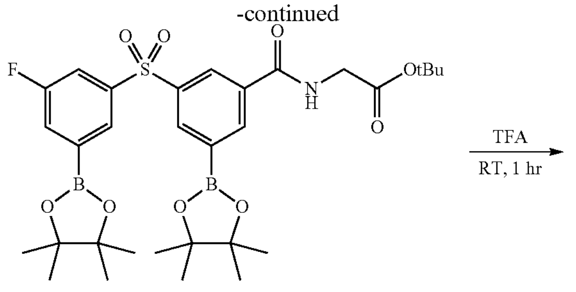

6

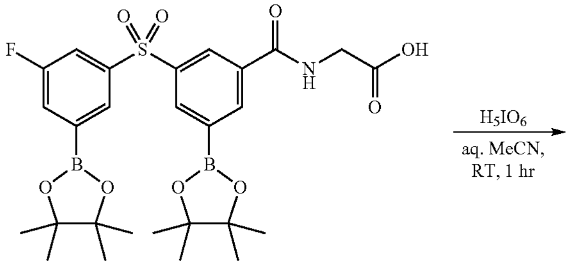

7

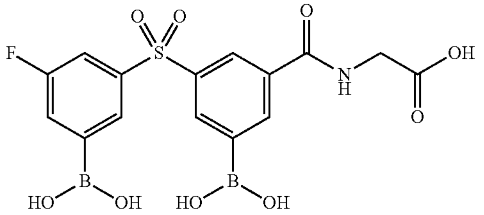

8 59% (from 5)

A mixture of 3-bromo-5-fluorobenzenethiol (1, 1.55 g, 7.49 mmol), methyl 3-bromo-5-iodobenzoate (2, 2.81 g, 8.24 mmol), copper(I) iodide (143 mg, 749 μmol), potassium carbonate (2.07 g, 15.0 mmol) and dry 1,2-dimethoxyethane (30.0 mL) was heated at 80° C. under argon over weekend. The reaction mixture was cooled to room temperature; diluted with ethyl acetate (30 mL); filtered over Celite and evaporated to dryness. The residue was re-dissolved in ethyl acetate (100 mL); washed with 0.5 M aqueous hydrochloric acid (50 mL), 0.5 M aqueous sodium hydroxide (2×50 mL) and 0.5 M aqueous hydrochloric acid (50 mL); dried over anhydrous sodium sulfate and evaporated to dryness. The residue was subjected to flash column chromatography (Silicagel 60, 0.040-0.063 mm; eluent: cyclohexane/ethyl acetate 97:3) to afford methyl 3-bromo-5-((3-bromo-5-fluorophenyl)thio)benzoate (3) contaminated with methyl 3-bromo-5-iodobenzoate (2) as pale yellow oil.

Yield: 2.54 g (40%).

Content: 50% ($^1$H NMR).

$R_F$ ($SiO_2$, n-hexane/ethyl acetate 9:1): 0.50.

$^1$H NMR spectrum (300 MHz, $CDCl_3$, $\delta_H$): 8.13 (m, 1H); 7.99 (t, J=1.6 Hz, 1H); 7.70 (t, J=1.7 Hz, 1H); 7.24 (td, J=1.6 and 0.6 Hz, 1H); 7.16 (ddd, J=8.0, 2.3 and 1.7 Hz, 1H); 6.93 (ddd, J=8.5, 2.4 and 1.6 Hz, 1H); 3.94 (s, 3H).

$^{19}$F NMR spectrum (282 MHz, $CDCl_3$, $\delta_F$): −108.98 (s).

LC-MS purity: 73% (UV 254 nm).

LC-MS Rt (Kinetex C18, 4.6 mm×50 mm, acetonitrile/water 70:30 to 100:0+0.1% FA): 3.47 min.

LC-MS m/z: 421.3 (M+H)+.

Potassium peroxymonosulfate (2.75 g, 4.48 mmol) was added to a solution of the above methyl 3-bromo-5-((3-bromo-5-fluorophenyl)thio)benzoate (3, 50%, 2.53 g, 2.99 mmol) in N,N-dimethylformamide (30 mL) and water (5 mL) and the reaction mixture was stirred at room temperature overnight. One more portion of Oxone® (2.75 g, 4.48 mmol) was added and the reaction mixture was stirred at room temperature overnight. Solvents were removed in vacuo; 15% aqueous solution of potassium hydrogencarbonate (60 mL) and 15% aqueous solution of sodium sulfite (60 mL) were subsequently added to the residue followed by ethyl acetate (300 mL). The phases were separated; the organic one was washed with water (100 mL) and brine (50 mL); dried over anhydrous sodium sulfate and evaporated to dryness. The residue was purified by flash column chromatography (Silicagel 60, 0.040-0.063 mm; eluent: cyclohexane/ethyl acetate 95:5 to 9:1) to give methyl 3-bromo-5-((3-bromo-5-fluorophenyl)sulfonyl)benzoate (4) as white solid.

Yield: 1.23 g (91%).

$R_F$ ($SiO_2$, n-hexane/ethyl acetate 9:1): 0.20.

$^1$H NMR spectrum (300 MHz, $CDCl_3$, $\delta_H$): 8.49 (m, 1H); 8.40 (dd, J=2.0 and 1.5 Hz, 1H); 8.24 (t, J=1.8 Hz, 1H); 7.90 (td, J=1.6 and 0.6 Hz, 1H); 7.62 (ddd, J=7.3, 2.3 and 1.6 Hz, 1H); 7.50 (ddd, J=7.7, 2.4 and 1.7 Hz, 1H); 3.98 (s, 3H).

$^{19}$F NMR spectrum (282 MHz, $CDCl_3$, $\delta_F$): −105.73 (s).

LC-MS purity: 100% (ELSD, UV 254 nm).

LC-MS Rt (Kinetex C18, 4.6 mm×50 mm, acetonitrile/water 35:65 to 100:0+0.1% FA): 4.14 min.

LC-MS m/z: 453.2 (M+H)+.

A solution of sodium hydroxide (535 mg, 13.4 mmol) in water (10 mL) was added to a solution of methyl 3-bromo-5-((3-bromo-5-fluorophenyl)sulfonyl)benzoate (4, 1.21 g, 2.68 mmol) in tetrahydrofuran (20 mL) and methanol (10 mL) and the resulting solution was stirred at room temperature over weekend. The mixture was concentrated in vacuo; acidified with 1 M aqueous hydrochloric acid (25 mL) and extracted with ethyl acetate (50 mL, 2×25 mL). Combined organic extracts were dried over anhydrous sodium sulfate and evaporated to dryness. The residue was dissolved in anhydrous N,N-dimethylformamide (20 mL), followed by addition of 1-((dimethylamino) (dimethyliminio)methyl)-1H-[1,2,3]triazolo[4,5-b]pyridine 3-oxide hexafluorophosphate (V) (HATU, 1.12 g, 2.95 mmol) and N,N-diisopropylethylamine (1.84 mL, 10.7 mmol). The mixture was stirred at room temperature for 5 minutes; then tert-butyl glycinate hydrochloride (483 mg, 3.22 mmol) was added and stirring continued for 2 hours. The reaction mixture was partitioned between 0.5 M aqueous hydrochloric acid (100 mL) and ethyl acetate (400 mL). The phases were separated and the organic one was washed with 0.5 M aqueous hydrochloric acid (100 mL), water (100 mL), 5% aqueous solution of sodium carbonate (100 mL) and brine; dried over anhydrous sodium sulfate and evaporated to dryness. The residue was purified by flash column chromatography (Silicagel 60, 0.040-0.063 mm; eluent: cyclohexane/ethyl acetate 9:1) to afford tert-butyl (3-bromo-5-((3-bromo-5-fluorophenyl) sulfonyl)benzoyl)glycinate (5) as colorless foam.

Yield: 900 mg (61%).

$R_F$ ($SiO_2$, n-hexane/ethyl acetate 3:2): 0.55.

$^1$H NMR spectrum (300 MHz, $CDCl_3$, $\delta_H$): 8.26 (t, J=1.6 Hz, 1H); 8.20-8.16 (m, 2H); 7.89 (td, J=1.5 and 0.7 Hz, 1H); 7.63-7.58 (m, 1H); 7.52-7.47 (m, 1H); 6.75 (bs, 1H); 4.14 (d, J=5.0 Hz, 2H); 1.52 (s, 9H).

$^{19}$F NMR spectrum (282 MHz, $CDCl_3$, $\delta_F$): −105.69 (s).

LC-MS purity: 100% (ELSD, UV 254 nm).

LC-MS Rt (Kinetex C18, 4.6 mm×50 mm, acetonitrile/water 50:50 to 100:0+0.1% FA): 3.27 min.

LC-MS m/z: 552.2 (M+H)+.

A 50 mL reaction flask was charged with potassium acetate (533 mg, 5.43 mmol) and the salt was dried for 1 hour at 110° C. in vacuo. After cooling to room temperature, the reaction flask was backfilled with argon and charged with tert-butyl (3-bromo-5-((3-bromo-5-fluorophenyl)sulfonyl)benzoyl)glycinate (5, 599 mg, 1.09 mmol), palladium acetate (12.2 mg, 54.0 μmol), 2-dicyclohexylphosphino-2',4',6'-triisopropylbiphenyl (XPhos, 51.8 mg, 109 μmol) and bis(pinacolato)diboron (607 mg, 2.39 mmol). The reaction flask was then evacuated and backfilled with argon (this procedure was repeated twice), anhydrous tetrahydrofuran (7 mL) was added with syringe, the flask was immersed in an oil bath pre-heated to 60° C. Reaction mixture was stirred at 60° C. for 20 hours, and then was cooled to ambient temperature, diluted with dichloromethane (7 mL) and filtered through a short plug of silicagel topped with Celite S and washed with dichloromethane (50 mL). The filtrate was concentrated under reduced pressure to afford the crude tert-butyl (3-((3-fluoro-5-(4,4,5,5-tetramethyl-1,3,2-dioxaborolan-2-yl)phenyl)sulfonyl)-5-(4,4,5,5-tetramethyl-1,3,2-dioxaborolan-2-yl)benzoyl)glycinate (6) as yellow foam.

Yield: 772 mg (crude product).

$R_F$ ($SiO_2$, n-hexane/ethyl acetate 3:2): 0.15.

$^1$H NMR spectrum (300 MHz, $CDCl_3$, $\delta_H$): 8.53-8.47 (m, 2H); 8.35 (dd, J=1.7 and 1.0 Hz, 1H); 8.17 (dd, J=1.7 and 0.8 Hz, 1H); 7.76-7.71 (m, 1H); 7.70-7.64 (m, 1H); 6.75 (t, J=4.9 Hz, 1H); 4.15 (d, J=5.0 Hz, 2H); 1.51 (s, 9H); 1.36 (s, 12H); 1.34 (s, 12H).

$^{19}$F NMR spectrum (282 MHz, $CDCl_3$, $\delta_F$): −110.47 (s).

LC-MS purity: 96% (ELSD).

LC-MS Rt (Kinetex C18, 4.6 mm×50 mm, acetonitrile/water 50:50 to 100:0+0.1% FA): 4.69 min.

LC-MS m/z: 646.7 (M+H)+.

A mixture of the above crude tert-butyl (3-((3-fluoro-5-(4,4,5,5-tetramethyl-1,3,2-dioxaborolan-2-yl)phenyl)sulfonyl)-5-(4,4,5,5-tetramethyl-1,3,2-dioxaborolan-2-yl)benzoyl)glycinate (6, 772 mg, <1.09 mmol) and trifluoroacetic acid (8.00 mL) was stirred for 1 hr at room temperature. The mixture was evaporated to dryness in vacuo, and the residue was evaporated from dichloromethane (5×10 mL) to afford crude (3-((3-fluoro-5-(4,4,5,5-tetramethyl-1,3,2-dioxaborolan-2-yl)phenyl)sulfonyl)-5-(4,4,5,5-tetramethyl-1,3,2-dioxaborolan-2-yl)benzoyl)glycine (7) as yellow foam.

Yield: 791 mg (crude product).

$^1$H NMR spectrum (300 MHz, $CDCl_3$, $\delta_H$): 8.54-8.48 (m, 2H); 8.43 (m, 1H); 8.16 (dd, J=1.7 and 0.8 Hz, 1H); 7.76-7.71 (m, 1H); 7.70-7.65 (m, 1H); 7.39 (t, J=5.3 Hz, 1H); 4.34 (d, J=5.3 Hz, 2H); 1.36 (s, 12H); 1.34 (s, 12H).

LC-MS purity: 85% (ELSD).

LC-MS Rt (Kinetex C18, 4.6 mm×50 mm, acetonitrile/water 50:50 to 100:0+0.1% FA): 3.16 min.

LC-MS m/z: 590.5 (M+H)+.

A solution of the above crude (3-((3-fluoro-5-(4,4,5,5-tetramethyl-1,3,2-dioxaborolan-2-yl)phenyl)sulfonyl)-5-(4,4,5,5-tetramethyl-1,3,2-dioxaborolan-2-yl)benzoyl)glycine (7, 791 mg, <1.09 mmol) in acetonitrile (6.5 mL) was diluted with water (1.3 mL) followed by addition of periodic acid (991 mg, 4.35 mmol). The resulting mixture was stirred for 1 hr; and then it was partitioned between ethyl acetate (80 mL) and water (20 mL). The phases were separated; the organic one was washed with brine (2×20 mL); dried over anhydrous sodium sulphate and evaporated to dryness. The residue was dissolved in a minimal amount of wet ethyl acetate (3 mL) and the resulting solution was slowly added to stirred n-hexane (50 mL) cooled to 0° C. Precipitated solid was decanted and dried to give 472 mg of crude product (8). A portion of the solid (8, 172 mg) was purified by preparative LC/MS (Synergi Polar-RP 80, 4 μm, 150×21.2 mm, acetonitrile/water 0:100 to 100:0+0.1% FA). Pure fractions were combined and freeze-dried to give the title compound (8) as white powder.

Yield: 100 mg (59%).

$R_F$ ($SiO_2$, acetonitrile/water/formic acid 89:10:1): 0.25.

$^1$H NMR spectrum (300 MHz, DMSO-$d_6$+DCl, $\delta_H$): 8.55 (dd, J=1.7 and 1.2 Hz, 1H); 8.50 (dd, J=1.8 and 1.1 Hz, 1H); 8.47 (t, J=1.8 Hz, 1H); 8.23 (dd, J=1.7 and 0.7 Hz, 1H); 7.90-7.85 (m, 1H); 7.85-7.79 (m, 1H); 3.93 (s, 2H).

$^{19}$F NMR spectrum (282 MHz, DMSO-$d_6$+DCl, $\delta_F$): −110.92 (s).

LC-MS purity: 100% (ELSD, UV 254 nm).

LC-MS Rt (Kinetex C18, 4.6 mm×50 mm, acetonitrile/water 5:95 to 100:0+0.1% FA): 3.12 min.

LC-MS m/z: 426.4 (M+H)+.

Example 25

N-(1-Hydroxy-4-(trifluoromethyl)-1,3-dihydrobenzo[c][1,2]oxaborole-6-carbonyl)-N-(2-(1-hydroxy-4-(trifluoromethyl)-1,3-dihydrobenzo[c][1,2]oxaborole-6-carboxamido)ethyl)glycine

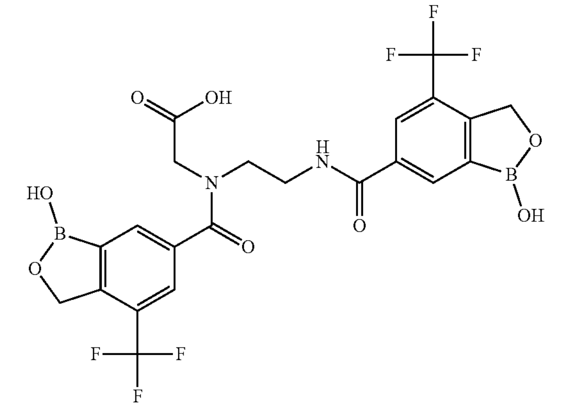 [SMILES: O=C(O)CN(CCNC(=O)c1cc2c(c(C(F)(F)F)c1)COB2O)C(=O)c1cc2c(c(C(F)(F)F)c1)COB2O]

N-(1-Hydroxy-4-(trifluoromethyl)-1,3-dihydrobenzo[c][1,2]oxaborole-6-carbonyl)-N-(2-(1-hydroxy-4-(trifluoromethyl)-1,3-dihydrobenzo[c][1,2]oxaborole-6-carboxamido)ethyl)glycine was synthesized according to the reaction scheme shown in Chem. 30 and following the procedure described below.

Chem. 30

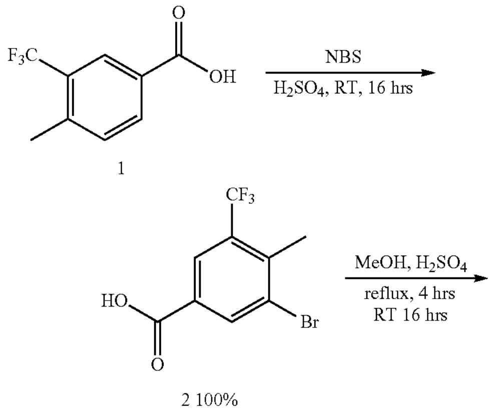

-continued

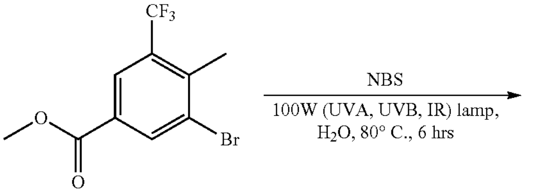

3 98%

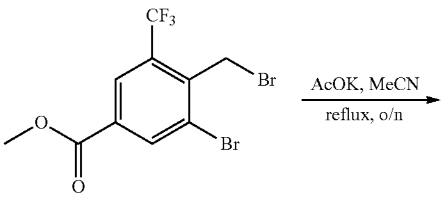

4 100%

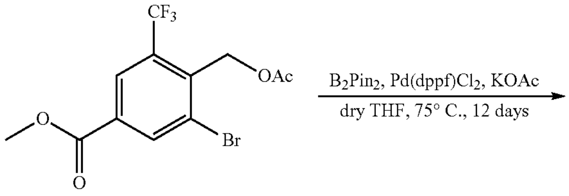

5 97%

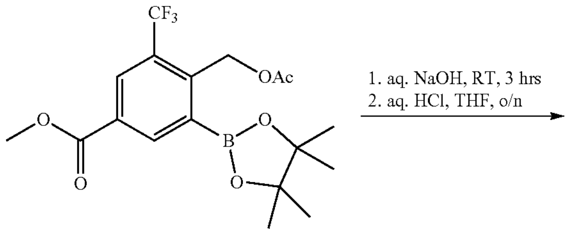

6 77%

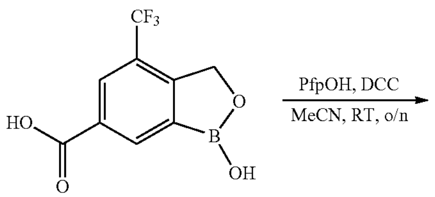

7 82%

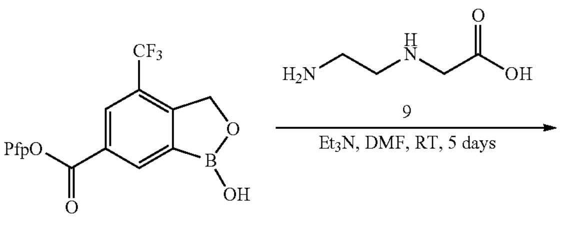

8 91%

-continued

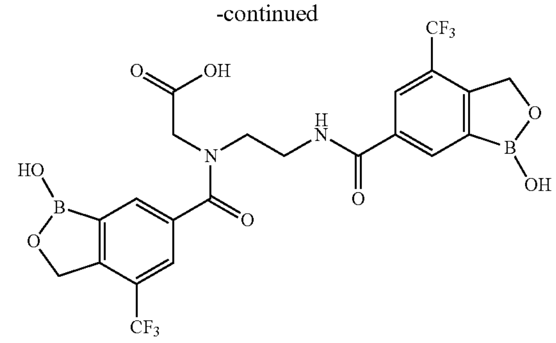

10 12%

1-Bromopyrrolidine-2,5-dione (NBS, 34.9 g, 196 mmol) was added to a solution of 3-trifluoromethyl-4-methylbenzoic acid (1, 40.0 g, 196 mmol) in concentrated sulfuric acid (400 mL) and the reaction mixture was allowed to stir at ambient temperature for 16 hours. The reaction mixture was then poured into ice-water (2 L). Resulting precipitate was filtered off, washed with water (500 mL) and dissolved in ethyl acetate (400 mL); dried over anhydrous sodium sulfate, filtered and evaporated to provide 3-bromo-4-methyl-5-trifluoromethylbenzoic acid (2) as white solid.

Yield: 55.4 g (100%).

$^1$H NMR spectrum (300 MHz, DMSO-$d_6$, $\delta_H$): 13.71 (bs, 1H); 8.35 (d, J=0.4 Hz, 1H); 8.15 (d, J=0.9 Hz, 1H); 2.56 (s, 3H).

Concentrated sulfuric acid (24 mL) was added to a solution 3-bromo-4-methyl-5-trifluoromethylbenzoic acid (2, 35.0 g, 124 mmol) in methanol (500 mL) and the reaction mixture was allowed to stir under reflux for 4 hours and at ambient temperature for 16 hours. The reaction mixture was then evaporated under reduced pressure, dissolved in diethyl ether (250 mL), extracted with water (2×100 mL) and mixture of saturated solution of potassium carbonate (100 mL) and brine (100 mL). Organic layer was separated, dried over anhydrous sodium sulfate, filtered and evaporated to provide methyl 3-bromo-4-methyl-5-trifluoromethylbenzoate (3) as white solid.

Yield: 36 g (98%).

$^1$H NMR spectrum (300 MHz, DMSO-$d_6$, $\delta_H$): 8.36 (d, J=1.1 Hz, 1H); 8.13 (d, J=1.1 Hz, 1H); 3.90 (s, 3H); 2.55 (d, J=1.3 Hz, 3H).

The suspension of 1-bromopyrrolidine-2,5-dione (NBS, 32.3 g, 181 mmol) and methyl 3-bromo-4-methyl-5-trifluoromethylbenzoate (3, 35.9 g, 121 mmol) in water (300 mL) was stirred for 6 hours under 100 W light bulb at 80° C. Reaction mixture was extracted with diethyl ether (2×200 mL). Organic layers were washed with brine (150 mL). Organic layer was separated, dried over anhydrous sodium sulfate, filtered and evaporated to provide methyl 3-bromo-4-bromomethyl-5-trifluoromethylbenzoate (4) as yellow solid.

Yield: 45.5 g (100%).

$^1$H NMR spectrum (300 MHz, $CDCl_3$, $\delta_H$): 8.47 (d, J=1.5 Hz, 1H); 8.31 (d, J=1.3 Hz, 1H); 4.75 (s, 2H); 3.98 (s, 3H).

Solution of 3-bromo-4-bromomethyl-5-trifluoromethylbenzoate (4, 45.5 g, 121 mmol) and potassium acetate (23.7 g, 142 mmol) in acetonitrile (0.5 L) was stirred at 75° C. overnight. The suspension was filtered through cotton-wool and evaporated. The crude product was dissolved in dichloromethane and filtered again. Evaporation provided methyl 3-bromo-4-(acetoxymethyl)-5-(trifluoromethyl)benzoate (5) as white solid.

Yield: 41.6 g (97%).

$^1$H NMR spectrum (300 MHz, $CDCl_3$, $\delta_H$): 8.49 (d, J=1.3 Hz, 1H); 8.34 (d, J=1.3 Hz, 1H); 5.37 (s, 2H); 3.99 (s, 3H); 2.11 (s, 3H).

Solution of methyl 3-bromo-4-acetylmethyl-5-trifluoromethylbenzoate (5, 40.5 g, 114 mmol), bis(pinacolato)diboron (31.9 g, 126 mmol), potassium acetate (33.6 g, 343 mmol) and [1,1'-bis(diphenylphosphino)ferrocene]dichloropalladium(II) (2.50 g, 3.42 mmol) in dry tetrahydrofuran (500 mL) was allowed to stir at 75° C. under argon atmosphere for 12 days. Then the reaction mixture was cooled to ambient temperature, filtered and evaporated. The crude product was filtered through silica gel (Silicagel, 0.063-0.200 mm; eluent: cyclohexane/ethyl acetate 8:1) to provide methyl 4-(acetoxymethyl)-3-(4,4,5,5-tetramethyl-1,3,2-dioxaborolan-2-yl)-5-(trifluoromethyl)benzoate (6).

Yield: 35.3 g (77%).

$R_F$ ($SiO_2$, cyclohexane/ethyl acetate 8:1): 0.40.

$^1$H NMR spectrum (300 MHz, $CDCl_3$, $\delta_H$): 8.65 (s, 1H); 8.43 (s, 1H); 5.48 (s, 2H); 3.97 (s, 3H); 2.05 (s, 3H); 1.36 (s, 12H).

Solution of methyl 4-(acetoxymethyl)-3-(4,4,5,5-tetramethyl-1,3,2-dioxaborolan-2-yl)-5-(trifluoromethyl)benzoate (6, 34.0 g, 84.6 mmol) and sodium hydroxide (17.0 g, 425 mmol) in water (300 mL) was stirred at ambient temperature for 3 hours. Then solution of hydrochloric acid (35%, 37 mL) in water (100 mL) was added to lower the pH to 1. The reaction mixture was stirred overnight. Precipitate was filtered and dried to provide 1-hydroxy-4-(trifluoromethyl)-1,3-dihydrobenzo[c][1,2]oxaborole-6-carboxylic acid (7) as white solid.

Yield: 17.0 g (82%).

$^1$H NMR spectrum (300 MHz, DMSO-$d_6$, $\delta_H$): 13.47 (bs, 1H); 9.66 (s, 1H); 8.62 (s, 1H); 8.24 (s, 1H); 5.22 (s, 2H).

Solution of 2,3,4,5,6-pentafluorophenol (497 mg, 2.70 mmol), 1-hydroxy-4-(trifluoromethyl)-1,3-dihydrobenzo[c][1,2]oxaborole-6-carboxylic acid (7, 665 mg, 2.70 mmol) and N,N'-dicyclohexylcarbodiimide (DCC, 556 mg, 2.70 mmol) in acetonitrile (15 mL) was stirred at ambient temperature overnight. The reaction mixture was filtered, washed with acetonitrile and evaporated to give the perfluorophenyl 1-hydroxy-4-(trifluoromethyl)-1,3-dihydrobenzo[c][1,2]oxaborole-6-carboxylate (8) as white solid.

Yield: 1.00 g (91%).

$^1$H NMR spectrum (300 MHz, DMSO-$d_6$, $\delta_H$): 9.79 (s, 1H); 8.86 (s, 1H); 8.46 (s, 1H); 5.30 (s, 2H).

Solution of the perfluorophenyl 1-hydroxy-4-(trifluoromethyl)-1,3-dihydrobenzo [c][1,2]oxaborole-6-carboxylate (8, 850 mg, 2.06 mmol), (2-aminoethyl)glycine (9, 122 mg, 1.03 mmol) and triethylamine (1.15 mL, 8.27 mmol) in N,N-dimethylformamide (25 mL) was stirred at ambient temperature for 5 days. The reaction mixture was then evaporated and crude product 10 was filtered through short pad of silica gel (eluent: dichloromethane/methanol 10:1 to 4:1), purified by preparative HPLC (SunFire Prep C18, 5 μm, 19×100 mm, acetonitrile/water 5:95 to 100:0+0.1% FA) and freeze-dried to N-(1-hydroxy-4-(trifluoromethyl)-1,3-dihydrobenzo[c][1,2]oxaborole-6-carbonyl)-N-(2-(1-hydroxy-4-(trifluoromethyl)-1,3-dihydrobenzo[c][1,2]oxaborole-6-carboxamido) ethyl)glycine (10) as white solid.

Yield: 70.0 mg (12%).

$^1$H NMR spectrum (300 MHz, DMSO-$d_6$, $\delta_H$): 12.91 (bs, 1H); 9.91-9.40 (m, 2H); 9.02-8.65 (m, 1H); 8.67-7.41 (m, 4H); 5.28-5.03 (m, 4H); 4.37-3.90 (m, 2H); 3.79-3.42 (m, 4H).

LC-MS purity: 100% (ELSD).

LC-MS Rt (Kinetex C18, 4.6 mm×50 mm, acetonitrile/water 5:95 to 100:0+0.1% FA): 3.63 min.

LC-MS m/z: 575.5 $(M+H)^+$.

Example 26

(S)-2,3-Bis(1-hydroxy-4-(trifluoromethyl)-1,3-dihydrobenzo[c][1,2]oxaborole-6-carboxamido)propanoic acid

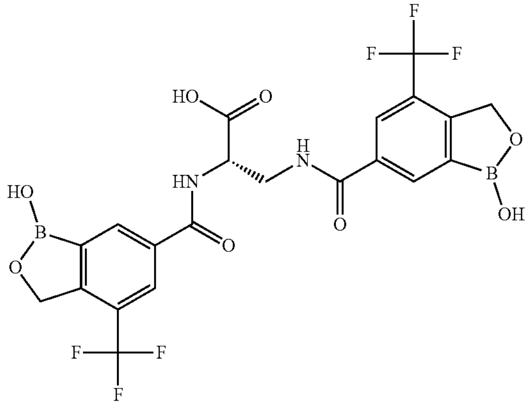 [SMILES: O=C(NC[C@H](NC(=O)c1cc2c(c(C(F)(F)F)c1)COB2O)C(=O)O)c1cc2c(c(C(F)(F)F)c1)COB2O]

(S)-2,3-Bis(1-hydroxy-4-(trifluoromethyl)-1,3-dihydrobenzo[c][1,2]oxaborole-6-carboxamido)propanoic acid was synthesized according to the reaction scheme shown in Chem. 31 and following the procedure described below.

Chem. 31

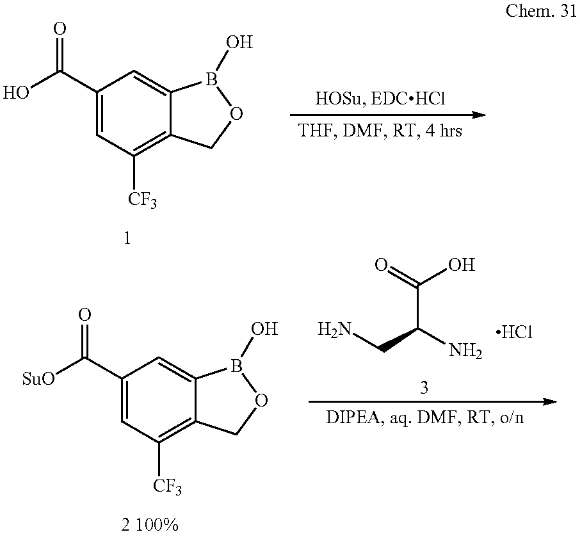

-continued

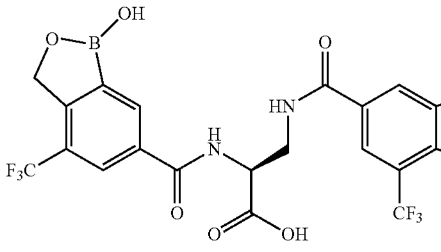

4 39%

1-Hydroxy-4-(trifluoromethyl)-1,3-dihydrobenzo[c][1,2]oxaborole-6-carboxylic acid (1, 3.50 g, 14.2 mmol), N-hydroxysuccinimide (1.64 g, 14.2 mmol) and 1-ethyl-3-(3'-dimethylaminopropyl) carbodiimide hydrochloride (2.72 g, 14.2 mmol) were stirred in tetrahydrofuran (70 mL) and N,N-dimethylformamide (10 mL) for 4 hours at ambient temperature. The reaction mixture was evaporated and extracted with ethyl acetate (3×100 mL) and 1 M aqueous solution of hydrochloric acid (100 mL). The organic phase was dried over anhydrous sodium sulfate, filtered and evaporated to afford 2,5-dioxopyrrolidin-1-yl 1-hydroxy-4-(trifluoromethyl)-1,3-dihydrobenzo[c][1,2]oxaborole-6-carboxylate (2) as white solid.

Yield: 4.87 g (100%).

LC-MS purity: 100% (ELSD).

LC-MS Rt (Kinetex C18, 4.6 mm×50 mm, acetonitrile/water 35:65 to 100:0+0.1% FA): 2.32 min.

LC-MS m/z: 344.3 $(M+H)^+$.

Solution of afforded 2,5-dioxopyrrolidin-1-yl 1-hydroxy-4-(trifluoromethyl)-1,3-dihydrobenzo[c][1,2]oxaborole-6-carboxylate (2, 515 mg, 1.50 mmol), (S)-2,3-diaminopropanoic acid hydrochloride (3, 98.0 mg, 0.70 mmol) and N,N-diisopropylethylamine (0.75 mL, 4.20 mmol) in N,N-dimethylformamide (15 mL) and water (4 mL) was stirred at ambient temperature overnight. The reaction mixture was evaporated, purified by preparative HPLC (SunFire Prep C18, 5 μm, 19×100 mm, acetonitrile/water 5:95 to 100:0+0.1% FA) and freeze-dried to afford (S)-2,3-bis(1-hydroxy-4-(trifluoromethyl)-1,3-dihydrobenzo[c][1,2]oxaborole-6-carboxamido)propanoic acid (4) as white solid.

Yield: 153 mg (39%).

$^1$H NMR spectrum (300 MHz, DMSO-$d_6$, $\delta_H$): 12.90 (bs, 1H); 9.62 (d, J=4.2 Hz, 2H); 9.10 (d, J=8.1 Hz, 1H); 8.99 (t, J=5.2 Hz, 1H); 8.50 (d, J=15.0 Hz, 2H); 8.25 (d, J=21.1 Hz, 2H); 5.21 (d, J=5.5 Hz, 4H); 4.84-4.63 (m, 1H); 3.99-3.81 (m, 1H); 3.79-3.59 (m, 1H).

LC-MS purity: 100% (ELSD).

LC-MS Rt (Kinetex C18, 4.6 mm×50 mm, acetonitrile/water 5:95 to 100:0+0.1% FA): 3.70 min.

LC-MS m/z: 561.5 $(M+H)^+$.

Example 27

4-((3S,4S)-3,4-Bis(1-hydroxy-4-(trifluoromethyl)-1,3-dihydrobenzo[c][1,2]oxaborole-6-carboxamido)pyrrolidin-1-yl)-4-oxobutanoic acid

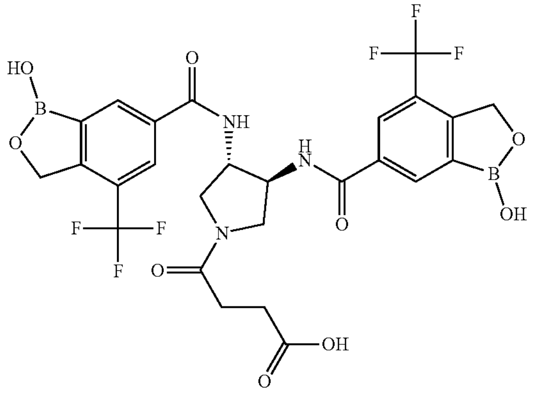 [SMILES: O=C(O)CCC(=O)N1C[C@H](NC(=O)c2cc3c(c(C(F)(F)F)c2)COB3O)[C@@H](NC(=O)c2cc3c(c(C(F)(F)F)c2)COB3O)C1]

4-((3S,4S)-3,4-Bis(1-hydroxy-4-(trifluoromethyl)-1,3-dihydrobenzo[c][1,2]oxaborole-6-carboxamido)pyrrolidin-1-yl)-4-oxobutanoic acid was synthesized according to the reaction scheme shown in Chem. 32 and following the procedure described below.

Chem. 32

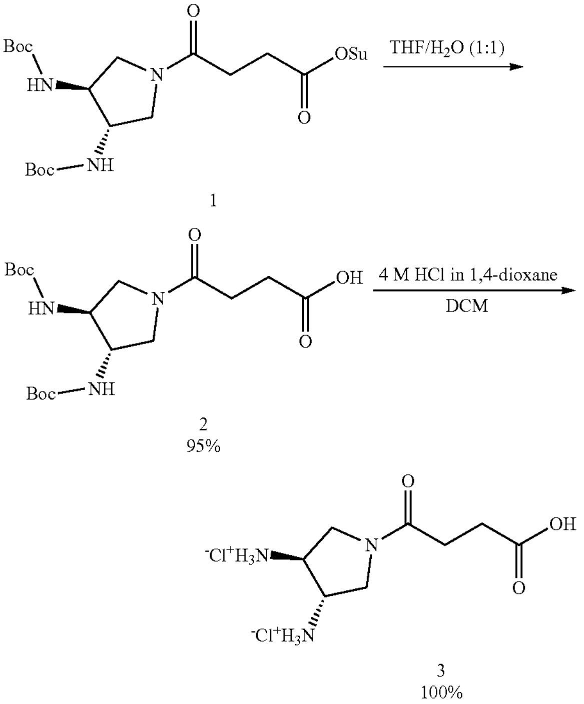

-continued

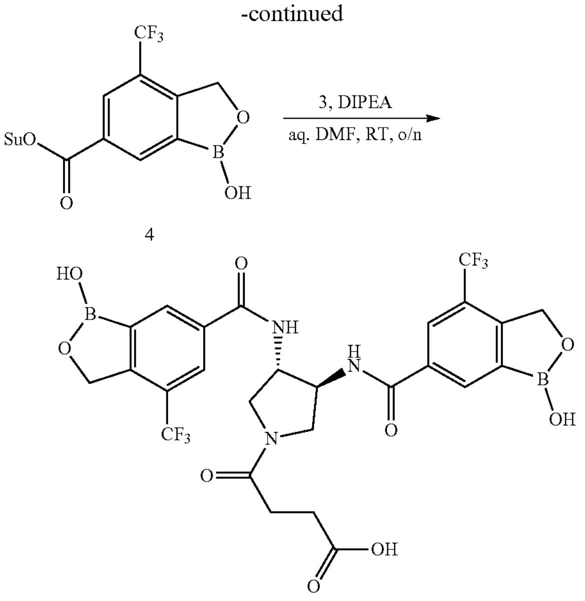

4

5
31%

2,5-Dioxopyrrolidin-1-yl 4-((3S,4S)-3,4-bis((tert-butoxycarbonyl)amino) pyrrolidin-1-yl)-4-oxobutanoate (1, 6.57 g, 13.2 mmol) was dissolved in tetrahydrofuran/water mixture (1:1, 100 mL) and left to stay for 5 days. The mixture was diluted with ethyl acetate (100 mL) and washed with 1 M aqueous solution of hydrochloric acid (1×100 mL), water (2×100 mL) and brine (1×100 mL). Organic layer was dried over anhydrous sodium sulfate, filtered and evaporated to dryness affording 4-((3S,4S)-3,4-bis((tert-butoxycarbonyl)amino)pyrrolidin-1-yl)-4-oxobutanoic acid (2) as white solid.

Yield: 4.60 g (95%).

$^1$H NMR spectrum (300 MHz, $CDCl_3$, $\delta_H$): 5.54-5.43 (m, 1H); 5.37-5.24 (m, 1H); 4.11-3.80 (m, 4H); 3.33-3.17 (m, 2H); 2.74-2.42 (m, 4H); 1.45 (s, 18H).

The acid (2, 4.59 g, 11.4 mmol) was dissolved in dichloromethane (10 mL) and 4 M solution of hydrogen chloride in 1,4-dioxane (100 mL) was added. After 30 minutes the solvent was evaporated. The residue was suspended in ethyl acetate (100 mL), the insoluble material was filtered, washed with ethyl acetate and dried in vacuo to yield 4-((3S,4S)-3,4-diaminopyrrolidin-1-yl)-4-oxobutanoic acid dihydrochloride (3) as white powder.

Yield: 3.33 g (100%).

$^1$H NMR spectrum (300 MHz, $D_2O$, $\delta_H$): 4.32-4.17 (m, 3H); 4.09-3.99 (m, 1H); 3.91-3.84 (m, 1H); 3.77-3.68 (m, 1H); 2.67 (s, 4H).

Solution of 4-((3S,4S)-3,4-diaminopyrrolidin-1-yl)-4-oxobutanoic acid dihydrochloride (3, 137 mg, 0.50 mmol), 2,5-dioxopyrrolidin-1-yl 1-hydroxy-4-(trifluoromethyl)-1,3-dihydrobenzo[c][1,2]oxaborole-6-carboxylate (4, 343 mg, 1.00 mmol) and N,N-diisopropylethylamine (0.54 mL, 3.00 mmol) in N,N-dimethylformamide (12 mL) and water (3 mL) was stirred at ambient temperature overnight. The reaction mixture was evaporated, purified by preparative HPLC (SunFire Prep C18, 5 μm, 19×100 mm, acetonitrile/water 5:95 to 100:0+0.1% FA) and freeze-dried to afford 4-((3S,4S)-3,4-bis(1-hydroxy-4-(trifluoromethyl)-1,3-dihydrobenzo[c][1,2]oxaborole-6-carboxamido)pyrrolidin-1-yl)-4-oxobutanoic acid (5) as white solid.

Yield: 103 mg (31%).

$^1$H NMR spectrum (300 MHz, DMSO-$d_6$, $\delta_H$) 12.12 (bs, 1H); 9.63 (s, 2H); 9.01 (dd, J=10.2 and 7.2 Hz, 2H); 8.48 (s, 2H); 8.23 (s, 2H); 5.20 (s, 4H); 4.82-4.55 (m, 2H); 4.01 (dd, J=10.4 and 6.3 Hz, 1H); 3.86 (dd, J=12.3 and 7.0 Hz, 1H); 3.50 (dd, J=10.7 and 7.4 Hz, 2H); 2.49-2.37 (m, 4H).

LC-MS purity: 100% (ELSD).

LC-MS Rt (Kinetex C18, 4.6 mm×50 mm, acetonitrile/water 5:95 to 100:0+0.1% FA): 3.66 min.

LC-MS m/z: 658.7 $(M+H)^+$.

Example 28

(3-Borono-5-((3-borono-5-(pentafluoro-$\lambda^6$-sulfanyl)phenyl)sulfonyl)benzoyl)glycine

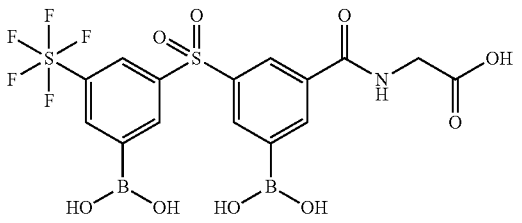 [SMILES: O=C(O)CNC(=O)c1cc(B(O)O)cc(S(=O)(=O)c2cc(B(O)O)cc(S(F)(F)(F)(F)F)c2)c1]

(3-Borono-5-((3-borono-5-(pentafluoro-$\lambda^6$-sulfanyl)phenyl)sulfonyl)benzoyl)glycine was synthesized according to the reaction scheme shown in Chem. 33 and following the procedure described below.

Chem. 33

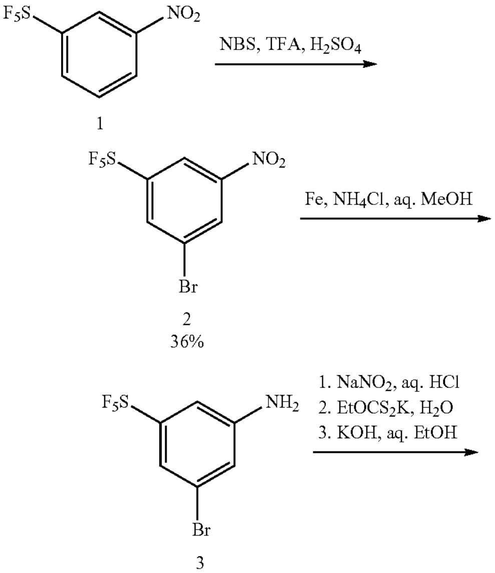

1

2
36%

3
91%

-continued

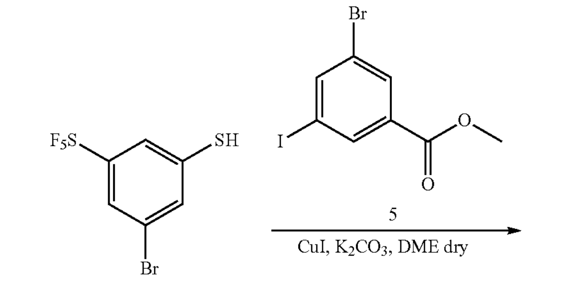

4
<41%

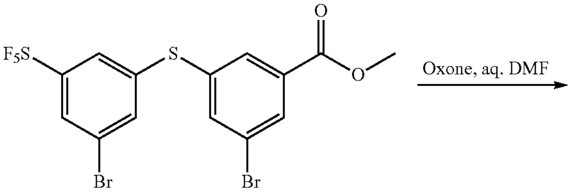

6

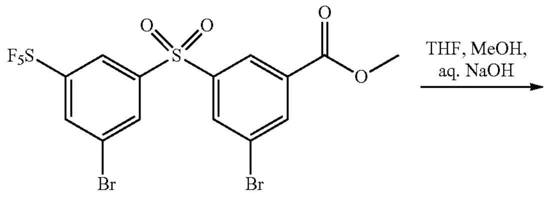

7
6% (from 3)

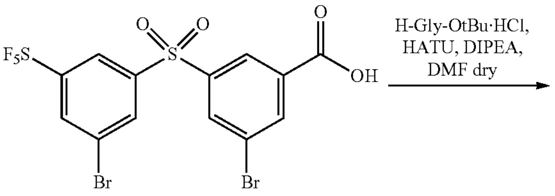

8
97%

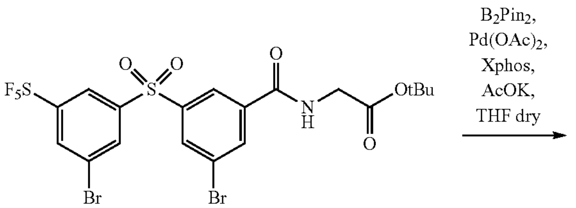

9
85%

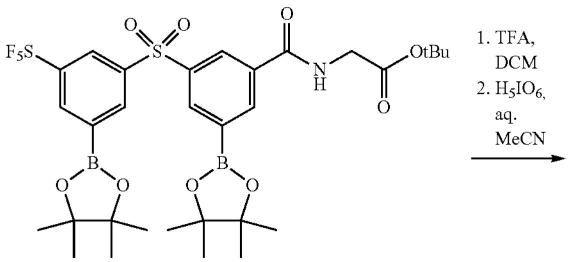

10

-continued

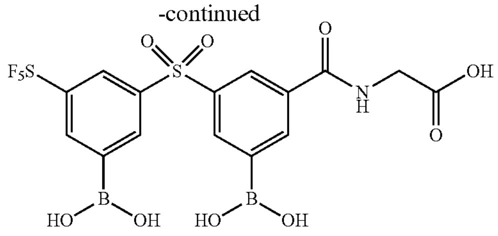

11
40% (from 9)

N-Bromosuccinimide (25.2 g, 142 mmol) was added in ten equal portions to a mixture of pentafluoro(3-nitrophenyl)-$\lambda^6$-sulfane (1, 23.3 g, 93.5 mmol), trifluoroacetic acid (75 mL) and 98% sulfuric acid (25 mL) at 40° C. during 8 hours. The reaction mixture was stirred at 40° C. overnight. Then the mixture was portioned between ethyl acetate (0.5 L) and ice-cold water (1 L). Organic phase was washed with 10% aqueous solution of potassium carbonate (1 L), 10% aqueous solution of sodium sulfite (1 L) and brine (1 L) prior to drying over anhydrous magnesium sulfate. Solvent was removed in vacuo and the residue was purified twice by flash column chromatography (Silicagel 60, 0.040-0.063 mm; eluent: cyclohexane/ethyl acetate 100:0 to 90:10) to give (3-bromo-5-nitrophenyl)pentafluoro-$\lambda^6$-sulfane (2) as yellowish crystalline solid.

Yield: 10.9 g (36%).

$^1$H NMR spectrum (300 MHz, $CDCl_3$, $\delta_H$): 8.62-8.51 (m, 2H); 8.24 (t, J=1.7 Hz, 1H).

A thoroughly degassed mixture of (3-bromo-5-nitrophenyl)pentafluoro-$\lambda^6$-sulfane (2, 5.88 g, 17.9 mmol), iron (5.01 g, 89.6 mmol) and ammonium chloride (9.59 g, 179 mmol) in methanol/water (2:1, 36 mL) was heated under argon atmosphere to 90° C. for 1.5 hours. Insolubles were removed by filtration, and volatiles were removed under reduced pressure. The residue was dissolved in ethyl acetate (400 mL) and washed with brine (2×500 mL) prior to drying over anhydrous magnesium sulfate. Solvent was removed in vacuo, and the residue was purified by flash column chromatography (Silicagel 60, 0.040-0.063 mm; eluent: cyclohexane/ethyl acetate 10:0 to 9:1) to give 3-bromo-5-(pentafluoro-$\lambda^6$-sulfanyl)aniline (3) as yellowish crystalline solid.

Yield: 4.86 g (91%).

$^1$H NMR spectrum (300 MHz, $CDCl_3$, $\delta_H$): 7.25 (t, J=1.7 Hz, 1H); 7.02-6.89 (m, 2H); 3.95 (bs, 2H).

A solution of sodium nitrite (915 mg, 13.2 mmol) in water (10 mL) was added drop-wise to a mixture of 3-bromo-5-(pentafluoro-$\lambda^6$-sulfanyl)aniline (3, 3.76 g, 12.6 mmol) and 35% hydrochloric acid (3.5 mL) in water (10 mL) at 0° C. The mixture was stirred for further 30 minutes at 0° C. Then this solution was added to a solution of potassium O-ethyldithiocarbonate (5.05 g, 31.5 mmol) in water (50 mL) at 50° C., and it was heated and stirred for further 60 minutes. The mixture was cooled to room temperature and extracted with ethyl acetate (300 mL). The organic phase was washed with 10% aqueous solution of sodium hydroxide (500 mL), brine (500 mL), 0.5 M aqueous solution hydrochloric acid (500 mL) and brine (500 mL) prior to drying over anhydrous magnesium sulfate. Solvent was removed under reduced pressure. The residue was dissolved in ethanol (50 mL) and solution of potassium hydroxide (7.08 g, 126 mmol) in water (50 mL) was added. The resulting mixture was heated to 80° C. for 12 hours. Volatiles were removed under reduced pressure. The residue was diluted with water (350 mL) and washed with diethyl ether (500 mL). Aqueous phase was acidified with 35% hydrochloric acid to pH 1 and then extracted with ethyl acetate (500 mL). Organic phase was washed with brine (2×500 mL) prior to drying over anhydrous magnesium sulfate. Solvent was removed in vacuo and the residue was purified by flash column chromatography (Silicagel 60, 0.040-0.063 mm; eluent: cyclohexane) to give 3-bromo-5-(pentafluoro-$\lambda^6$-sulfanyl)benzenethiol (4) contaminated with unidentified inseparable impurities as colorless crystalline solid.

Yield: 1.64 g (<41%).

$^1$H NMR spectrum (300 MHz, $CDCl_3$, $\delta_H$): 7.70-7.65 (m, 1H); 7.62-7.35 (m, 2H); 3.69 (s, 1H).

A mixture of 3-bromo-5-(pentafluoro-$\lambda^6$-sulfanyl)benzenethiol (4, 1.62 g, 5.14 mmol), methyl 3-bromo-5-iodobenzoate (5, 1.75 g, 5.14 mmol), copper(I) iodide (98.0 mg, 0.51 mol), potassium carbonate (1.42 g, 10.3 mmol) and dry 1,2-dimethoxyethane (20 mL) was heated at 80° C. under argon for 48 hours. The reaction mixture was cooled to room temperature; diluted with ethyl acetate (30 mL); filtered over Celite and evaporated to dryness. The residue was dissolved in ethyl acetate (250 mL); washed with 1 M aqueous solution of hydrochloric acid (250 mL) and brine (250 mL); dried over anhydrous sodium sulfate and evaporated to dryness. The residue was subjected to flash column chromatography (Silicagel 60, 0.040-0.063 mm; eluent: cyclohexane/ethyl acetate 100:0 to 98:2) to give methyl 3-bromo-5-((3-bromo-5-(pentafluoro-$\lambda^6$-sulfanyl)phenyl)thio) benzoate (6) contaminated with methyl 3-bromo-5-iodobenzoate (5) as pale yellow oil.

Yield: 1.46 g.

Content: ~60% ($^1$H NMR).

$^1$H NMR spectrum (300 MHz, $CDCl_3$, $\delta_H$): 8.16 (t, J=1.7 Hz, 1H); 8.01 (t, J=1.7 Hz, 1H); 7.79 (t, J=1.7 Hz, 1H); 7.72 (t, J=1.7 Hz, 1H); 7.63 (t, J=1.7 Hz, 1H); 7.51 (s, 1H); 3.94 (s, 3H).

Potassium peroxymonosulfate (2.52 g, 4.10 mmol) was added to a solution of methyl 3-bromo-5-((3-bromo-5-(pentafluoro-$\lambda^6$-sulfanyl)phenyl)thio)benzoate (6, 1.45 g, <2.74 mmol) in N,N-dimethylformamide (30 mL) and water (5 mL), and the reaction mixture was stirred at room temperature overnight. One more portion of potassium peroxymonosulfate (2.52 g, 4.10 mmol) was added and the reaction mixture was stirred at room temperature overnight. Solvents were removed in vacuo; 15% aqueous solution of potassium hydrogencarbonate (60 mL) and 15% aqueous solution of sodium sulfite (60 mL) were subsequently added to the residue followed by ethyl acetate (300 mL). The phases were separated; the organic one was washed with water (100 mL) and brine (50 mL); dried over anhydrous sodium sulfate and evaporated to dryness. The residue was purified by flash column chromatography (Silicagel 60, 0.040-0.063 mm; eluent: cyclohexane/ethyl acetate 100:0 to 95:5) to give methyl 3-bromo-5-((3-bromo-5-(pentafluoro-$\lambda^6$-sulfanyl) phenyl) sulfonyl)benzoate (7) as white solid.

Yield: 421 mg (6% from 3).

$^1$H NMR spectrum (300 MHz, $CDCl_3$, $\delta_H$): 8.54-8.48 (m, 1H); 8.45-8.40 (m, 1H); 8.28 (t, J=1.7 Hz, 1H); 8.26 (t, J=1.7 Hz, 1H); 8.21 (t, J=1.8 Hz, 1H); 8.12 (t, J=1.8 Hz, 1H); 3.99 (s, 3H).

LC-MS purity: 100% (ELSD).

LC-MS Rt (Kinetex C18, 4.6 mm×50 mm, acetonitrile/water 70:30 to 100:0+0.1% FA): 2.25 min.

LC-MS m/z: mass not found.

Solution of sodium hydroxide (169 mg, 4.22 mmol) in water (10 mL) was added to a solution of methyl 3-bromo-5-((3-bromo-5-(pentafluoro-$\lambda^6$-sulfanyl)phenyl)sulfonyl) benzoate (7, 472 mg, 10.9 mmol) in tetrahydrofuran/methanol (2:1, 30 mL). The mixture was stirred at room temperature for 20 hours. Volatiles were removed under reduced pressure. The residue was acidified with 1 M aqueous solution of hydrochloric acid (100 mL) and extracted with ethyl acetate (2×150 mL). Combined organic phase was washed brine (250 mL) prior to drying over anhydrous magnesium sulfate. Solvent was removed in vacuo to give 3-bromo-5-((3-bromo-5-(pentafluoro-$\lambda^6$-sulfanyl)phenyl) sulfonyl)benzoic acid (8) as yellowish solid which was used in the next step without further purification.

Yield: 448 mg (97%).

$^1$H NMR spectrum (300 MHz, $CDCl_3$, $\delta_H$): 8.57 (t, J=1.6 Hz, 1H); 8.50-8.46 (m, 1H); 8.33-8.28 (m, 2H); 8.23 (t, J=1.8 Hz, 1H); 8.13 (t, J=1.8 Hz, 1H).

LC-MS purity: 100% (ELSD).

LC-MS Rt (Kinetex C18, 4.6 mm×50 mm, acetonitrile/water 5:95 to 100:0+0.1% FA): 4.82 min.

LC-MS m/z: mass not found.

A mixture of 3-bromo-5-((3-bromo-5-(pentafluoro-$\lambda^6$-sulfanyl)phenyl)sulfonyl) benzoic acid (8, 448 mg, 0.82 mmol), tert-butyl glycinate hydrochloride (166 mg, 0.99 mmol), N,N-diisopropylethylamine (0.57 mL, 3.29 mmol) and 1-((dimethylamino) (dimethyliminio)methyl)-1H-[1,2,3]triazolo[4,5-b]pyridine 3-oxide hexafluorophosphate (V) (HATU, 344 mg, 0.91 mmol) in anhydrous N,N-dimethylformamide (20 mL) was stirred at room temperature for 16 hours. The mixture was portioned between ethyl acetate (150 mL) and 0.5 M aqueous solution of hydrochloric acid (150 mL). Organic phase was washed brine (150 mL) prior to drying over anhydrous magnesium sulfate. Solvent was removed in vacuo and the residue was purified by flash column chromatography (Silicagel 60, 0.040-0.063 mm; eluent: cyclohexane/ethyl acetate 95:5 to 9:1) to give tert-butyl (3-bromo-5-((3-bromo-5-(pentafluoro-$\lambda^6$-sulfanyl) phenyl) sulfonyl)benzoyl)glycinate (9) as colorless foam.

Yield: 462 mg (85%).

$^1$H NMR spectrum (300 MHz, $CDCl_3$, $\delta_H$): 8.28 (s, 2H); 8.24-8.16 (m, 3H); 8.12 (t, J=1.7 Hz, 1H); 6.70 (t, J=4.6 Hz, 1H); 4.14 (d, J=5.0 Hz, 2H); 1.52 (s, 9H).

LC-MS purity: 100% (ELSD), 100% (UV, 254 nm).

LC-MS Rt (Kinetex C18, 4.6 mm×50 mm, acetonitrile/water 50:50 to 100:0+0.1% FA): 3.27 min.

LC-MS m/z: 604.2 $(M\text{-}tBu)^+$.

A mixture of tert-butyl (3-bromo-5-((3-bromo-5-(pentafluoro-$\lambda^6$-sulfanyl) phenyl)sulfonyl)benzoyl)glycinate (9, 444 mg, 0.67 mmol), palladium acetate (8.00 mg, 34.0 μmol), 2-dicyclohexylphosphino-2',4',6'-triisopropylbiphenyl (XPhos, 32.0 mg, 67.0 μmol), bis(pinacolato)diboron (376 mg, 1.48 mmol) and potassium acetate (330 mg, 3.36 mmol) in anhydrous tetrahydrofuran (25 mL) was heated under argon atmosphere at 60° C. for 23 hours. The mixture was cooled down to room temperature, diluted with dichloromethane (200 mL) and passed through a short plug of silica (Silicagel 60, 0.040-0.060 mm; eluent: dichloromethane). Solvents were removed under reduced pressure to give crude tert-butyl (3-((3-(pentafluoro-$\lambda^6$-sulfanyl)-5-(4,4,5,5-tetramethyl-1,3,2-dioxaborolan-2-yl)phenyl)sulfonyl)-5-(4,4,5,5-tetramethyl-1,3,2-dioxaborolan-2-yl) benzoyl)glycinate (10) as brownish foam. It was dissolved in dichloromethane (15 mL) and trifluoroacetic acid (15 mL) was added. Resulting solution was stirred at room temperature for 2 hours. Volatiles were removed under reduced pressure. The residue was dissolved in aqueous acetonitrile (3:1, 50 mL) and periodic acid (617 mg, 2.70 mmol) was added. Resulting mixture was stirred at room temperature for one hour. Volatiles were removed under reduced pressure and the residue was portioned between ethyl acetate (250 mL) and water (250 mL). Organic phase was washed with brine (250 mL) prior to drying over anhydrous magnesium sulfate. Solvent was removed in vacuo and the residue was purified twice by preparative LC/MS (SunFire Prep C18, 5 μm, 19×100 mm, acetonitrile/water 5:95 to 100:0+0.1% FA). Fractions containing product were freeze-dried to give (3-borono-5-((3-borono-5-(pentafluoro-$\lambda^6$-sulfanyl)phenyl) sulfonyl)benzoyl)glycine (11) as white solid.

Yield: 142 mg (40%).

$^1$H NMR spectrum (300 MHz, DMSO-$d_6$+one drop of 20% DCl in $D_2O$, $\delta_H$): 8.67 (s, 1H); 8.62-8.52 (m, 3H); 8.52-8.47 (m, 1H); 8.41-8.34 (m, 1H); 3.94 (s, 2H).

LC-MS purity: 100% (ELSD), 100% (UV, 254 nm).

LC-MS Rt (Kinetex C18, 4.6 mm×50 mm, acetonitrile/water 5:95 to 100:0+0.1% FA): 3.44 min.

LC-MS m/z: 534.3 $(M+H)^+$.

Example 29

4-[(3R,4R)-3,4-bis[[1-hydroxy-4-(trifluoromethyl)-3H-2,1-benzoxaborole-6-carbonyl]amino]pyrrolidin-1-yl]-4-oxobutanoic acid

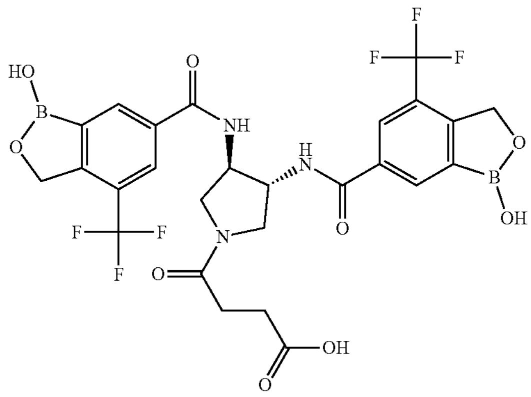 [SMILES: O=C(O)CCC(=O)N1C[C@@H](NC(=O)c2cc3c(c(C(F)(F)F)c2)COB3O)[C@H](NC(=O)c2cc3c(c(C(F)(F)F)c2)COB3O)C1]

4-[(3R,4R)-3,4-bis[[1-hydroxy-4-(trifluoromethyl)-3H-2,1-benzoxaborole-6-carbonyl]amino]pyrrolidin-1-yl]-4-oxobutanoic acid was prepared similarly to the compound of Example 27 from 4-((3R,4R)-3,4-bis((tert-butoxycarbonyl)amino)pyrrolidin-1-yl)-4-oxobutanoic acid.

Example 30

2-((Bis(3-borono-5-(trifluoromethyl)phenyl)(oxo)-λ6-sulfanylidene)amino)acetic acid

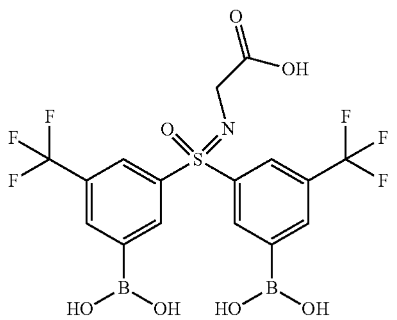 [SMILES: O=C(O)CN=S(=O)(c1cc(B(O)O)cc(C(F)(F)F)c1)c1cc(B(O)O)cc(C(F)(F)F)c1]

2-((Bis(3-borono-5-(trifluoromethyl)phenyl)(oxo)-λ6-sulfanylidene)amino)acetic acid was synthesized according to the reaction scheme shown in Chem. 34 and following the procedure described below.

Chem. 34

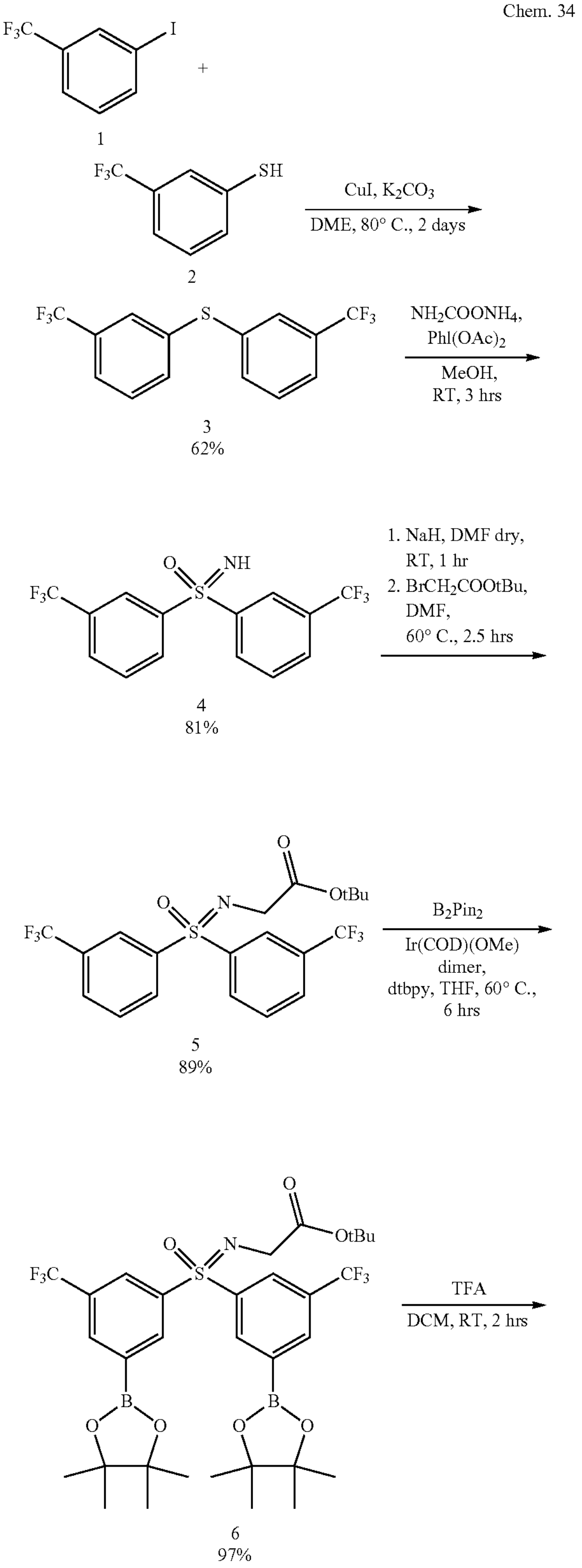

-continued

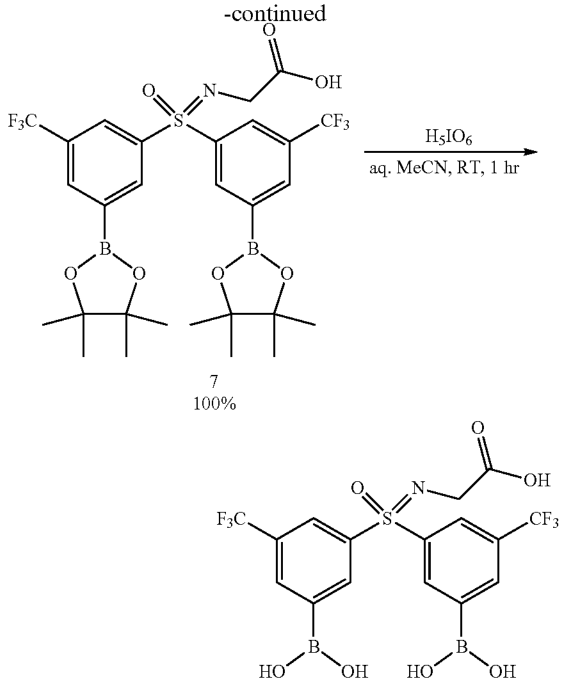

7
100%

8
79%

A mixture of 1-iodo-3-(trifluoromethyl)-benzene (1, 5.44 g, 20.0 mmol), 3-(trifluoromethyl)-benzenethiol (2, 4.28 g, 24.0 mmol), copper(I) iodide (380 mg, 2.00 mmol), potassium carbonate (6.63 g, 48.0 mmol) and dry 1,2-dimethoxyethane (40 mL) was heated at 80 C under argon for two days. The reaction mixture was cooled to room temperature; diluted with ethyl acetate (80 mL); filtered over Celite and evaporated to dryness. The residue was re-dissolved in ethyl acetate (300 mL); washed with water (100 mL), 5% aqueous solution of sodium carbonate (2×100 mL) and 1 M aqueous solution of hydrochloric acid (50 mL); dried over anhydrous sodium sulfate and evaporated to dryness. The residue (contaminated with unwanted diaryl disulfide) was dissolved in acetic acid (80 mL). Zinc powder (7.00 g) was added and the mixture was heated at 60 C for 3 hours; then it was cooled to room temperature, diluted with toluene (80 mL), filtered over Celite and evaporated to dryness. The residue was partitioned between toluene (300 mL) and water (150 mL). The phases were separated, and the organic one was washed with 1 M aqueous solution of sodium hydroxide (2×200 mL) and brine (100 mL), dried over anhydrous sodium sulfate and evaporated to dryness. The residue was subjected to flash column chromatography (Silicagel 60, 0.040-0.063 mm; eluent: cyclohexane) to afford bis(3-(trifluoromethyl)phenyl)sulfane (3) as colorless liquid.

Yield: 4.01 g (62%).

$R_F$ ($SiO_2$, cyclohexane/ethyl acetate 95:5): 0.50.

$^1H$ NMR spectrum (300 MHz, $CDCl_3$, $\delta_H$): 7.65-7.61 (m, 2H); 7.58-7.42 (m, 6H).

$^{19}F$ NMR spectrum (282 MHz, $CDCl_3$, $\delta_F$): −62.90 (s).

LC-MS purity: 93% (UV 254 nm).

LC-MS Rt (Kinetex C18, 4.6 mm×50 mm, acetonitrile/water 70:30 to 100:0+0.1% FA): 2.96 min.

LC-MS m/z: 323.4 $(M+H)^+$.

(Diacetoxyiodo)benzene (9.82 g, 30.5 mmol) was added to a mixture of bis(3-(trifluoromethyl)phenyl)sulfane (3, 3.93 g, 12.2 mmol) and ammonium carbamate (1.90 g, 24.4 mmol) in methanol (24.4 mL). The resulting pale yellow solution was stirred at room temperature for 3 hours, and then it was evaporated to dryness in vacuo. A solution of potassium hydrogen carbonate (20 g) and sodium thiosulfate (20 g) in water (200 mL) was added to the residue, followed by ethyl acetate (200 mL). The phases were separated and the aqueous one was extracted with ethyl acetate (3×100 mL). The organic fractions were combined, dried over anhydrous sodium sulfate and evaporated in vacuo. The residue was purified by flash column chromatography (Silicagel 60, 0.040-0.063 mm; eluent: cyclohexane/ethyl acetate 99:1 to 70:30) to give iminobis(3-(trifluoromethyl)phenyl)-$\lambda^6$-sulfanone (4) as pale yellow oil.

Yield: 3.50 g (81%).

$R_F$ ($SiO_2$, n-hexane/ethyl acetate 1:1): 0.50.

$^1H$ NMR spectrum (300 MHz, $CDCl_3$, $\delta_H$): 8.37-8.34 (m, 2H); 8.29-8.24 (m, 2H); 7.88-7.81 (m, 2H); 7.73-7.65 (m, 2H); 3.28 (bs, 1H).

$^{19}F$ NMR spectrum (282 MHz, $CDCl_3$, $\delta_F$): −62.78 (s).

LC-MS purity: 100% (ELSD, UV 254 nm).

LC-MS Rt (Kinetex C18, 4.6 mm×50 mm, acetonitrile/water 35:65 to 100:0+0.1% FA): 3.53 min.

LC-MS m/z: 354.4 $(M+H)^+$.

Sodium hydride (60% dispersion in mineral oil, 310 mg, 7.75 mmol) was added to a solution of iminobis(3-(trifluoromethyl)phenyl)-$\lambda^6$-sulfanone (4, 2.49 g, 7.05 mmol) in dry N,N-dimethylformamide (20 mL) and the mixture was stirred at room temperature for 1 hour. tert-Butyl bromoacetate (2.36 mL, 10.6 mmol) was added; the mixture was heated to 60° C. and stirred at this temperature for 2.5 hours. The mixture was cooled to room temperature and partitioned between 10% aqueous solution of sodium hydrogensulfate (300 mL) and ethyl acetate (600 mL). Separated organic layer was washed with water (3×200 mL) and brine (100 mL); dried over anhydrous sodium sulfate and evaporated in vacuo. The residue was purified by flash column chromatography (Silicagel 60, 0.040-0.063 mm; eluent: cyclohexane/ethyl acetate 99:1 to 70:30) to yield tert-butyl 2-((oxobis(3-(trifluoromethyl)phenyl)-$\lambda^6$-sulfanylidene)amino)acetate (5) as white solid.

Yield: 2.94 g (89%).

$R_F$ ($SiO_2$, n-hexane/ethyl acetate 1:1): 0.55.

$^1H$ NMR spectrum (300 MHz, $CDCl_3$, $\delta_H$): 8.34 (s, 2H); 8.28 (d, J=7.9 Hz, 2H); 7.83 (d, J=7.9 Hz, 2H); 7.67 (t, J=7.9, 2 H); 3.77 (s, 2H); 1.48 (s, 9H).

$^{19}F$ NMR spectrum (282 MHz, $CDCl_3$, $\delta_F$): −62.77 (s).

LC-MS purity: 100% (ELSD, UV 254 nm).

LC-MS Rt (Kinetex C18, 4.6 mm×50 mm, acetonitrile/water 35:65 to 100:0+0.1% FA): 4.62 min.

LC-MS m/z: 468.4 $(M+H)^+$.

tert-Butyl 2-((oxobis(3-(trifluoromethyl)phenyl)-$\lambda^6$-sulfanylidene)amino)acetate (5, 501 mg, 1.07 mmol), bis(pinacolato)diboron (680 mg, 2.68 mmol), (1,5-cyclooctadiene)(methoxy)iridium(I) dimer (21.0 mg, 0.03 mmol) and 4,4-di-tert-butyl-2,2-dipyridyl (20.0 mg, 0.08 mmol) were dissolved in degassed tetrahydrofuran (3 mL) under argon. The resulting mixture was warmed to 60 C and heated at this temperature for 6 hours. The mixture was evaporated to dryness; and the residue purified by quick flash column chromatography (Silicagel 60, 0.040-0.063 mm; eluent: dichloromethane) to give tert-butyl 2-((oxobis(3-(4,4,5,5- tetramethyl-1,3,2-dioxaborolan-2-yl)-5-(trifluoromethyl) phenyl)-$\lambda^6$-sulfanylidene)amino)acetate (6) as off-white foam.

Yield: 748 mg (97%).

$^1$H NMR spectrum (300 MHz, $CDCl_3$, $\delta_H$): 8.59 (s, 2H); 8.42 (s, 2H); 8.21 (s, 2H); 3.76 (s, 2H); 1.51 (s, 9H); 1.36 (s, 12H); 1.35 (s, 12H).

$^{19}$F NMR spectrum (282 MHz, $CDCl_3$, $\delta_F$): −62.59 (s).

LC-MS purity: 100% (ELSD).

LC-MS Rt (Kinetex C18, 4.6 mm×50 mm, acetonitrile/water 85:15 to 100:0+0.1% FA): 1.32 min (M-2×pinacol), 1.65 (M-pinacol), 5.11 min (M).

LC-MS m/z: 556.6 $(M-2\times pinacol+H)^+$, 638.8 $(M-pinacol+H)^+$, 721.0 $(M+H)^+$.

Trifluoroacetic acid (6 mL) was added to a solution of tert-butyl 2-((oxobis(3-(4,4,5,5-tetramethyl-1,3,2-dioxaborolan-2-yl)-5-(trifluoromethyl)phenyl)-$\lambda^6$-sulfanylidene) amino)acetate (6, 735 mg, 1.02 mmol) in dichloromethane (2 mL) and the mixture was stirred for 2 hours at room temperature. The mixture was evaporated to dryness in vacuo, and the residue was evaporated from dichloromethane (5×10 mL) to afford 2-((oxobis(3-(4,4,5,5-tetramethyl-1,3,2-dioxaborolan-2-yl)-5-(trifluoromethyl)phenyl)-$\lambda^6$-sulfanylidene)amino)acetic acid (7) as off-white foam.

Yield: 678 mg (100%).

$^1$H NMR spectrum (300 MHz, $CDCl_3$, $\delta_H$): 8.54 (s, 2H); 8.33 (s, 2H); 8.27 (s, 2H); 3.85 (s, 2H); 1.37 (s, 12H); 1.37 (s, 12H).

$^{19}$F NMR spectrum (282 MHz, $CDCl_3$, $\delta_F$): −62.68 (s).

LC-MS purity: 100% (ELSD).

LC-MS Rt (Kinetex C18, 4.6 mm×50 mm, acetonitrile/water 85:15 to 100:0+0.1% FA): 0.67 min (M-2×pinacol), 0.84 (M-pinacol), 2.04 min (M).

LC-MS m/z: 550.5 $(M-2\times pinacol+H)^+$, 582.7 $(M-pinacol+H)^+$, 664.8 $(M+H)^+$.

A solution of 2-((oxobis(3-(4,4,5,5-tetramethyl-1,3,2-dioxaborolan-2-yl)-5-(trifluoromethyl)phenyl)-$\lambda^6$-sulfanylidene)amino)acetic acid (7, 568 mg, 856 μmol) in acetonitrile (6 mL) was diluted with water (2.4 mL) followed by addition of periodic acid (780 mg, 3.42 mmol). The resulting mixture was stirred for 1 hour; and then it was partitioned between ethyl acetate (120 mL) and water (30 mL). The phases were separated; the organic one was washed with brine (2×30 mL); dried over anhydrous sodium sulfate and evaporated to dryness. The residue was dissolved in 0.5 M aqueous solution of sodium hydroxide (30 mL) and washed with dichloromethane (3×40 mL). The aqueous layer was acidified with 1 M aqueous solution of hydrochloric acid (30 mL) and extracted with ethyl acetate (2×60 mL). Ethyl acetate extracts were combined, dried over anhydrous sodium sulfate and concentrated in vacuo until the product started to precipitate (approx. 10 mL volume). The suspension was diluted with n-hexane (50 mL) and placed into a freezer for 30 minutes. The precipitate was collected by filtration, washed with n-hexane (3×5 mL), dried in vacuo and dissolved in 50% aqueous acetonitrile (60 mL). The resulting solution was freeze-dried to afford the title compound (8) as white powder.

Yield: 338 mg (79%).

$^1$H NMR spectrum (300 MHz, DMSO-$d_6$+DCl, $\delta_H$): 8.60 (s, 2H); 8.35 (s, 4H); 3.70 (s, 2H)

$^{19}$F NMR spectrum (282 MHz, DMSO-$d_6$+DCl, $\delta_F$): −61.24 (s).

LC-MS purity: 100% (ELSD, UV 254 nm).

LC-MS Rt (Kinetex C18, 4.6 mm×50 mm, acetonitrile/water 5:95 to 100:0+0.1% FA): 3.89 min.

LC-MS m/z: 500.5 (M+H)+.

Example 31

N-(4-(Difluoromethyl)-1-hydroxy-1,3-dihydrobenzo[c][1,2]oxaborole-6-carbonyl)-N-(2-(4-(difluoromethyl)-1-hydroxy-1,3-dihydrobenzo[c][1,2]oxaborole-6-carboxamido)ethyl)glycine

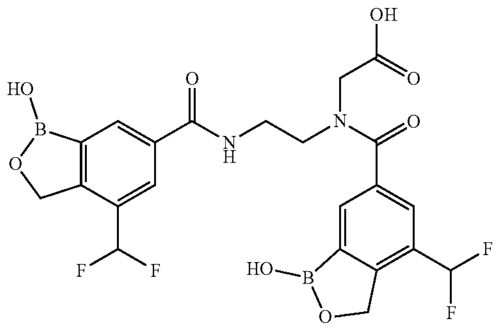 [SMILES: O=C(O)CN(CCNC(=O)c1cc2c(c(C(F)F)c1)COB2O)C(=O)c1cc2c(c(C(F)F)c1)COB2O]

N-(4-(Difluoromethyl)-1-hydroxy-1,3-dihydrobenzo[c][1,2]oxaborole-6-carbonyl)-N-(2-(4-(difluoromethyl)-1-hydroxy-1,3-dihydrobenzo[c][1,2]oxaborole-6-carboxamido)ethyl)glycine was synthesized according to the reaction scheme shown in Chem. 35 and following the procedure described below.

Chem. 35

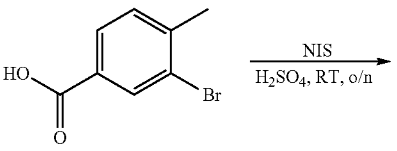

1

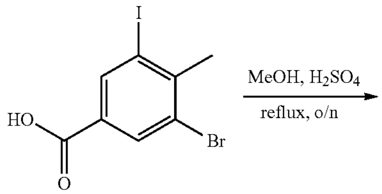

2
99%

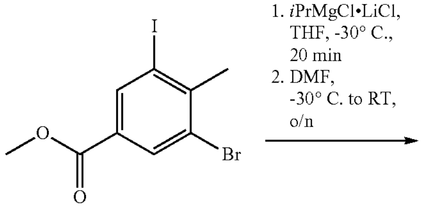

3
84%

-continued

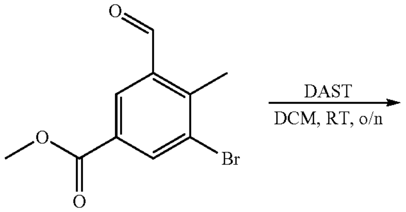

4
96%

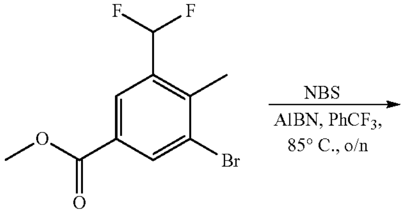

5
96%

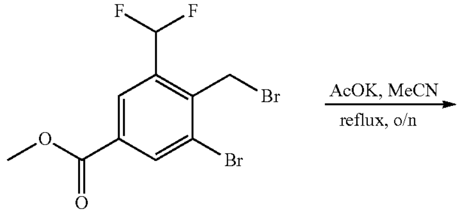

6

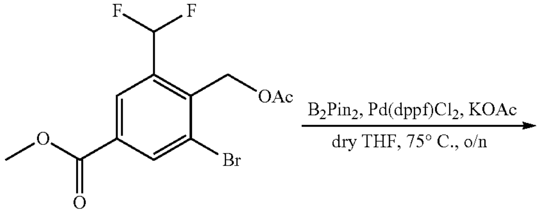

7
54%

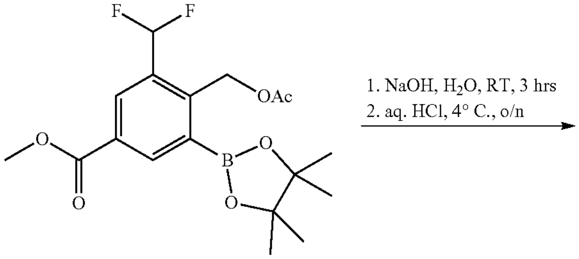

8
53%

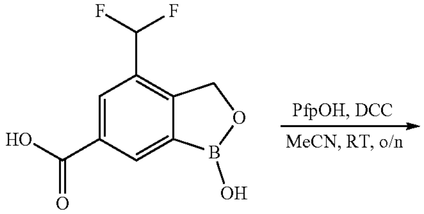

9
79%

-continued

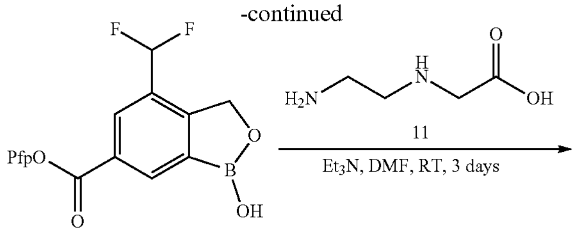

10
100%

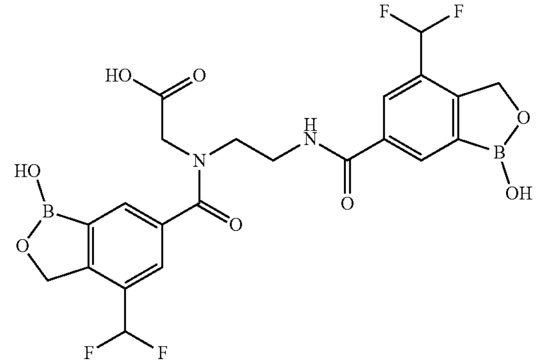

12
31%

N-Iodosuccinimide (NIS, 61.5 g, 274 mmol) was added to a solution of 3-bromo-4-methylbenzoic acid (1, 56.0 g, 260 mmol) in concentrated sulfuric acid (1 L) and the reaction mixture was allowed to stir at ambient temperature for 16 hours. The reaction mixture was then poured into ice-water (2 L). Resulting mixture was poured onto ice bath (2 L), precipitate was filtered, washed with water and dried in vacuo to provide 3-bromo-5-iodo-4-methylbenzoic acid (2) as off-white solid.

Yield: 87.8 g (99%).

$^1$H NMR spectrum (300 MHz, DMSO-$d_6$, $\delta_H$): 8.30 (d, J=1.7 Hz, 1H); 8.06 (d, J=1.7 Hz, 1H); 2.64 (s, 3H).

Concentrated sulfuric acid (25 mL) was added to a solution of 3-bromo-5-iodo-4-methylbenzoic acid (2, 30.0 g, 88.0 mmol) in methanol (1 L) and the reaction mixture was allowed to stir under reflux overnight. The reaction mixture was then evaporated under reduced pressure, dissolved in diethyl ether (500 mL), washed with water (2×200 mL) and saturated solution of potassium carbonate (200 mL). Organic layer was separated, dried over anhydrous sodium sulfate, filtered and evaporated to provide methyl 3-bromo-5-iodo-4-methylbenzoate (3) as white solid.

Yield: 26.1 g (84%).

$^1$H NMR spectrum (300 MHz, DMSO-$d_6$, $\delta_H$): 8.32 (d, J=1.7 Hz, 1H); 8.09 (d, J=1.3 Hz, 1H); 3.86 (s, 3H); 2.65 (s, 3H).

To a solution of methyl 3-bromo-5-iodo-4-methylbenzoate (3, 9.00 g, 25.4 mmol) in dry tetrahydrofuran (250 mL) 1.3 M solution of isopropylmagnesium chloride lithium chloride complex in tetrahydrofuran (21.6 mL, 28.0 mmol) was added dropwise at −30 C under inert atmosphere and was stirred for 20 minutes. Then N,N-dimethylformamide (3.60 mL, 38.1 mmol) was added at −30 C. The reaction mixture was allowed to warm to ambient temperature and stirred for 16 hours. The reaction mixture was then evaporated under reduced pressure, dissolved in ethyl acetate (200 mL) and washed with water (2×100 mL). Organic layer was separated, dried over anhydrous sodium sulfate, filtered and evaporated to provide methyl 3-bromo-5-formyl-4-methylbenzoate (4) as white solid.

Yield: 6.24 g (96%).

$^1$H NMR spectrum (300 MHz, $CDCl_3$, $\delta_H$): 10.27 (s, 1H); 8.53-8.34 (m, 2H); 3.97 (s, 3H); 2.82 (s, 3H).

Solution of 3-bromo-5-formyl-4-methylbenzoate (4, 6.23 g, 24.3 mmol) and (diethylamino)sulfur trifluoride (DAST, 6.40 mL, 48.5 mmol) in dichloromethane (150 mL) was stirred at ambient temperature for 16 hours. Reaction was quenched by addition of water (75 mL) and extracted with dichloromethane (2×100 mL). Organic layers were combined, dried over anhydrous sodium sulfate, filtered and evaporated to provide methyl 3-bromo-5-(difluoromethyl)-4-methylbenzoate (5) as white solid.

Yield: 6.53 g (96%).

$^1$H NMR spectrum (300 MHz, $CDCl_3$, $\delta_H$): 8.35 (d, J=1.1 Hz, 1H); 8.14 (d, J=0.9 Hz, 1H); 6.78 (t, J=54.8 Hz, 1H); 3.93 (s, 3H); 2.55 (t, J=1.4 Hz, 3H).

Solution of 1-bromopyrrolidine-2,5-dione (NBS, 4.57 g, 25.7 mmol), methyl 3-bromo-5-(difluoromethyl)-4-methylbenzoate (5, 6.53 g, 23.4 mmol) and 2,2-azobis(2-methylpropionitrile) (AIBN, 192 mg, 1.17 mmol) in $PhCF_3$ (200 mL) was stirred overnight at 85 C. Reaction mixture was evaporated and then extracted with diethyl ether (2×200 mL). Organic layers were washed with brine (150 mL). Organic layer was separated, dried over anhydrous sodium sulfate, filtered and evaporated. The crude product 6 was stirred with potassium acetate (4.59 g, 46.8 mmol) in acetonitrile (200 mL) at 75 C overnight. The suspension was filtered through filtering paper and evaporated. The crude product was dissolved in dichloromethane and filtered again. The filtrate was evaporated and purified by column chromatography (Silicagel 60, 0.040-0.063 mm; eluent: cyclohexane/ethyl acetate 7:1) to give methyl 4-(acetoxymethyl)-3-bromo-5-(difluoromethyl)benzoate (7) as white solid.

Yield: 4.24 g (54%).

$^1$H NMR spectrum (300 MHz, $CDCl_3$, $\delta_H$): 8.40 (s, 1H); 8.26 (s, 1H); 7.02 (t, J=54.7 Hz, 1H); 5.38 (s, 2H); 3.97 (s, 3H); 2.11 (s, 3H).

Solution of methyl 4-(acetoxymethyl)-3-bromo-5-(difluoromethyl)benzoate (7, 4.24 g, 12.6 mmol), bis(pinacolato) diboron (3.52 g, 13.9 mmol), potassium acetate (3.70 g, 37.8 mmol) and [1,1-bis(diphenylphosphino)ferrocene]dichloropalladium(II) (513 mg, 0.63 mmol) in dry tetrahydrofuran (100 mL) was allowed to stir at 75 C under argon atmosphere for 10 days. Then the reaction mixture was cooled to ambient temperature, filtered and evaporated. The crude product was filtered through silica gel column (Silicagel, 0.063-0.200 mm; eluent: cyclohexane/ethyl acetate 9:1) to provide methyl 4-(acetoxymethyl)-3-(difluoromethyl)-5-(4,4,5,5-tetramethyl-1,3,2-dioxaborolan-2-yl)benzoate (8).

Yield: 2.82 g (53%).

$R_F$ ($SiO_2$, cyclohexane/ethyl acetate 9:1): 0.40.

$^1$H NMR spectrum (300 MHz, $CDCl_3$, $\delta_H$): 8.57 (s, 1H); 8.38 (s, 1H); 7.04 (t, J=55.1 Hz, 1H); 5.54 (s, 2H); 3.97 (s, 3H); 2.06 (s, 3H); 1.39 (s, 12H).

Solution of methyl 4-(acetoxymethyl)-3-(difluoromethyl)-5-(4,4,5,5-tetramethyl-1,3,2-dioxaborolan-2-yl)benzoate (8, 2.82 g, 7.34 mmol) and sodium hydroxide (1.47 g, 36.7 mmol) in water (50 mL) was stirred at ambient temperature for 3 hours. Then solution of concentrated hydrochloric acid (4 mL) in water (10 mL) was added to lower the pH to 1. The reaction mixture was left in the fridge overnight. Precipitate was filtered and dried to provide 4-(difluoromethyl)-1-hydroxy-1,3-dihydrobenzo[c][1,2]oxaborole-6-carboxylic acid (9) as white solid.

Yield: 1.32 g (79%).

$^1$H NMR spectrum (300 MHz, DMSO-$d_6$, $\delta_H$): 13.25 (bs, 1H); 9.54 (s, 1H); 8.51 (s, 1H); 8.20 (s, 1H); 7.22 (t, J=55.1 Hz, 1H); 5.19 (s, 2H).

Solution of 2,3,4,5,6-pentafluorophenol (242 mg, 1.32 mmol), 4-(difluoromethyl)-1-hydroxy-1,3-dihydrobenzo[c][1,2]oxaborole-6-carboxylic acid (9, 300 mg, 1.32 mmol) and N,N'-dicyclohexylcarbodiimide (DCC, 272 mg, 1.32 mmol) in acetonitrile (20 mL) was stirred at ambient temperature overnight. The reaction mixture was filtered, evaporated, dissolved in acetonitrile, re-filtered and evaporated to give the perfluorophenyl 4-(difluoromethyl)-1-hydroxy-1,3-dihydrobenzo[c][1,2]oxaborole-6-carboxylate (10) as white solid.

Yield: 520 mg (100%).

LC-MS purity: 100% (ELSD).

LC-MS Rt (Kinetex C18, 4.6 mm×50 mm, acetonitrile/water 20:80 to 100:0+0.1% FA): 4.65 min.

LC-MS m/z: 395.5 $(M+H)^+$.

Solution of the perfluorophenyl 4-(difluoromethyl)-1-hydroxy-1,3-dihydrobenzo[c][1,2]oxaborole-6-carboxylate (10, 520 mg, 1.32 mmol), (2-aminoethyl)glycine (11, 78.0 mg, 0.66 mmol) and triethylamine (1.84 mL, 6.60 mmol) in N,N-dimethylformamide (10 mL) was stirred at ambient temperature for 3 days. The reaction mixture was then evaporated and crude product 12 was purified by preparative HPLC (SunFire Prep C18 OBD, 5 m, 19×100 mm, acetonitrile/water 5:95 to 100:0+0.1% FA) and freeze-dried to afford N-(4-(difluoromethyl)-1-hydroxy-1,3-dihydrobenzo[c][1,2]oxaborole-6-carbonyl)-N-(2-(4-(difluoromethyl)-1-hydroxy-1,3-dihydrobenzo[c][1,2]oxaborole-6-carboxamido)ethyl)glycine (12) as white solid.

Yield: 110 mg (31%).

$^1$H NMR spectrum (300 MHz, DMSO-$d_6$, $\delta_H$): 12.89 (bs, 1H); 9.63-9.35 (m, 2H); 8.92-6.70 (m, 7H); 5.25-5.08 (m, 4H); 4.28-3.94 (m, 2H); 3.74-3.35 (m, 4H).

LC-MS purity: 100% (ELSD).

LC-MS Rt (Kinetex C18, 4.6 mm×50 mm, acetonitrile/water 5:95 to 100:0+0.1% FA): 3.30 min.

LC-MS m/z: 539.4 $(M+H)^+$.

Example 32

N-(4-Chloro-1-hydroxy-1,3-dihydrobenzo[c][1,2]oxaborole-6-carbonyl)-N-(2-(4-chloro-1-hydroxy-1,3-dihydrobenzo[c][1,2]oxaborole-6-carboxamido)ethyl)glycine

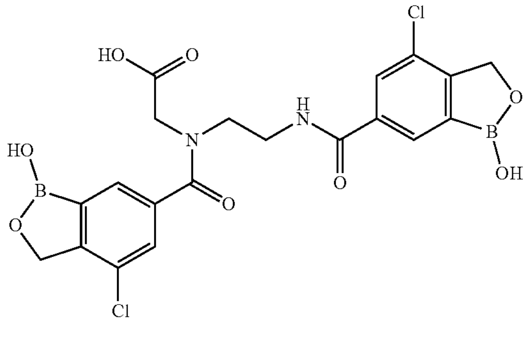

N-(4-Chloro-1-hydroxy-1,3-dihydrobenzo[c][1,2]oxaborole-6-carbonyl)-N-(2-(4-chloro-1-hydroxy-1,3-dihydrobenzo[c][1,2]oxaborole-6-carboxamido)ethyl)glycine was synthesized according to the reaction scheme shown in Chem. 36 and following the procedure described below.

Chem. 36

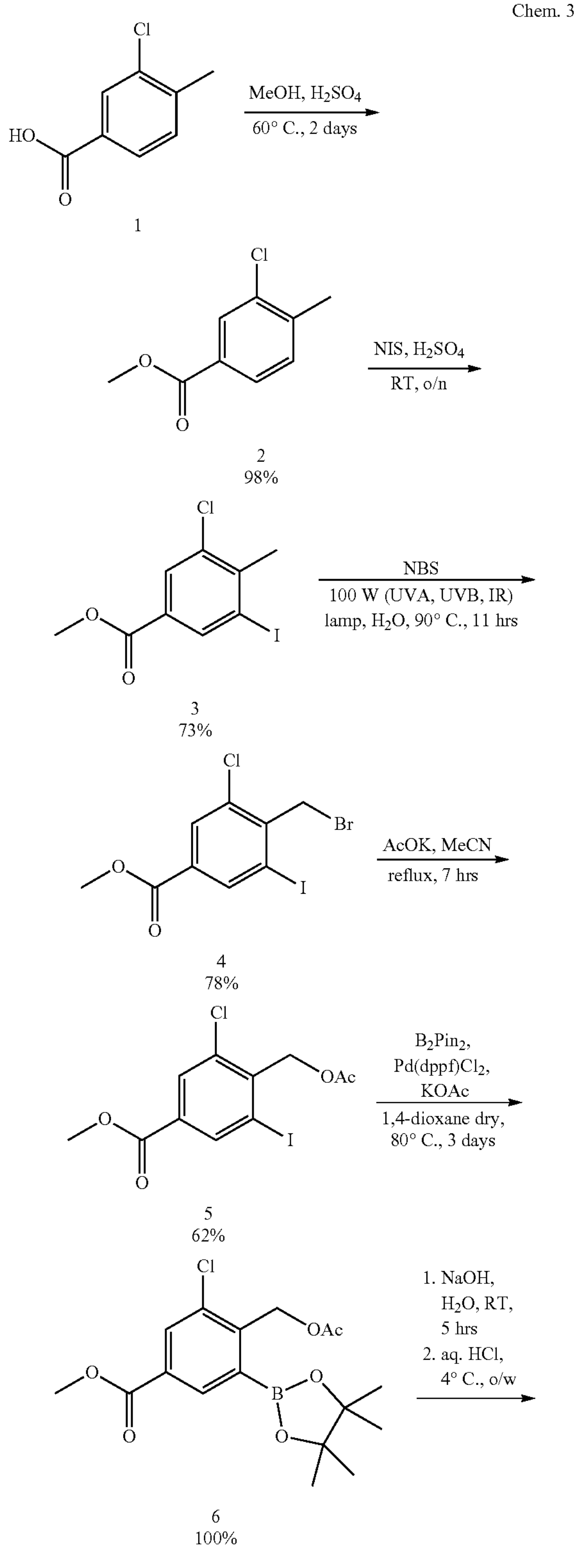

1

2
98%

3
73%

4
78%

5
62%

6
100%

-continued

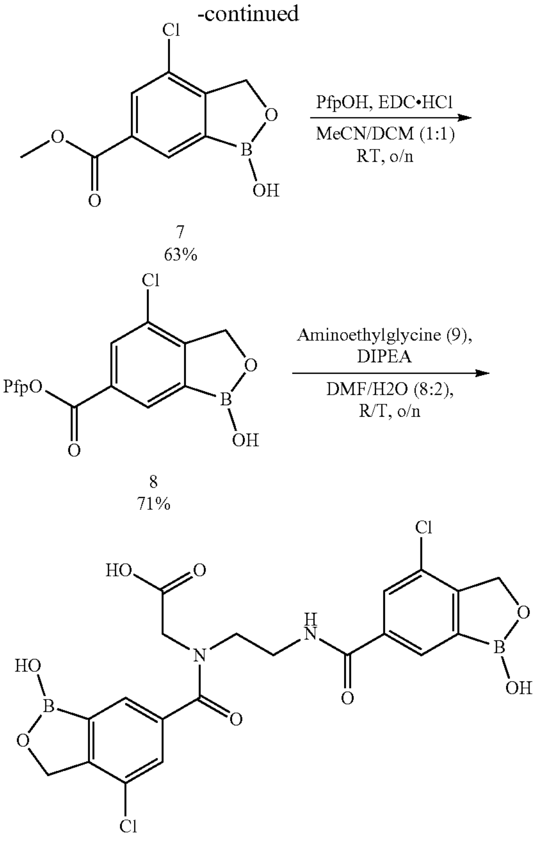

7
63%

8
71%

10
21%

Concentrated sulfuric acid (4.00 mL, 73.3 mmol) was added to a solution of 3-chloro-4-methylbenzoic acid (1, 25.0 g, 147 mmol) in methanol (200 mL) and the reaction mixture was allowed to stir at 60 C for 2 days. The solution was cooled to room temperature, sodium hydrogencarbonate (6.80 g, 80.0 mmol) was added, and the mixture was evaporated under reduced pressure. The residue was partitioned between ethyl acetate (300 mL) and water (250 mL). The organic layer was separated; washed with 0.5 M aqueous solution of sodium hydroxide (2×250 mL), 0.5 M aqueous solution of hydrochloric acid (200 mL) and brine (150 mL); dried over anhydrous sodium sulfate and evaporated in vacuo to give methyl 3-chloro-4-methylbenzoate (2) as orange oil.

Yield: 27.0 g (98%).

$R_F$ ($SiO_2$, dichloromethane/methanol 95:5): 0.80.

$^1H$ NMR spectrum (300 MHz, $CDCl_3$, $\delta_H$): 8.00 (d, J=1.65 Hz, 1H); 7.80 (dd, J=7.9 and 1.5 Hz, 1H); 7.28 (d, J=8.1 Hz, 1H); 3.90 (s, 3H); 2.42 (s, 3H).

Methyl 3-chloro-4-methylbenzoate (2, 26.0 g, 141 mmol) was dissolved in sulfuric acid (150 mL) followed by addition of N-iodosuccinimide (38.0 g, 169 mmol). The resulting mixture was stirred overnight at room temperature then it was poured onto ice. When ice was completely melted the mixture was extracted with ethyl acetate (300 mL). Organic layer was washed with 5% aqueous solution of sodium thiosulfate (3×100 mL) and water (1×100 mL), dried over anhydrous sodium sulfate, filtered and evaporated to dryness. Product was re-crystallized from hot heptane (150 mL) affording methyl 3-chloro-5-iodo-4-methylbenzoate (3) as white powder.

Yield: 32.0 g (73%).

$R_F$ ($SiO_2$, dichloromethane/methanol 95:5): 0.80.

$^1H$ NMR spectrum (300 MHz, DMSO-$d_6$, $\delta_H$): 8.38 (dd, J=1.3 Hz, 1H); 8.00 (dd, J=1.3 Hz, 1H); 3.87 (s, 3H); 2.54 (s, 3H).

A stirred mixture of methyl 3-chloro-4-methylbenzoate (3, 30.0 g, 96.6 mmol), 1-bromopyrrolidine-2,5-dione (NBS, 18.9 g, 106 mmol) and water (400 mL) in a wide beaker was placed under D3 basking lamp for reptiles (100 W, UVA, UVB, IR) and heated to 90-100° C. from suspension to oily consistency. Another portion of 1-bromopyrrolidine-2,5-dione (0.00 g, 11.3 mmol) was added after 6 hours, and the mixture was stirred for an additional 5 hours. The mixture was cooled to room temperature followed by extraction with ethyl acetate (3×200 mL). Combined organic layers were washed with 5% aqueous solution of sodium thiosulfate (3×100 mL), water (1×100 mL), brine (1×100 mL), dried over anhydrous sodium sulfate and evaporated in vacuo to afford crude methyl 4-(bromomethyl)-3-chloro-5-iodobenzoate (4) as yellow solid.

Yield: 29.5 g (78%).

$R_F$ ($SiO_2$, cyclohexane/ethyl acetate 8:2): 0.70.

$^1H$ NMR spectrum (300 MHz, DMSO-$d_6$, $\delta_H$): 8.80 (s, 1H); 8.41 (s, 1H); 4.81 (s, 2H); 3.94 (s, 3H).

A mixture of the above crude methyl 4-(bromomethyl)-3-chloro-5-iodobenzoate (4, 28.0 g, 71.9 mmol) and potassium acetate (21.2 g, 216 mmol) in acetonitrile (600 mL) was heated at 80 C for 7 hours. The mixture was cooled to room temperature, the solid was removed by filtration and washed with ethyl acetate (3×50 mL). The filtrate was evaporated to dryness, and the residue was partitioned between ethyl acetate (500 mL) and water (200 mL). The organic layer was separated, washed with water (200 mL) and brine (2×200 mL), dried over anhydrous sodium sulfate and evaporated in vacuo. The residue was purified by flash column chromatography (Silicagel, 0.063-0.200 mm; eluent: cyclohexane/ethyl acetate 97:3) and after was recrystallized from hot cyclohexane to give pure methyl 4-(acetoxymethyl)-3-chloro-5-iodobenzoate (5) as white solid.

Yield: 19.3 g (62%).

$R_F$ ($SiO_2$, cyclohexane/ethyl acetate 4:1): 0.60.

$^1H$ NMR spectrum (300 MHz, $CDCl_3$, $\delta_H$): 8.42 (d, J=3.3 Hz, 1H); 8.04 (d, J=3.6 Hz, 1H); 5.40 (s, 2H); 3.94 (s, 3H); 2.12 (s, 3H).

LC-MS purity: 100% (UV 254 nm).

LC-MS Rt (Kinetex C18, 4.6 mm×50 mm, acetonitrile/water 50:50 to 100:0+0.1% FA): 2.62 min.

LC-MS m/z: 369.5 $(M+H)^+$.

[1,1-Bis(diphenylphosphino)ferrocene]dichloropalladium(II) (2.48 g, 3.39 mmol) was added to a degassed solution of methyl 4-(acetoxymethyl)-3-chloro-5-iodobenzoate (5, 25.0 g, 63.8 mmol), bis(pinacolato)diboron (19.0 g, 74.6 mmol) and potassium acetate (20.0 g, 204 mmol) in dry 1,4-dioxane (300 mL) under argon. The mixture was warmed to 80 C and stirred at this temperature for 3 days. The mixture was cooled to room temperature; then it was diluted with dichloromethane (200 mL) and passed through a short column of silicagel topped with Celite followed by elution with dichloromethane. Fractions containing the product were combined and evaporated to dryness. The residue was purified by flash column chromatography (Silicagel, 0.063-0.200 mm; eluent: cyclohexane/ethyl acetate 9:1 to 7:3) to affording methyl 4-(acetoxymethyl)-3-chloro-5-(4,4,5,5-tetramethyl-1,3,2-dioxaborolan-2-yl)benzoate (6) yellow oil.

Yield: 25.0 g (100%).

$R_F$ ($SiO_2$, cyclohexane/ethyl acetate 8:2): 0.4.

$^1H$ NMR spectrum (300 MHz, $CDCl_3$, $\delta_H$): 8.34 (d, J=1.65 Hz, 1H); 8.12 (d, J=8.2 and 2.0 Hz, 1H); 5.52 (s, 2H); 3.93 (s, 3H); 2.05 (s, 3H); 1.34 (s, 12H).

LC-MS purity: 100% (ELSD), 88% (UV 254 nm).

LC-MS Rt (Kinetex C18, 4.6 mm×50 mm, acetonitrile/water 50:50 to 100:0+0.1% FA): 3.54 min.

LC-MS m/z: 369.6 $(M+H)^+$.

Methyl 4-(acetoxymethyl)-3-chloro-5-(4,4,5,5-tetramethyl-1,3,2-dioxaborolan-2-yl)benzoate (6, 25.0 g, <63.8 mmol) was added to a solution of sodium hydroxide (12.8 g, 319 mmol) in water (300 mL) and the resulting mixture was stirred at room temperature for 5 hours. The mixture was filtered and acidified with 35% hydrochloric acid (39.6 mL, 444 mmol). The resulting white suspension was stirred for another one hour. The precipitate was filtered, washed with water (5×50 mL) and dissolved in 80% aqueous solution of acetonitrile (500 mL), filtered and solution mixture was freeze-dried to afford 4-chloro-1-hydroxy-1,3-dihydrobenzo[c][1,2]oxaborole-6-carboxylic acid (7) as white powder.

Yield: 9.00 g (63%).

$^1H$ NMR spectrum (300 MHz, DMSO-$d_6$, $\delta_H$): 13.30 (s, 1H); 9.60 (s, 1H); 8.32 (d, J=1.1 Hz, 1H); 8.00 (d, J=1.1 Hz, 1H); 5.06 (s, 2H).

LC-MS purity: 99% (ELSD).

LC-MS Rt (Kinetex C18, 4.6 mm×50 mm, acetonitrile/water 5:95 to 100:0+0.1% FA): 3.90 min.

LC-MS m/z: 213.3 $(M+H)^+$.

N-(3-Dimethylaminopropyl)-N-ethylcarbodiimide hydrochloride (3.40 g, 17.9 mmol) was added to a suspension of 4-chloro-1-hydroxy-1,3-dihydrobenzo[c][1,2]oxaborole-6-carboxylic acid (7, 3.80 g, 17.9 mmol) and pentafluorophenol (3.30 g, 17.9 mmol) in solution acetonitrile/dichloromethane (1:1, 150 mL) and the mixture was stirred at room temperature overnight. Solvent was evaporated to dryness. Residue was partionated between ethyl acetate (200 mL) and 10% aqueous solution of potassium hydrogensulfate (200 mL). Organic layer was separate and washed with water (2×100 mL), dried over anhydrous sodium sulfate and evaporated in vacuo. Residue dissolved in dichloromethane placed in the fridge overnight. The solid was filtered off and washed with ethyl acetate (2×20 mL). The filtrates were combined and evaporated to dryness. Cyclohexane (100 mL) was added to the residue and the mixture was stirred at room temperature for 15 minutes. The mixture was decanted and the sediment was dried in vacuo to give perfluorophenyl 4-chloro-1-hydroxy-1,3-dihydrobenzo[c][1,2]oxaborole-6-carboxylate (8) as off-white solid.

Yield: 4.80 g (71%).

LC-MS purity: 98% (ELSD).

LC-MS Rt (Kinetex C18, 4.6 mm×50 mm, acetonitrile/water 5:95 to 100:0+0.1% FA): 4.48 min.

LC-MS m/z: 379.4 $(M+H)^+$.

N,N-Diisopropylethylamine (2.35 mL, 13.5 mmol) was added to a mixture of perfluorophenyl 1-hydroxy-1,3-dihydrobenzo[c][1,2]oxaborole-6-carboxylate (9, 1.40 g, 3.72 mmol) and L-2,3-diaminopropionic acid hydrochloride (9, N-2-aminoethylglycine, 200 mg, 1.70 mmol) in solution N,N-dimethylformamide/water (4:1, 20 mL) and the resulting solution was stirred at room temperature overnight. The mixture was evaporated to dryness in vacuo, and the residue was partitioned between 1 M aqueous solution of hydrochloric acid (40 mL) and ethyl acetate (50 mL). The phases were separated and the organic one was extracted with ethyl acetate (2×25 mL). All organic layers was combined, dried over anhydrous sodium sulfate and concentrated in vacuo. Mixture was evaporated with toluene three time. Dichloromethane (50 mL) was added and the resulting suspension was stirred at room temperature 2 hours. Solid was decanted and all was repeat another one. The precipitate was triturated with a mixture of dichloromethane/methanol/formic acid (1000:20:3), the solid was collected by filtration, washed with cyclohexane (2×5 mL) and air-dried to give title compound (10) as white powder.

Yield: 180 mg (21%).

$^1$H NMR spectrum (300 MHz, DMSO-$d_6$, $\delta_H$): 12.87 (bs, 1H); 9.67-9.37 (m, 1H); 8.87-7.09 (m, 5H); 5.15-4.86 (m, 4H); 4.34-3.92 (m, 2H); 3.60-3.24 (m, 4H).

LC-MS purity: 100% (ELSD).

LC-MS Rt (Kinetex C18, 4.6 mm×50 mm, acetonitrile/water 5:95 to 100:0+0.1% FA): 2.58 min.

LC-MS m/z: 507.3 $(M+H)^+$.

Example 33

(S)-3-(2,3-Bis(4-chloro-1-hydroxy-1,3-dihydrobenzo[c][1,2]oxaborole-6-carboxamido)propanamido)propanoic acid

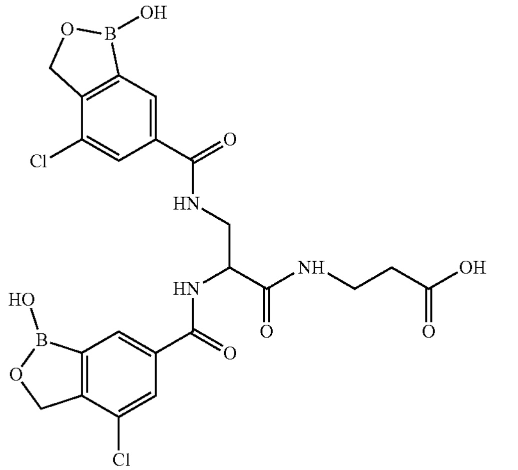

(S)-3-(2,3-Bis(4-chloro-1-hydroxy-1,3-dihydrobenzo[c][1,2]oxaborole-6-carboxamido)propanamido)propanoic acid was synthesized according to the reaction scheme shown in Chem. 37 and following the procedure described below.

Chem. 37

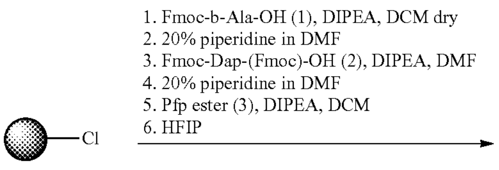

2-Chlorotrityl chloride resin

-continued

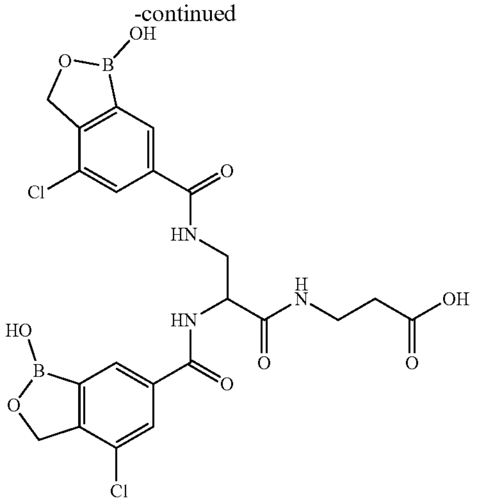

4

11%

2-Chlorotrityl chloride resin 100-200 mesh 1.5 mmol/g (3.30 g, 4.95 mmol) was left to swell in dry dichloromethane (300 mL) for 30 minutes. A solution of 3-((((9H-fluoren-9-yl)methoxy)carbonyl)amino)propanoic acid (1, Fmoc-beta-Ala-OH, 0.50 g, 1.60 mmol) in dry dichloromethane (100 mL) and N,N-diisopropylethylamine (2.00 mL, 15.5 mmol) was added and the mixture was shaken overnight. Then resin was filtered and treated with a solution of N,N-diisopropylethylamine/methanol/dichloromethane mixture (1:2:8, 2×5 min, 2×50 mL). The resin was washed with dichloromethane (3×100 mL), 2-propanol (3×100 mL) and N,N-dimethylformamide (3×100 mL). Fmoc group was removed by treatment with 20% piperidine in N,N-dimethylformamide (1×5 min, 1×30 min, 2×100 mL). Resin was washed with N,N-dimethylformamide (3×100 mL), 2-propanol (3×100 mL) and dichloromethane (3×100 mL). A solution of (S)-2,3-bis((((8a9H-fluoren-9-yl)methoxy)carbonyl)amino)propanoic acid (2, Fmoc-Dap(Fmoc)-OH, 1.00 g, 1.82 mmol) and N,N-diisopropylethylamine (3.00 mL, 4.04 mmol) in dichloromethane (100 mL) was added to resin and mixture was shaken for 5 hours. Resin was filtered and washed with dichloromethane (3×100 mL), 2-propanol (3×100 mL) and dichloromethane (3×100 mL). Fmoc groups were removed by treatment with 20% piperidine in N,N-dimethylformamide (1×5 min, 1×30 min, 2×100 mL). Resin was washed with dichloromethane (3×100 mL), 2-propanol (3×100 mL) and dichloromethane (3×100 mL). A solution of pentafluorophenyl 1-hydroxy-1,3-dihydrobenzo[c][1,2]oxaborole-6-carboxylate (3, 1.40 g, 3.72 mmol; #8 in example above) and N,N-diisopropylethylamine (6.00 mL, 60.0 mmol) in N,N-dimethylformamide (50 mL) was added to resin and mixture was shaken for 5 hours. The resin was washed with dichloromethane (3×100 mL), 2-propanol (3×100 mL), N,N-dimethylformamide (3×100 mL) and dichloromethane (5×100 mL).

The product was cleaved from resin by treatment with 1,1,1,3,3,3-hexafluoroisopropanol in dichloromethane (3:1, 100 mL). Resin was filtered and washed with dichloromethane (3×100 mL). Solutions were combined and solvents were evaporated to dryness to give crude mixture was subjected to purification by preparative LC/MS (SunFire Prep C18 OBD, 5 m, 19×100 mm, acetonitrile/water 5:95 to 100:0+0.1% FA). Pure fractions were combined and freeze-dried to give title compound (4) as white powder.

Yield: 103 mg (11%).

$^1$H NMR spectrum (300 MHz, DMSO-$d_6$, $\delta_H$): 12.16 (bs, 1H); 9.54 (d, J=6.24 Hz, 2H); 8.74-8.63 (m, 2H); 8.19 (d, J=1.1 Hz, 1H); 8.15-8.08 (m, 2H); 8.02 (d, J=1.28 Hz, 1H); 7.09 (d, J=1.1 Hz, 1H); 5.03 (d, J=7.34 Hz, 4H); 4.71-4.61 (m, 1H); 3.59 (t, J=5.59 Hz, 2H); 3.30-3.23 (m, 2H); 2.37 (t, J=7.15 Hz, 2H).

LC-MS purity: 100% (ELSD, UV 254 nm).

LC-MS Rt (Kinetex C18, 4.6 mm×50 mm, acetonitrile/water 5:95 to 100:0+0.1% FA): 3.63 min.

LC-MS m/z: 563.0 $(M+H)^+$.

Example 34

2-((Bis(3-borono-5-(difluoromethyl)phenyl)(oxo)-λ6-sulfanylidene)amino)acetic acid

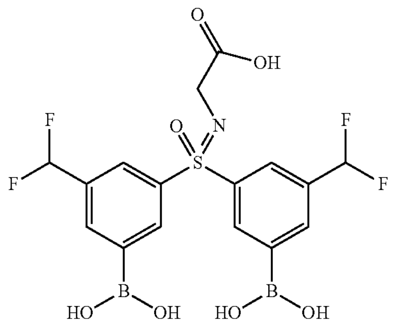 [SMILES: O=C(O)CN=S(=O)(c1cc(B(O)O)cc(C(F)F)c1)c1cc(B(O)O)cc(C(F)F)c1]

2-((Bis(3-borono-5-(difluoromethyl)phenyl)(oxo)-λ6-sulfanylidene)amino)acetic acid was synthesized according to the reaction scheme shown in Chem. 38 and following the procedure described below.

Chem. 38

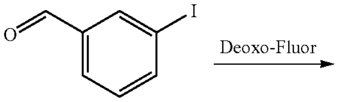

1

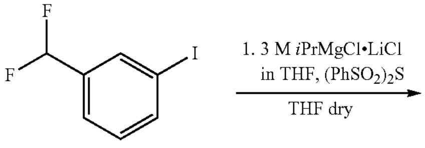

2
74%

-continued

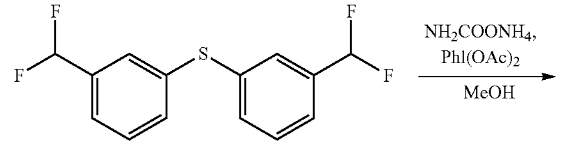

3
76%

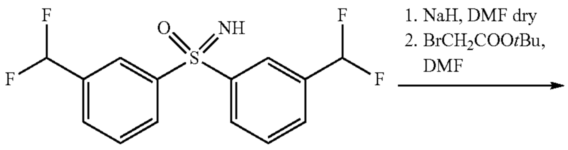

4
89%

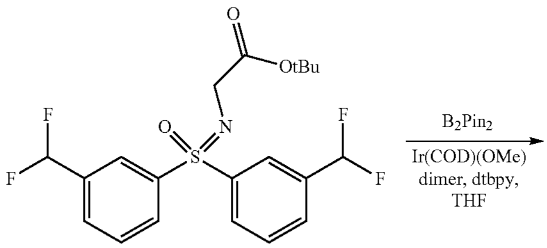

5
96%

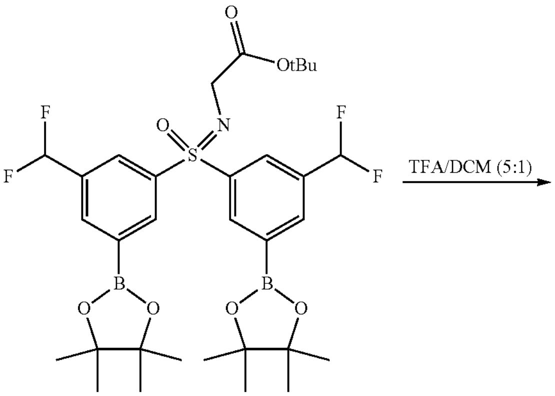

6
85%

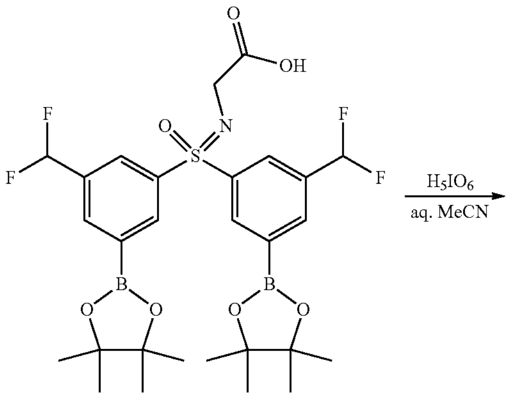

7
100%

-continued

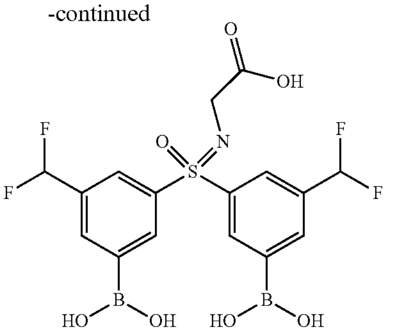

8
85%

The mixture of 3-iodobenzaldehyde (1, 4.00 g, 17.2 mmol) in Deoxo-Fluor (12 mL) was stirred at room temperature overnight. Then it was diluted with dichloromethane (150 mL) followed by dropwise addition of 10% aqueous solution of potassium carbonate (200 mL) at 0 C. Phases were separated; organic layer was dried over anhydrous sodium sulfate, filtered and evaporated. The residue was subjected to flash column chromatography (Silicagel 60, 0.040-0.063 mm; eluent: cyclohexane) to afford 1-(difluoromethyl)-3-iodobenzene (2) as colorless oil.

Yield: 3.22 g (74%).

$R_F$ ($SiO_2$, cyclohexane): 0.50.

$^1$H NMR spectrum (300 MHz, $CDCl_3$, $\delta_H$): 7.89-7.85 (m, 1H); 7.85-7.79 (m, 1H); 7.52-7.46 (m, 1H); 7.24-7.17 (m, 1H); 6.59 (t, J=56.2 Hz, 1H).

Iodide (2, 1.48 g, 5.81 mmol) was dissolved in dry tetrahydrofuran (20 mL) under nitrogen atmosphere and cooled down to −30 C. 1.3 M Solution of isopropylmagnesium chloride lithium chloride complex in tetrahydrofuran (4.69 mL, 6.10 mmol) was added dropwise. Resulting solution was stirred for 1.5 hours at −30 C. Then a solution of bis(phenylsulfonyl)sulfide (0.82 g, 2.61 mmol) in degassed tetrahydrofuran (10 mL) was added. The mixture was left to warm up to room temperature (approx. 2 hours). The reaction was quenched by addition of 20% aqueous solution of ammonium chloride (30 mL) and extracted with diethyl ether (50 mL). Organic layer was washed with water (3×50 mL) and brine (1×50 mL), dried over anhydrous sodium sulfate, filtered and evaporated. The residue was subjected to flash column chromatography (Silicagel 60, 0.040-0.063 mm; eluent: cyclohexane) to afford bis(3-(difluoromethyl)phenyl)sulfane (3) as colorless oil which crystallized in fridge.

Yield: 568 mg (76%).

$R_F$ ($SiO_2$, cyclohexane): 0.20.

$^1$H NMR spectrum (300 MHz, $CDCl_3$, $\delta_H$): 7.52-7.48 (m, 2H); 7.48-7.37 (m, 6H); 6.61 (t, J=56.3 Hz, 2H).

$^{19}$F NMR spectrum (282 MHz, $CDCl_3$, $\delta_F$): −111.21 (s); −111.40 (s).

(Diacetoxyiodo)benzene (966 mg, 3.00 mmol) was added to a mixture of sulfide (3, 343 mg, 1.20 mmol) and ammonium carbamate (187 mg, 2.40 mmol) in methanol (5.5 mL). The resulting pale yellow solution was stirred at room temperature for 3 hours, and then it was evaporated to dryness in vacuo. A solution of potassium hydrogen carbonate (2 g) and sodium thiosulfate (2 g) in water (20 mL) was added to the residue, followed by ethyl acetate (70 mL). The phases were separated and the aqueous one was extracted with ethyl acetate (2×70 mL). The organic fractions were combined, dried over anhydrous sodium sulfate and evaporated in vacuo. The residue was purified by flash column chromatography (Silicagel 60, 0.040-0.063 mm; eluent: cyclohexane/ethyl acetate 2:1) to afford bis(3-(difluoromethyl)phenyl)(imino)-$\lambda^6$-sulfanone (4) as white solid.

Yield: 553 mg (89%).

$R_F$ ($SiO_2$, n-hexane/ethyl acetate 1:1): 0.45.

$^1$H NMR spectrum (300 MHz, $CDCl_3$, $\delta_H$): 8.24-8.12 (m, 4H); 7.75-7.68 (m, 2H); 7.68-7.58 (m, 2H); 6.70 (t, J=56.0 Hz, 2H); 3.20 (bs, 1H).

$^{19}$F NMR spectrum (282 MHz, $CDCl_3$, $\delta_F$): −111.74 (s); −111.94 (s).

LC-MS purity: 100% (ELSD).

LC-MS Rt (Kinetex C18, 4.6 mm×50 mm, acetonitrile/water 35:65 to 100:0+0.1% FA): 2.70 min.

LC-MS m/z: 317.3 $(M+H)^+$.

60% Sodium hydride dispersion in mineral oil (0.08 g, 1.88 mmol) was added to a solution of the above compound (4, 543 mg, 1.71 mmol) in dry N,Ndimethylformamide (5 mL) and the mixture was stirred at room temperature for 1 hour. tert-Butyl bromoacetate (0.38 mL, 2.57 mmol) was added; the mixture was heated to 60 C and stirred at this temperature for 2.5 hours. The mixture was cooled to room temperature and partitioned between 10% aqueous solution of sodium hydrogensulfate (30 mL) and ethyl acetate (60 mL). Separated organic layer was washed with water (3×30 mL), dried over anhydrous sodium sulfate and evaporated in vacuo. The residue was purified by flash column chromatography (Silicagel 60, 0.040-0.063 mm; eluent: cyclohexane/ethyl acetate 4:1) to yield tert-butyl 2-((bis(3-(difluoromethyl)phenyl)(oxo)-$\lambda^6$-sulfanylidene)amino)acetate (5) as colorless oil.

Yield: 708 mg (96%).

$R_F$ ($SiO_2$, n-hexane/ethyl acetate 1:1): 0.65.

$^1$H NMR spectrum (300 MHz, $CDCl_3$, $\delta_H$): 8.23-8.16 (m, 4H); 7.75-7.70 (m, 2H); 7.67-7.58 (m, 2H); 6.69 (t, J=56.0 Hz, 2H); 3.76 (s, 2H); 1.47 (s, 9H).

$^{19}$F NMR spectrum (282 MHz, $CDCl_3$, $\delta_F$): −111.56 (s); −111.76 (s).

The above prepared compound (5, 700 mg, 1.62 mmol), bis(pinacolato)diboron (1.03 g, 4.05 mmol), (1,5-cyclooctadiene)(methoxy)iridium(I) dimer (33.0 mg, 0.05 mmol) and 4,4-di-tert-butyl-2,2-dipyridyl (dtbpy, 30.0 mg, 0.11 mmol) were dissolved in degassed tetrahydrofuran (16 mL) under nitrogen. The resulting mixture was warmed to 50 C and heated at this temperature overnight. The mixture was evaporated to dryness; and the residue purified by quick flash column chromatography (Silicagel 60, 0.040-0.063 mm; eluent: dichloromethane) to give tert-butyl 2-((bis(3-(difluoromethyl)-5-(4,4,5,5-tetramethyl-1,3,2-dioxaborolan-2-yl)phenyl)(oxo)-$\lambda^6$-sulfanylidene)amino)acetate (6) as beige foam.

Yield: 945 mg (85%).

$^1$H NMR spectrum (300 MHz, $CDCl_3$, $\delta_H$): 8.53 (s, 2H); 8.30 (s, 2H); 8.11 (s, 4H); 6.69 (t, J=56.0 Hz, 2H); 3.75 (s, 2H); 1.51 (s, 9H); 1.35 (s, 12H); 1.35 (s, 12H).

$^{19}$F NMR spectrum (282 MHz, $CDCl_3$, $\delta_F$): −111.26 (s); −111.49 (s).

Trifluoroacetic acid (20 mL) was added to a solution of the above compound (6, 935 mg, 1.04 mmol) in dichloromethane (4 mL) and the mixture was stirred for 2 hours at room temperature. The mixture was evaporated to dryness in vacuo, and the residue was evaporated from dichloromethane (5×10 mL) to afford 2-((bis(3-(difluoromethyl)-5-(4,4, 5,5-tetramethyl-1,3,2-dioxaborolan-2-yl)phenyl)(oxo)-$\lambda^6$-sulfanylidene)amino)acetic acid (7) as beige foam.

Yield: 858 mg (100%).

$^1H$ NMR spectrum (300 MHz, $CDCl_3$, $\delta_H$): 8.49 (s, 2H); 8.22 (s, 2H); 8.18 (s, 2H); 6.72 (t, J=55.8 Hz, 2H); 3.88 (s, 2H); 1.37 (s, 12H); 1.37 (s, 12H).

$^{19}F$ NMR spectrum (282 MHz, $CDCl_3$, $\delta_F$): −111.84 (s); −112.03 (s).

A solution of the acid (7, 858 mg, 1.37 mmol) in acetonitrile (16 mL) was diluted with water (4 mL) followed by addition of periodic acid (1.25 g, 5.48 mmol). The resulting mixture was stirred for 1 hour; and then it was partitioned between ethyl acetate (120 mL) and water (30 mL). The phases were separated; the organic one was washed with water (1×60 mL); dried over anhydrous sodium sulfate and evaporated to dryness. The residue was dissolved in 0.5 M aqueous solution of sodium hydroxide (50 mL) and washed with dichloromethane (2×80 mL). The aqueous layer was acidified with 1 M aqueous solution of hydrochloric acid (80 mL) and extracted with ethyl acetate (3×120 mL). Ethyl acetate extracts were combined, dried over anhydrous sodium sulfate, filtered and evaporated. Part of the residual material (0.20 g) was purified by preparative LC/MS (SunFire Prep C18 OBD, 5 m, 19×100 mm, acetonitrile/water 5:95 to 100:0+0.1% FA) to give title compound (8) as white powder.

Yield: 170 mg (85%).

$^1H$ NMR spectrum (300 MHz, DMSO-$d_6$+DCl, $\delta_H$): 8.48 (s, 2H); 8.19 (s, 4H); 7.14 (t, J=55.6 Hz, 2H); 3.65 (s, 2H).

$^{19}F$ NMR spectrum (282 MHz, DMSO-$d_6$+DCl, $\delta_F$): −110.64 (s); −110.84 (s).

LC-MS purity: 100% (ELSD).

LC-MS Rt (Kinetex C18, 4.6 mm×50 mm, acetonitrile/water 5:95 to 100:0+0.1% FA): 3.27 min.

LC-MS m/z: 462.9 $(M+H)^+$.

Example 35

2-((Bis(3-borono-5-chlorophenyl)(oxo)-λ6-sulfanylidene)amino)acetic acid

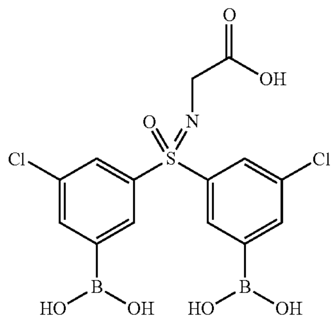 [SMILES: O=C(O)CN=S(=O)(c1cc(Cl)cc(B(O)O)c1)c1cc(Cl)cc(B(O)O)c1]

2-((Bis(3-borono-5-chlorophenyl)(oxo)-λ6-sulfanylidene)amino)acetic acid was synthesized according to the reaction scheme shown in Chem. 39 and following the procedure described below.

Chem. 39

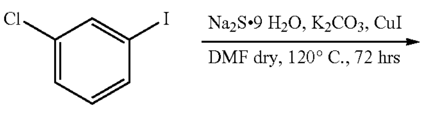

1

-continued

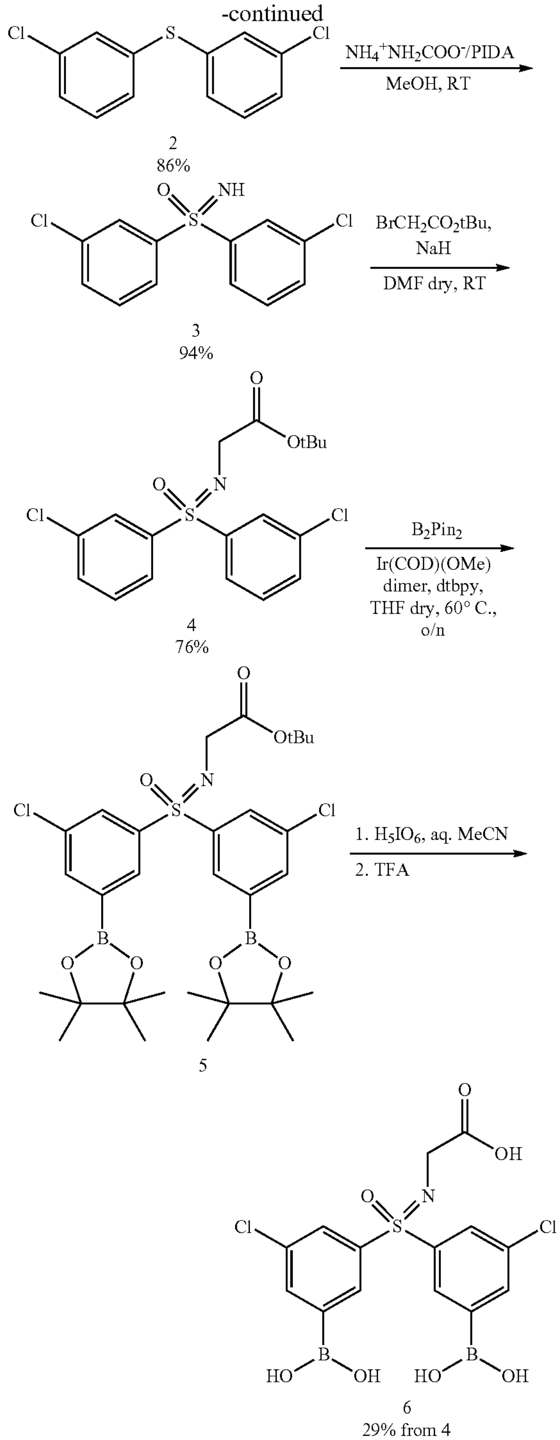

A well stirred suspension of 3-chloroiodobenzene (1, 10.2 g, 42.6 mmol), sodium sulfide nonahydrate (7.16 g, 29.8 mmol), potassium carbonate (5.89 g, 42.6 mmol) and copper (I) iodide (811 mg, 4.26 mmol) in dry N,N-dimethylformamide (85 mL) was heated to 120° C. (oil bath) for 72 hours. After cooling to ambient temperature, the reaction mixture was diluted with diethyl ether (150 mL) and filtered through a pad of Celite, the pad was washed with more diethyl ether (3×100 mL). The filtrate was transferred to a separatory funnel and washed with water (200 mL) and 1 M aqueous solution of sodium hydroxide (2×150 mL). The organic layer was dried over anhydrous sodium sulfate, filtered and evaporated. The residue was subjected to flash column chromatography (Silicagel 60, 0.063-0.200 mm; eluent: cyclohexane) to give bis(3-chlorophenyl)sulfane (2) as colorless oil.

Yield: 4.66 g (86%).

$^1$H NMR spectrum (300 MHz, DMSO-d$_6$, $\delta_H$): 7.45-7.38 (m, 6H); 7.35-7.29 (m, 2H).

LC-MS purity: 97% (UV 254).

LC-MS Rt (Kinetex C18, 4.6 mm×50 mm, acetonitrile/water 70:30 to 100:0+0.1% FA): 3.25 min.

LC-MS m/z: 254.1 $(M+H)^+$.

To a well-stirred solution of bis(3-chlorophenyl)sulfane (2, 4.00 g, 15.7 mmol) in methanol (37 mL) was added ammonium carbamate (2.84 g, 31.4 mmol) and bis(acetoxy)iodobenzene (14.7 g, 39.3 mmol). After 2 hours, the reaction mixture was evaporated in vacuo and the residue was dissolved in ethyl acetate (40 mL) and washed with 10% aqueous solution of sodium thiosulfate (40 mL), 10% aqueous solution of potassium bicarbonate (40 mL) and brine (40 mL). The organic layer was separated, dried over anhydrous sodium sulfate, filtered and evaporated. The residue was subjected to flash column chromatography (Silicagel 60, 0.063-0.200 mm; eluent: cyclohexane/ethyl acetate 3:1) to give bis(3-chlorophenyl)(imino)-λ$^6$-sulfanone (3) as yellowish oil.

Yield: 4.13 g (94%).

$^1$H NMR spectrum (300 MHz, $CDCl_3$, $\delta_H$): 8.03 (t, J=1.8 Hz, 2H); 7.95-7.88 (m, 2H); 7.55-7.49 (m, 2H); 7.44 (t, J=7.9 Hz, 2H); 3.15 (bs, 1H).

LC-MS purity: 100% (ELSD, UV 242).

LC-MS Rt (Kinetex C18, 4.6 mm×50 mm, acetonitrile/water 40:60 to 100:0+0.1% FA): 2.65 min.

LC-MS m/z: 286.2 $(M+H)^+$.

To an ice-cold, well-stirred solution of bis(3-chlorophenyl)(imino)-λ$^6$-sulfanone (3, 4.13 g, 16.2 mmol) in anhydrous N,N-dimethylformamide (45 mL) was added sodium hydride (712 mg, 17.8 mmol) under nitrogen. After 5 minutes, tert-butyl bromoacetate (4.74 mL, 24.3 mmol) was added. The reaction mixture was allowed to reach ambient temperature and stirred for an hour. The reaction mixture was then taken up in ethyl acetate (160 mL) and washed with 10% aqueous solution of ammonium chloride (160 mL), water (2×160 mL) and brine (160 mL). The organic layer was dried over anhydrous sodium sulfate, filtered and evaporated. The crude product was purified by column chromatography (Silicagel, 0.063-0.200 mm; eluent: cyclohexane/ethyl acetate 20:1 to 3:1) to provide tert-butyl 2-((bis(3-chlorophenyl)(oxo)-λ$^6$-sulfanylidene)amino)acetate (4) as yellowish oil.

Yield: 4.73 g (76%).

$^1$H NMR spectrum (300 MHz, $CDCl_3$, $\delta_H$): 8.04 (t, J=1.8 Hz, 2H); 7.94 (dt, J=7.7, 1.4 Hz and 2H); 7.55-7.49 (m, 2H); 7.44 (t, J=7.9 Hz, 2H); 3.76 (s, 2H); 1.48 (s, 9H).

LC-MS purity: 100% (ELSD, UV 242).

LC-MS Rt (Kinetex C18, 4.6 mm×50 mm, acetonitrile/water 40:60 to 100:0+0.1% FA): 4.29 min.

LC-MS m/z: 400.3 $(M+H)^+$.

tert-Butyl 2-((bis(3-chlorophenyl)(oxo)-λ$^6$-sulfanylidene)amino)acetate (4, 400 mg, 1.00 mmol), bis(pinacolato)diboron (635 mg, 2.50 mmol), (1,5-cyclooctadiene)(methoxy)iridium(I) dimer (26.5 mg, 0.04 mmol) and 4,4'-di-tert-butyl-2,2'-dipyridyl (dtbpy, 26.5 mg, 0.04 mmol) were dissolved in dry, degassed tetrahydrofuran (4 mL) under nitrogen. The reaction mixture was stirred at 60° C. (oil bath) for 16 hours. Afterwards, the reaction mixture was evaporated to dryness and the residue was dissolved in dichloromethane (10 mL) and filtered through a plug of silicagel (7.00 g) topped with Celite with the aid of dichloromethane (4×15 mL). The filtrate was evaporated to give crude tert-butyl 2-((oxobis(3-(4,4,5,5-tetramethyl-1,3,2-dioxaborolan-2-yl)-5-(trifluoromethyl)phenyl)-λ$^6$-sulfanylidene)amino)acetate (5) as yellowish foam.

It was dissolved in acetonitrile (6 mL) and water (2 mL) and periodic acid (1596 mg, 7.00 mmol) was added. The resulting mixture was stirred for 1 hour and it was then partitioned between ethyl acetate (30 mL) and water (30 mL). The phases were separated and the organic layer was washed with brine (2×30 mL), dried over anhydrous sodium sulfate, filtered and evaporated to give a yellowish waxy solid.

The solid was dissolved in trifluoroacetic acid (5 mL) and the mixture was stirred for 1 hour at room temperature. The mixture was evaporated to dryness in vacuo, and the residue was co-distilled with ethyl acetate (5×10 mL) and acetonitrile (5×5 mL). A part of the residue was dissolved in acetonitrile/water mixture (3:1, 4 mL) and purified by preparative LC/MS, SunFire Prep C18 OBD, 5 μm, 19×100 mm, acetonitrile/water 5:95 to 100:0+0.1% FA) to afford 2-((bis(3-borono-5-chlorophenyl)(oxo)-λ$^6$-sulfanylidene)amino)acetic acid (6) as colorless solid.

Yield: 125 mg (29%).

$^1$H NMR spectrum (300 MHz, Acetone-d$_6$+$D_2O$, $\delta_H$): 8.39 (bs, 2H); 8.10 (bs, 2H); 7.99 (bs, 2H); 3.77 (s, 2H, overlapping with water signal).

LC-MS purity: 100% (ELSD).

LC-MS Rt (Kinetex C18, 4.6 mm×50 mm, acetonitrile/water 20:80 to 100:0+0.1% FA): 2.70 min.

LC-MS m/z: 432.2 $(M+H)^+$.

Example 36

2-((Bis(3-boronophenyl)(oxo)-λ6-sulfanylidene)amino)acetic acid

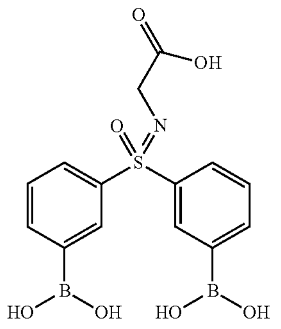 [SMILES: O=C(O)CN=S(=O)(c1cccc(B(O)O)c1)c1cccc(B(O)O)c1]

2-((Bis(3-boronophenyl)(oxo)-λ6-sulfanylidene)amino)acetic acid was synthesized according to the reaction scheme shown in Chem. 40 and following the procedure described below.

Chem. 40

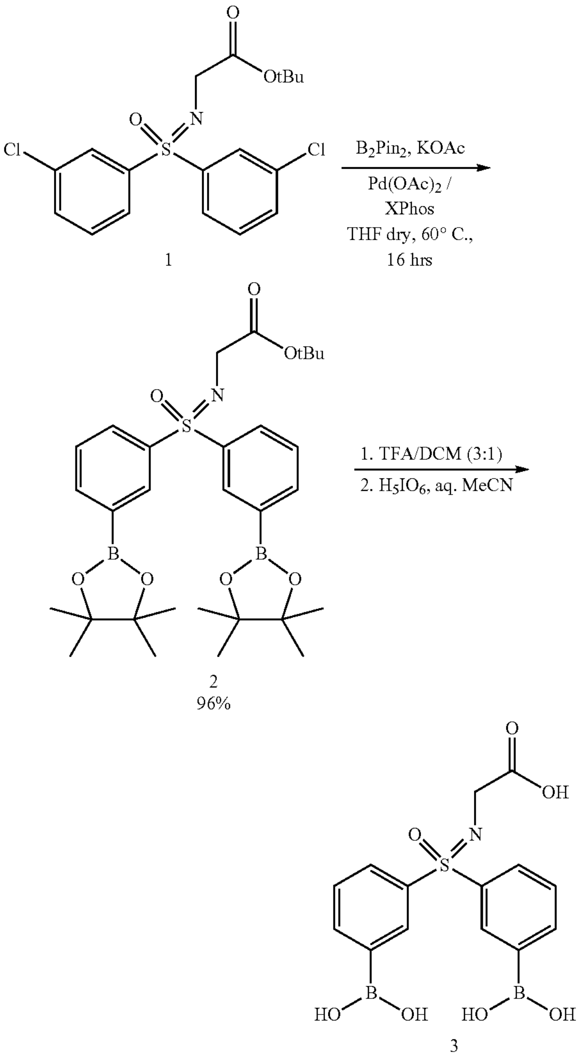

1

2
96%

3
80%

A 25 mL reaction vessel was charged with potassium acetate (1.14 g, 11.6 mmol) and the salt was dried for 1 hour at 110 C in vacuo. After cooling to room temperature, the reaction vessel was backfilled with nitrogen and charged with tert-butyl 2-((bis(3-chlorophenyl)(oxo)-λ6-sulfanylidene)amino)acetate (1, 925 mg, 2.32 mmol), palladium acetate (20.8 mg, 93.0 mol), 2-dicyclohexylphosphino-2,4,6-triisopropylbiphenyl (XPhos, 88.2 mg, 0.19 mmol) and bis(pinacolato)diboron (1.18 g, 4.64 mmol). The reaction vessel was then evacuated and backfilled with nitrogen (this procedure was repeated twice), anhydrous tetrahydrofuran (10 mL) was added with syringe, the vessel was sealed with a plastic stopper and submerged in the heating bath pre-heated to 60 C. After stirring at 400 rpm for 16 hours the reaction mixture was cooled to ambient temperature, diluted with ethyl acetate (40 mL) and filtered through a short plug of silica (25 g) topped with Celite S with the aid of ethyl acetate (3×40 mL). The filtrate was concentrated under reduced pressure to afford the crude product 2 as yellowish oil. It was triturated with acetonitrile (10 mL) and the precipitate (XPhos oxide) was filtered. The filtrate was evaporated in vacuo and co-distilled with cyclohexane (3×20 mL) to afford a yellowish foam, which was pulverized to give tert-butyl 2-((oxobis(3-(4,4,5,5-tetramethyl-1,3,2-dioxaborolan-2-yl)phenyl)-λ$^6$-sulfanylidene)amino)acetate (2) as yellow oil.

Yield: 1.30 g (96%).

$^1$H NMR spectrum (300 MHz, $CDCl_3$, $\delta_H$): 8.45 (s, 2H); 8.15 (s, 2H); 7.94 (d, J=7.3 Hz, 2H); 7.48 (t, J=7.7 Hz, 2H); 3.75 (s, 2H); 1.49 (s, 9H); 1.34 (s, 24H).

LC-MS purity: 100% (ELSD, UV 270 nm).

LC-MS Rt (Kinetex C18, 4.6 mm×50 mm, acetonitrile/water 70:30 to 100:0+0.1% FA): 2.8 min.

LC-MS m/z: 584.6 $(M+H)^+$.

Trifluoroacetic acid (12 mL) was added to a solution of tert-butyl 2-((oxobis(3-(4,4,5,5-tetramethyl-1,3,2-dioxaborolan-2-yl)phenyl)-λ$^6$-sulfanylidene)amino)acetate (2, 1.30 g, 2.20 mmol) in dichloromethane (4 mL) and the mixture was stirred for 2 hours at room temperature. The mixture was evaporated to dryness in vacuo, and the residue was evaporated from dichloromethane (5×10 mL) to afford of 2-((oxobis(3-(4,4,5,5-tetramethyl-1,3,2-dioxaborolan-2-yl)phenyl)-λ$^6$-sulfanylidene)amino)acetic acid as off-white foam.

A solution of 2-((oxobis(3-(4,4,5,5-tetramethyl-1,3,2-dioxaborolan-2-yl)phenyl)-λ$^6$-sulfanylidene)amino)acetic acid (1.00 g, 1.90 mmol) in acetonitrile (12 mL) was diluted with water (4 mL) followed by addition of periodic acid (1.73 g, 7.60 mmol). The resulting mixture was stirred for 1 hour; and then it was diluted with ethyl acetate (100 mL) and washed with 5% brine (3×100 mL). Organic phase was dried over anhydrous sodium sulfate and evaporated to dryness. A part of the residue was dissolved in acetonitrile/water mixture (3:1, 4 mL) and purified by preparative LC/MS (SunFire Prep C18 OBD, 5 m, 19×100 mm, acetonitrile/water 5:95 to 100:0+0.1% FA). The resulting solution was freeze-dried to afford 2-((bis(3-boronophenyl)(oxo)-λ$^6$-sulfanylidene)amino)acetic acid (3) as white powder.

Yield: 700 mg (80%).

$^1$H NMR spectrum (300 MHz, Acetone-$d_6$+$D_2O$, $\delta_H$): 8.50 (s, 2H); 8.05 (t, J=7.8 Hz, 4H); 7.55 (t, J=7.7 Hz, 4H); 3.72 (s, 2H).

LC-MS purity: 100% (ELSD, UV 260 nm).

LC-MS Rt (Kinetex C18, 4.6 mm×50 mm, acetonitrile/water 5:95 to 100:0+0.1% FA): 3.19 min.

Example 37

N-(1-Hydroxy-5-(trifluoromethyl)-1,3-dihydrobenzo[c][1,2]oxaborole-6-carbonyl)-N-(2-(1-hydroxy-5-(trifluoromethyl)-1,3-dihydrobenzo[c][1,2]oxaborole-6-carboxamido)ethyl)glycine

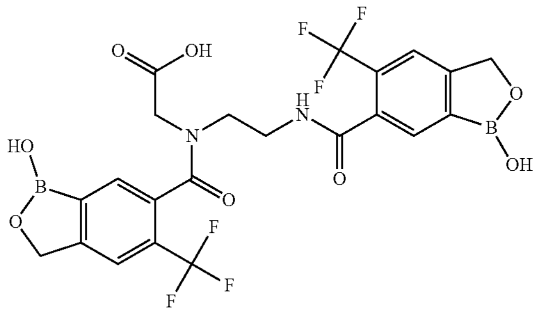 [SMILES: O=C(O)CN(CCNC(=O)c1cc2c(cc1C(F)(F)F)COB2O)C(=O)c1cc2c(cc1C(F)(F)F)COB2O]

N-(1-Hydroxy-5-(trifluoromethyl)-1,3-dihydrobenzo[c][1,2]oxaborole-6-carbonyl)-N-(2-(1-hydroxy-5-(trifluoromethyl)-1,3-dihydrobenzo[c][1,2]oxaborole-6-carboxamido)ethyl)glycine was synthesized according to the reaction scheme shown in Chem. 41 and following the procedure described below.

Chem. 41

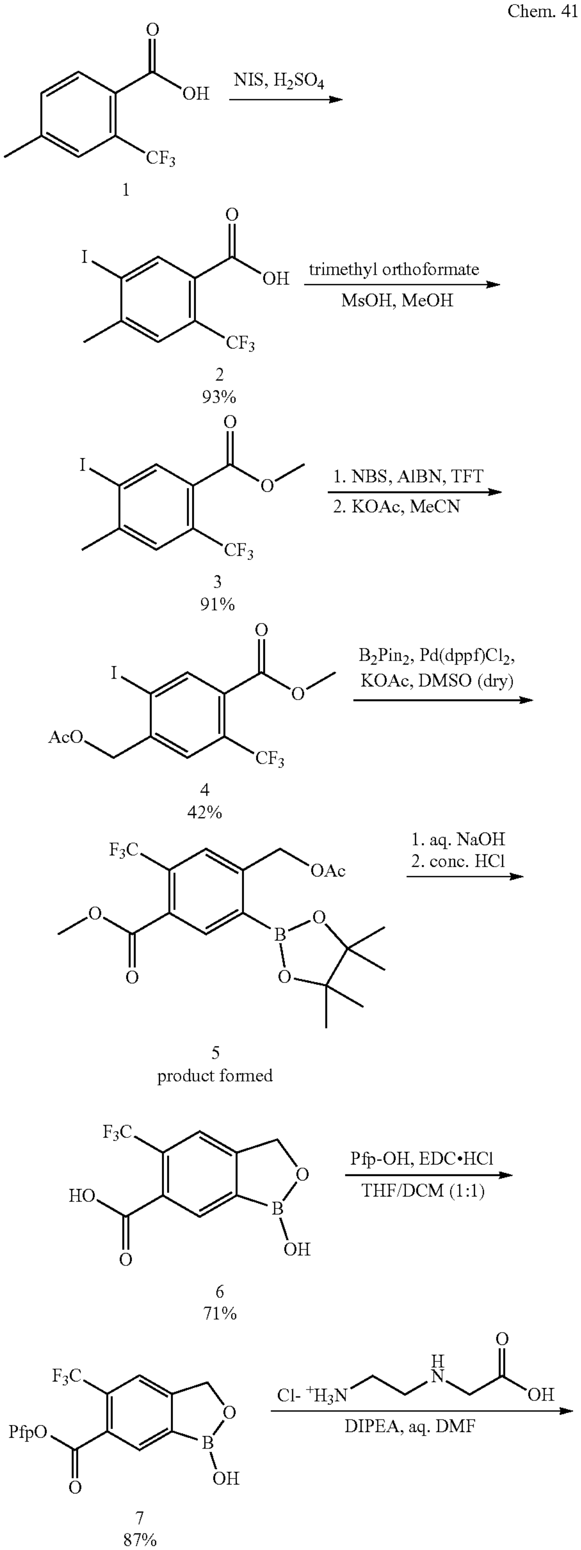

-continued

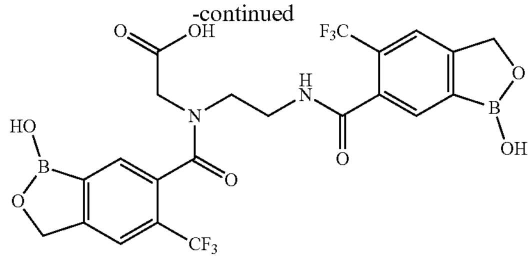

9
55%

4-Methyl-2-(trifluoromethyl)benzoic acid (1, 25.0 g, 123 mmol) was dissolved in sulfuric acid (183 mL) followed by addition of N-iodosuccinimide (33.1 g, 147 mmol). The resulting mixture was stirred overnight at room temperature then it was poured onto ice. When ice was completely melted the mixture was extracted with ethyl acetate (500 mL). Organic layer was washed with 5% aqueous solution of sodium thiosulfate (2×250 mL) and water (1×250 mL), dried over anhydrous sodium sulfate, filtered and evaporated to dryness affording 5-iodo-4-methyl-2-(trifluoromethyl)benzoic acid (2) as beige powder.

Yield: 37.7 g (93%).

$^1$H NMR spectrum (300 MHz, DMSO-$d_6$, $\delta_H$): 13.68 (bs, 1H); 8.22 (s, 1H); 7.76 (s, 1H); 2.47 (s, 3H).

Mixture of 5-iodo-4-methyl-2-(trifluoromethyl)benzoic acid (2, 22.2 g, 67.2 mmol), trimethyl orthoformate (14.7 mL, 134 mmol) and methanesulfonic acid (2.8 mL) in methanol (135 mL) was refluxed at 80° C. under nitrogen atmosphere overnight. Solvent was evaporated. The residue was dissolved in 5% aqueous solution of sodium carbonate (200 mL) and extracted with ethyl acetate (3×250 mL). Combined organic layers were washed with water (1×300 mL) and brine (1×200 mL), dried over anhydrous sodium sulfate, filtered and evaporated. The residue was purified by quick flash column chromatography (Silicagel 60, 0.040-0.063 mm; eluent: cyclohexane/ethyl acetate 9:1) to give methyl 5-iodo-4-methyl-2-(trifluoromethyl)benzoate (3) as white crystals. Yield: 35.9 g (91%).

$R_F$ (cyclohexane/ethyl acetate 9:1): 0.50.

$^1$H NMR spectrum (300 MHz, $CDCl_3$, $\delta_H$): 8.26 (s, 1H); 7.57 (s, 1H); 3.93 (s, 3H); 2.53 (s, 3H).

A mixture of methyl 5-iodo-4-methyl-2-(trifluoromethyl)benzoate (3, 35.9 g, 104 mmol), N-bromosuccinimide (20.4 g, 114 mmol) and 2,2-azobis(2-methylpropionitrile) (AIBN, 5.12 g, 31.2 mmol) in benzotrifluoride (95 mL) was stirred at 85° C. overnight. Full conversion was not achieved but the reaction was worked up. Dichloromethane (150 mL) was added and the mixture was washed with water (3×100 mL). Organic layer was dried over anhydrous sodium sulfate, filtered and evaporated. The residue was dissolved in acetonitrile (440 mL) and potassium acetate (10.2 g, 104 mmol) was added. The mixture was stirred at 75 C overnight. The insoluble material was filtered off and the filtrate was evaporated. The residue was purified by flash column chromatography (Silicagel 60, 0.040-0.063 mm; eluent: cyclohexane/dichloromethane 4:1 to 1:1.5) to give methyl 4-(acetoxymethyl)-5-iodo-2-(trifluoromethyl)benzoate (4) as white powder. Yield: 17.5 g (42%).

$R_F$ (cyclohexane/ethyl acetate 9:1): 0.35.

$^1H$ NMR spectrum (300 MHz, $CDCl_3$, $\delta_H$): 8.28 (s, 1H); 7.70 (s, 1H); 5.16 (s, 2H); 3.95 (s, 3H); 2.20 (s, 3H).

$^{19}F$ NMR spectrum (282 MHz, $CDCl_3$, $\delta_F$): −59.96 (s).

A mixture of methyl 4-(acetoxymethyl)-5-iodo-2-(trifluoromethyl)benzoate (4, 17.5 g, 43.5 mmol), bis(pinacolato) diboron (14.3 g, 56.5 mmol) and dry potassium acetate (21.3 g, 217 mmol) in dry N,N-dimethylsulfoxide (110 mL) was degassed; then [1,1-bis(diphenylphosphino)ferrocene]dichloropalladium (1.59 g, 2.17 mmol) was added. Reaction mixture was stirred under nitrogen atmosphere at 95° C. overnight. After cooling down diethyl ether (500 mL) was added and the precipitate was filtered off through celite pad. The filtrate was washed with 5% aqueous solution of sodium chloride (3×500 mL). Organic layer was dried over anhydrous sodium sulfate, filtered and evaporated affording methyl 4-(acetoxymethyl)-5-(4,4,5,5-tetramethyl-1,3,2-dioxaborolan-2-yl)-2-(trifluoromethyl)benzoate (5) as black oil. This oil was used in the next step without further purification. Yield: 22.5 g.

$^1H$ NMR spectrum (300 MHz, $CDCl_3$, $\delta_H$): 8.22 (s, 1H); 7.74 (s, 1H); 5.44 (s, 2H); 3.94 (s, 3H); 2.14 (s, 3H); 1.36 (s, 12H).

$^{19}F$ NMR spectrum (282 MHz, $CDCl_3$, $\delta_F$): −60.07 (s).

Methyl 4-(acetoxymethyl)-5-(4,4,5,5-tetramethyl-1,3,2-dioxaborolan-2-yl)-2-(trifluoromethyl)benzoate (5, 17.5 g, 43.5 mmol) was suspended in a solution of sodium hydroxide (8.70 g, 217 mmol) in water (150 mL). The mixture was stirred for 6 hours at room temperature then it was extracted with diethyl ether (2×200 mL). Aqueous phase was acidified with concentrated hydrochloric acid (18.9 mL) and resulting mixture was stirred overnight at room temperature. The precipitate was filtered, washed with water and dried to give 1-hydroxy-5-(trifluoromethyl)-1,3-dihydrobenzo[c][1,2] oxaborole-6-carboxylic acid (6) as grey powder.

Yield: 7.62 g (71%).

$^1H$ NMR spectrum (300 MHz, DMSO-$d_6$, $\delta_H$): 13.50 (bs, 1H); 9.57 (s, 1H); 8.16 (s, 1H); 7.92 (s, 1H); 5.11 (s, 2H).

$^{19}F$ NMR spectrum (282 MHz, DMSO-$d_6$, $\delta_F$): −57.91 (s).

LC-MS purity: 100% (ELSD).

LC-MS Rt (Kinetex C18, 4.6 mm×50 mm, acetonitrile/water 5:95 to 100:0+0.1% FA): 2.77 min.

LC-MS m/z: 245.9 $(M-H)^-$.

1-Hydroxy-5-(trifluoromethyl)-1,3-dihydrobenzo[c][1,2] oxaborole-6-carboxylic acid (6, 6.71 g, 27.3 mmol) was dissolved in tetrahydrofuran/dichloromethane mixture (1:1, 50 mL) followed by addition of 2,3,4,5,6-pentrafluorophenol (5.03 g, 27.3 mmol) and N-(3-dimethylaminopropyl)-N-ethylcarbodiimide hydrochloride (5.23 g, 27.3 mmol). The mixture was stirred overnight at room temperature. Solvent was evaporated. The residue was dissolved in ethyl acetate (150 mL) and washed with water (3×100 mL) and brine (1×100 mL). Organic layer was dried over anhydrous sodium sulfate, filtered and evaporated. The residue was dissolved in diethyl ether (10 mL) and n-hexane (200 mL) was added. The precipitate was filtered off and the filtrate was evaporated. The same procedure was repeated with the precipitate twice. All the filtrates were combined together and evaporated to dryness to afford perfluorophenyl 1-hydroxy-5-(trifluoromethyl)-1,3-dihydrobenzo[c][1,2]oxaborole-6-carboxylate (7) as yellow tough oil.

Yield: 9.76 g (87%).

$^1H$ NMR spectrum (300 MHz, DMSO-$d_6$, $\delta_H$): 9.74 (s, 1H); 8.53 (s, 1H); 8.16 (s, 1H); 5.18 (s, 2H).

Perfluorophenyl 1-hydroxy-5-(trifluoromethyl)-1,3-dihydrobenzo[c][1,2]oxaborole-6-carboxylate (7, 9.51 g, 23.1 mmol) was dissolved in N,N-dimethylformamide (30 mL). Subsequently N,N-diisopropylethylamine (10.1 mL, 57.7 mmol) and a solution of (2-aminoethyl)glycine hydrochloride (8, 1.78 g, 11.5 mmol) in water (30 mL) were added. Resulting mixture was stirred overnight at room temperature. Then the solvents were evaporated. The residue was dissolved in ethyl acetate (200 mL) and washed 1 M aqueous solution of hydrochloric acid (1×200 mL), water (2×200 mL) and brine (1×150 mL). Organic layer was dried over anhydrous sodium sulfate, filtered and evaporated. The residue was treated with cyclohexane. The precipitate was filtered, washed with cyclohexane and purified by flash column chromatography (Silicagel 60, 0.040-0.063 mm; eluent: dichloromethane/methanol/formic acid 10:1:0.05). Fractions containing product were combined and evaporated. The residue was treated with cyclohexane. The precipitate was filtered, washed with cyclohexane, dissolved in acetonitrile (50 mL) and freeze-dried to give the title compound (9) as beige powder. Yield: 3.63 g (55%).

$^1H$ NMR spectrum (300 MHz, AcOD-$d_4$, 80 C, $\delta_H$): 8.04-7.66 (m, 4H); 5.28-5.04 (m, 4H); 4.63-4.34 (m, 1H); 4.22-3.78 (m, 3H); 3.72-3.49 (m, 2H).

LC-MS purity: 100% (ELSD).

LC-MS Rt (Kinetex C18, 4.6 mm×50 mm, acetonitrile/water 5:95 to 100:0+0.1% FA): 4.15 min.

LC-MS m/z: 574.0 $(M+H)^+$.

Example 38

2-((Bis(1-hydroxy-4-(trifluoromethyl)-1,3-dihydrobenzo[c][1,2]oxaborol-6-yl)(oxo)-λ6-sulfanylidene)amino)acetic acid

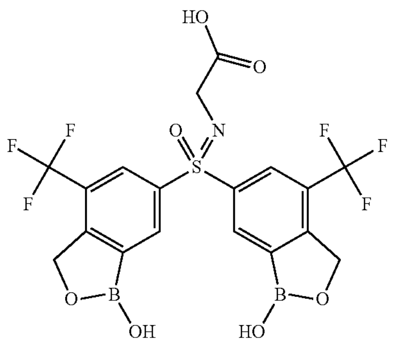 [SMILES: O=C(O)CN=S(=O)(c1cc2c(c(C(F)(F)F)c1)COB2O)c1cc2c(c(C(F)(F)F)c1)COB2O]

2-((Bis(1-hydroxy-4-(trifluoromethyl)-1,3-dihydrobenzo [c][1,2]oxaborol-6-yl)(oxo)-λ6-sulfanylidene)amino)acetic acid was synthesized according to the reaction scheme shown in Chem. 42 and Chem. 43 and following the procedure described below.

Chem. 42

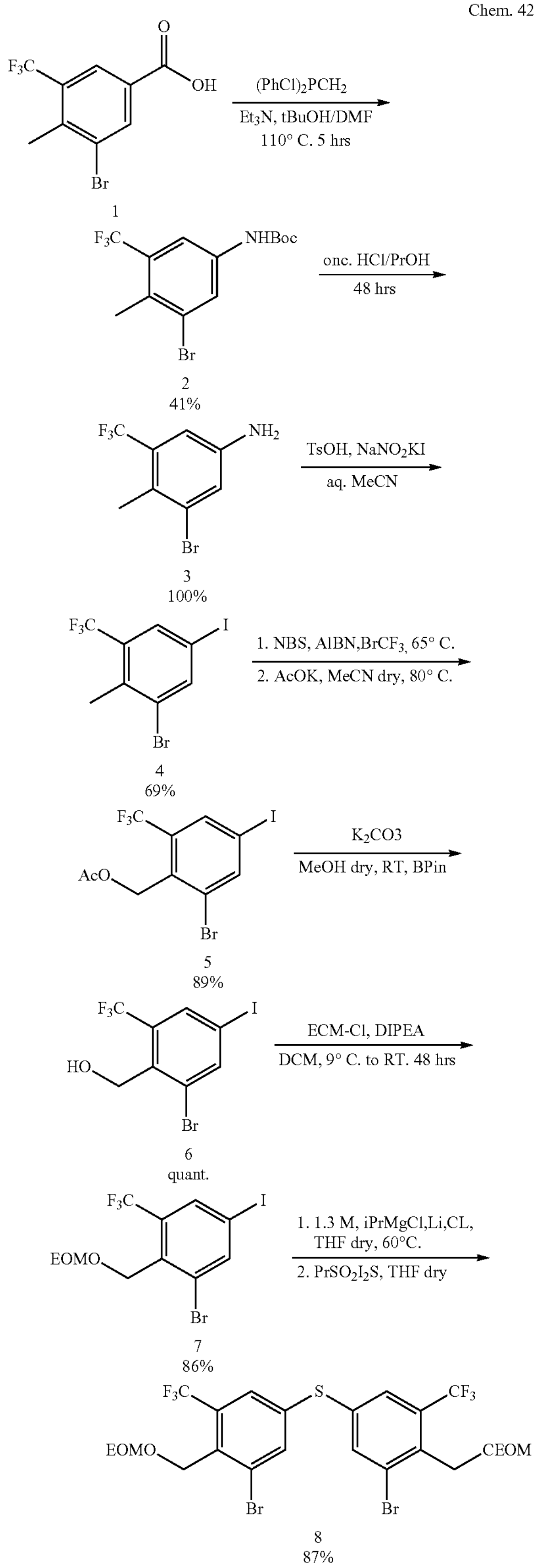

Solution of 3-bromo-4-methyl-5-trifluoromethylbenzoic acid (1, 26.6 g, 94.0 mmol), triethylamine (16.0 mL, 113 mmol) and diphenyl phosphoryl azide (24.0 mL, 113 mmol) in mixture of N,N-dimethylformamide and tert-butanol (1:5, 0.5 L) was stirred at 110° C. for 5 hours. The reaction mixture was then evaporated and crude product was dissolved in ethyl acetate (0.5 L) and washed with 10% aqueous solution of citric acid (300 mL), 10% aqueous solution of sodium bicarbonate (300 mL) and brine (300 mL). Organic layer was separated, dried over anhydrous sodium sulfate, filtered and evaporated. Crude product was purified by column chromatography (Silicagel, 0.063-0.200 mm; eluent: cyclohexane/ethyl acetate 9:1) to provide tert-butyl (3-bromo-4-methyl-5-(trifluoromethyl)phenyl)carbamate (2) as white solid.

Yield: 13.5 g (41%).

$^1$H NMR spectrum (300 MHz, DMSO-$d_6$, $\delta_H$): 7.91 (s, 1H); 7.55 (d, J=2.4 Hz, 1H); 6.49 (bs, 1H); 2.47 (d, J=1.5 Hz, 3H); 1.54 (s, 9H).

tert-Butyl (3-bromo-4-methyl-5-(trifluoromethyl)phenyl) carbamate (2, 10.0 g, 28.2 mmol) was dissolved in 2-propanol (60 mL) and concentrated aqueous hydrochloric acid (15 mL) was added. After 48 hours, the reaction mixture was evaporated, taken up in diethyl ether (100 mL) and washed with 1 M aqueous solution of sodium hydroxide (100 mL) and brine (100 mL). Organic layer was dried over anhydrous sodium sulfate, filtered and evaporated to give the crude 3-bromo-4-methyl-5-(trifluoromethyl)aniline (3) as yellowish oil, which was taken to the next step without purification.

3-Bromo-4-methyl-5-(trifluoromethyl)aniline (3) was dissolved in ice-cold acetonitrile (110 mL) and 4-toluenesulfonic acid monohydrate (16.1 g, 84.6 mmol) was added. Ice-cold water (45 mL) was added to the mixture to improve stirring. A solution of sodium nitrite (3.90 g, 56.4 mmol) and potassium iodide (11.7 g, 70.5 mmol) in water (30 mL) was then added dropwise to the acetonitrile solution (cooled in an ice-bath). After the addition had been completed and the gas evolution had ceased, the reaction mixture was allowed to reach ambient temperature and stirred for 2 hours. The reaction mixture was concentrated under reduced pressure and taken up in diethyl ether (100 mL) and washed with 10% aqueous solution of potassium carbonate (100 mL) and 10% aqueous solution of sodium thiosulfate (50 mL). Organic layer was dried over anhydrous sodium sulfate, filtered and evaporated to give the crude product, which was subjected to flash column chromatography (Silicagel 60, 0.063-0.200 mm; eluent: neat cyclohexane) to give 1-bromo-5-iodo-2-methyl-3-(trifluoromethyl)benzene (4) as yellow oil. Yield: 7.06 g (69%).

$^1$H NMR spectrum (300 MHz, $CDCl_3$, $\delta_H$): 8.09 (s, 1H); 7.89 (s, 1H); 2.49 (s, 3H).

A mixture of 1-bromo-5-iodo-2-methyl-3-(trifluoromethyl)benzene (4, 6.65 g, 18.2 mmol), N-bromosuccinimide (4.22 g, 23.7 mmol) and AIBN (299 mg, 1.82 mmol) was suspended in benzotrifluoride (27 mL) and heated to 85° C. (oil bath) for 24 hours. More AIBN (299 mg, 1.82 mmol) was added and the reaction mixture was heated with stirring for additional 24 hours. After cooling to ambient temperature, the reaction mixture was taken in diethyl ether (100 mL) and washed with 10% aqueous solution of potassium bicarbonate (100 mL), water (100 mL), 10% aqueous solution of sodium thiosulfate (50 mL), water (50 mL) and brine (50 mL). Organic layer was dried over anhydrous sodium sulfate, filtered and evaporated to give the crude benzylic bromide. It was dissolved in dry acetonitrile (27 mL) and potassium acetate (3.60 g, 36.0 mmol) was added. The resulting suspension was heated to 80° C. (oil bath) for 24 hours. After cooling to ambient temperature, the reaction mixture was taken in diethyl ether (100 mL) and filtered through a short plug of Silica gel (50 g) topped with Celite. Filtrate was evaporated in vacuo and the residue was subjected to flash column chromatography (Silicagel 60, 0.063-0.200 mm; eluent: cyclohexane/ethyl acetate 10:1) to give 2-bromo-4-iodo-6-(trifluoromethyl)benzyl acetate (5) as colorless solid.

Yield: 6.60 g (85%).

$^{1}$H NMR spectrum (300 MHz, $CDCl_3$, $\delta_H$): 8.20 (s, 1H); 8.00 (s, 1H); 5.27 (s, 2H); 2.09 (s, 3H).

2-Bromo-4-iodo-6-(trifluoromethyl)benzyl acetate (5, 5.16 g, 12.2 mmol) was dissolved in dry methanol (36 mL) and potassium carbonate (5.00 g, 36.2 mmol) was added. After 90 minutes, the reaction mixture was taken in diethyl ether (100 mL) and filtered through a short plug of Silica gel (50 g) topped with Celite. The filtrate was evaporated in vacuo to give pure 2-bromo-4-iodo-6-(trifluoromethyl)phenyl)methanol (6) as colorless solid.

Yield: 4.64 g (quant.).

$^{1}$H NMR spectrum (300 MHz, $CDCl_3$, $\delta_H$): 8.18 (s, 1H); 7.98 (s, 1H); 4.87 (d, J=6.9 Hz, 2H), 2.08 (t, J=6.9 Hz, 1H).

2-Bromo-4-iodo-6-(trifluoromethyl)phenyl)methanol (6, 4.64 g, 12.2 mmol) was dissolved in dry ice-cold dichloromethane (36 mL) and N,N-diisopropylethylamine (DIPEA, 4.20 mL, 24.4 mmol) was added, followed by ethoxymethyl chloride (1.45 mL, 15.6 mmol). The reaction mixture was allowed to reach ambient temperature and stirred for 48 hours before it was quenched with methanol (5 mL). After 2 hours, the reaction mixture was evaporated in vacuo and the residue was taken up in diethyl ether (100 mL) and washed with 10% aqueous solution of potassium bisulfate (100 mL), water (100 mL) and brine (50 mL). Organic layer was dried over anhydrous sodium sulfate, filtered and evaporated. The residue was subjected to flash column chromatography (Silicagel 60, 0.063-0.200 mm; eluent: cyclohexane/ethyl acetate 20:1) to give 1-bromo-2-((ethoxymethoxy)methyl)-5-iodo-3-(trifluoromethyl)benzene (7) as colorless solid.

Yield: 4.57 g (85%).

$^{1}$H NMR spectrum (300 MHz, $CDCl_3$, $\delta_H$): 8.20 (s, 1H); 7.98 (s, 1H); 4.83 (s, 2H); 4.75 (s, 2H); 3.71 (q, J=7.1 Hz, 2H); 1.27 (t, J=7.1 Hz, 3H).

1-Bromo-2-((ethoxymethoxy)methyl)-5-iodo-3-(trifluoromethyl)benzene (7, 3.32 g, 7.57 mmol) was dissolved in dry tetrahydrofuran (23 mL) under inert atmosphere and cooled to 30 C (methanol/dry ice bath). 1.3 M Solution isopropylmagnesium chloride-lithium chloride complex in tetrahydrofuran (6.10 mL, 7.93 mmol) was added dropwise with stirring. After 30 minutes, a solution of bis(phenylsulfonyl)sulfide (1.07 mg, 3.41 mmol) in dry tetrahydrofuran (10 mL) was added dropwise. The reaction mixture was then allowed to reach slowly ambient temperature (cooling bath was allowed to expire) and then quenched with 10% aqueous solution of ammonium chloride (15 mL). The reaction mixture was taken up in diethyl ether (50 mL) and washed with water (50 mL) and brine (50 mL). Organic layer was dried over anhydrous sodium sulfate, filtered and evaporated. The residue was subjected to flash column chromatography (Silicagel 60, 0.063-0.200 mm; eluent: cyclohexane/ethyl acetate 30:1) to give bis(3-bromo-4-((ethoxymethoxy)methyl)-5-(trifluoromethyl)phenyl)sulfane (8) as colorless solid. Yield: 1.96 g (87%).

$^{1}$H NMR spectrum (300 MHz, $CDCl_3$, $\delta_H$): 7.76 (s, 2H); 7.65 (s, 2H); 4.84 (s, 4H); 4.79 (s, 4H); 3.71 (q, J=7.1 Hz, 4H); 1.26 (t, J=7.1 Hz, 6H).

Chem. 43

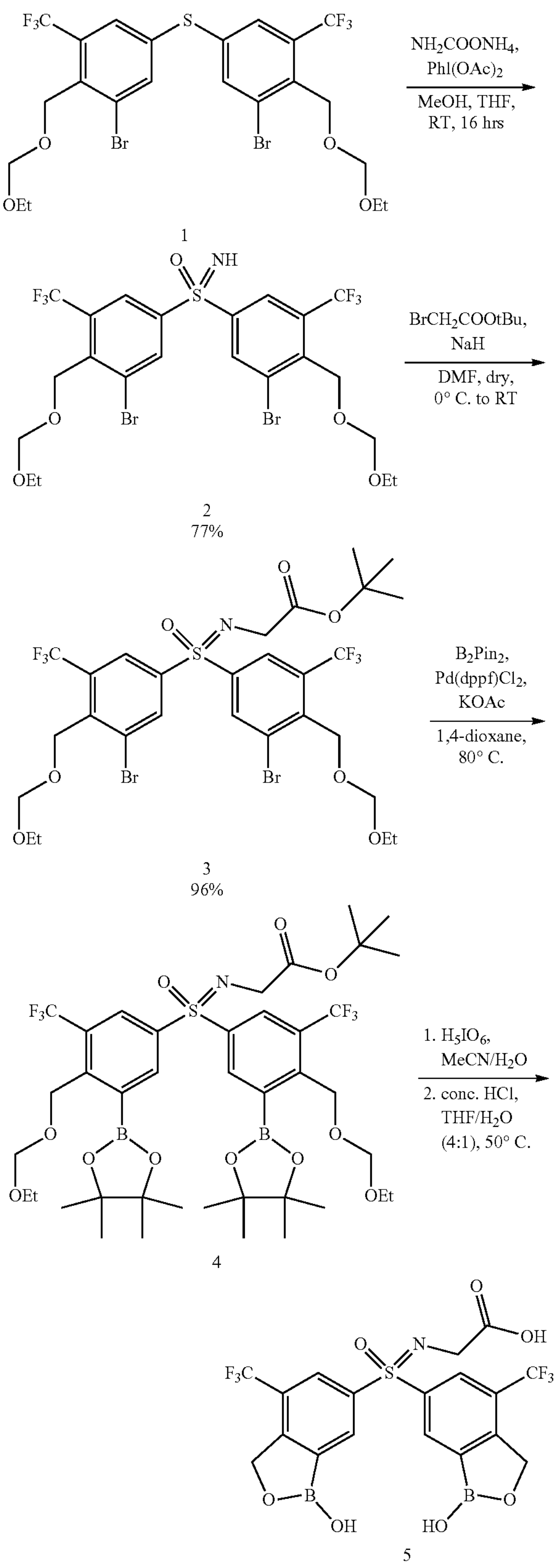

1

2
77%

3
96%

4

5
78% from 3

To a well-stirred solution of bis(3-bromo-4-((ethoxymethoxy)methyl)-5-(trifluoromethyl)phenyl)sulfane (1, 997 mg, 1.52 mmol, compound)) in mixture of tetrahydrofuran (3 mL) and methanol (6 mL) was added ammonium carbamate (238 mg, 3.04 mmol) and bis(acetoxy)iodobenzene (1.22 g, 3.80 mmol). After 3 hours, to the reaction mixture more ammonium carbamate (119 mg, 1.52 mmol) and bis(acetoxy)iodobenzene (611 mg, 1.90 mmol) were added. After six more hours, to the reaction mixture more ammonium carbamate (119 mg, 1.52 mmol) and bis(acetoxy)iodobenzene (611 mg, 1.90 mmol) were added and stirred for 10 more hours. The reaction mixture was then evaporated and crude product was dissolved in ethyl acetate (40 mL) and washed with 10% aqueous solution of sodium thiosulfate (40 mL), 10% aqueous solution of potassium bicarbonate (40 mL) and brine (40 mL). Organic layer was separated, dried over anhydrous sodium sulfate, filtered and evaporated. The crude product was recrystallized from hexane to give bis(3-bromo-4-((ethoxymethoxy)methyl)-5-(trifluoromethyl)phenyl)(imino)-$\lambda^6$-sulfanone 2. Yield: 800 mg (77%).

$^1$H NMR spectrum (300 MHz, $CDCl_3$, $\delta_H$): 8.45 (s, 2H); 8.27 (s, 2H); 4.81 (app. s, 8H); 3.67 (q, J=7.0 Hz, 4H); 3.33 (bs, 1H); 1.23 (t, J=7.0 Hz, 6H).

LC-MS purity: 100% (ELSD, UV 242).

LC-MS Rt (Kinetex C18, 4.6 mm×50 mm, acetonitrile/water 85:15 to 100:0+0.1% FA): 1.56 min.

LC-MS m/z: 688.3 $(M+H)^+$.

To an ice-cold, well-stirred solution of bis(3-bromo-4-((ethoxymethoxy)methyl)-5-(trifluoromethyl)phenyl)(imino)-$\lambda^6$-sulfanone (2, 756 mg, 1.10 mmol) in anhydrous N,N-dimethylformamide was added sodium hydride (58.0 mg, 1.43 mmol) under nitrogen. After 5 minutes, tert-butyl bromoacetate (321 mg, 1.65 mmol) was added. The reaction mixture was allowed to reach ambient temperature and stirred for an hour. The reaction mixture was then taken up in ethyl acetate (40 mL) and washed with 10% aqueous solution of ammonium chloride (40 mL), water (2×40 mL) and brine (40 mL). Organic layer was separated, dried over anhydrous sodium sulfate, filtered and evaporated. The crude product was purified by column chromatography (Silicagel, 0.063-0.200 mm; eluent: cyclohexane/ethyl acetate 10:1) to provide tert-butyl 2-((bis(3-bromo-4-((ethoxymethoxy)methyl)-5-(trifluoromethyl)phenyl)(oxo)-$\lambda^6$-sulfanylidene)amino)acetate (3) as colorless oil. Yield: 847 mg (96%).

$^1$H NMR spectrum (300 MHz, $CDCl_3$, $\delta_H$): 8.47 (s, 2H); 8.28 (s, 2H); 4.81 (app. s, 8H); 3.77 (s, 2H); 3.67 (q, J=7.0 Hz, 4H); 1.49 (s, 9H); 1.23 (t, J=7.0 Hz, 6H).

LC-MS purity: 100% (ELSD, UV 242).

LC-MS Rt (Kinetex C18, 4.6 mm×50 mm, acetonitrile/water 85:15 to 100:0+0.1% FA): 3.04 min.

LC-MS m/z: 802.5 $(M+H)^+$.

A 50 mL reaction vessel was charged with potassium acetate (490 mg, 5.00 mmol) and the salt was dried for 1 hour at 110° C. in vacuo. After cooling to room temperature, the reaction vessel was backfilled with nitrogen and charged with tert-butyl 2-((bis(3-bromo-4-((ethoxymethoxy)methyl)-5-(trifluoromethyl)phenyl)(oxo)-$\lambda^6$-sulfanylidene)amino)acetate (3, 801 mg, 1.00 mmol), (1,1-bis(diphenylphosphino)ferrocene)dichloropalladium(II), complex with dichloromethane (41.0 mg, 50.0 mol) and bis(pinacolato)diboron (635 mg, 2.50 mmol). The reaction vessel was then evacuated and backfilled with nitrogen (this procedure was repeated twice), anhydrous 1,4-dioxane (5 mL) was added with syringe, the vessel was sealed with a plastic stopper and submerged in the heating bath preheated to 80° C. After stirring at 400 rpm for 16 hours (overnight) the reaction mixture was cooled to ambient temperature, diluted with ethyl acetate (30 mL) and filtered through a short plug of silica (10 g) topped with Celite S with the aid of ethyl acetate (3×30 mL). The filtrate was concentrated under reduced pressure to afford the tert-butyl 2-((bis(4-((ethoxymethoxy)methyl)-3-(4,4,5,5-tetramethyl-1,3,2-dioxaborolan-2-yl)-5-(trifluoromethyl)phenyl)(oxo)-$\lambda^6$-sulfanylidene)amino)acetate (4) as brownish waxy foam. It was dissolved in acetonitrile (6 mL) and water (1 mL) and periodic acid (912 mg, 4.00 mmol) was added. After two hours, the reaction mixture was taken up was taken up in ethyl acetate (30 mL) and washed with water (2×30 mL) and brine (40 mL). Organic layer was dried over anhydrous sodium sulfate, filtered and evaporated to give the crude product as orange wax. It was dissolved in tetrahydrofuran (4 mL) and water (1 mL) and concentrated solution of hydrochloric acid (1 mL) was added. After two hours, the reaction mixture was taken heated to 50 C and stirred for 5 hours. Afterwards, it was taken up in ethyl acetate (30 mL) and washed with water (30 mL) and brine (40 mL). Organic layer was dried over anhydrous sodium sulfate, filtered and evaporated to give the crude product as beige solid. It was dissolved in a minimum amount of diethyl ether and hexane (3 volumes) was added. The precipitated product was collected by filtration, washed with cold hexane (2×5 mL) and air dried to give 2-((bis(1-hydroxy-4-(trifluoromethyl)-1,3-dihydrobenzo-[c][1,2]oxaborol-6-yl)(oxo)-$\lambda^6$-sulfanylidene)amino)acetic acid (5) as off-white solid.

Yield: 405 mg (78%).

$^1$H NMR spectrum (300 MHz, Acetone-$d_6$/$D_2O$, $\delta_H$): 8.68 (s, 2H); 8.47 (s, 2H); 5.21 (s, 4H); 3.83 (s, 2H) partly overlapping with water signal.

LC-MS purity: 100% (ELSD)

LC-MS Rt (Kinetex C18, 4.6 mm×50 mm, acetonitrile/water 20:80 to 100:0+0.1% FA): 3.84 min.

LC-MS m/z: 524.3 $(M+H)^+$

Example 39

(3-Borono-5-((3-boronophenyl)sulfonyl)benzoyl)glycine

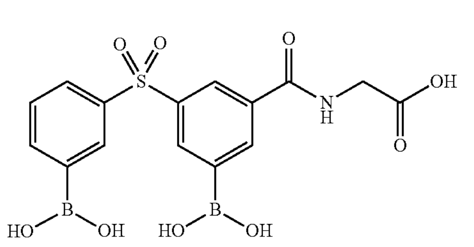 [SMILES: O=C(O)CNC(=O)c1cc(B(O)O)cc(S(=O)(=O)c2cccc(B(O)O)c2)c1]

(3-Borono-5-((3-boronophenyl)sulfonyl)benzoyl)glycine was synthesized according to the reaction scheme shown in Chem. 44 and following the procedure described below.

Chem. 44

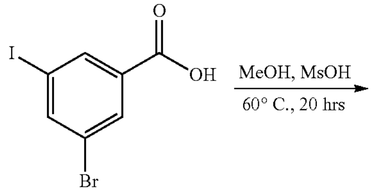

1

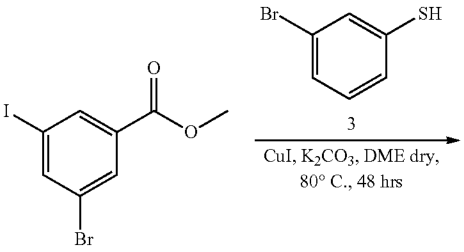

3

2
76%

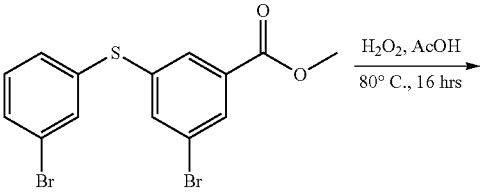

4

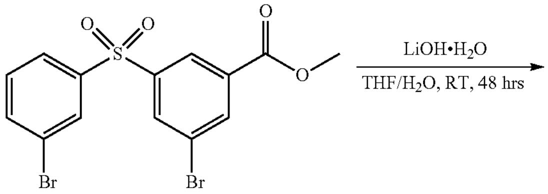

5

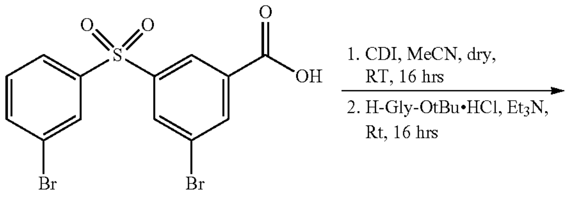

6
40% from 2

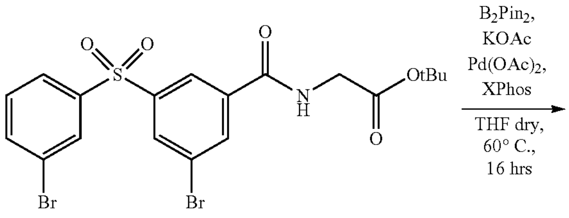

7
92%

-continued

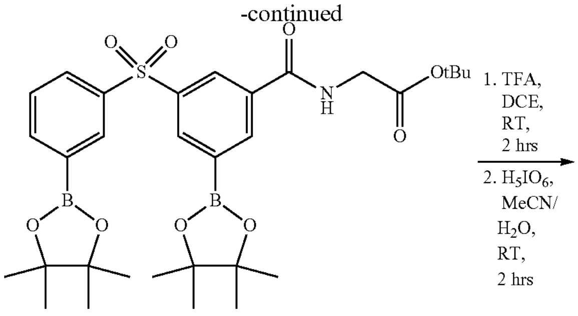

8

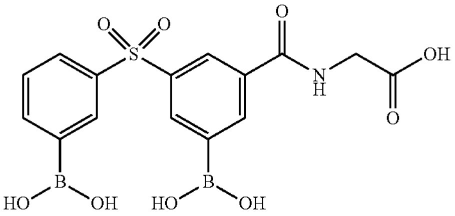

9
54% from 7

3-Bromo-5-iodobenzoic acid (1, 32.7 g, 100 mmol) was suspended in methanol (150 mL) and methanesulfonic acid (3 mL) was added. The resulting mixture was stirred for 20 hours at 60° C. (oil bath). The resulting clear solution was cooled to −20° C. in the freezer for 20 hours and the resulting solid was collected by filtration, washed with chilled (−20° C.) methanol and dried in vacuo to give methyl 3-bromo-5-iodobenzoate (2) as an off-white solid.

Yield: 26.0 g (76%).

$^1H$ NMR spectrum (300 MHz, $CDCl_3$, $\delta_H$): 8.30 (s, 1H); 8.14 (s, 1H); 8.04 (s, 1H); 3.93 (s, 1H).

Methyl 3-bromo-5-iodobenzoate (2, 2.62 g, 10.0 mmol), anhydrous potassium carbonate (3.45 g, 25.0 mmol), copper iodide (381 mg, 2.00 mmol) and 3-bromobenzenethiol (3, 1.78 mL, 15.0 mmol) were suspended in dry 1,2-dimethoxyethane (25 mL) and the resulting suspension was stirred for 48 hours at 80° C. After cooling to ambient temperature, the reaction mixture was diluted with cyclohexane (80 mL), filtered through a pad of silicagel (40 g) topped with Celite (washed with ethyl acetate/cyclohexane 1:10, 3×30 mL) and evaporated in vacuo. The residue was dissolved in acetic acid (30 mL) and 30% aqueous solution of hydrogen peroxide (4.00 mL, 39.2 mmol) was added in portions (heat evolution). After stirring for 16 hours at 80° C. (oil bath), the reaction mixture was evaporated in vacuo, taken up in ethyl acetate (100 mL) and washed with water (100 mL) and brine (100 mL). Drying of the organic layer with anhydrous sodium sulfate, filtration and evaporation in vacuo gave the methyl ester 5 as yellow oil. It was dissolved in tetrahydrofuran (30 mL) and water (15 mL) and lithium hydroxide monohydrate (840 mg, 20.0 mmol) was added. After stirring for 48 hours, the reaction mixture was evaporated in vacuo, taken up in ethyl acetate (100 mL) and washed with 1 M aqueous solution of hydrochloric acid (100 mL) and brine (100 mL). Drying of the organic layer with anhydrous sodium sulfate, filtration and evaporation in vacuo gave the crude product as brownish solid. It was purified by recrystallization from toluene to give pure 3-bromo-5-((3-bromophenyl)sulfonyl)benzoic acid (6) as beige solid. Yield: 1.67 g (40%).

$^1$H NMR spectrum (300 MHz, Acetone-$d_6$, $\delta_H$): 8.53 (s, 1H); 8.45 (s, 1H); 8.38 (s, 1H); 8.27 (s, 1H); 8.12 (d, J=8.0 Hz, 1H); 7.92 (d, J=7.9 Hz, 1H); 7.64 (t, J=8.0 Hz, 1H).

LC-MS purity: 100% (ELSD, UV 242 nm).

LC-MS Rt (Kinetex C18, 4.6 mm×50 mm, acetonitrile/water 35:65 to 100:0+0.1% FA): 3.63 min.

LC-MS m/z: 421.2 $(M+H)^+$.

A solution of 3-bromo-5-((3-bromophenyl)sulfonyl)benzoic acid (6, 924 mg, 2.20 mmol) and carbonyldiimidazole (CDI, 428 mg, 2.64 mmol) in anhydrous acetonitrile (8.0 mL) was stirred for 16 hours. Glycine tert-butyl ester hydrochloride (480 mg, 2.86 mmol) was then added, followed by triethylamine (1 mL). After stirring for 16 hours, the reaction mixture was evaporated in vacuo, taken up in ethyl acetate (30 mL) and washed with 1 M aqueous solution of potassium bisulfate (100 mL) and brine (100 mL). Drying of the organic layer with anhydrous sodium sulfate, filtration and evaporation in vacuo gave the crude product as yellowish solid, which was subjected to flash column chromatography (Silicagel 60, 0.063-0.200 mm; eluent: cyclohexane/ethyl acetate 5:1 to 4:1) to give tert-butyl (3-bromo-5-((3-bromophenyl)sulfonyl)benzoyl)glycinate (7) as white foam.

Yield: 1.08 g (92%).

$^1$H NMR spectrum (300 MHz, $CDCl_3$, $\delta_H$): 8.26 (s, 1H); 8.18 (s, 1H); 8.15 (s, 1H); 8.09 (s, 1H); 7.89 (d, J=7.9 Hz, 1H); 7.79-7.69 (m, 1H); 7.43 (t, J=7.9 Hz, 1H); 6.76 (bs, 1H); 4.13 (d, J=5.0 Hz, 2H); 1.51 (s, 9H).

LC-MS purity: 100% (ELSD, UV 242 nm).

LC-MS Rt (Kinetex C18, 4.6 mm×50 mm, acetonitrile/water 35:65 to 100:0+0.1% FA): 4.13 min.

LC-MS m/z: 534.3 $(M+H)^+$.

A 25 mL reaction vessel was charged with potassium acetate (490 mg, 5.00 mmol) and the salt was dried for 1 hour at 110° C. in vacuo. After cooling to room temperature, the reaction vessel was backfilled with nitrogen and charged with methyl tert-butyl (3-bromo-5-((3-bromophenyl)sulfonyl)benzoyl)glycinate (7, 533 mg, 1.00 mmol), palladium acetate (8.90 mg, 0.04 mmol), 2-dicyclohexylphosphino-2,4,6-triisopropylbiphenyl (XPhos, 39.0 mg, 0.08 mmol) and bis(pinacolato)diboron (610 mg, 2.40 mmol). The reaction vessel was then evacuated and backfilled with nitrogen (this procedure was repeated twice), anhydrous tetrahydrofuran (5 mL) was added with syringe, the vessel was sealed with rubber septum and submerged in the heating bath preheated to 60° C. After stirring at 400 rpm for 16 hours (overnight) the reaction mixture was cooled to ambient temperature, diluted with cyclohexane (24 mL) and filtered through a short plug of silica (7 g) topped with Celite S with the aid of dichloromethane (3×15 mL). The filtrate was concentrated under reduced pressure to afford the intermediate tert-butyl (3-(4,4,5,5-tetramethyl-1,3,2-dioxaborolan-2-yl)-5-((3-(4,4,5,5-tetramethyl-1,3,2-dioxaborolan-2-yl)phenyl)sulfonyl)benzoyl)glycinate (8) as brownish waxy solid. It was dissolved in a mixture of 1,2-dichloroethane (2.5 mL) and trifluoroacetic acid (2.5 mL). After two hours, the reaction mixture was evaporated in vacuo and the residue was co-distilled with ethyl acetate (3×10 mL). The resulting foam was dissolved in acetonitrile (6 mL) and water (2 mL) and periodic acid (1.37 g, 6.00 mmol) was added. The resulting mixture was vigorously stirred at ambient temperature for two hours. The reaction mixture was taken up in ethyl acetate (30 mL) and washed with water (2×20 mL) and brine (20 mL). The organic layer was extracted with 1 M aqueous solution of sodium hydroxide (20 mL) and water (10 mL), the aqueous extracts were combined and washed with dichloromethane (2×10 mL). The aqueous phase was acidified by the addition of concentrated hydrochloric acid (3 mL) and extracted with ethyl acetate (2×20 mL). The combined organic extracts were washed with brine (15 mL), dried over anhydrous sodium sulfate, filtered and evaporated. The crude product was dissolved in a minimum amount of wet (shaken thoroughly with water) ethyl acetate and the solution added dropwise to an ice-cold n-hexane (5 mL) with stirring, resulting in the precipitation of a product. The solid was collected by filtration and washed with hexane (2×5 mL) to give the title (3-borono-5-((3-boronophenyl)sulfonyl)benzoyl)glycine (9) as colorless solid.

Yield: 221.0 mg (54%).

$^1$H NMR spectrum (300 MHz, Acetone-$d_6$/$D_2O$; 10:1, $\delta_H$): 8.64-8.50 (m, 3H); 8.46 (s, 1H); 8.15-7.99 (m, 2H); 7.59 (t, J=7.7 Hz, 1H); 4.22-4.04 (m, 2H).

LC-MS purity: 100% (ELSD, UV 242 nm).

LC-MS Rt (Kinetex C18, 4.6 mm×50 mm, acetonitrile/water 20:80 to 100:0+0.1% FA): 2.45 min.

LC-MS m/z: 408.4 $(M+H)^+$.

Example 40

(S)-2,3-Bis(1-hydroxy-1,3-dihydrobenzo[c][1,2]oxaborole-6-carboxamido)propanoic acid

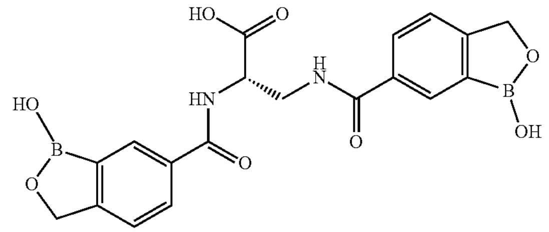

(S)-2,3-Bis(1-hydroxy-1,3-dihydrobenzo[c][1,2]oxaborole-6-carboxamido)propanoic acid was synthesized according to the reaction scheme shown in Chem. 45 and following the procedure described below.

Chem. 45

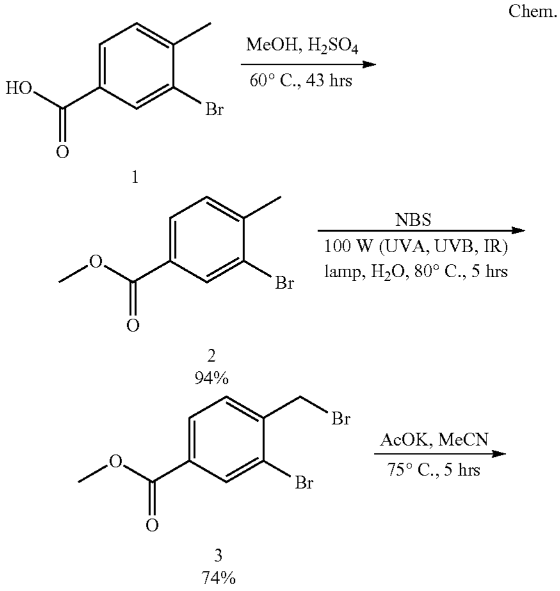

-continued

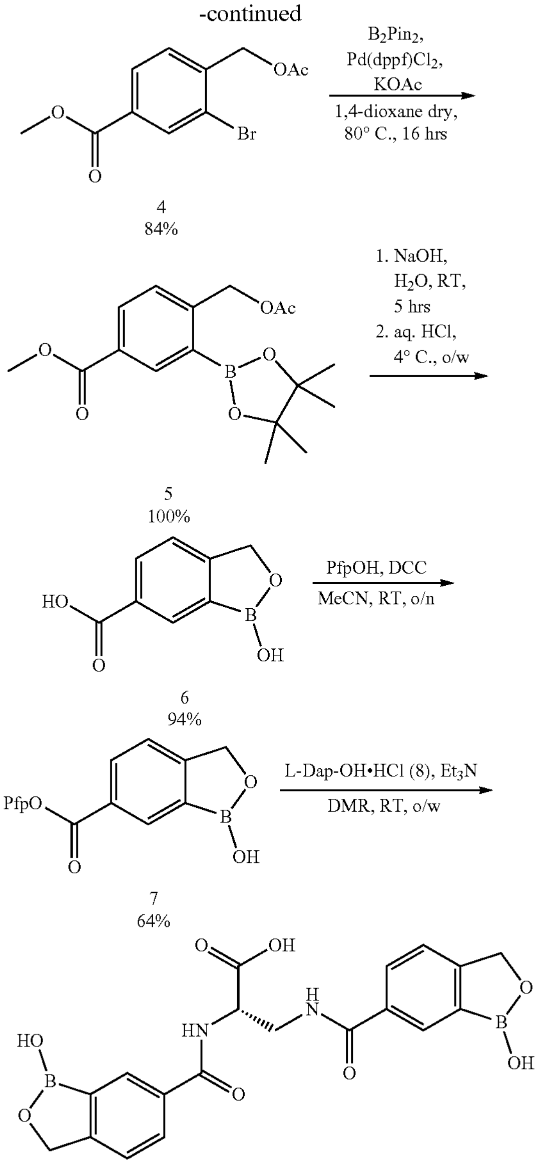

4
84%

5
100%

6
94%

7
64%

9
28%

Concentrated sulfuric acid (96%, 1.00 mL, 18.0 mmol) was added to a solution of 3-bromo-4-methylbenzoic acid (1, 25.0 g, 116 mmol) in methanol (500 mL) and the reaction mixture was allowed to stir at 60° C. for 43 hours. The solution was cooled to room temperature, sodium hydrogencarbonate (4.39 g, 53.3 mmol) was added, and the mixture was evaporated under reduced pressure. The residue was partitioned between ethyl acetate (600 mL) and water (250 mL). The organic layer was separated; washed with 0.5 M aqueous solution of sodium hydroxide (2×250 mL), 5% aqueous solution of sodium carbonate (2×200 mL), 0.5 M aqueous solution of hydrochloric acid (200 mL), water (200 mL) and brine (150 mL); dried over anhydrous sodium sulfate and evaporated in vacuo to give methyl 3-bromo-4-methylbenzoate (2) as orange oil. Yield: 25.16 g (94%).

$R_F$ ($SiO_2$, cyclohexane/ethyl acetate 9:1): 0.45.

$^1$H NMR spectrum (300 MHz, $CDCl_3$, $\delta_H$): 8.21 (d, J=1.7 Hz, 1H); 7.87 (dd, J=7.9 and 1.7 Hz, 1H); 7.30 (d, J=7.9 Hz, 1H); 3.92 (s, 3H); 2.46 (s, 3H).

A stirred mixture of 3-bromo-4-methylbenzoate (2, 24.8 g, 108 mmol), 1-bromopyrrolidine-2,5-dione (NBS, 21.2 g, 119 mmol) and water (360 mL) in a wide beaker was placed under D3 basking lamp for reptiles (100 W, UVA, UVB, IR) and heated to 70-80° C. Another portion of 1-bromopyrrolidine-2,5-dione (NBS, 3.86 g, 21.7 mmol) was added after 4 hours, and the mixture was stirred for an additional one hour. The mixture was cooled to room temperature followed by extraction with ethyl acetate (2×250 mL). Combined organic layers were washed with water (4×200 mL), dried over anhydrous sodium sulfate and evaporated in vacuo to afford crude methyl 3-bromo-4-(bromomethyl)benzoate (3) as yellow oil. Yield: 34.06 g (74%).

$R_F$ ($SiO_2$, cyclohexane/ethyl acetate 9:1): 0.30.

$^1$H NMR purity: 72 wt %.

$^1$H NMR spectrum (300 MHz, $CDCl_3$, $\delta_H$): 8.25 (d, J=1.7 Hz, 1H); 7.96 (dd, J=8.1 and 1.7 Hz, 1H); 7.54 (d, J=8.1 Hz, 1H); 4.61 (s, 2H); 3.94 (s, 3H).

A mixture of the above crude methyl 3-bromo-4-(bromomethyl)benzoate (3, 72%, 34.1 g, 80.1 mmol) and potassium acetate (23.6 g, 240 mmol) in acetonitrile (800 mL) was heated at 75° C. for 5 hours. The mixture was cooled to room temperature, the solid was removed by filtration and washed with ethyl acetate (3×50 mL). The filtrate was evaporated to dryness, and the residue was partitioned between ethyl acetate (700 mL) and water (200 mL). The organic layer was separated, washed with water (200 mL) and brine (2×200 mL), dried over anhydrous sodium sulfate and evaporated in vacuo. The residue was purified by flash column chromatography (Silicagel, 0.063-0.200 mm; eluent: cyclohexane/ethyl acetate 97:3) to give pure methyl 4-(acetoxymethyl)-3-bromobenzoate (4) as white solid. Yield: 19.39 g (84%).

$R_F$ ($SiO_2$, n-hexane/ethyl acetate 4:1): 0.25.

$^1$H NMR spectrum (300 MHz, $CDCl_3$, $\delta_H$): 8.24 (d, J=1.5 Hz, 1H); 7.99 (dd, J=8.0 and 1.6 Hz, 1H); 7.48 (d, J=8.1 Hz, 1H); 5.23 (s, 2H); 3.94 (s, 3H); 2.18 (s, 3H).

LC-MS purity: 100% (UV 254 nm).

LC-MS Rt (Kinetex C18, 4.6 mm×50 mm, acetonitrile/water 50:50 to 100:0+0.1% FA): 2.41 min.

LC-MS m/z: 287.2; 289.2 $(M+H)^+$.

[1,1-Bis(diphenylphosphino)ferrocene]dichloropalladium(II) (2.32 g, 3.18 mmol) was added to a degassed solution of methyl 4-(acetoxymethyl)-3-bromobenzoate (4, 18.2 g, 63.5 mmol), bis(pinacolato)diboron (17.7 g, 69.9 mmol) and potassium acetate (18.7 g, 191 mmol) in dry 1,4-dioxane (165 mL) under argon. The mixture was warmed to 80° C. and stirred at this temperature for 16 hours. The mixture was cooled to room temperature; then it was diluted with dichloromethane (165 mL) and passed through a short column of silicagel topped with Celite followed by elution with dichloromethane. Fractions containing the product were combined and evaporated to dryness. The residue was purified by flash column chromatography (Silicagel, 0.063-0.200 mm; eluent: cyclohexane/ethyl acetate 9:1 to 7:3) to yield methyl 4-(acetoxymethyl)-3-(4,4,5,5-tetramethyl-1,3,2-dioxaborolan-2-yl)benzoate (5) as yellow solid. Yield: 21.80 g (>100%).

$R_F$ ($SiO_2$, cyclohexane/ethyl acetate 9:1): 0.15.

$^1$H NMR spectrum (300 MHz, $CDCl_3$, $\delta_H$): 8.49 (d, J=1.8 Hz, 1H); 8.10 (dd, J=8.1 and 2.0 Hz, 1H); 7.46 (d, J=8.1 Hz, 1H); 5.43 (s, 2H); 3.93 (s, 3H); 2.12 (s, 3H), 1.36 (s, 12H).

LC-MS purity: 100% (ELSD), 88% (UV 254 nm).

LC-MS Rt (Kinetex C18, 4.6 mm×50 mm, acetonitrile/water 50:50 to 100:0+0.1% FA): 3.26 min.

LC-MS m/z: 335.5 $(M+H)^+$.

Methyl 4-(acetoxymethyl)-3-(4,4,5,5-tetramethyl-1,3,2-dioxaborolan-2-yl)benzoate (5, 21.8 g, <63.5 mmol) was added to a solution of sodium hydroxide (12.7 g, 318 mmol) in water (200 mL) and the resulting mixture was stirred at room temperature for 5 hours. The mixture was filtered, washed with diethyl ether (200 mL) and acidified with 35% hydrochloric acid (39.6 mL, 444 mmol). The resulting white suspension was placed in the fridge over weekend. The precipitate was filtered, washed with water (3×50 mL) and suspended in 20% aqueous solution of acetonitrile (100 mL). The mixture was freeze-dried to afford 1-hydroxy-1,3-dihydrobenzo[c][1,2]oxaborole-6-carboxylic acid (6) as white powder. Yield: 10.63 g (94%).

$^1$H NMR spectrum (300 MHz, DMSO-$d_6$, $\delta_H$): 12.90 (s, 1H); 9.35 (s, 1H); 8.37 (s, 1H); 8.04 (dd, J=8.0 and 1.6 Hz, 1H); 7.52 (d, J=7.9 Hz, 1H); 5.05 (s, 2H).

LC-MS purity: 100% (ELSD).

LC-MS Rt (Kinetex C18, 4.6 mm×50 mm, acetonitrile/water 5:95 to 100:0+0.1% FA): 3.90 min.

LC-MS m/z: 179.2 $(M+H)^+$.

N,N'-Dicyclohexylcarbodiimide (DCC, 2.50 g, 12.1 mmol) was added to a suspension of 1-hydroxy-1,3-dihydrobenzo[c][1,2]oxaborole-6-carboxylic acid (6, 2.16 g, 12.1 mmol) and pentafluorophenol (PfpOH, 2.23 g, 12.1 mmol) in acetonitrile (150 mL) and the mixture was stirred at room temperature overnight. The solid was filtered off and washed with ethyl acetate (5×20 mL). The filtrates were combined and evaporated to dryness. Cyclohexane (100 mL) was added to the residue and the mixture was stirred at room temperature for 15 minutes. The mixture was decanted and the sediment was dried in vacuo to give perfluorophenyl 1-hydroxy-1,3-dihydrobenzo[c][1,2]oxaborole-6-carboxylate (7) as off-white solid. Yield: 2.67 g (64%).

$^1$H NMR spectrum (300 MHz, $CDCl_3$, $\delta_H$): 8.62 (s, 1H); 8.32 (dd, J=8.1 and 1.7 Hz, 1H); 7.55 (d, J=8.3 Hz, 1H); 5.22 (s, 2H).

LC-MS purity: 98% (ELSD).

LC-MS Rt (Kinetex C18, 4.6 mm×50 mm, acetonitrile/water 35:65 to 100:0+0.1% FA): 4.08 min.

LC-MS m/z: 345.3 $(M+H)^+$.

Triethylamine (1.65 mL, 11.8 mmol) was added to a mixture of perfluorophenyl 1-hydroxy-1,3-dihydrobenzo[c][1,2]oxaborole-6-carboxylate (7, 713 mg, 2.07 mmol) and L-2,3-diaminopropionic acid hydrochloride (8, L-Dap-OHHCl, 139 mg, 0.99 mmol) in N,N-dimethylformamide (10.0 mL) and the resulting solution was stirred at room temperature over weekend. The mixture was evaporated to dryness in vacuo, and the residue was partitioned between 1 M aqueous solution of hydrochloric acid (25 mL) and ethyl acetate (50 mL). The phases were separated and the organic one was extracted with ethyl acetate (2×25 mL). All organic layers was combined, dried over anhydrous sodium sulfate and concentrated in vacuo to approx. 3 mL volume. Cyclohexane (100 mL) was added and the resulting suspension was stirred at room temperature overnight. The precipitate was collected by filtration and dried in vacuo. The precipitate (crude 9, 288 mg) was dissolved in 50% aqueous solution of acetonitrile (4.8 mL) and subjected to purification by preparative LC/MS (SunFire Prep C18 OBD, 5 m, 19×100 mm, acetonitrile/water 5:95 to 100:0+0.1% FA). Pure fractions were combined and freeze-dried to give title compound (9) as white powder. Yield: 116 mg (28%).

$^1$H NMR spectrum (300 MHz, DMSO-$d_6$, $\delta_H$): 12.73 (bs, 1H); 9.33 (s, 1H); 9.30 (s, 1H); 8.76 (d, J=7.5 Hz, 1H); 8.70 (t, J=5.9 Hz, 1H); 8.25 (d, J=0.7 Hz, 1H); 8.20 (d, J=0.9 Hz, 1H); 7.96 (dd, J=8.1 and 1.7 Hz, 1H); 7.90 (dd, J=7.9 and 1.7 Hz, 1H); 7.52 (d, J=8.8 Hz, 1H); 7.48 (d, J=8.3 Hz, 1H); 5.05 (s, 2H); 5.03 (s, 2H); 4.71-4.62 (m, 1H); 3.81-3.73 (m, 2H).

LC-MS purity: 100% (ELSD, UV 254 nm).

LC-MS Rt (Kinetex C18, 4.6 mm×50 mm, acetonitrile/water 5:95 to 100:0+0.1% FA): 3.56 min.

LC-MS m/z: 425.4 $(M+H)^+$.

Example 41

N-(1-Hydroxy-4-(methylsulfonyl)-1,3-dihydrobenzo[c][1,2]oxaborole-6-carbonyl)-N-(2-(1-hydroxy-4-(methylsulfonyl)-1,3-dihydrobenzo[c][1,2]oxaborole-6-carboxamido)ethyl)glycine

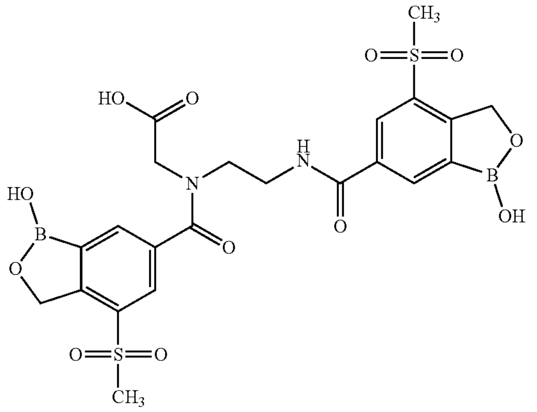 [SMILES: CS(=O)(=O)c1cc(C(=O)NCCN(CC(=O)O)C(=O)c2cc3c(c(S(C)(=O)=O)c2)COB3O)cc2c1COB2O]

N-(1-Hydroxy-4-(methylsulfonyl)-1,3-dihydrobenzo[c][1,2]oxaborole-6-carbonyl)-N-(2-(1-hydroxy-4-(methylsulfonyl)-1,3-dihydrobenzo[c][1,2]oxaborole-6-carboxamido)ethyl)glycine was synthesized according to the reaction scheme shown in Chem. 46 and following the procedure described below.

Chem. 46

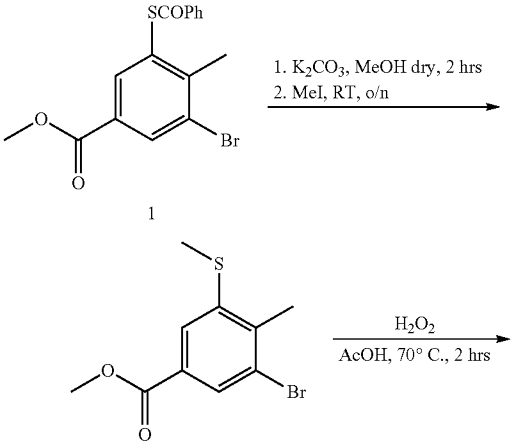

2
84%

-continued

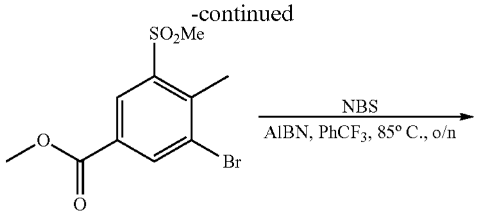

3
100%

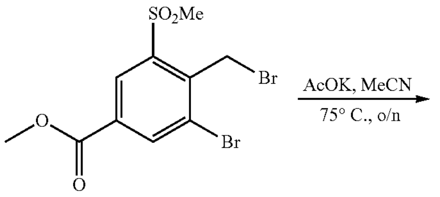

4
96%

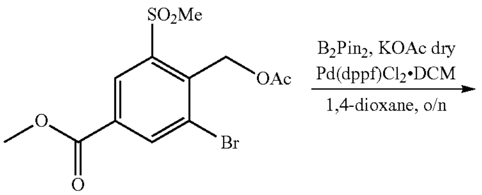

5
54%

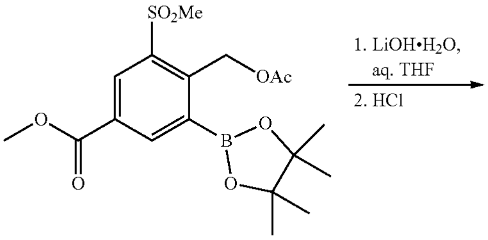

6

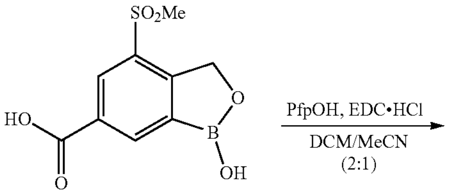

7
87%

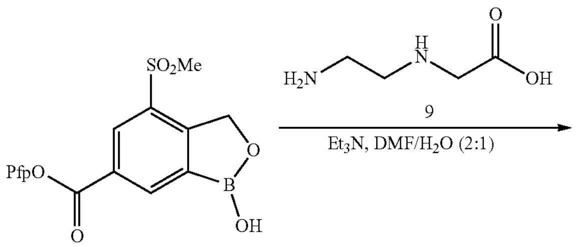

8
98%

-continued

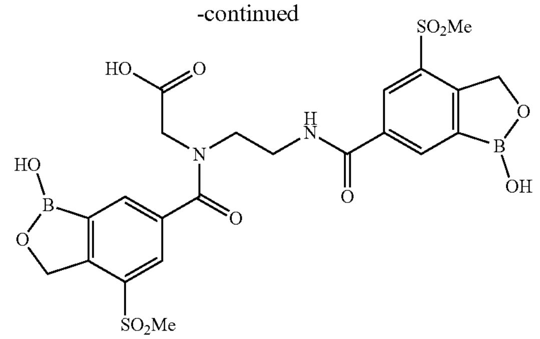

10
32%

Mixture of methyl 3-(benzoylthio)-5-bromo-4-methylbenzoate (1, 2.90 g, 7.95 mmol) and potassium carbonate (2.19 g, 15.9 mmol) was dissolved while heated in dry methanol (100 mL) and then was stirred under nitrogen atmosphere at room temperature for 2 hours. The solvent was evaporated and co-evaporated with toluene. Then methyl iodide (70 mL) was added and the reaction mixture was stirred overnight at room temperature. The solvent was evaporated and then several times co-evaporated with dichloromethane. Crude product was extracted with ethyl acetate (100 mL) and 1 M aqueous solution of hydrochloric acid (50 mL), water (50 mL) and brine (50 mL). Organic layer was separated, dried over anhydrous sodium sulfate, filtered and evaporated. The crude product was purified by column chromatography (Silicagel, 0.063-0.200 mm; eluent: cyclohexane/ethyl acetate 9:1) to provide methyl 3-bromo-4-methyl-5-(methylthio)benzoate (2) as white solid. Yield: 1.83 g (84%).

$^1$H NMR spectrum (300 MHz, $CDCl_3$, $\delta_H$): 8.01 (d, J=1.3 Hz, 1H); 7.75 (s, 1H); 3.93 (s, 3H); 2.53 (s, 3H); 2.50 (s, 3H).

Hydrogen peroxide (5 mL) was added to a solution of methyl 3-bromo-4-methyl-5-(methylthio)benzoate (2, 1.83 g, 6.65 mmol) in acetic acid (70 mL) and the reaction mixture was allowed to stir at 70° C. for 2 hours. The solvents were then evaporated to provide methyl 3-bromo-4-methyl-5-(methylsulfonyl)benzoate (3) as off-white solid. Yield: 2.05 g (100%).

$^1$H NMR spectrum (300 MHz, DMSO-$d_6$, $\delta_H$): 8.46 (d, J=1.7 Hz, 1H); 8.40 (d, J=1.8 Hz, 1H); 3.91 (s, 3H); 3.34 (s, 3H); 2.79 (s, 3H).

Solution of 1-bromopyrrolidine-2,5-dione (NBS, 1.31 g, 7.35 mmol), 3-bromo-4-methyl-5-(methylsulfonyl)benzoate (3, 2.05 g, 6.65 mmol) and 2,2-azobis(2-methylpropionitrile) (AIBN, 55.0 mg, 0.33 mmol) in $PhCF_3$ (20 mL) was stirred overnight at 85 C. Reaction mixture was evaporated and then extracted with diethyl ether (2x50 mL). Organic layers were washed with brine (50 mL). Organic layer was separated, dried over anhydrous sodium sulfate, filtered and evaporated to provide methyl 3-bromo-4-(bromomethyl)-5-(methylsulfonyl)benzoate (4) as yellowish solid. Yield: 2.43 g (94%).

$^1$H NMR spectrum (300 MHz, DMSO-$d_6$, $\delta_H$): 8.47 (d, J=1.1 Hz, 2H); 5.14 (bs, 2H); 3.92 (s, 3H); 3.44 (s, 3H).

Methyl 3-bromo-4-(bromomethyl)-5-(methylsulfonyl) benzoate (4, 2.70 g, 7.00 mmol) was stirred with potassium acetate (1.37 g, 14.0 mmol) in acetonitrile (70 mL) at 75 C overnight. The suspension was filtered through Celite pad and evaporated in vacuo. The crude product was dissolved in dichloromethane and filtered again. The filtrate was evaporated and purified by column chromatography (Silica-gel 60, 0.040-0.063 mm; eluent: cyclohexane/ethyl acetate 7:1) to give methyl 4-(acetoxymethyl)-3-bromo-5-(methylsulfonyl)benzoate (5) as white solid. Yield: 4.24 g (54%).

$^1$H NMR spectrum (300 MHz, $CDCl_3$, $\delta_H$): 8.74 (s, 1H); 8.55 (s, 1H); 5.76 (s, 2H); 3.99 (s, 3H); 3.21 (s, 3H); 2.11 (s, 3H).

LC-MS purity: 100% (ELSD).

LC-MS Rt (Kinetex C18, 4.6 mm×50 mm, acetonitrile/water 30:70 to 100:0+0.1% FA): 2.46 min.

LC-MS m/z: 366.9 $(M+H)^+$.

A mixture of methyl 4-(acetoxymethyl)-3-bromo-5-((trifluoromethyl)sulfonyl)benzoate (5, 1.97 g, 5.38 mmol), bis (pinacolato)diboron (1.64 g, 6.46 mmol) and dry potassium acetate (1.58 g, 16.1 mmol) and [1,1-bis(diphenylphosphino)ferrocene]-dichloropalladium-dichloromethane complex (220 mg, 269 mol) were suspended in dry, degassed 1,4-dioxane (20 mL). Reaction mixture was stirred under nitrogen atmosphere at 90° C. overnight. The crude reaction mixture was then taken up in ethyl acetate (60 mL) and filtered through a short pad of silica gel (20 g) topped with Celite (with the aid of ethyl acetate, 3×60 mL). The filtrate was evaporated in vacuo to give crude methyl 4-(acetoxymethyl)-3-(methylsulfonyl)-5-(4,4,5,5-tetramethyl-1,3,2-dioxaborolan-2-yl)benzoate (6) a yellowish solid.

It was dissolved in tetrahydrofuran (15 mL) and water (15 mL) and solid lithium hydroxide monohydrate (1.13 g, 26.9 mmol) was added. The mixture was stirred at room temperature for 2 hours and then diluted with water (60 mL) and transferred into a separatory funnel, where it was extracted with dichloromethane (2×40 mL) and diethyl ether (40 mL). Aqueous phase was acidified with concentrated hydrochloric acid to pH=2 and the resulting mixture was stirred for 30 minutes at room temperature. The precipitate was filtered, washed well with water and dried to give 1-hydroxy-4-(methylsulfonyl)-1,3-dihydrobenzo[c][1,2]oxaborole-6-carboxylic acid (7) as off-white solid. Yield: 1.20 g (87%).

$^1$H NMR spectrum (300 MHz, Acetone-$d_6$/$D_2O$, $\delta_H$): 8.67 (s, 1H); 8.54 (s, 1H); 5.40 (s, 2H); 3.23 (s, 3H).

LC-MS purity: 100% (ELSD, UV 240 nm).

LC-MS Rt (Kinetex C18, 4.6 mm×50 mm, acetonitrile/water 10:90 to 100:0+0.1% FA): 2.10 min.

LC-MS m/z: 255.2 $(M-H)^-$.

1-Hydroxy-4-(methylsulfonyl)-1,3-dihydrobenzo[c][1,2] oxaborole-6-carboxylic acid (7, 1.02 g, 4.00 mmol), 2,3,4,5,6-pentrafluorophenol (1030 mg, 5.60 mmol) and N-(3-dimethylaminopropyl)-N-ethylcarbodiimide hydrochloride (1.07 g, 5.60 mmol) were suspended in dichloromethane (20 mL) and acetonitrile (10 mL). The mixture was stirred overnight at room temperature. Then the solvent was evaporated. The residue was dissolved in ethyl acetate (70 mL) and washed with water (2×40 mL) and brine (1×40 mL). Organic layer was dried over anhydrous sodium sulfate, filtered and evaporated.

The crude product was dissolved in hot ethyl acetate (10 mL) and cyclohexane (30 mL) was slowly added. After cooling to ambient temperature, the solid precipitated. After 2 hours, it was collected by filtration, washed with cyclohexane and air dried to give perfluorophenyl 1-hydroxy-4-(methylsulfonyl)-1,3-dihydrobenzo[c][1,2]oxaborole-6-carboxylate (8) as off-white solid. Yield: 1.65 mg (98%).

$^1$H NMR spectrum (300 MHz, Acetone-$d_6$/$D_2O$, $\delta_H$): 8.88 (s, 1H); 8.73 (s, 1H); 5.49 (s, 2H); 3.30 (s, 3H).

$^{19}$F NMR spectrum (282 MHz, Acetone-$d_6$/$D_2O$, $\delta_F$): −154.63 (d, J=17.0 Hz); −159.62 (t, J=21.3 Hz); 164.43 (t, J=19.1 Hz).

LC-MS purity: 100% (ELSD, UV 240 nm).

LC-MS Rt (Kinetex C18, 4.6 mm×50 mm, acetonitrile/water 10:90 to 100:0+0.1% FA): 3.44 min.

LC-MS m/z: 421.0 $(M-H)^-$.

Perfluorophenyl 1-hydroxy-4-(methylsulfonyl)-1,3-dihydrobenzo[c][1,2]oxaborole-6-carboxylate (8, 422 mg, 1.00 mmol) and (2-aminoethyl)glycine (9, 59.0 mg, 0.50 mmol) were dissolved in N,N-dimethylformamide/water mixture (2:1, 3 mL). Triethylamine (500 L) was then added and the resulting mixture was stirred overnight at room temperature. Afterwards, it was acidified with 1 M aqueous solution of potassium bisulfate (15 mL) and extracted with ethyl acetate (3×15 mL). The organic layer was dried over anhydrous sodium sulfate, filtered and evaporated. The residue was co-distilled with toluene (3×10 mL) and triturated with diethyl ether (3 mL). The precipitate was filtered, washed with diethyl ether (2×2 mL) and air dried. The obtained powder was purified by preparative LC/MS (SunFire Prep C18 OBD, 5 m, 19×100 mm, acetonitrile/water 5:95 to 100:0+0.1% FA) and freeze-dried to give the title N-(1-hydroxy-4-(methylsulfonyl)-1,3-dihydrobenzo[c][1,2]oxaborole-6-carbonyl)-N-(2-(1-hydroxy-4-(methylsulfonyl)-1,3-dihydrobenzo[c][1,2]oxaborole-6-carboxamido)ethyl) glycine (10) as colorless solid. Yield: 99.0 mg (32%).

$^1$H NMR spectrum (300 MHz, AcOD-$d_4$, $\delta_H$): 8.74-8.46 (m, 1H); 8.35 (app. d, 1H); 8.06 (app. d, 1H); 7.96 (bs, 1H); 5.49-5.32 (m, 4H); 4.39 (app. d, 2H); 4.03-3.61 (m, 4H); 3.21-3.03 (m, 6H).

LC-MS purity: 100% (ELSD, UV 254 nm).

LC-MS Rt (Kinetex C18, 4.6 mm×50 mm, acetonitrile/water 5:95 to 100:0+0.1% FA): 3.14 min.

LC-MS m/z: 595.0 $(M+H)^+$.

Example 42

N-(1-Hydroxy-4-((trifluoromethyl)sulfonyl)-1,3-dihydrobenzo[c][1,2]oxaborole-6-carbonyl)-N-(2-(1-hydroxy-4-((trifluoromethyl)sulfonyl)-1,3-dihydrobenzo-[c][1,2]oxaborole-6-carboxamido)ethyl) glycine

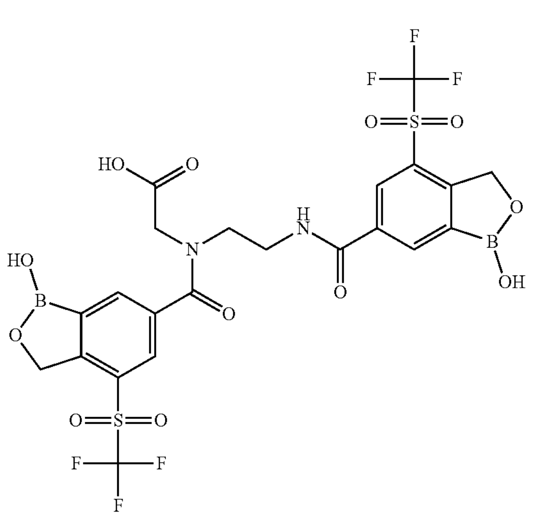 [SMILES: O=C(O)CN(CCNC(=O)c1cc2c(c(S(=O)(=O)C(F)(F)F)c1)COB2O)C(=O)c1cc2c(c(S(=O)(=O)C(F)(F)F)c1)COB2O]

N-(1-Hydroxy-4-((trifluoromethyl)sulfonyl)-1,3-dihydrobenzo[c][1,2]oxaborole-6-carbonyl)-N-(2-(1-hydroxy-4-((trifluoromethyl)sulfonyl)-1,3-dihydrobenzo-[c][1,2]oxaborole-6-carboxamido)ethyl)glycine was synthesized according to the reaction scheme shown in Chem. 47 and following the procedure described below.

Chem. 47

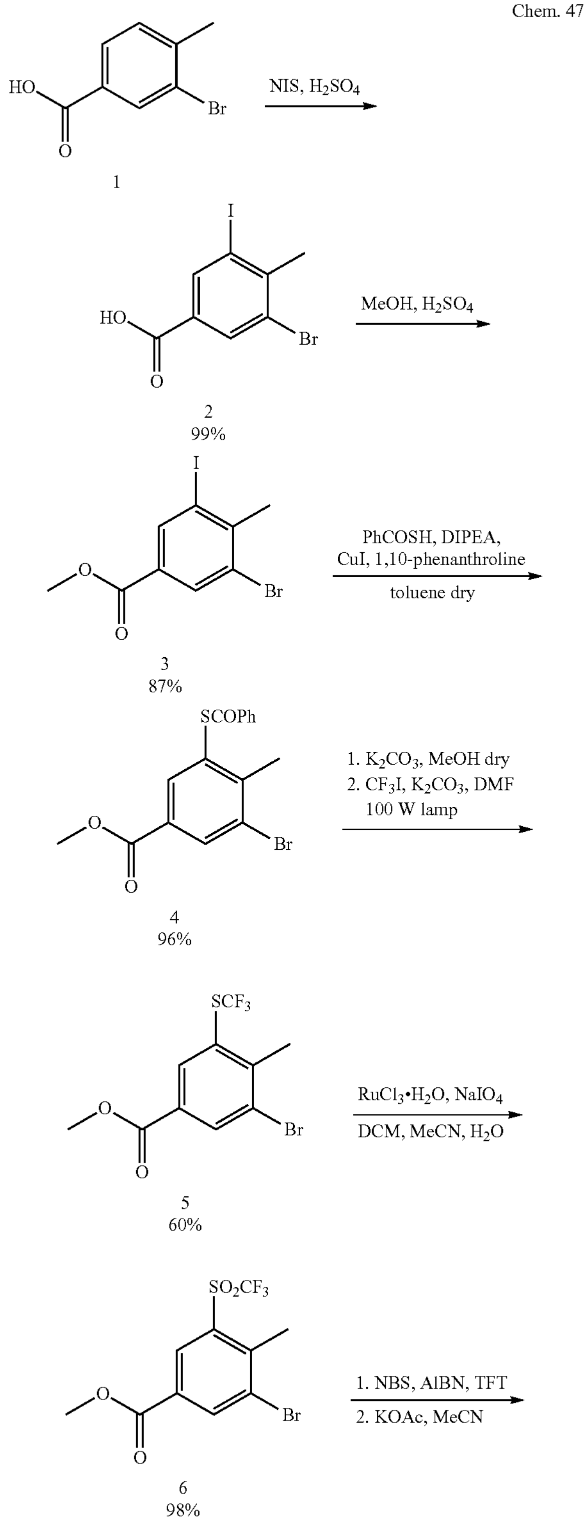

-continued

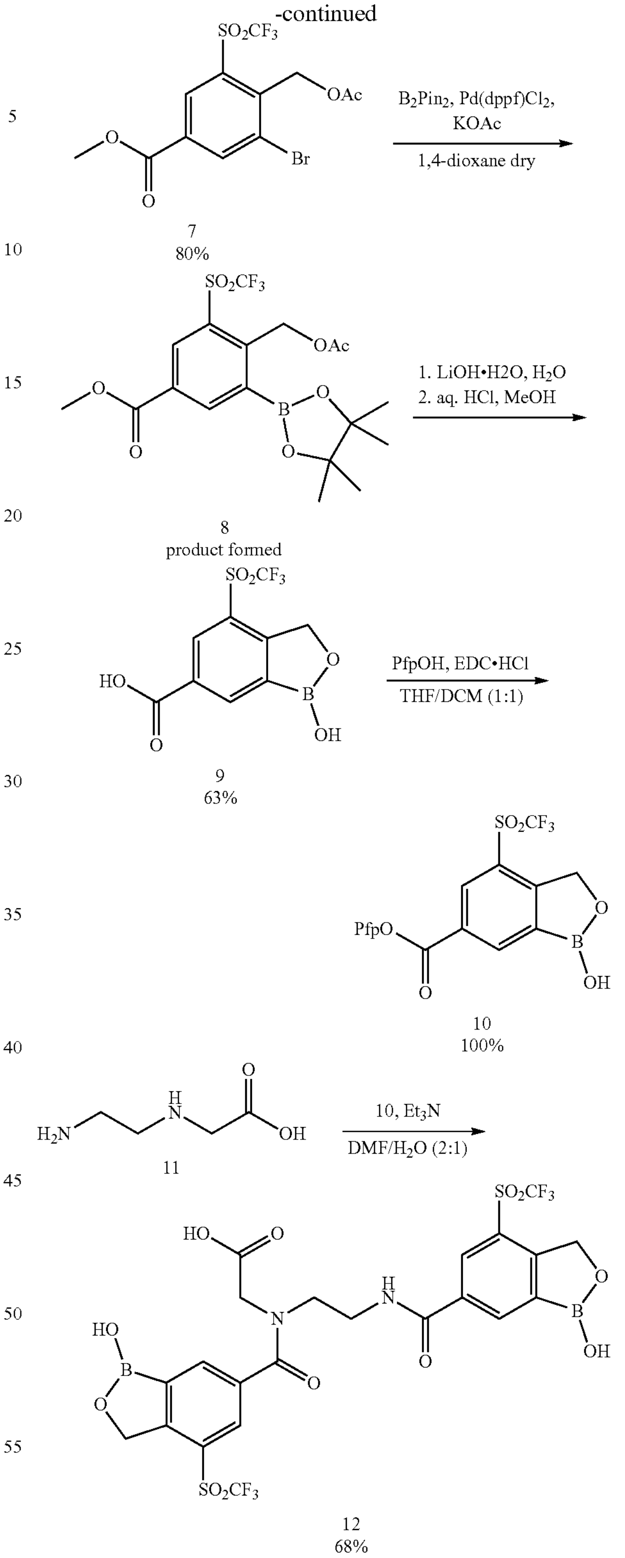

N-Iodosuccinimide (NIS, 61.5 g, 274 mmol) was added to a solution of 3-bromo-4-methylbenzoic acid (1, 56.0 g, 260 mmol) in concentrated sulfuric acid (1 L) and the reaction mixture was allowed to stir at ambient temperature for 16 hours. The reaction mixture was then poured into ice-water (2 L). Resulting mixture was poured onto ice bath (2 L), precipitate was filtered, washed with water and dried in vacuo to provide 3-bromo-5-iodo-4-methylbenzoic acid (2) as off-white solid. Yield: 87.8 g (99%).

$^1$H NMR spectrum (300 MHz, DMSO-$d_6$, $\delta_H$): 8.30 (d, J=1.7 Hz, 1H); 8.06 (d, J=1.7 Hz, 1H); 2.64 (s, 3H).

Concentrated sulfuric acid (35 mL) was added to a solution of 3-bromo-5-iodo-4-methylbenzoic acid (2, 55.4 g, 162 mmol) in methanol (1.5 L) and the reaction mixture was allowed to stir under reflux overnight. The reaction mixture was then evaporated under reduced pressure, dissolved in diethyl ether (1 L), washed with water (2×500 mL) and saturated aqueous solution of potassium carbonate (500 mL). Organic layer was separated, dried over anhydrous sodium sulfate, filtered and evaporated to provide methyl 3-bromo-5-iodo-4-methylbenzoate (3) as white solid.

Yield: 50.0 g (87%).

$^1$H NMR spectrum (300 MHz, DMSO-$d_6$, $\delta_H$): 8.32 (d, J=1.7 Hz, 1H); 8.09 (d, J=1.3 Hz, 1H); 3.86 (s, 3H); 2.65 (s, 3H).

Mixture of methyl 3-bromo-5-iodo-4-methylbenzoate (3, 15.1 g, 42.5 mmol), thiobenzoic acid (6.00 mL, 51.0 mmol), copper(I) iodide (0.81 g, 4.25 mmol), N,N-diisopropylethylamine (14.8 mL, 85.0 mmol) and 1,10-phenanthroline (1.53 g, 8.50 mmol) in dry toluene (120 mL) was stirred under nitrogen atmosphere at 100° C. overnight. After cooling down the suspension was filtered through celite pad and the solvent was evaporated. The residue was purified by 2 rounds of flash column chromatography (Silicagel 60, 0.040-0.063 mm; eluent: cyclohexane/dichloromethane 1:1) to give methyl 3-(benzoylthio)-5-bromo-4-methylbenzoate (4) as off-white solid. Yield: 14.9 g (96%).

$R_F$ ($SiO_2$, cyclohexane/dichloromethane 1:1): 0.30.

$^1$H NMR spectrum (300 MHz, $CDCl_3$, $\delta_H$): 8.33 (d, J=1.7 Hz, 1H); 8.14 (d, J=1.8 Hz, 1H); 8.08-8.00 (m, 2H); 7.69-7.61 (m, 1H); 7.56-7.49 (m, 2H); 3.93 (s, 3H); 2.59 (s, 3H).

Mixture of methyl 3-(benzoylthio)-5-bromo-4-methylbenzoate (4, 8.81 g, 24.1 mmol) and potassium carbonate (6.66 g, 48.2 mmol) in dry methanol (100 mL) was stirred under nitrogen atmosphere at room temperature for 1 hour. The solvent was evaporated and co-evaporated with toluene. Then potassium carbonate (19.9 g, 145 mmol) and N,N-dimethylformamide (130 mL) were added and the suspension was degassed and trifluoromethyl iodide was added (using balloon filled with trifluoromethyl iodide). The mixture was stirred for 1.5 hours under 100 W light bulb and then overnight at room temperature. Ethyl acetate (400 mL) was added and the mixture was washed with water (2×300 mL), 1 M aqueous solution of hydrochloric acid (1×300 mL) and brine (1×300 mL). Organic layer was dried over anhydrous sodium sulfate, filtered and evaporated. The residue was purified by flash column chromatography (Silicagel 60, 0.040-0.063 mm; eluent: cyclohexane/ethyl acetate 4:1) to give methyl 3-bromo-4-methyl-5-((trifluoromethyl)thio) benzoate (5) as colorless oil which crystallized in fridge. Yield: 4.78 g (60%).

$R_F$ ($SiO_2$, cyclohexane/ethyl acetate 9:1): 0.65.

$^1$H NMR spectrum (300 MHz, $CDCl_3$, $\delta_H$): 8.35 (s, 1H); 8.31 (s, 1H); 3.95 (s, 3H); 2.74 (s, 3H).

$^{19}$F NMR spectrum (282 MHz, $CDCl_3$, $\delta_F$): −42.18 (s).

Methyl 3-bromo-4-methyl-5-((trifluoromethyl)thio)benzoate (5, 4.75 g, 14.5 mmol) was dissolved in dichloromethane (20 mL) followed by addition of acetonitrile (20 mL), water (40 mL) and sodium periodate (9.29 g, 43.4 mmol). Then ruthenium(III) chloride hydrate (52.0 mg) was added at 0 C. The mixture was stirred for 2 hours at room temperature. Water (40 mL) was added and the mixture was extracted with dichloromethane (2×80 mL). Organic layers were combined, washed with 10% aqueous solution of hydrogen peroxide (1×30 mL) dried over anhydrous sodium sulfate, filtered through celite pad and evaporated. The residue was purified by flash column chromatography (Silicagel 60, 0.040-0.063 mm; eluent: cyclohexane/ethyl acetate 4:1) to give methyl 3-bromo-4-methyl-5-((trifluoromethyl) sulfonyl)benzoate (6) as white crystals. Yield: 5.14 g (98%).

$R_F$ ($SiO_2$, cyclohexane/ethyl acetate 9:1): 0.45.

$^1$H NMR spectrum (300 MHz, $CDCl_3$, $\delta_H$): 8.73 (d, J=1.8 Hz, 1H); 8.63 (d, J=1.7 Hz, 1H); 3.99 (s, 3H); 2.87 (s, 3H).

$^{19}$F NMR spectrum (282 MHz, $CDCl_3$, $\delta_F$): −77.13 (s).

A mixture of methyl 3-bromo-4-methyl-5-((trifluoromethyl)sulfonyl)benzoate (6, 5.13 g, 14.2 mmol), N-bromosuccinimide (3.28 g, 18.5 mmol) and 2,2-azobis(2-methylpropionitrile) (AIBN, 0.23 g, 1.42 mmol) in benzotrifluoride (25 mL) was stirred at 85° C. overnight. Full conversion was not achieved therefore N-bromosuccinimide (1.09 g, 6.17 mmol) and 2,2-azobis(2-methylpropionitrile) (AIBN, 0.23 g, 1.42 mmol) were added and the mixture was stirred at 85° C. overnight. Dichloromethane (100 mL) was added and the mixture was washed with water (3×100 mL). Organic layer was dried over anhydrous sodium sulfate, filtered and evaporated. The residue was dissolved in acetonitrile (75 mL) and potassium acetate (1.39 g, 14.2 mmol) was added. The mixture was stirred at 75° C. overnight. The insoluble material was filtered off and the filtrate was evaporated. The residue was purified by flash column chromatography (Silicagel 60, 0.040-0.063 mm; eluent: cyclohexane/dichloromethane 2:1 to 1:1) to give methyl 4-(acetoxymethyl)-3-bromo-5-((trifluoromethyl)sulfonyl)benzoate (7) as white powder.

Yield: 4.76 g (80%).

$R_F$ ($SiO_2$, cyclohexane/ethyl acetate 4:1): 0.35.

$^1$H NMR spectrum (300 MHz, $CDCl_3$, $\delta_H$): 8.78 (d, J=1.7 Hz, 1H); 8.70 (d, J=1.7 Hz, 1H); 5.63 (s, 2H); 4.02 (s, 3H); 2.11 (s, 3H).

$^{19}$F NMR spectrum (282 MHz, $CDCl_3$, $\delta_F$): −77.08 (s).

A mixture of methyl 4-(acetoxymethyl)-3-bromo-5-((trifluoromethyl)sulfonyl)benzoate (7, 4.75 g, 11.3 mmol), bis (pinacolato)diboron (3.74 g, 14.7 mmol) and dry potassium acetate (5.56 g, 56.6 mmol) in dry 1,4-dioxane (60 mL) was degassed; then [1,1-bis(diphenylphosphino)ferrocene]dichloropalladium (0.42 g, 0.57 mmol) was added. Reaction mixture was stirred under nitrogen atmosphere at 80° C. overnight. The solvent was evaporated. The residue was filtered through a short silica gel column in dichloromethane affording methyl 4-(acetoxymethyl)-3-(4,4,5,5-tetramethyl-1,3,2-dioxaborolan-2-yl)-5-((trifluoromethyl)sulfonyl)benzoate (8) as yellow solid. Yield: 6.00 g.

$^1$H NMR spectrum (300 MHz, $CDCl_3$, $\delta_H$): 8.85 (s, 2H); 5.75 (s, 2H); 4.00 (s, 3H); 2.05 (s, 3H); 1.37 (s, 12H).

$^{19}$F NMR spectrum (282 MHz, $CDCl_3$, $\delta_F$): −77.39 (s).

Methyl 4-(acetoxymethyl)-3-(4,4,5,5-tetramethyl-1,3,2-dioxaborolan-2-yl)-5-((trifluoromethyl)sulfonyl)benzoate (8, 0.47 g, 1.00 mmol) was dissolved in methanol (4 mL) and a solution of lithium hydroxide monohydrate (0.21 g, 5.00 mmol) in water (2 mL) was added. The mixture was stirred for 35 minutes at room temperature then it was extracted with diethyl ether (2×10 mL). Aqueous phase was acidified with concentrated hydrochloric acid (434 L) and resulting mixture was stirred for 30 minutes at room temperature. The precipitate was filtered, washed with water and dried to give 1-hydroxy-4-((trifluoromethyl)sulfonyl)-1,3-dihydrobenzo[c][1,2]oxaborole-6-carboxylic acid (9) as white solid. Yield: 195 mg (63%).

$^1$H NMR spectrum (300 MHz, DMSO-$d_6$, $\delta_H$): 9.85 (s, 1H); 8.88 (s, 1H); 8.49 (s, 1H); 5.35 (s, 2H).

$^{19}$F NMR spectrum (282 MHz, $CDCl_3$, $\delta_F$): −78.52 (s).

LC-MS purity: 100% (ELSD).

LC-MS Rt (Kinetex C18, 4.6 mm×50 mm, acetonitrile/water 5:95 to 100:0+0.1% FA): 3.69 min.

LC-MS m/z: 310.0 $(M-H)^-$.

1-Hydroxy-4-((trifluoromethyl)sulfonyl)-1,3-dihydrobenzo[c][1,2]oxaborole-6-carboxylic acid (9, 195 mg, 0.63 mmol) was dissolved in tetrahydrofuran/dichloromethane mixture (1:1, 10 mL) followed by addition of 2,3,4,5,6-pentrafluorophenol (116 mg, 0.63 mmol) and N-(3-dimethylaminopropyl)-N-ethylcarbodiimide hydrochloride (121 mg, 0.63 mmol). The mixture was stirred overnight at room temperature. Then the solvent was evaporated. The residue was dissolved in ethyl acetate (70 mL) and washed with water (2×40 mL) and brine (1×40 mL). Organic layer was dried over anhydrous sodium sulfate, filtered and evaporated to dryness to give perfluorophenyl 1-hydroxy-4-((trifluoromethyl)sulfonyl)-1,3-dihydrobenzo[c][1,2]oxaborole-6-carboxylate (10) as pale pink powder. Yield: 300 mg (100%).

$^1$H NMR spectrum (300 MHz, DMSO-$d_6$, $\delta_H$): 9.93 (s, 1H); 9.09 (s, 1H); 8.65 (s, 1H); 5.41 (s, 2H).

Perfluorophenyl 1-hydroxy-4-((trifluoromethyl)sulfonyl)-1,3-dihydrobenzo-[c][1,2]oxaborole-6-carboxylate (10, 238 mg, 0.50 mmol) and (2-aminoethyl)glycine (11, 29.5 mg, 0.25 mmol) were dissolved in N,N-dimethylformamide/water mixture (2:1, 1.5 mL). Triethylamine (250 L) was then added and the resulting mixture was stirred overnight at room temperature. Afterwards, it was acidified with 1 M aqueous solution of potassium bisulfate (15 mL) and extracted with ethyl acetate (3×15 mL). The organic layer was dried over anhydrous sodium sulfate, filtered and evaporated. The residue was co-distilled with toluene (3×10 mL) and triturated with diethyl ether (3 mL). The precipitate was filtered, washed with diethyl ether (2×1 mL) and air dried. The obtained powder was dissolved in acetonitrile/water mixture (2:1, 20 mL) and freeze-dried to give the title N-(1-hydroxy-4-((trifluoromethyl)sulfonyl)-1,3-dihydrobenzo-[c][1,2]oxaborole-6-carbonyl)-N-(2-(1-hydroxy-4-((trifluoromethyl)sulfonyl)-1,3-dihydrobenzo[c][1,2]oxaborole-6-carboxamido)ethyl)glycine (12) as colorless solid. Yield: 120 mg (68%).

$^1$H NMR spectrum (300 MHz, AcOD-$d_6$, 80 C, $\delta_H$): 8.68 (bs, 1H); 8.53 (bs, 1H); 8.27 (s, 1H); 8.10 (s, 1H); 5.46 (s, 2H); 5.42 (s, 2H); 4.44-4.29 (m, 2H); 3.99-3.72 (m, 4H)

LC-MS purity: 100% (ELSD, UV 254 nm).

LC-MS Rt (Kinetex C18, 4.6 mm×50 mm, acetonitrile/water 5:95 to 100:0+0.1% FA): 5.06 min.

LC-MS m/z: 702.1 $(M+H)^+$.

Example 43

4-Borono-2-((3-borono-5-(trifluoromethyl)phenyl)sulfonyl)-6-(trifluoromethyl)benzoic acid

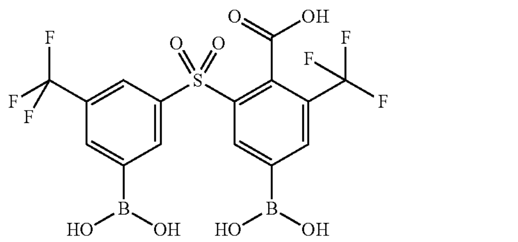 [SMILES: O=C(O)c1c(C(F)(F)F)cc(B(O)O)cc1S(=O)(=O)c1cc(B(O)O)cc(C(F)(F)F)c1]

4-Borono-2-((3-borono-5-(trifluoromethyl)phenyl)sulfonyl)-6-(trifluoromethyl)benzoic acid was synthesized according to the reaction scheme shown in Chem. 48 and following the procedure described below.

Chem. 48

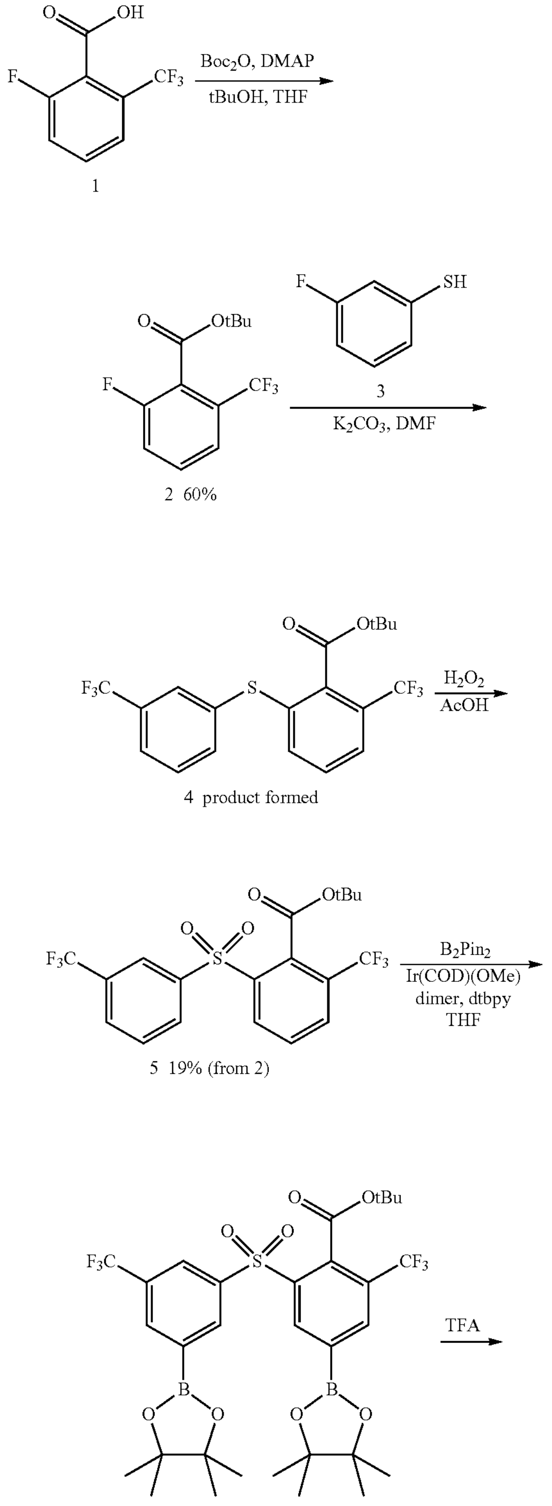

-continued

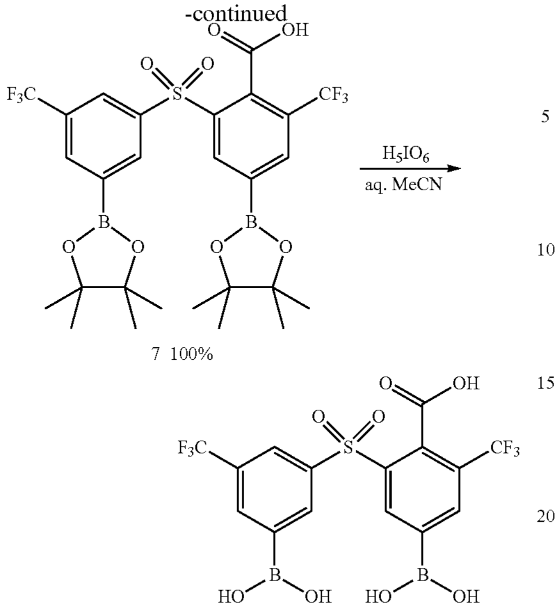

7 100%

8 88%

Mixture of 2-fluoro-6-(trifluoromethyl)benzoic acid (1, 1.00 g, 4.81 mmol), di-tert-butyl dicarbonate (1.47 g, 6.73 mmol), 4-(dimethylamino)pyridine (0.18 g, 1.44 mmol) and tert-butanol (5 mL) in tetrahydrofuran (10 mL) was stirred overnight at room temperature. The mixture was diluted with ethyl acetate (40 mL) and washed with water (1×40 mL), 1 M aqueous solution of hydrochloric acid (1×40 mL), 5% aqueous solution of sodium carbonate (1×40 mL), water (1×40 mL) and brine (1×40 mL). Organic layer was dried over anhydrous sodium sulfate, filtered and evaporated to dryness to give tert-butyl 2-fluoro-6-(trifluoromethyl)benzoate (2) as colorless oil. Yield: 0.77 g (60%).

$^1$H NMR spectrum (300 MHz, $CDCl_3$, $\delta_H$): 7.53-7.44 (m, 2H); 7.36-7.29 (m, 1H); 1.60 (s, 9H).

Mixture of ester (2, 0.76 g, 2.87 mmol), 3-(trifluoromethyl)benzenethiol (3, 0.61 g, 3.44 mmol) and potassium carbonate (0.87 g, 6.31 mmol) in N,N-dimethylformamide (30 mL) was stirred under nitrogen atmosphere overnight at 100° C. Reaction mixture was then diluted with ethyl acetate (30 mL) and washed with water (3×30 mL). Organic layer was dried over anhydrous sodium sulfate, filtered and evaporated to afford mixture of starting ester (2) and tert-butyl 2-(trifluoromethyl)-6-((3-(trifluoromethyl)phenyl)thio)benzoate (4) (1:1.8). This mixture was dissolved in acetic acid (20 mL) and hydrogen peroxide (2 mL) was added. Resulting mixture was stirred at 70° C. for 7 hours. Reaction mixture was then diluted with ethyl acetate (30 mL) and washed with water (3×30 mL). Organic layer was dried over anhydrous sodium sulfate, filtered and evaporated. The residue was purified by flash column chromatography (Silicagel 60, 0.040-0.063 mm; eluent: cyclohexane/ethyl acetate 4:1) to yield tert-butyl 2-(trifluoromethyl)-6-((3-(trifluoromethyl)phenyl)sulfonyl)benzoate (5) as white powder. Yield: 0.25 g (19%).

$R_F$ ($SiO_2$, cyclohexane/ethyl acetate 4:1): 0.45.

$^1$H NMR spectrum (300 MHz, $CDCl_3$, $\delta_H$): 8.37 (d, J=8.1 Hz, 1H); 8.27-8.18 (m, 2H); 7.95 (d, J=7.7 Hz, 1H); 7.86 (d, J=7.9 Hz, 1H); 7.77-7.64 (m, 2H); 1.67 (s, 9H).

LC-MS purity: 100% (ELSD).

LC-MS Rt (Kinetex C18, 4.6 mm×50 mm, acetonitrile/water 70:30 to 100:0+0.1% FA): 3.39 min.

LC-MS m/z: 477.3 $(M+Na)^+$.

The sulfone (5, 0.25 g, 0.55 mmol), bis(pinacolato)diboron (350 mg, 1.38 mmol), (1,5-cyclooctadiene)(methoxy)iridium(I) dimer (11.0 mg, 0.02 mmol) and 4,4-di-tert-butyl-2,2-dipyridyl (dtbpy, 10.0 mg, 0.04 mmol) were dissolved in degassed tetrahydrofuran (5 mL) under nitrogen. The resulting mixture was warmed to 50° C. and heated at this temperature overnight. The mixture was evaporated to dryness; and the residue purified by quick flash column chromatography (Silicagel 60, 0.040-0.063 mm; eluent: dichloromethane) to give tert-butyl 4-(4,4,5,5-tetramethyl-1,3,2-dioxaborolan-2-yl)-2-((3-(4,4,5,5-tetramethyl-1,3,2-dioxaborolan-2-yl)-5-(trifluoromethyl)phenyl)sulfonyl)-6-(trifluoromethyl)benzoate (6) as white foam. Yield: 240 mg (62%).

$^1$H NMR spectrum (300 MHz, $CDCl_3$, $\delta_H$): 8.75 (s, 1H); 8.52 (s, 1H); 8.34 (s, 1H); 8.31 (s, 1H); 8.24 (s, 1H); 1.66 (s, 9H); 1.38 (s, 12H); 1.36 (s, 12H).

Trifluoroacetic acid (5 mL) was added to a solution of tert-butyl 4-(4,4,5,5-tetramethyl-1,3,2-dioxaborolan-2-yl)-2-((3-(4,4,5,5-tetramethyl-1,3,2-dioxaborolan-2-yl)-5-(trifluoromethyl)phenyl)sulfonyl)-6-(trifluoromethyl)benzoate (6, 235 mg, 0.33 mmol) in dichloromethane (1 mL) and the mixture was stirred for 2 hours at room temperature. The mixture was evaporated to dryness in vacuo, and the residue was evaporated from dichloromethane (5×10 mL) to afford 4-(4,4,5,5-tetramethyl-1,3,2-dioxaborolan-2-yl)-2-((3-(4,4,5,5-tetramethyl-1,3,2-dioxaborolan-2-yl)-5-(trifluoromethyl)phenyl)sulfonyl)-6-(trifluoromethyl)benzoic acid (7) as white foam. Yield: 214 mg (100%).

$^1$H NMR spectrum (300 MHz, $CDCl_3$, $\delta_H$): 8.78 (s, 1H); 8.60 (s, 1H); 8.34 (s, 2H); 8.25 (s, 1H); 1.39 (s, 12H); 1.36 (s, 12H).

A solution of the above acid (7, 210 mg, 0.33 mmol) in acetonitrile (4 mL) was diluted with water (1 mL) followed by addition of periodic acid (301 mg, 1.32 mmol). The resulting mixture was stirred for 1 hour; and then it was partitioned between ethyl acetate (30 mL) and water (30 mL). The phases were separated; the organic one was washed with water (1×30 mL) and brine (1×30 mL); dried over anhydrous sodium sulfate, filtered and evaporated to dryness. The residue was dissolved in 20% aqueous solution of sodium hydroxide (10 mL) and washed with dichloromethane (2×40 mL). The aqueous layer was acidified with 1 M aqueous solution of hydrochloric acid (30 mL) and extracted with ethyl acetate (2×50 mL). Ethyl acetate extracts were combined, dried over anhydrous sodium sulfate, filtered and concentrated in vacuo until the product started to precipitate. The suspension was diluted with n-hexane (50 mL). The precipitate was collected by filtration, washed with n-hexane, dissolved in acetonitrile (30 mL) and freeze-dried to afford the title compound (8) as beige powder. Yield: 138 mg (88%).

$^1$H NMR spectrum (300 MHz, DMSO-$d_6$/DCl, $\delta_H$): 8.86 (s, 1H); 8.62 (s, 1H); 8.42 (s, 1H); 8.37 (s, 1H); 8.26 (s, 1H).

$^{19}$F NMR spectrum (282 MHz, DMSO-$d_6$, $\delta_F$): −58.17 (s); −61.40 (s).

LC-MS purity: 100% (ELSD).

LC-MS Rt (Kinetex C18, 4.6 mm×50 mm, acetonitrile/water 20:80 to 100:0+0.1% FA): 4.05 min.

LC-MS m/z: 467.9 $(M-H_2O+H)^+$.

Example 44

2-((Bis(3-borono-5-(trifluoromethoxy)phenyl)(oxo)-λ6-sulfanylidene)amino)acetic acid

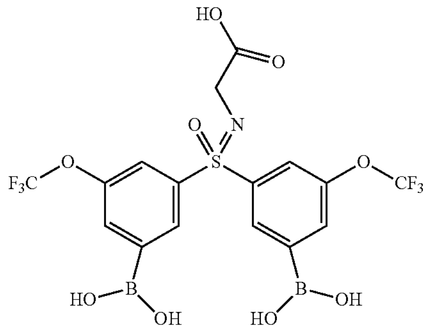 [SMILES: O=C(O)CN=S(=O)(c1cc(OC(F)(F)F)cc(B(O)O)c1)c1cc(OC(F)(F)F)cc(B(O)O)c1]

2-((Bis(3-borono-5-(trifluoromethoxy)phenyl)(oxo)-λ6-sulfanylidene)amino)acetic acid was synthesized according to the reaction scheme shown in Chem. 49 and following the procedure described below.

Chem. 49

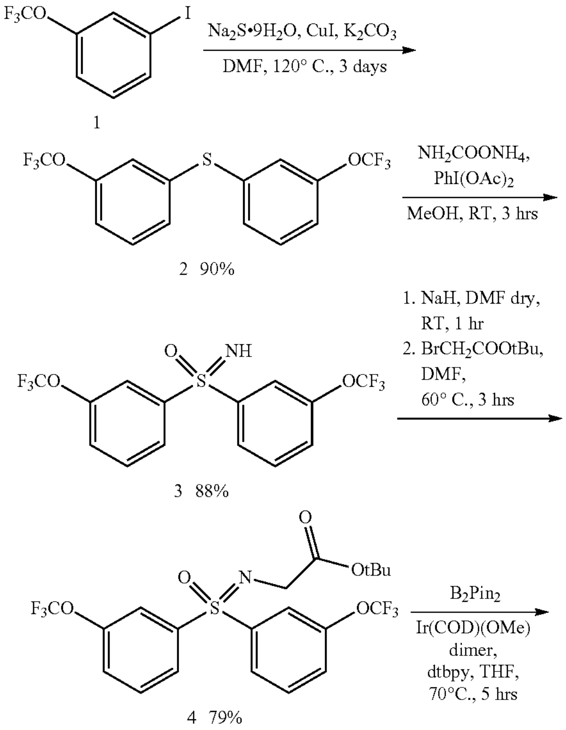

-continued

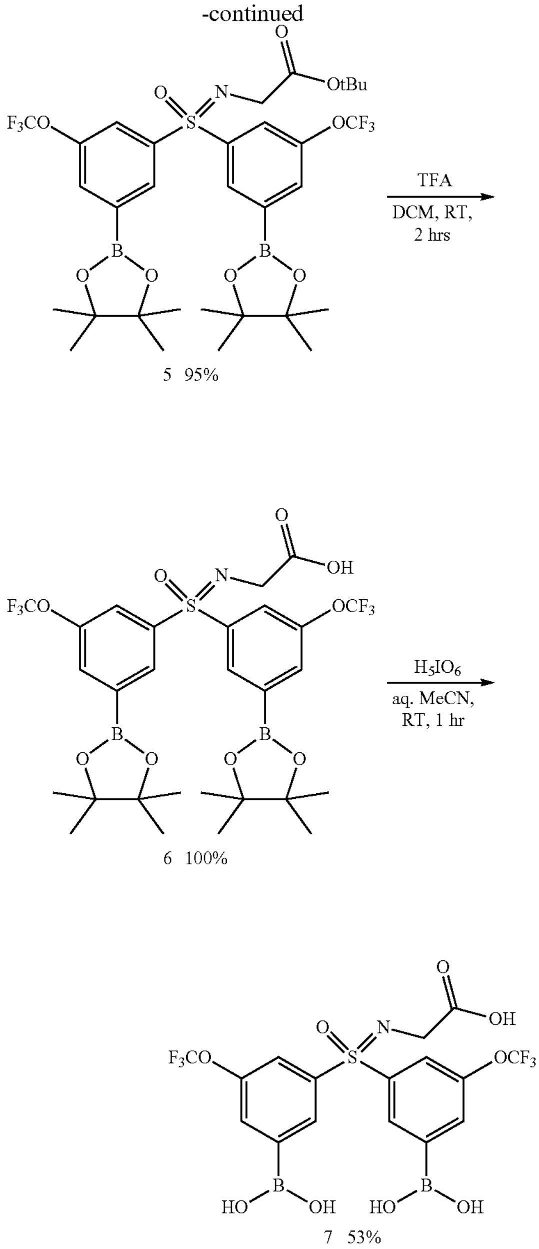

A solution of 1-iodo-3-(trifluoromethoxy)benzene (1, 9.08 g, 31.5 mmol) in N,N-dimethylformamide (63 mL) was added to sodium sulfide nonahydrate (5.30 g, 22.1 mmol) and potassium carbonate (4.36 g, 31.5 mmol) in a pressure reactor. The mixture was degassed and backfilled with argon. Cuprous iodide (600 mg, 3.15 mmol) was added, the reactor was sealed and heated to 120° C. The mixture was heated at 120° C. for 3 days, then it was cooled to room temperature and diluted with diethyl ether (100 mL). The resulting mixture was filtered over Celite. The filtrate was washed with water (150 mL), and the aqueous layer was re-extracted with diethyl ether (2×100 mL). All organic fractions were combined, washed 1 M aqueous solution of sodium hydroxide (2×100 mL), water (100 mL) and brine (70 mL); dried over anhydrous sodium sulfate and evaporated to dryness in vacuo. The residue was purified by flash column chromatography (Silicagel 60, 0.040-0.063 mm; eluent: cyclohexane) to give bis(3-(trifluoromethoxy)phenyl)sulfane (2) as colorless liquid. Yield: 5.04 g (90%).

$R_F$ ($SiO_2$, cyclohexane/ethyl acetate 95:5): 0.45.

$^1H$ NMR spectrum (300 MHz, $CDCl_3$, $\delta_H$): 7.41-7.33 (m, 2H); 7.30-7.25 (m, 2H); 7.20 (s, 20H); 7.18-7.12 (m, 2H).

$^{19}F$ NMR spectrum (282 MHz, $CDCl_3$, $\delta_F$): −57.91 (s).

LC-MS purity: 97% (UV 254 nm).

LC-MS Rt (Kinetex C18, 4.6 mm×50 mm, acetonitrile/water 70:30 to 100:0+0.1% FA): 3.48 min.

LC-MS m/z: 355.2 $(M+H)^+$.

(Diacetoxyiodo)benzene (PIDA, 12.8 g, 39.7 mmol) was added to a mixture of bis(3-(trifluoromethoxy)phenyl)sulfane (2, 5.63 g, 15.9 mmol) and powdered ammonium carbamate (2.48 g, 31.8 mmol) in methanol (32 mL). The resulting pale yellow solution was stirred at room temperature for 3 hours, and then it was evaporated to dryness in vacuo. A solution of potassium carbonate (12.5 g) and sodium thiosulfate (25 g) in water (200 mL) was added to the residue, followed by ethyl acetate (200 mL). The phases were separated and the aqueous one was extracted with ethyl acetate (3×100 mL). The organic fractions were combined, dried over anhydrous sodium sulfate and evaporated in vacuo. The residue was purified by flash column chromatography (Silicagel 60, 0.040-0.063 mm; eluent: cyclohexane/ethyl acetate 95:5 to 70:30) to give iminobis(3-(trifluoromethoxy)phenyl)-$\lambda^6$-sulfanone (3) as pale yellow liquid. Yield: 5.38 g (88%).

$R_F$ ($SiO_2$, n-hexane/ethyl acetate 1:1): 0.45.

$^1H$ NMR spectrum (300 MHz, $CDCl_3$, $\delta_H$): 8.00-7.94 (m, 2H); 7.92 (s, 2H); 7.56 (t, J=8.1 Hz, 2H); 7.45-7.38 (m, 2H); 3.20 (bs, 1H).

$^{19}F$ NMR spectrum (282 MHz, $CDCl_3$, $\delta_F$): −58.00 (s).

LC-MS purity: 100% (ELSD, UV 254 nm).

LC-MS Rt (Kinetex C18, 4.6 mm×50 mm, acetonitrile/water 35:65 to 100:0+0.1% FA): 3.78 min.

LC-MS m/z: 386.3 $(M+H)^+$.

Sodium hydride (60% dispersion in mineral oil, 614 mg, 15.4 mmol) was added to a solution of iminobis(3-(trifluoromethoxy)phenyl)-$\lambda^6$-sulfanone (3, 5.38 g, 14.0 mmol) in dry N,N-dimethylformamide (42 mL) and the mixture was stirred at room temperature for 1 hour. tert-Butyl bromoacetate (4.68 mL, 21.0 mmol) was added; the mixture was heated to 60° C. and stirred at this temperature for 3 hours. The mixture was cooled to room temperature, diluted with 10% aqueous solution of potassium hydrogensulfate (200 mL) and extracted with ethyl acetate (2×100 mL). Separated organic layers were combined, washed with water (4×150 mL) and brine (100 mL); dried over anhydrous sodium sulfate and evaporated in vacuo. The residue was subjected to flash column chromatography (Silicagel 60, 0.040-0.063 mm; eluent: cyclohexane/ethyl acetate 95:5) to give pure fraction of tert-butyl 2-((oxobis(3-(trifluoromethoxy)phenyl)-$\lambda^6$-sulfanylidene)amino)acetate (4) as colorless oil. Yield: 5.51 g (79%).

$R_F$ ($SiO_2$, n-hexane/ethyl acetate 1:1): 0.60.

$^1H$ NMR spectrum (300 MHz, $CDCl_3$, $\delta_H$): 8.02-7.96 (m, 2H); 7.93 (s, 2H); 7.56 (d, J=8.0 Hz, 2H); 7.44-7.38 (m, 2H); 3.77 (s, 2H); 1.48 (s, 9H).

$^{19}F$ NMR spectrum (282 MHz, $CDCl_3$, $\delta_F$): −57.99 (s).

LC-MS purity: 100% (ELSD, UV 254 nm).

LC-MS Rt (Kinetex C18, 4.6 mm×50 mm, acetonitrile/water 35:65 to 100:0+0.1% FA): 4.88 min.

LC-MS m/z: 500.4 $(M+H)^+$.

tert-Butyl 2-((oxobis(3-(trifluoromethoxy)phenyl)-$\lambda^6$-sulfanylidene)amino)acetate (4, 810 mg, 1.62 mmol), bis(pinacolato)diboron (906 mg, 3.57 mmol), (1,5-cyclooctadiene)(methoxy)iridium(I) dimer (10.8 mg, 16.2 µmol) and 4,4-di-tert-butyl-2,2-dipyridyl (dtbpy, 10.9 mg, 40.5 µmol) were dissolved in degassed tetrahydrofuran (3.2 mL) under argon. The resulting mixture was warmed to 70° C. and heated at this temperature for 5 hours. The mixture was evaporated to dryness and re-dissolved in dichloromethane (20 mL). Methanol (40 mL) was added; the solution was stirred for 30 minutes, and then it was evaporated in vacuo. The residue was purified by flash column chromatography (Silicagel 60, 0.040-0.063 mm; eluent: dichloromethane/ethyl acetate 10:0 to 4:1) to give tert-butyl 2-((oxobis(3-(4,4,5,5-tetramethyl-1,3,2-dioxaborolan-2-yl)-5-(trifluoromethoxy)phenyl)-$\lambda^6$-sulfanylidene)amino)acetate (5) as pale orange foam. Yield: 1.15 g (95%).

$^1H$ NMR spectrum (300 MHz, $CDCl_3$, $\delta_H$): 8.32 (s, 2H); 8.03 (s, 2H); 7.79 (s, 2H); 3.76 (s, 2H); 1.51 (s, 9H); 1.34 (s, 24H).

$^{19}F$ NMR spectrum (282 MHz, $CDCl_3$, $\delta_F$): −57.87 (s).

LC-MS purity: 92% (ELSD).

LC-MS Rt (Kinetex C18, 4.6 mm×50 mm, acetonitrile/water 85:15 to 100:0+0.1% FA): 4.63 min.

LC-MS m/z: 752.9 $(M+H)^+$.

Trifluoroacetic acid (6 mL) was added to a solution of tert-butyl 2-((oxobis(3-(4,4,5,5-tetramethyl-1,3,2-dioxaborolan-2-yl)-5-(trifluoromethoxy)phenyl)-$\lambda^6$-sulfanylidene)amino)acetate (5, 1.14 g, 1.52 mmol) in dichloromethane (3.00 mL) and the mixture was stirred for 2 hours at room temperature. The mixture was evaporated to dryness in vacuo, and the residue was evaporated from toluene (3×20 mL) and dichloromethane (3×20 mL). The residue was dissolved in 0.5 M aqueous solution of sodium hydroxide (30 mL). The resulting cloudy solution was washed with dichloromethane (2×10 mL), acidified with 1 M aqueous solution of hydrochloric acid (20 mL) and extracted with ethyl acetate (3×25 mL). Combined ethyl acetate extracts were dried over anhydrous sodium sulfate and evaporated in vacuo to give 2-((oxobis(3-(4,4,5,5-tetramethyl-1,3,2-dioxaborolan-2-yl)-5-(trifluoromethoxy)phenyl)-$\lambda^6$-sulfanylidene)amino)acetic acid (6) as off-white foam. Yield: 1.06 g (100%).

$^1H$ NMR spectrum (300 MHz, $CDCl_3$, $\delta_H$): 8.27 (s, 2H); 7.92 (s, 2H); 7.85 (s, 2H); 3.85 (s, 2H); 1.36 (s, 12H); 1.35 (s, 12H).

$^{19}F$ NMR spectrum (282 MHz, $CDCl_3$, $\delta_F$): −57.92 (s).

LC-MS purity: 100% (ELSD).

LC-MS Rt (Kinetex C18, 4.6 mm×50 mm, acetonitrile/water 85:15 to 100:0+0.1% FA): 0.89 min (M-pinacol), 2.23 min (M).

LC-MS m/z: 614.6 $(M\text{-pinacol}+H)^+$, 696.8 $(M+H)^+$.

A solution of 2-((oxobis(3-(4,4,5,5-tetramethyl-1,3,2-dioxaborolan-2-yl)-5-(trifluoromethoxy)phenyl)-$\lambda^6$-sulfanylidene)amino)acetic acid (6, 1.06 g, 1.52 mmol) in acetonitrile (10.7 mL) was diluted with water (2.1 mL) followed by addition of periodic acid (1.39 g, 6.08 mmol). The resulting mixture was stirred for 1 hour; and then it was partitioned between ethyl acetate (240 mL) and water (60 mL). The phases were separated; the organic one was washed with saturated aqueous solution of potassium chloride (2×100 mL); dried over anhydrous sodium sulfate and evaporated to dryness. The residue was dissolved in 0.5 M aqueous solution of sodium hydroxide (60 mL) and washed with dichloromethane (3×60 mL). The aqueous layer was acidified with 1 M aqueous solution of hydrochloric acid (60 mL) and extracted with ethyl acetate (2×120 mL). Ethyl acetate extracts were combined, dried over anhydrous sodium sulfate and concentrated in vacuo until the product started to precipitate (approx. 20 mL volume). The suspension was diluted with n-hexane (50 mL) and placed into a fridge for 1 hour. The precipitate was collected by filtration, washed with n-hexane (3×10 mL) and dried in vacuo to give 623 mg of crude title compound (7). A portion of the precipitate (210 mg) was purified by preparative HPLC (SunFire Prep C18 OBD, 5 m, 19×100 mm, acetonitrile/water 5:95 to 100:0+0.1% FA) and freeze-dried to afford the title compound (7) as white powder. Yield: 146 mg (53%).

$^1$H NMR spectrum (300 MHz, DMSO-$d_6$+DCl, $\delta_H$): 8.34 (dd, J=1.7 and 0.7 Hz, 2H); 7.98 (s, 2H); 7.94 (s, 2H); 3.68 (s, 2H).

$^{19}$F NMR spectrum (282 MHz, DMSO-$d_6$+DCl, $\delta_F$): −56.99 (s).

LC-MS purity: 100% (ELSD, UV 254 nm).

LC-MS Rt (Kinetex C18, 4.6 mm×50 mm, acetonitrile/water 5:95 to 100:0+0.1% FA): 3.26 min.

LC-MS m/z: 532.0 $(M+H)^+$.

Example 45

Carbohydrates and Diboronate Binding Affinity—The Alizarin Assay (ARS)

The alizarin-red binding assay is a colorimetric assay used to determine the inhibition affinity of boronate compounds to glucose. The assay is based on a colour shift of alizarin-red upon binding to boronate, which shift can be followed by change in absorbance in the 330-340 nm region.

Determination of the Dissociation Constant (Kd)

For determination of the dissociation constant (Kd) between the Alizarin Red (ARS) and the boronate compound, 200 μM of ARS is dissolved in a 20 mM of phosphate buffer pH 7.4, and titrated in triplicate into a 96 well plate with 1, 0.5, 0.25, 0.125, 62.5, 31.25, 15.625, 7.812, 3.906, 1.953, 0.9767, 0.488 and 0.244 mM of boronic acid. After 5 minutes of centrifugation at 4000 rpm, the plate is placed in a multi-well spectrometer (SpectraMax, Molecular Devices) for absorption detection.

The analysis is carried out at room temperature with absorption readings at 330, 340 and 520 nm, respectively. Data obtained for absorption versus concentration of boronate is then fitted (Prism 7, GraphPad) with a sigmoidal function to obtain the Kd value of boronate and ARS.

Determination of the Displacement Constant ($K_d$)

For determination of the inhibitory constant (Ki) between the boronate and the carbohydrate, 400 μM of boronic acids is dissolved in a 20 mM phosphate buffer pH 7.4 under gentle stirring. Upon complete dissolution of the compound, 200 μM of Alizarin red (ARS) is added to the solution. The ARS-boronate solution is then aliquoted into a 96 multiwell plate (black, flat and clear bottom) 1:1 with appropriate carbohydrate. In particular, D-glucose and L-lactate solutions are prepared in a 20 mM phosphate buffer pH 7.4 at these concentrations respectively: 1000, 500, 250, 100, 50, 25, 10, 5, 2.5, 1, 0.25, 0.1 mM and 2500, 1000, 500, 100, 50, 10, 5, 1, 0.5, 0.1, 0.05, 0.01 mM. The plate with ARS-boronate mixed with carbohydrate is incubated 20 minutes at room temperature. After 5 minutes of centrifugation at 4000 rpm the plate is placed in a multiwell spectrometer (Spectra Max, Molecular Devices) for absorption detection.

The analysis is carried out at room temperature with absorption readings at 330, 340 and 520 nm, respectively. Data obtained for absorption versus concentration of carbohydrate is then fitted (Prism 7, GraphPad) with a one site Ki equation constrained for the value of Kd of the obtained for ARS-boronate and for the concentration of the ARS (100 μM) to obtain the Ki value of the boronate for the chosen carbohydrate.

Example 46

Glucose Affinity by $^{13}$C NMR Assay

The $^{13}$C Glucose assay is an NMR based assay that takes advantage of the slow chemical shift exchange between the unbound glucose (A state) and the glucose bound to diboronates (B state). If $$A \underset{Koff}{\overset{Kon}{\rightleftarrows}} B;\ k_{ex} = K_{on} + K_{off}$$

and the chemical shift difference between state A and B is $\Delta\omega$, the process is in slow exchange (on NMR time scale) when $k_{ex} \ll \Delta\omega$ In a slow exchange regime NMR signals from both states (A and B) are observed and reflect the distinct chemical shifts of the two states as there is not significant interconversion in the timescale of the NMR experiments. Therefore the intensity of each peak directly reports on the population of that state.

The dissociation constant (Kd) could be defined as Kd=([A][B])/[AB], given At as the total concentration of specie A and Bt as total concentration of specie B, in the case in which At−Bt, the product at the equilibrium AB is given by the following equation:

$$AB = \frac{(At + Bt + Kd) - \sqrt{(At + Bt + Kd)^2 - 4(AtBt)}}{2} \quad (1)$$

so that knowing At, Bt and AB at the equilibrium is possible to determine Kd. Binding of glucose to boronates happens in a NMR slow exchange regime so that is possible to define the concentration of AB by investigating the intensities of the C13 Glucose peaks before and after the binding of diboronates.

Determination of the Dissociation Constant (Kd)

For determination of the dissociation constant (Kd) between glucose and the boronate compound, samples of 1 mM of glucose C13 with and without 1 mM of boronate at pH 7.4 in 10 mM phosphate buffer and 5% D2O are prepared. The samples are then investigated with a standard Carbon HSQC in a Bruker NMR instrument (RT, 32 scans). The intensities of the peaks of free glucose and glucose bound to boronates are determined by the use of TOPSPIN program (Bruker). Difference between intensity of free glucose and glucose bound peaks gives the concentration of product AB at the equilibrium so that Kd can be calculated using equation 1.

Data in table 1 show that the diboron compounds of the invention bind glucose with Kd values in the low millimolar range (0.2 to 4.5 mM), and that the diboron compounds of the invention have higher affinity towards glucose than towards lactate.

TABLE 1

Glucose and lactate Kd-values as determined by the alizarin assay described in Example 45 for diboron compounds representative of the invention.

| Compound of Example No. | Formula | Binding Affinity [Kd Glucose (mM)] | Binding Affinity [Kd Lactate (mM)] |
|---|---|---|---|
| Example 1 | Ia + IIa | 3.1 | 8.6 |
| Example 2 | Ia + IIa | 3.4 | 5.4 |
| Example 3 | Ib + IIa | 2.7 | 16.0 |
| Example 4 | Ic + IIa | 2.6 | 6.5 |
| Example 5 | Ib + IIb | 0.8 | 40.0 |
| Example 6 | Ia + IIb | 1.1 | N.D. |
| Example 7 | Ib + IIb | 1.5 | 24.1 |
| Example 8 | Ib + IIb | 2.7 | 34.0 |
| Example 9 | Ib + IIb | 2.6 | 67.9 |
| Example 10 | Ic + IIb | 3.2 | 352.0 |
| Example 11 | Ig + IIa | 1.8 | 17.0 |
| Example 12 | Ie + IIa | 1.1 | 18.0 |
| Example 13 | Ie + IIa | 0.3 | 4.0 |
| Example 14 | Ic + IIb | 3.2 | 16.0 |
| Example 15 | Ic + IIb | 0.5 | 10.0 |
| Example 16 | Ic + IIb | 4.2 | 37.0 |
| Example 17 | Ic + IIb | 1.6 | 107.0 |
| Example 18 | Ih + IIa | 0.4 | 13.0 |
| Example 19 | Ie + IIa | 1.5 | 17.0 |
| Example 20 | Ig + IIa | 1.7 | 31.0 |
| Example 21 | Id + IIb | 2.6 | N.D. |
| Example 22 | Ie + IIa | 2.0 | 20.0 |
| Example 24 | Ig + IIa | 1.2 | 34.0 |
| Example 25 | Ib + IIb | 1.3 | 11.0 |
| Example 26 | Ic + IIb | 0.2 | 10.0 |
| Example 27 | Id + IIb | 1.1 | 41.0 |
| Example 28 | Ig + IIa | 0.3 | N.D. |
| Example 29 | Id + IIb | 2.3 | 230 |
| Example 30 | Ii + IIa | 0.06* | N.D. |
| Example 31 | Ib + IIb | 0.8 | 100.0 |
| Example 32 | Ib + IIb | 3.2 | 60.6 |
| Example 33 | Ic + IIb | 4.5 | 152.7 |
| Example 34 | Ii + IIa | 2.1 | 24.9 |
| Example 35 | Ii + IIa | 0.6 | 20.0 |
| Example 36 | Ii + IIa | 2.3 | 20.0 |
| Example 37 | Ib + IIb | 4.2 | 13.0 |
| Example 38 | Ii + IIb | 3.7 | N.D. |
| Example 39 | Ig + IIa | 2.4 | 27.0 |
| Example 40 | Ic + IIb | 2.0 | N.D. |
| Example 41 | Ib + IIb | 1.4 | 4.4 |
| Example 42 | Ib + IIb | 1.1 | N.D. |
| Example 43 | Ig + IIa | 0.7 | 22.0 |
| Example 44 | Ii + IIa | 0.8 | 41.0 |

N.D. = not detectable.
*measured by 13C-NMR as described in Example 46

Example 47

Fluorine NMR Assay

This assay describes how to determine the $^{19}F$ NMR spectrum, which shows diboron compound binding to albumin, and glucose sensitive albumin binding of the diboron compound.

Diboron compound is dissolved at a 0.1 mM concentration in a 50 mM phosphate buffer pH 7.4, 10% deuterated water (D2O), and mixed with 0, 0.1, 0.2, 0.5, 1 and 2 mM human serum albumin (HSA). An additional sample with diboron compound in the presence of 1 mM HSA and 50 mM glucose is prepared.

The samples are then placed into 3 mm standard NMR tube (Bruker) and transferred for analysis to a 400 Mhz Bruker spectrometer equipped with a cryoprobe suitable for fluorine detection. The experiment is carried out with standard Bruker zgflqn pulse sequence at room temperature with enough scans to have a S/N ratio over 50 for the 0 mM HSA sample. The spectra are processed, visualized and compared by TopSpin program (Bruker).

The binding of diboron compound to HSA is qualitatively assessed by decrease of the fluorine signal of the diboron compound upon binding to HSA. Release of the diboron compound from HSA upon addition of glucose is assessed by reappearance/increase of fluorine signal in the spectra.

Figure 3:
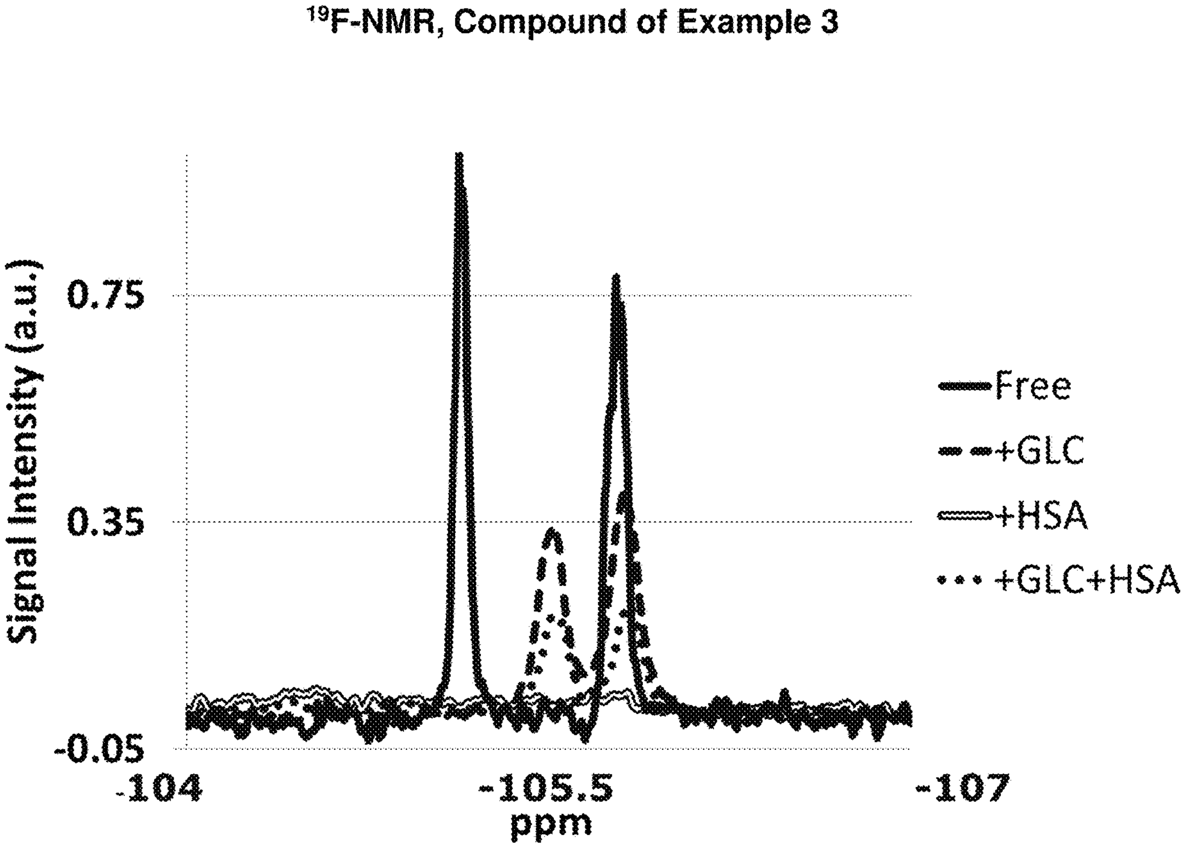
FIG. 3 shows $^{19}F$-NMR signals from the diboron compound of Example 3 in free form (0.1 mM), and upon treatment with albumin (HSA, 1 mM), or with glucose (50 mM) or with albumin (1 mM)+glucose (50 mM), thus illustrating glucose-sensitive albumin binding.
Figure 4:
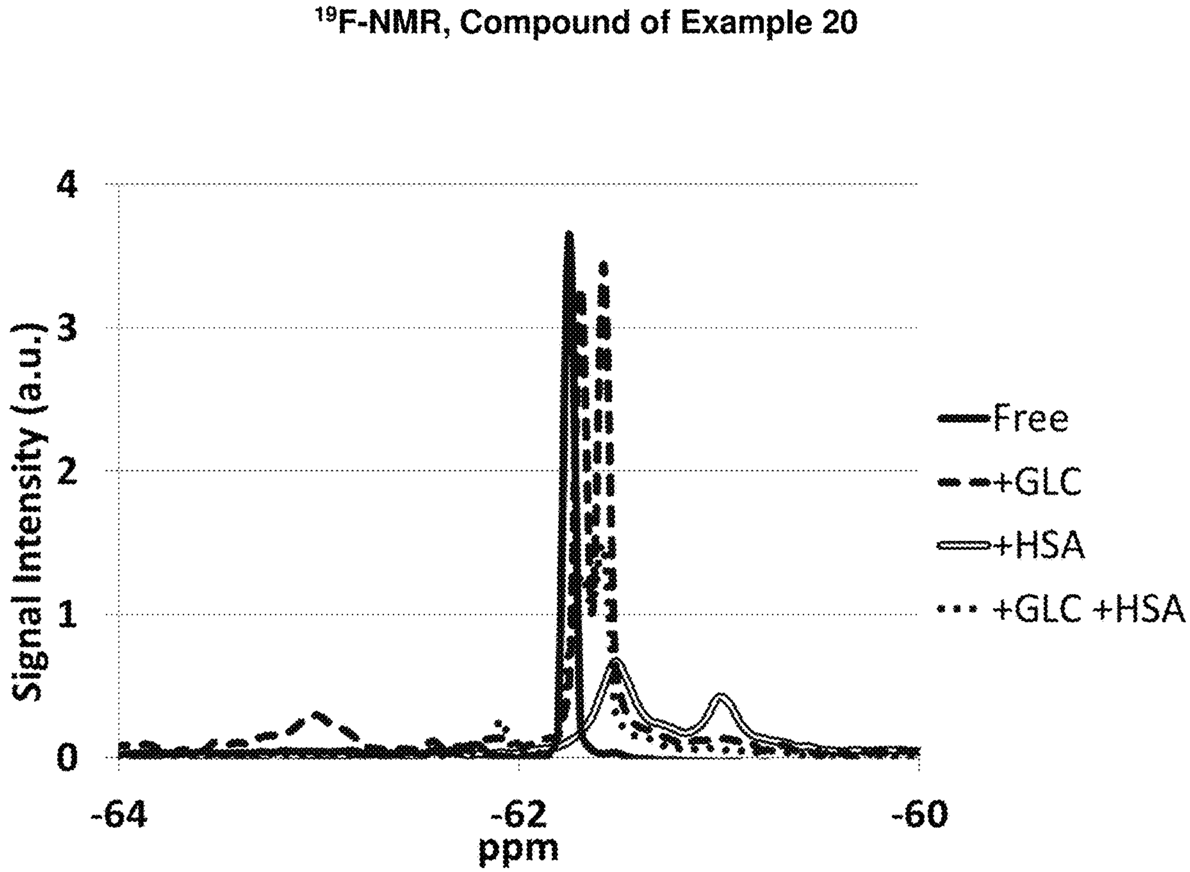
FIG. 4 shows $^{19}F$-NMR signals from the diboron compound of example 20 with and without albumin and glucose like FIG. 3.
Figure 5:
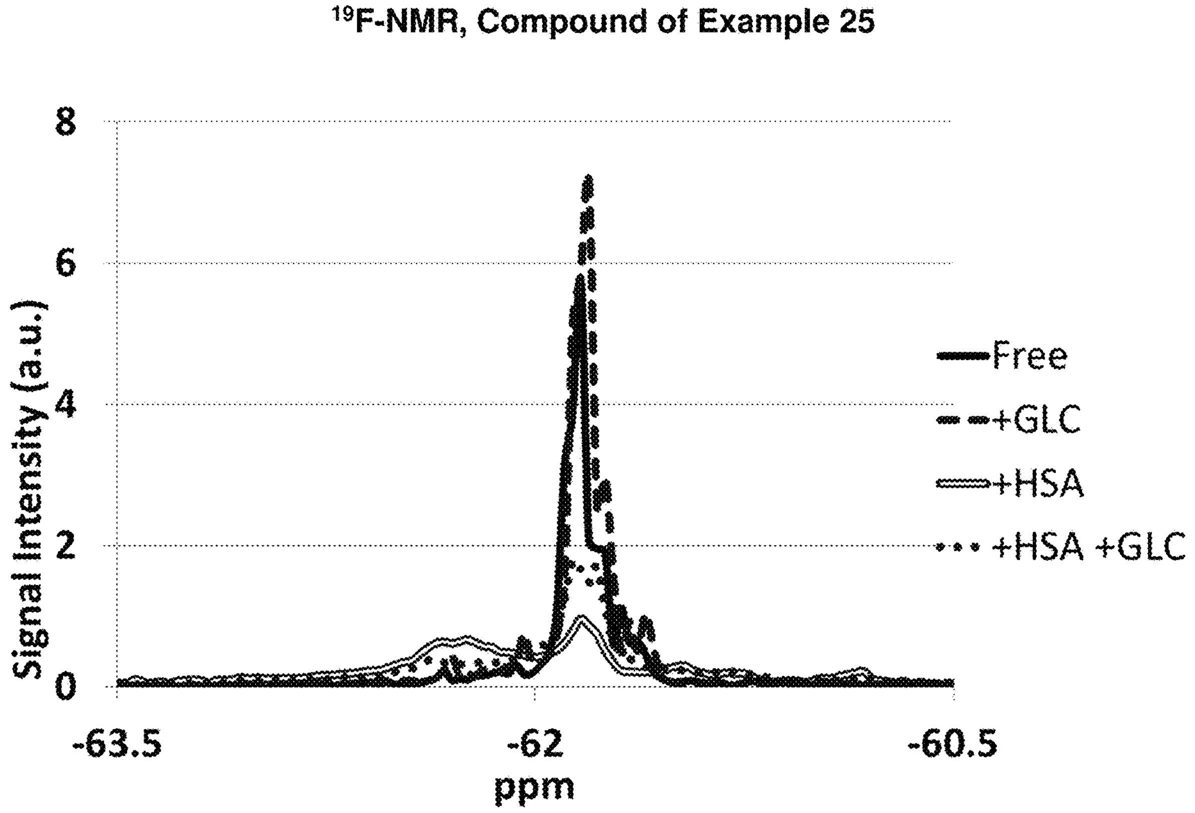
FIG. 5 shows $^{19}F$-NMR signals from the diboron compound of example 25 in with and without albumin and glucose like FIG. 3.
Figure 6:
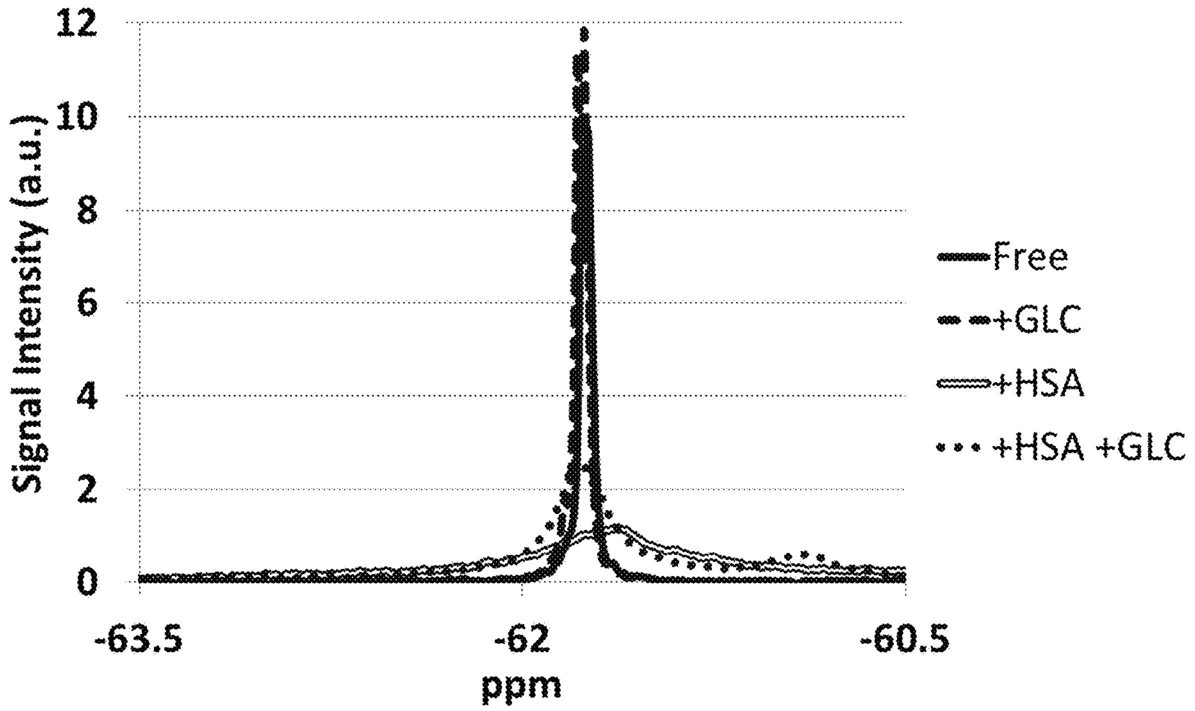
FIG. 6 shows $^{19}F$-NMR signals from the diboron compound of example 26 in with and without albumin and glucose like FIG. 3.

F-NMR signals are depicted in FIG. 3, 4, 5, 6 and show that the diboron compounds (exemplified by the diboron compounds of Example 3, 22, 25 and 26) bind to albumin in a glucose-dependent manner.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A diboron conjugate represented by the general Formula I'

$R^{1'}$—X'—$R^{2'}$ in which Formula I',

X' represents a linker of Formula Ia':

(Formula Ia')

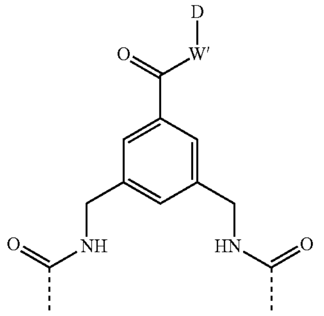

wherein

---- represents a covalent bond towards $R^{1'}$ or $R^{2'}$;

D represents a drug substance; and

W' represents a covalent bond, or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing an L-gamma-Glu or a D-gamma-Glu residue); or X' represents a linker of Formula Ib':

(Formula Ib')

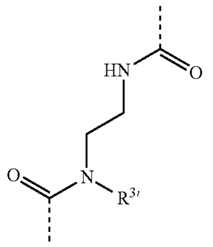

wherein,

---- represents a covalent bond towards $R^{1'}$ or $R^{2'}$; and $R^{3'}$ represent —$(CH_2)_{m'}(C{=}O)$—W'-D, wherein m' represents an integer in the range of 1 to 4;

W' represents a covalent bond or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing an L-gamma-Glu or a D-gamma-Glu residue); and D represents a drug substance; or X' represents a linker of Formula Ic':

(Formula Ic')

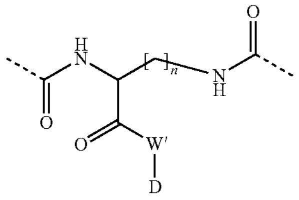

which represents a D- or an L-amino acid form; and wherein,

---- represents a covalent bond towards $R^{1'}$ or $R^{2'}$;

n' represents an integer in the range of 1 to 4;

W' represents a covalent bond or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing an L-gamma-Glu or a D-gamma-Glu residue); and D represents a drug substance; or X' represents a linker of Formula Id':

(Formula Id')

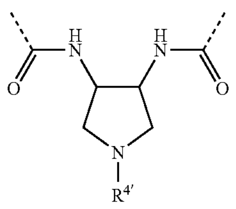

which represents a R,R or S,S, or R,S or R,S stereoisomer of the 3,4-diamino-pyrrolidine;

wherein,

---- represents a covalent bond towards $R^{1'}$ or $R^{2'}$;

$R^{4'}$ represents —$(C{=}O)(CH_2)_{p'}(C{=}O)$—W'-D; where

W' represents a covalent bond or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing an L-gamma-Glu or a D-gamma-Glu residue);

wherein p' represents an integer in the range of 1 to 4; and

D represents a drug substance; or

X' represents a linker of Formula Ie':

(Formula Ie')

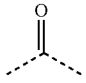

wherein,

--- represents a covalent bond towards $R^{1'}$ or $R^{2'}$; or

X' represents a linker of Formula If':

(Formula If')

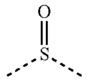

wherein,

---- represents a covalent bond towards $R^{1'}$ or $R^{2'}$; or

X' represents a linker of Formula Ig':

(Formula Ig')

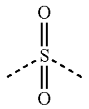

wherein,

--- represents a covalent bond towards $R^{1'}$ or $R^{2'}$; or

X' represents a linker of Formula Ih':

(Formula Ih')

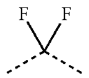

wherein,

--- represents a covalent bond towards $R^{1'}$ or $R^{2'}$; or

X' represents a linker of Formula Ii':

(Formula Ii')

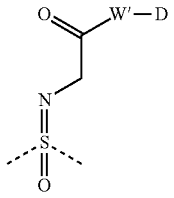

wherein,

---- represents a covalent bond towards $R^{1'}$ or $R^{2'}$; and

W' represents a covalent bond or a linker selected from the group consisting of —$NHCH_2(C{=}O)$—, —$NHCH_2CH_2(C{=}O)$—, —$NHCH_2CH_2CH_2(C{=}O)$—, and —$NHCH(COOH)CH_2CH_2(C{=}O)$— (the latter representing an L-gamma-Glu or a D-gamma-Glu residue); and $R^{1'}$ and $R^{2'}$, which may be identical or different, each represents a group of Formula IIa' or Formula IIb':

(Formula IIa')

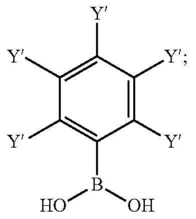

or

-continued (Formula IIb')

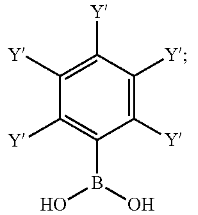

wherein, one to four Y' represents H; and none, one or two Y' represents F, Cl, $CF_2$, $CF_3$, $SF_5$, $OCF_3$, $SO_2CH_3$ and/or $SO_2CF_3$; and one Y' represents (a covalent bond representing) the attachment point to X' of Formula I'; and when X' is Formula Ie', If', Ig' or Ih', one Y in either $R^{1'}$ or $R^{2'}$ represents —(C═O)—W'-D, where W' represents a covalent bond, or a linker selected from the group consisting of —$NHCH_2$(C═O)—, —$NHCH_2CH_2$(C═O)—, —$NHCH_2CH_2CH_2$(C═O)—, and —NHCH(COOH)$CH_2CH_2$(C═O)— (the latter representing an L-gamma-Glu or a D-gamma-Glu residue); and wherein D represents a drug substance.

2. A diboron conjugate, wherein the diboron compound according to claim 1 is conjugated to a drug substance via an optional linker.

3. The diboron conjugate of claim 2, wherein the diboron compound is conjugated to the drug substance via an optional linker by derivatisation of the carboxylic acid moiety of the diboron compound.

* * * * *

UNITED STATES PATENT AND TRADEMARK OFFICE

CERTIFICATE OF CORRECTION

PATENT NO. : 11,767,332 B2
APPLICATION NO. : 17/500242
DATED : September 26, 2023
INVENTOR(S) : Thomas Kruse et al.

It is certified that error appears in the above-identified patent and that said Letters Patent is hereby corrected as shown below:

In the Claims

At Column 185, Claim number 1, Formula IIb', please replace as follows:

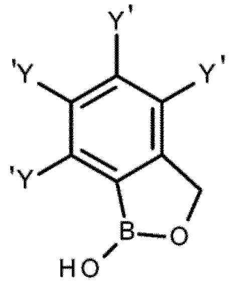

Signed and Sealed this
Twenty-seventh Day of August, 2024

Katherine Kelly Vidal

Katherine Kelly Vidal
*Director of the United States Patent and Trademark Office*